(12) United States Patent
Vaccaro et al.

(10) Patent No.: US 7,723,336 B2
(45) Date of Patent: May 25, 2010

(54) FUSED HETEROCYCLIC COMPOUNDS USEFUL AS KINASE MODULATORS

(75) Inventors: Wayne Vaccaro, Yardley, PA (US); Zhong Chen, Princeton, NJ (US); Dharmpal S. Dodd, Princeton, NJ (US); Tram N. Huynh, Pennington, NJ (US); James Lin, Lawrenceville, NJ (US); Chunjian Liu, Pennington, NJ (US); Christopher P. Mussari, Princeton, NJ (US); John S. Tokarski, Princeton, NJ (US); David R. Tortolani, Skillman, NJ (US); Stephen T. Wrobleski, Whitehouse Station, NJ (US); Shuqun Lin, Newtown, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 205 days.

(21) Appl. No.: 11/689,132

(22) Filed: Mar. 21, 2007

(65) Prior Publication Data

US 2008/0045536 A1 Feb. 21, 2008

Related U.S. Application Data

(63) Continuation-in-part of application No. 11/524,996, filed on Sep. 21, 2006, now abandoned.

(60) Provisional application No. 60/719,519, filed on Sep. 22, 2005.

(51) Int. Cl.
C07D 487/04 (2006.01)
A61K 31/5025 (2006.01)
A61P 19/02 (2006.01)

(52) U.S. Cl. ...................... 514/248; 544/236
(58) Field of Classification Search ................. 544/236; 514/248

See application file for complete search history.

(56) References Cited

U.S. PATENT DOCUMENTS

| | | | |
|---|---|---|---|
| 4,183,930 A | 1/1980 | Cohen | |
| 4,464,372 A | 8/1984 | Bristol et al. | |
| 4,716,169 A | 12/1987 | Heider et al. | |
| 4,838,925 A | 6/1989 | Tseng | |
| 2004/0048849 A1 | 3/2004 | Prevost et al. | |
| 2004/0138245 A1 | 7/2004 | Prevost et al. | |

FOREIGN PATENT DOCUMENTS

| | | |
|---|---|---|
| EP | 0 185 346 | 6/1986 |
| EP | 0 244 166 | 11/1987 |
| EP | 0 306 408 | 3/1989 |
| EP | 0 490 587 | 6/1992 |
| WO | WO 00/56734 | 9/2000 |
| WO | WO 01/83481 | 11/2001 |
| WO | WO 02/50079 | 6/2002 |
| WO | WO 02/066481 | 8/2002 |
| WO | WO 02/096348 | 12/2002 |
| WO | WO 03/076441 | 9/2003 |
| WO | WO 2004/076458 | 9/2004 |
| WO | WO 2004/092175 | 10/2004 |
| WO | WO 2005/000852 | 1/2005 |
| WO | WO 2005/026126 | 3/2005 |
| WO | WO 2006/016715 | 2/2006 |
| WO | WO 2006/070943 | 7/2006 |
| WO | WO 2006/098519 | 9/2006 |
| WO | WO 2006/099972 | 9/2006 |
| WO | WO 2006/102194 | 9/2006 |
| WO | WO 2006/107784 | 10/2006 |
| WO | WO 2007/013673 | 2/2007 |

OTHER PUBLICATIONS

Mass, R. D., Int. Jo Radiation Oncology Bio. Phys.vol. 58(3): 932-940, 2004.*
Fabbro et al. Pharmacology & therapeutics 93, 79-98, 2002.*
Graninger et al. Curr. Opin. Rhematol. 13(3)209-13, 2001.*
Barlin, G.B. et al., "Condensation Reactions of Some α-Aminodiazines with Pyruvaldehyde Dimethyl Acetal", Aust. J. Chem., vol. 35, pp. 423-430 (1982).
Checchi, S. et al., "Derivatives of 5-aminopyrazole. IV. Synthesis of heterocyclic derivatives", Gazzetta Chimica Italiana, vol. 87, pp. 597-614 (1957), (English abstract only).
Dudfield, P.J. et al., "Synthesis of C-ribosyl imidazo[2,1-*f*][1,2,4]triazines as inhibitors of adenosine and AMP deaminases", J. Chem. Soc., Perkin Trans. 1, pp. 2929-2936 (1999).
Elgemeie, G.H. et al., "The Design and Synthesis of Structurally Related Mercaptopurine Analogues: Reaction of Dimethyl N-Cyanodithioiminocarbonate with 5-Aminopyrazoles", Synthetic Communications, vol. 31, No. 22, pp. 3453-3458 (2001).

(Continued)

Primary Examiner—Venkataraman Balasubramanian
(74) Attorney, Agent, or Firm—Hong Liu; Laurelee A. Duncan

(57) ABSTRACT

Compounds having the formula (I), and enantiomers, and diastereomers, pharmaceutically-acceptable salts, thereof,

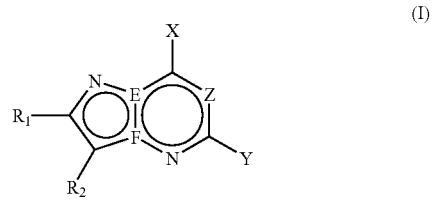

(I)

are useful as kinase modulators, including MK2 modulation, wherein one of E and F is a nitrogen atom and the other of E and F is a carbon atom, Z is N or $CR_3$, and $R_1$, $R_2$, $R_3$, X and Y are as defined herein.

16 Claims, No Drawings

OTHER PUBLICATIONS

Elgemeie, G.H. et al., "The reaction of dimethyl N-cyanodithioiminocarbonate with amino- and oxo-azoles: a new general synthesis of methylsulfanylazoloazines", Journal of Chemical Research (Synopsis), pp. 439-441 (2001).

Freshney, N.W. et al., "Interleukin-1 Activates a Novel Protein Kinase Cascade that Results in the Phosphorylation of Hsp27", Cell, vol. 78, pp. 1039-1049 (1994).

Hajos, G. et al., "Product Class 5: Azaindolizines with Two Nitrogen Atoms in the Five-Membered Ring", Science of Synthesis: Houben-Weyl Methods of Molecular Transformations, vol. 12, No. 5, Georg Thieme Verlag, publ., Neier, R., ed., pp. 613-678 (2002).

Henry, J.R. et al., "p38 mitogen-activated protein kinase as a target for drug discovery", Drugs of the Future, vol. 24, No. 12, pp. 1345-1354 (1999).

Kobe, B. et al., "Use of distance geometry approach for the in vitro antiviral activity evaluation of N-bridgehead C-nucleosides", Eur. J. Med. Chem., vol. 27, pp. 259-266 (1992).

Kotlyarov, A. et al., "MAPKAP kinase 2 is essential for LPS-induced TNF-α biosynthesis", Nature Cell Biology, vol. 1, pp. 94-97 (1999).

Lehner, M.D. et al., "Mitogen-Activated Protein Kinase-Activated Protein Kinase 2-Deficient Mice Show Increased Susceptibility to *Listeria monocytogenes* Infection", The Journal of Immunology, vol. 168, pp. 4667-4673 (2002).

Moreland, L.W. et al., "Etanercept Therapy in Rheumatoid Arthritis: A Randomized, Controlled Trial", Annals of Internal Medicine, vol. 130, No. 6, pp. 478-486 (1999).

Polanc, S. et al., "Synthesis of Some Tricyclic Heterocycles Fused at the N-1-C-8 Bond of Imidazo[1,2-*b*]pyridazines", Synthesis, pp. 175-176 (1975).

Rankin, E.C.C. et al., "The Therapeutic Effects of an Engineered Human Anti-Tumour Necrosis Factor Alpha Antibody (CDP571) in Rheumatoid Arthritis", British Journal of Rheumatology, vol. 34, No. 4, pp. 334-342 (1995).

Salituro, F.G. et al., "Inhibitors of p38 MAP Kinase: Therapeutic Intervention in Cytokine-Mediated Diseases", Current Medicinal Chemistry, vol. 6, No. 9, pp. 807-823 (1999).

Stanovnik, B., "Perchloroimidazo[1,2-*b*]pyridazine. Synthesis and Nucleophilic Substitution", Synthesis, pp. 424-425 (1971).

Stanovnik, B. et al., "Syntheses and Reactivity of 2,3,6,7,8-Pentachloroimidazo[1,2-*b*]pyridazine and 3,6,7,8-Tetrachloro-*s*-triazolo[4,3-*b*]pyridazine", Monatshefte für Chemie, vol. 103, pp. 1624-1631 (1972), (English abstract only).

Abignente, E. et al., "Imidazo[1,2-b]pyridazines: Studies on Chemical Structure-Antiinflammatory Activity Relationships", Acta Chimica Slovenica, vol. 41, pp. 131-148 (1994).

Abignente, E. et al., "Research on Heterocyclic Compounds. XXX. Synthesis and Pharmacological Activity of 2-Methylimidazo[1,2-b]pyridazine-3-carboxylic Acids", Il Farmaco, vol. 47, No. 6, pp. 931-944 (1992).

Almansa, C. et al., "Synthesis and SAR of a New Series of COX-2-Selective Inhibitors: Pyrazolo[1,5-*a*]pyrimidines", Journal of Medicinal Chemistry, vol. 44, No. 3, pp. 350-361 (2001).

Arnaud-Neu, F. et al., "Acid-Base Characteristics of Cholinomimetic 3-Alkylaminopyridazine Derivatives", J. Chem. Research (S), pp. 4-5 (1994).

Arnaud-Neu, F. et al., "Effect of structural modifications on the basicity and spectral characteristics of 3-aminopyridazines", Actualities de Chimie Therapeutique, vol. 16, pp. 291-301 (1989), (English Abstract only).

Galtier, C. et al., "Synthesis and antiviral activities of 3-aralkylthiomethylimidazo[1,2-*b*]pyridazine derivatives", Antiviral Chemistry & Chemotherapy, vol. 14, pp. 177-182 (2003).

Gehlert, D.R. et al., "3-(4-Chloro-2-Morpholin-4-yl-Thiazol-5-yl)-8-(1-Ethylpropyl)-2,6-Dimethyl-Imidazo[1,2-*b*]Pyridazine: A Novel Brain-Penetrant, Orally Available Corticotropin-Releasing Factor Receptor 1 Antagonist with Efficacy in Animal Models of Alcoholism", The Journal of Neuroscience, vol. 27, No. 10, pp. 2718-2726 (2007).

Green, B.G. et al., "Inhibitor of Bacterial Peptide Deformylase by Biaryl Acid Analogs", Archives of Biochemistry and Biophysics, vol. 375, No. 2, pp. 355-358 (2000).

Pollak, A. et al., "Synthesis of Pyridazine Derivatives—XVI: Methyl Substituted Imidazo(1,2-b)pyridazines by Synthesis and Homolytic Methylation", Tetrahedron, vol. 24, pp. 2623-2629 (1968).

Sacchi, A. et al., "Research on heterocyclic compounds, XLI. 2-Phenylimidazo[1,2-b]pyridazine-3-acetic derivatives: synthesis and anti-inflammatory activity", Eur. J. Med. Chem., vol. 34, pp. 1003-1008 (1999).

Walsh, T.F. et al., "Synthesis of New Imidazo[1,2-*b*]pyridazine Isosteres of Potent Imidazo[4,5-*b*]pyridine Angiotensin II Antagonists", Bioorganic & Medicinal Chemistry Letters, vol. 4, No. 1, pp. 219-222 (1994).

Registry No. 933034-91-4, 2007.
Registry No. 910607-63-5, 2006.
Registry No. 910607-62-4, 2006.
Registry No. 910607-61-3, 2006.
Registry No. 785012-64-8, 2004.

* cited by examiner

FUSED HETEROCYCLIC COMPOUNDS USEFUL AS KINASE MODULATORS

This application is a continuation-in-part of U.S. Non-Provisional application Ser. No. 11/524,996, filed Sep. 21, 2006, now abandoned, which claims the priority benefit to U.S. Provisional Application No. 60/719,519, filed Sep. 22, 2005, both of which are incorporated herein by reference in their entirety.

FIELD OF THE INVENTION

This invention relates to fused heterocyclic compounds useful as kinase modulators, including the modulation of MAPKAP kinase-2 (MK2). The invention further pertains to pharmaceutical compositions containing at least one compound according to the invention that are useful for the treatment of conditions related to kinase modulation and methods of inhibiting the activity of kinases, including MK2, in a mammal.

BACKGROUND OF THE INVENTION

A large number of cytokines participate in the inflammatory response, including IL-1, IL-6, IL-8 and TNF-α. The overproduction of cytokines such as IL-1 and TNF-α is implicated in a wide variety of diseases, including inflammatory bowel disease, rheumatoid arthritis, psoriasis, multiple sclerosis, endotoxin shock, osteoporosis, Alzheimer's disease, and congestive heart failure. See e.g. Henry et al., *Drugs Fut.*, Vol. 24 (1999), at pp. 1345-1354; and Salituro et al., *Curr. Med. Chem.*, Vol. 6 (1999), at pp. 807-823. Evidence in human patients indicates that protein antagonists of cytokines are effective in treating chronic inflammatory diseases, such as, for example, monoclonal antibody to TNF-α (Enbrel) (see Rankin et al., *Br. J. Rheumatol.*, Vol 34 (1995), at pp. 334-342), and soluble TNF-α receptor-Fc fusion protein (Etanercept) (see Moreland et al., *Ann. Intern. Med.*, Vol. 130 (1999), at pp. 478-486).

The biosynthesis of TNF-α occurs in many cell types in response to an external stimulus, such as, for example, a mitogen, an infectious organism, or trauma. Important mediators of TNF-α production are the mitogen-activated protein (MAP) kinases, including p38 kinase (p38). Activation of p38 requires dual phosphorylation by an upstream MAP kinase (MKK3 and MKK6) on threonine and tyrosine within a Thr-Gly-Tyr motif characteristic of p38 isozymes. The p38 kinase is an upstream kinase of mitogen-activated protein kinase-activated protein kinase-2 (MAPKAP K2 or MK2). See Freshney et al., *Cell*, Vol. 78 (1994), at pp. 1039-1049.

MK2 is a protein that appears to be predominantly regulated by p38 in cells. In fact, MK2 was the first substrate of p38α to be identified, and in vitro phosphorylation of MK2 by p38α is required for MK2 activation. MK2, in turn, phosphorylates substrates including, but not limited to, heat shock protein 27 (HSP27), lymphocyte-specific protein 1 (LAP-1), leukocyte-specific protein-1 (LSP-1), 5-lipoxygenase (5-LO), cAMP response element-binding protein (CREB), ATF1, serum response factor (SRF), tyrosine hydroxylase, and most importantly, adenosine and uridine-rich element (ARE) binding proteins. ARE binding proteins regulate the mRNA stability of inflammatory mediators such as TNFα and COX-2.

Targeted mutations have been introduced into the mouse MK2 gene that resulted in the generation of MK2-deficient mice. See Kotlyarov et al, *Nat. Cell Biol.*, Vol. 1 (1999), at pp. 94-97. These MK2-deficient mice exhibited increased stress resistance to LPS-induced endoxic shock and had a better survival rate compared to mice that retained the MK2 gene. See id. Isolated splenocytes from these mice challenged with LPS had reduced levels of TNFα, IL-1β, IL-6 and IFNγ. See id. More recently, Lehner et al. reported that MK2-deficient mice showed increased susceptibility to *Listeria moocytogenes* infection and concluded that MK2 had an essential role in host defense against intracellular bacteria, probably through the regulation of TNFα and IFNγ, two of the cytokines required for the activation of antibacterial effector mechanisms. See Lehner et al., *J. Immunol.*, Vol. 168 (2002), at pp. 4667-4673. Moreover, since MK2 is located immediately downstream of p38 in the p38 signaling pathway, it is recognized that MK2 could act as a focal point for more selectively modulating the inflammatory pathway thereby reducing the possibility of undesirable side effects.

Pyrazolo[1,5-a]pyrimidine derivatives have been disclosed in WO2004076458(A1) and described as having kinase inhibiting activity.

New compounds and methods of modulating the activity of kinases, including MK2, would be desirable in the treatment of diseases and disorders that are mediated by cytokines, such as TNFα. It would be even more desirable to provide MK2 inhibitors that have improved potency and reduced undesirable side effects.

SUMMARY OF THE INVENTION

The present invention provides compounds useful in treating inflammatory or immune disease having the formula (I):

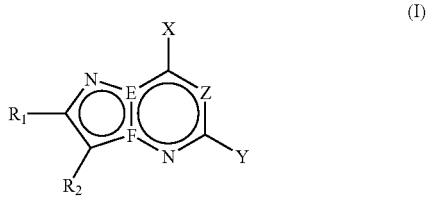

or an enantiomer, diastereomer, or a pharmaceutically-acceptable salt, thereof, wherein:

one of E or F is N, and the other of E or F is C;

X is $NR_4R_5$;

Z is N or $CR_3$, provided that if E is N then Z is N;

Y is selected from hydrogen, alkyl, substituted alkyl, alkenyl, substituted alkenyl, alkynyl, substituted alkynyl, halogen, nitro, cyano, $SR_8$, $S(O)_pR_8$, $OR_8$, $NR_6R_7$, $CO_2R_8$, $C(=O)R_8$, $O—C(=O)R_8$, $C(=O)NR_8R_9$, cycloalkyl, cycloalkenyl, cycloalkynyl, heterocyclo, aryl, and heteroaryl, provided that if Y is hydrogen then $R_4$ is phenyl substituted with a carboxamido group;

$R_1$ and $R_2$ are independently selected from (i) hydrogen, alkyl, substituted alkyl, alkenyl, substituted alkenyl, alkynyl, substituted alkynyl, halogen, nitro, cyano, $SR_{10}$, $OR_{10}$, $NR_{10}R_{11}$, $NR_{10}C(=O)R_{11}$, $CO_2R_{10}$, $C(=O)R_{10}$, $—O—C(=O)R_{10}$, $C(=O)NR_{10}R_{11}$, cycloalkyl, heterocyclo, aryl, and heteroaryl; or (ii) $R_1$ is taken together with $R_2$ and the ring atoms to which they are attached to form a fused 5-, 6-, or 7-membered cycloalkyl, aryl, heteroaryl, or cycloheteroalkyl;

$R_3$ is selected from hydrogen, halogen, alkyl, substituted alkyl, alkenyl, substituted alkenyl, alkynyl, substituted alkynyl, nitro, cyano, $SR_{13}$, $OR_{13}$, $NR_{13}R_{14}$, $NR_{13}C(=O)R_{14}$, $CO_2R_{13}$, $C(=O)R_{13}$, $—O—C(=O)R_{13}$, $—C(=O)NR_{13}R_{14}$, cycloalkyl, heterocyclo, aryl, and heteroaryl;

$R_4$, $R_5$, $R_6$, and $R_7$ are independently selected from hydrogen, alkyl, substituted alkyl, alkenyl, substituted alkenyl, alkynyl, substituted alkynyl, $OR_{15}$, $SR_{15}$, $C(=O)R_{15}$, $CO_2R_{15}$, $C(=O)NR_{15}R_{16}$, $C(W)OR_{16}$, $S(O)_pR_{17}$, $SO_2NR_{15}R_{16}$, cycloalkyl, heterocyclo, aryl, and heteroaryl; or (ii) $R_4$ is taken together with $R_5$ and the nitrogen atom to which they are both attached and/or $R_6$ is taken together with $R_7$ and the nitrogen atom to which they are both attached to form a heteroaryl or heterocyclo;

$R_8$, $R_9$, $R_{10}$, $R_{11}$, $R_{13}$, $R_{14}$, $R_{15}$, and $R_{16}$ at each occurrence are independently selected from (i) hydrogen, alkyl, substituted alkyl, alkenyl, substituted alkenyl, alkynyl, substituted alkynyl, cycloalkyl, aryl, heteroaryl, and heterocyclo; or (ii) together with the nitrogen atom to which they are attached, $R_8$ is taken together with $R_9$, and/or $R_{10}$ is taken together with $R_{11}$, and/or $R_{13}$ is taken together with $R_{14}$, and/or $R_{15}$ is taken together with $R_{16}$ to form a heteroaryl or heterocyclo;

$R_{17}$ at each occurrence is independently selected from alkyl, substituted alkyl, alkenyl, substituted alkenyl, alkynyl, substituted alkynyl, cycloalkyl, aryl, heteroaryl, and heterocyclo;

W at each occurrence is O, S, N, CN, or NH; and p is 1 or 2, with the following provisos:

(1) if E is C, F is N, Z is $CR_3$, and X is NH(Me), $N(Me)_2$, NH(unsubstituted phenyl), or $NHNH_2$, then Y is other than hydrogen or halogen; and (2) if E is N, F is C, Z is N, and Y is $NR_6R_7$;

(a) then X is other than $NH(C_{1-4}alkyl)$, $N(C_{1-4}alkyl)_2$, $NH(C_{2-4}alkenyl)$, $NH(—CH_2-furyl)$, $NHNH_2$, NH(methoxyalkylene), and NHAc;

(b) and if X is NH(—$CH_2$— (substituted or unsubstituted) pyridyl) or NH(—$CH_2$— (substituted or unsubstituted) phenyl), then Y is other than

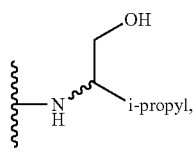

NH(substituted piperidine), or NH(—$CH_2$-pyridine);

(c) and if X is NH(cyclopentyl), then Y is other than NH(cyclopentyl);

(d) and if X is $N(CH_3)$(substituted phenyl) or $N(CH_3)$(pyridyl), then Y is other than

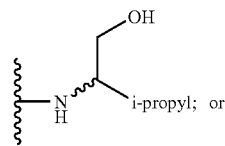

(e) and if X is NH(substituted phenyl), then Y is other than

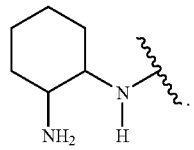

The present invention is also directed to pharmaceutical compositions useful in treating diseases associated with kinase modulation, including modulation (especially inhibition) of MK2, comprising compounds of formula (I), or pharmaceutically-acceptable salts thereof, and pharmaceutically-acceptable carriers or diluents. The invention further relates to methods of treating diseases associated with the kinase modulation, including the modulation of MK2, comprising administering to a patient in need of such treatment a therapeutically-effective amount of a compound according to formula (I).

DETAILED DESCRIPTION OF THE INVENTION

The following are definitions of terms used in this specification and appended claims. The initial definition provided for a group or term herein applies to that group or term throughout the specification and claims, individually or as part of another group, unless otherwise indicated.

The term "alkyl" refers to straight or branched chain hydrocarbon groups having 1 to 12 carbon atoms, preferably 1 to 8 carbon atoms. Lower alkyl groups, that is, alkyl groups of 1 to 4 carbon atoms, are most preferred. When numbers appear in a subscript after the symbol "C", the subscript defines with more specificity the number of carbon atoms that a particular group may contain. For example, "$C_{1-6}$alkyl" refers to straight and branched chain alkyl groups with one to six carbon atoms, such as methyl, ethyl, n-propyl, isopropyl, n-butyl, t-butyl, n-pentyl, and so forth. The subscript "0" refers to a bond. Thus, the term hydroxy($C_{0-2}$)alkyl or ($C_{0-2}$) hydroxyalkyl includes hydroxy, hydroxymethyl and hydroxyethyl.

The term "substituted alkyl" refers to an alkyl group as defined above having one, two, or three substituents selected from the group consisting of halo (e.g., trifluoromethyl), alkenyl, substituted alkenyl, alkynyl, nitro, cyano, oxo (=O), $OR_a$, $SR_a$, (=S), —$NR_aR_b$, —$N(alkyl)_3^+$, $NR_aSO_2$, —$NR_aSO_2R_c$, —$SO_2R_c$—$SO_2NR_aR_b$, —$SO_2NR_aC(=O)$ $R_b$, $SO_3H$, —$PO(OH)_2$, —$OC(O)R_a$, —$C(=O)R_a$, —$CO_2R_a$, —$C(=O)NR_aR_b$, —$C(=O)(C_{1-4}alkylene)$ $NR_aR_b$, —$C(=O)NR_a(SO_2)R_b$, —$CO_2(C_{1-4}alkylene)$ $NR_aR_b$, —$NR_aC(=O)R_b$, —$NR_aCO_2R_b$, —$NR_a(C_{1-4}alkylene)CO_2R_b$, =N—OH, =N—O-alkyl, aryl, cycloalkyl, heterocyclo, and/or heteroaryl, wherein $R_a$ and $R_b$ are selected from hydrogen, alkyl, alkenyl, $CO_2H$, $CO_2(alkyl)$, $C_{3-7}$cycloalkyl, phenyl, benzyl, phenylethyl, napthyl, a four to seven membered heterocyclo, or a five to six membered heteroaryl, or when attached to the same nitrogen atom may join to form a heterocyclo or heteroaryl, and $R_c$ is selected from same groups as $R_a$ and $R_b$ but is not hydrogen. Each group $R_a$ and $R_b$ when other than hydrogen, and each $R_c$ group optionally has up to three further substituents attached at any available carbon or nitrogen atom of $R_a$, $R_b$, and/or $R_c$, said substituent(s) being selected from the group consisting of $(C_{1-6})$alkyl, $(C_{2-6})$alkenyl, hydroxy, halogen, cyano, nitro, =O (as valence allows), $CF_3$, $O(C_{1-6}alkyl)$, $OCF_3$, $C(=O)H$, $C(=O)(C_{1-6}alkyl)$, $CO_2H$, $CO_2(C_{1-6}alkyl)$, $NHCO_2(C_1$-

$_6$alkyl), —S(C$_{1-6}$alkyl), —NH$_2$, NH(C$_{1-6}$alkyl), N(C$_{1-6}$alkyl)$_2$, N(CH$_3$)$_3$$^+$, SO$_2$(C$_{1-6}$alkyl), C(=O)(C$_{1-4}$alkylene)NH$_2$, C(=O)(C$_{1-4}$alkylene)NH(alkyl), C(=O)(C$_{1-4}$alkylene)N(C$_{1-4}$alkyl)$_2$, C$_{3-7}$cycloalkyl, phenyl, benzyl, phenylethyl, phenyloxy, benzyloxy, napthyl, a four to seven membered heterocyclo or cycloalkyl, or a five to six membered heteroaryl. When a substituted alkyl is substituted with an aryl (including, for example, phenyl and napthyl), heterocyclo, cycloalkyl, or heteroaryl group, said ringed systems are as defined below and thus may have zero, one, two, or three substituents, also as defined below.

One skilled in the field will understand that, when the designation "CO$_2$" is used herein, this is intended to refer to the group

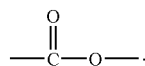

When the term "alkyl" is used together with another group, such as in "arylalkyl", this conjunction defines with more specificity at least one of the substituents that the substituted alkyl will contain. For example, "arylalkyl" refers to a substituted alkyl group as defined above where at least one of the substituents is an aryl, such as benzyl. Thus, the term aryl(C$_{0-4}$)alkyl includes a substituted lower alkyl having at least one aryl substituent and also includes an aryl directly bonded to another group, i.e., aryl(C$_0$)alkyl.

The term "alkenyl" refers to straight or branched chain hydrocarbon groups having 2 to 12 carbon atoms and at least one double bond. Alkenyl groups of 2 to 6 carbon atoms and having one double bond are most preferred.

The term "alkynyl" refers to straight or branched chain hydrocarbon groups having 2 to 12 carbon atoms and at least one triple bond. Alkynyl groups of 2 to 6 carbon atoms and having one triple bond are most preferred.

The term "alkylene" refers to bivalent straight or branched chain hydrocarbon groups having 1 to 12 carbon atoms, preferably 1 to 8 carbon atoms, e.g., {—CH$_2$—}$_n$, wherein n is 1 to 12, preferably 1-8. Lower alkylene groups, that is, alkylene groups of 1 to 4 carbon atoms, are most preferred. The terms "alkenylene" and "alkynylene" refer to bivalent radicals of alkenyl and alkynyl groups, respectively, as defined above.

When reference is made to a substituted alkenyl, alkynyl, alkylene, alkenylene, or alkynylene group, these groups are substituted with one to three substitutents as defined above for substituted alkyl groups.

The term "heteroalkylene" is used herein to refer to saturated and unsaturated bivalent straight or branched chain hydrocarbon groups having 2 to 12 carbon atoms, preferably 2 to 8 carbon atoms, wherein one or two carbon atoms in the straight chain are replaced by heteroatom(s) selected from —O—, —S—, —S(=O)—, —SO$_2$—, —NH—, and —NHSO$_2$—. Thus, the term "heteroalkylene" includes bivalent alkoxy, thioalkyl, and aminoalkyl groups, as defined below, as well as alkylene and alkenylene groups having a combination of heteroatoms in the alkyl chain. As an illustration, a "heteroalkylene" herein may comprise groups such as —S—(CH$_2$)$_{1-5}$NH—CH$_2$—, —O—(CH$_2$)$_{1-5}$S(=O)—CH$_2$—, —NHSO$_2$—CH$_2$—, —CH$_2$—NH—, and so forth. Preferably, a heteroalkylene does not have two adjacent atoms simultaneously selected from —O— and —S—. When a subscript is used with the term heteroalkylene, e.g., as in C$_{2-3}$heteroalkylene, the subscript refers to the number of carbon atoms in the group in addition to heteroatoms. Thus, for example, a C$_{1-2}$heteroalkylene may include groups such as —NH—CH$_2$—, —CH$_2$—NH—CH$_2$—, —CH$_2$—CH$_2$—NH—, —S—CH$_2$—, —CH$_2$—S—CH$_2$—, —O—CH$_2$—NH—CH$_2$—, CH$_2$—O—CH$_2$ and so forth.

The term "substituted heteroalkylene" refers to a heteroalkylene group as defined above wherein at least one of the nitrogen or carbon atoms in the heteroalkylene chain is bonded to (or substituted with) a group other than hydrogen. Carbon atoms in the heteroalkylene chain may be substituted with a group selected from those recited above for substituted alkyl groups, or with a further alkyl or substituted alkyl group. Nitrogen atoms of the heteroalkylene chain may be substituted with a group selected from alkyl, alkenyl, alkynyl, cyano, or A$_1$-Q-A$_2$-R$_h$, wherein A$_1$ is a bond, C$_{1-2}$alkylene, or C$_{2-3}$alkenylene; Q is a bond, —C(=O)—, —C(=O)NR$_d$—, —C(=S)NR$_d$—, —SO$_2$—, —SO$_2$NR$_d$—, —CO$_2$—, or —NR$_d$CO$_2$—; A$_2$ is a bond, C$_{1-3}$alkylene, C$_{2-3}$alkenylene, —C$_{1-4}$alkylene-NR$_d$—, —C$_{1-4}$alkylene-NR$_d$C(=O)—, —C$_{1-4}$alkylene-S—, —C$_{1-4}$alkylene-SO$_2$—, or —C$_{1-4}$alkylene-O—, wherein said A$_2$ alkylene groups are branched or straight chain and optionally substituted as defined herein for substituted alkylene; R$_h$ is hydrogen, alkyl, substituted alkyl, alkenyl, substituted alkenyl, aryl, heteroaryl, heterocyclo, or cycloalkyl; and R$_d$ is selected from hydrogen, alkyl, and substituted alkyl, as defined herein, provided, however, that for a substituted heteroalkylene R$_h$ is not hydrogen when A$_1$, Q and A$_2$ are each bonds. When R$_h$ is aryl, heteroaryl, cycloalkyl, or heterocyclo, these rings are, in turn, optionally substituted with one to three groups as defined below in the definitions for these terms.

The term "alkoxy" refers to an oxygen atom substituted by alkyl or substituted alkyl, as defined herein. For example, the term "alkoxy" or includes the group —O—C$_{1-6}$alkyl.

The term "alkylthio" refers to a sulfur atom that is substituted by an alkyl or substituted alkyl group as defined herein. For example, the term "thioalkyl" includes the group —S—C$_{1-6}$alkyl, and so forth.

The term "alkylamino" refers to an amino group substituted with an alkyl group or substituted alkyl group as defined above. For example, the term "alkylamino" includes the group —NR—C$_{1-12}$alkyl. (where R is preferably hydrogen but may include alkyl or substituted alkyl as defined above.)

When a subscript is used with reference to an alkoxy, thioalkyl or aminoalkyl, the subscript refers to the number of carbon atoms that the group may contain in addition to heteroatoms. Thus, for example, monovalent C$_{1-2}$aminoalkyl includes the groups —CH$_2$—N(CH$_3$)$_2$, and —(CH$_2$)$_2$—NH$_2$. A lower aminoalkyl comprises an aminoalkyl having one to four carbon atoms. The term (C$_{1-4}$alkyl)$_{0-2}$amino includes the groups NH$_2$, —NH(C$_{1-4}$alkyl), and —N(C$_{1-4}$alkyl)$_2$. "Amino" refers to the group NH$_2$. A "substituted amino" refers to an amino group substituted as described above for the nitrogen atom of a heteroalkylene chain and includes, for example, the terms alkylamino and acylamino (—NR$_d$C(O)R$_e$).

The alkoxy, thioalkyl, or aminoalkyl groups may be monovalent or bivalent. By "monovalent" it is meant that the group has a valency (i.e., ability to combine with another group), of one, and by "bivalent" it is meant that the group has a valency of two. Thus, for example, a monovalent alkoxy includes groups such as —O—C$_{1-12}$alkyl, whereas a bivalent alkoxy includes groups such as —O—C$_{1-12}$alkylene-.

It should be understood that the selections for all groups, including for examples, alkoxy, thioalkyl, and aminoalkyl, will be made by one skilled in the field to provide stable compounds. Thus, for example, in compounds of formula (I), when G is attached to a nitrogen atom (N*) of ring A and is selected from an alkoxy or alkylthio group, the alkoxy and alkylthio groups will have at least one carbon atom bonded directly to ring A (at N*), with the oxygen or sulfur atoms being at least one atom away from said nitrogen atom.

The term "carbonyl" refers to a bivalent carbonyl group —C(=O)—. When the term "carbonyl" is used together with another group, such as in "heterocyclocarbonyl", this conjunction defines with more specificity at least one of the substituents that the substituted carbonyl will contain. For example, "heterocyclocarbonyl" refers to a carbonyl group as defined above where at least one of the substituents is an heterocyclo, such as morpholinyl.

The term "acyl" refers to a carbonyl group linked to an organic radical, more particularly, the group $C(=O)R_c$. The group $R_c$ can be selected from alkyl, alkenyl, alkynyl, aminoalkyl, substituted alkyl (i.e. substituted alkylene), substituted alkenyl, substituted alkynyl, cycloalkyl, heterocyclo, aryl, or heteroaryl, as defined herein. When $R_c$ is aryl, heteroaryl, cycloalkyl, or heterocyclo, these rings are, in turn, optionally substituted with one to three groups as defined below in the definitions for these terms.

The term "alkoxycarbonyl" refers to a carboxy group

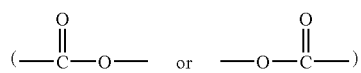

linked to an organic radical ($CO_2R_e$), as well as the bivalent groups —$CO_2$—, —$CO_2R_e$— which are linked to organic radicals in compounds of formula (I), wherein $R_e$ is as defined above for acyl. The organic radical to which the carboxy group is attached may be monovalent (e.g., —$CO_2$-alkyl or —OC(=O)alkyl), or bivalent (e.g. —$CO_2$-alkylene, —OC(=O)alkylene, etc.) Accordingly, in compounds of formula (I), when it is recited that G can be "alkoxycarbonyl," this is intended to encompass a selection for G of —$CO_2$— and also the groups —$CO_2R_e$— or —$R_eCO_2$—, wherein in this instance, the group $R_e$ will be selected from bivalent groups, e.g., alkylene, alkenylene, alkynylene, bivalent aminoalkyl, substituted alkylene, substituted alkenylene, or substituted alkynylene.

The term "carboxamide", "carboxamidyl", or "carboxamido" refers to the group —$NR_dC(=O)R_e$, wherein the groups $R_d$ and $R_e$ are defined as recited above in the definitions for heteroalkyl, alkoxycarbonyl and acyl. For example, the group

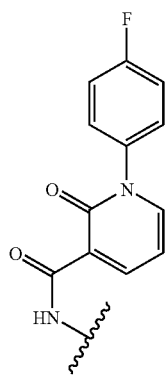

is a carboxamido group where $R_e$ is a substituted heterocyclo according to the definitions herein.

The term "amide", "amidyl", or "amido" refers to the group —C(=O)$NR_aR_b$, wherein the groups $R_a$ and $R_b$ are defined as recited above in the definition for substituted alkyl groups.

The term "urea" refers to the group —$NR_dC(=O)NR_aR_b$, wherein the groups $R_a$, $R_b$, and $R_d$ are defined as recited above in the definition for substituted alkyl groups. Additionally, the urea group may be bivalent, in which case one of the groups $R_a$ and $R_b$ will be a bond. Thus, in compounds of formula (I), when it is stated that G may be urea, it can mean that G is a group —$NR_d(C(=O)NR_a$— where appropriate.

The term "sulfonyl" refers to a sulphoxide group linked to an organic radical in compounds of formula (I), more particularly, the monovalent group —$S(O)_2$—$R_e$. Additionally, the sulfonyl group may be bivalent, in which case $R_e$ is a bond. Accordingly, in compounds of formula (I), when it is recited that G can be "sulfonyl," it can mean that G is a group —S(O) where appropriate. The group $R_e$ is selected from those recited above for acyl and alkoxycarbonyl groups, with the exception that $R_e$ is not hydrogen.

The terms "sulfonamide", "sulfonamidyl", or "sulfonamido" refers to the group —$S(O)_2NR_aR_b$, wherein $R_a$ and $R_b$ are as defined above for substituted alkyl groups.

The term "cycloalkyl" refers to fully saturated and partially unsaturated hydrocarbon rings (and therefore includes hydrocarbon rings also known as "cycloalkenyl rings") of 3 to 9, preferably 3 to 7 carbon atoms. The term "cycloalkyl" includes such rings having zero, one, two, or three substituents selected from the group consisting of halogen, trifluoromethyl, trifluoromethoxy, alkyl, substituted alkyl, alkenyl, substituted alkenyl, alkynyl, nitro, cyano, oxo (=O), $OR_a$, $SR_a$, (=S), —$NR_aR_b$, —N(alkyl)$_3^+$, $NR_aSO_2$, —$NR_aSO_2R_c$, —$SO_2R_c$—$SO_2NR_aR_b$, —$SO_2NR_aC(=O)R_b$, $SO_3H$, —$PO(OH)_2$, —$C(=O)R_a$, —$CO_2R_a$, —$C(=O)NR_aR_b$, —$C(=O)(C_{1-4}alkylene)NR_aR_b$, —$C(=O)NR_a(SO_2)R_b$, —$CO_2(C_{1-4}alkylene)NR_aR_b$, —$NR_aC(=O)R_b$, —$NR_aCO_2R_b$, —$NR_a(C_{1-4}alkylene)CO_2R_b$, =N—OH, =N—O-alkyl, aryl, cycloalkyl, heterocyclo, and/or heteroaryl, wherein $R_a$, $R_b$ and $R_c$ are as defined above for substituted alkyl groups, and are also in turn optionally substituted as recited above in the definition for substituted alkyl groups. The term "cycloalkyl" also includes such rings having a second ring fused thereto (e.g., including benzo, heterocyclo, or heteroaryl rings) or having a carbon-carbon bridge of 3 to 4 carbon atoms. When a cycloalkyl is substituted with a further ring (or has a second ring fused thereto), said ring in turn is optionally substituted with one to two of ($C_{1-4}$)alkyl, ($C_{2-4}$)alkenyl, ($C_{2-4}$)alkynyl, halogen, hydroxy, cyano, nitro, $CF_3$, O($C_{1-4}$alkyl), $OCF_3$, C(=O)H, C(=O)($C_{1-4}$alkyl), $CO_2H$, $CO_2(C_{1-4}$alkyl), $NHCO_2(C_{1-4}$alkyl), —S($C_{1-4}$alkyl), —$NH_2$, NH($C_{1-4}$alkyl), N($C_{1-4}$alkyl)$_2$, N($C_{1-4}$alkyl)$_3^+$, $SO_2$($C_{1-4}$alkyl), C(=O)($C_{1-4}$alkylene)$NH_2$, C(=O)($C_{1-4}$alkylene)NH(alkyl), C(=O)($C_{1-4}$alkylene)N($C_{1-4}$alkyl)$_2$ and/or phenyl optionally substituted with any of the preceeding groups. As valence allows, if said further ring is cycloalkyl or heterocyclo it is additionally optionally substituted with =O (oxo).

Accordingly, in compounds of formula (I), the term "cycloalkyl" includes cyclopropyl, cyclobutyl, cyclopentyl, cyclohexyl, cycloheptyl, bicyclooctyl, etc., as well as the following ring systems,

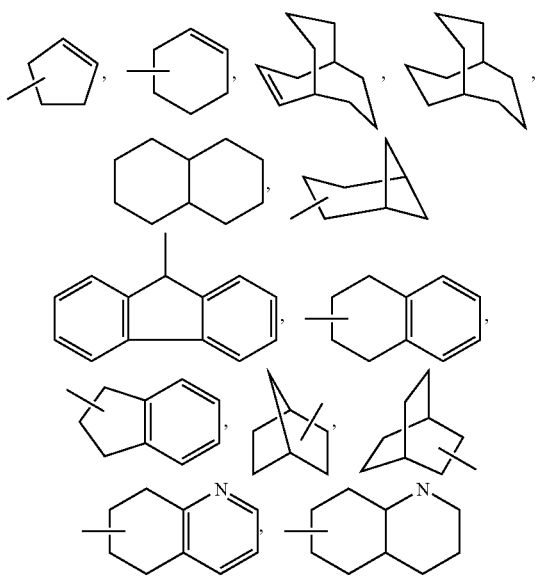

and the like, which optionally may be substituted at any available atoms of the ring(s). Preferred cycloalkyl groups include cyclopropyl, cyclopentyl, cyclohexyl, and

The term "halo" or "halogen" refers to chloro, bromo, fluoro and iodo.

The term "haloalkyl" means a substituted alkyl having one or more halo substituents. For example, "haloalkyl" includes mono, bi, and trifluoromethyl.

The term "haloalkoxy" means an alkoxy group having one or more halo substituents. For example, "haloalkoxy" includes $OCF_3$.

The term "aryl" refers to phenyl, biphenyl, fluorenyl, 1-naphthyl and 2-naphthyl. The term "aryl" includes such rings having zero, one, two or three substituents selected from the group consisting of halogen, trifluoromethyl, trifluoromethoxy, alkyl, substituted alkyl, alkenyl, substituted alkenyl, alkynyl, nitro, cyano, $OR_a$, $SR_a$, (=S), $SO_3H$, $-NR_aR_b$, $N(alkyl)_3^+$, $-NR_aSO_2$, $-NR_aSO_2R_c$, $-SO_2R_c$-$SO_2NR_aR_b$, $-SO_2NR_aC(=O)R_b$, $SO_3H$, $-PO(OH)_2$, $-C(=O)R_a$, $-CO_2R_a$, $-C(=O)NR_aR_b$, $-C(=O)(C_{1-4}alkylene)NR_aR_b$, $-C(=O)NR_a(SO_2)R_b$, $-CO_2(C_{1-4}alkylene)NR_aR_b$, $-NR_aC(=O)R_b$, $-NR_aCO_2R_b$, $-NR_a(C_{1-4}alkylene)CO_2R_b$, aryl, cycloalkyl, heterocyclo, and/or heteroaryl, wherein $R_a$, $R_b$ and $R_c$ are as defined above for substituted alkyl groups, and are also in turn optionally substituted as recited above. Additionally, two substituents attached to an aryl, particularly a phenyl group, may join to form a further ring such as a fused or spiro-ring, e.g. cyclopentyl or cyclohexyl, or fused heterocyclo or heteroaryl. When an aryl is substituted with a further ring (or has a second ring fused thereto), said ring in turn is optionally substituted with one to two of $(C_{1-4})$alkyl, $(C_{2-4})$alkenyl, $(C_{2-4})$alkynyl, halogen, hydroxy, cyano, nitro, $CF_3$, $O(C_{1-4}alkyl)$, $OCF_3$, $C(=O)H$, $C(=O)(C_{1-4}alkyl)$, $CO_2H$, $CO_2(C_{1-4}alkyl)$, $NHCO_2(C_{1-4}alkyl)$, $-S(C_{1-4}alkyl)$, $-NH_2$, $NH(C_{1-4}alkyl)$, $N(C_{1-4}alkyl)_2$, $N(C_{1-4}alkyl)_3^+$, $SO_2(C_{1-4}alkyl)$, $C(=O)(C_{1-4}alkylene)NH_2$, $C(=O)(C_{1-4}alkylene)NH(alkyl)$, $C(=O)(C_{1-4}alkylene)N(C_{1-4}alkyl)_2$ and/or phenyl optionally substituted with any of the preceeding groups. As valence allows, if said further ring is cycloalkyl or heterocyclo it is additionally optionally substituted with =O (oxo).

Thus, examples of aryl groups include:

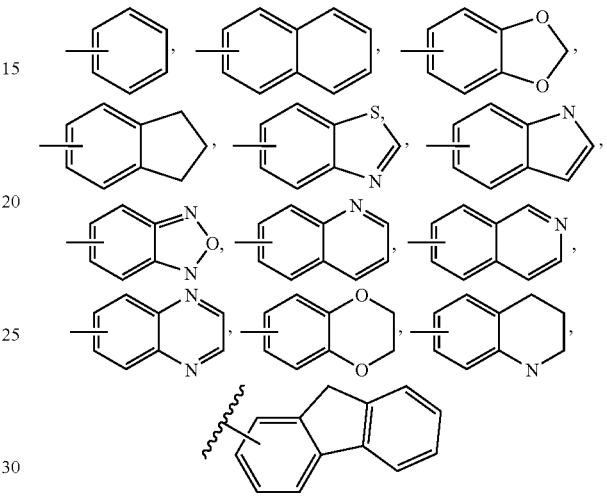

(fluorenyl) and the like, which optionally may be substituted at any available carbon or nitrogen atom. A preferred aryl group is optionally-substituted phenyl.

The terms "heterocycloalkyl", "heterocyclo" or "heterocyclic" may be used interchangeably and refer to substituted and unsubstituted non-aromatic 3- to 7-membered monocyclic groups, 7- to 11-membered bicyclic groups, and 10- to 15-membered tricyclic groups, in which at least one of the rings has at least one heteroatom (O, S or N), said heteroatom containing ring preferably having 1, 2, or 3 heteroatoms selected from O, S, and N. Each ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The fused rings completing the bicyclic and tricyclic groups may contain only carbon atoms and may be saturated, partially saturated, or unsaturated. The heterocyclo group may be attached at any available nitrogen or carbon atom. The heterocyclo ring may contain zero, one, two or three substituents selected from the group consisting of halogen, trifluoromethyl, trifluoromethoxy, alkyl, substituted alkyl, alkenyl, substituted alkenyl, alkynyl, nitro, cyano, oxo (=O), $OR_a$, $SR_a$, (=S), $-NR_aR_b$, $-N(alkyl)_3^+$, $-NR_aSO_2$, $-NR_aSO_2R_c$, $-SO_2R_c$-$SO_2NR_aR_b$, $-SO_2NR_aC(=O)R_b$, $SO_3H$, $-PO(OH)_2$, $-C(=O)R_a$, $-CO_2R_a$, $-C(=O)NR_aR_b$, $-C(=O)(C_{1-4}alkylene)NR_aR_b$, $-C(=O)NR_a(SO_2)R_b$, $-CO_2(C_{1-4}alkylene)NR_aR_b$, $-NR_aC(=O)R_b$, $-NR_aCO_2R_b$, $-NR_a(C_{1-4}alkylene)CO_2R_b$, =N-OH, =N-O-alkyl, aryl, cycloalkyl, heterocyclo, and/or heteroaryl, wherein $R_a$, $R_b$ and $R_c$ are as defined above for substituted alkyl groups, and are also in turn optionally substituted as recited above. When a heterocyclo is substituted with a further ring, said ring in turn is optionally substituted with one to two of $(C_{1-4})$alkyl, $(C_{2-4})$alkenyl, $(C_{2-4})$alkynyl, halogen, hydroxy, cyano, nitro, $CF_3$, $O(C_{1-4}alkyl)$, $OCF_3$, $C(\!=\!O)H$, $C(\!=\!O)(C_{1-4}alkyl)$, $CO_2H$, $CO_2(C_{1-4}alkyl)$, $NHCO_2(C_{1-4}alkyl)$, $-S(C_{1-4}alkyl)$, $-NH_2$, $NH(C_{1-4}alkyl)$, $N(C_{1-4}alkyl)_2$, $N(C_{1-4}alkyl)_3{}^+$, $SO_2(C_{1-4}alkyl)$, $C(\!=\!O)(C_{1-4}alkylene)NH_2$, $C(\!=\!O)(C_{1-4}alkylene)NH(alkyl)$, $C(\!=\!O)(C_{1-4}alkylene)N(C_{1-4}alkyl)_2$ and/or phenyl optionally substituted with any of the preceeding groups. As valence allows, if said further ring is cycloalkyl or heterocyclo it is additionally optionally substituted with =O (oxo).

Exemplary monocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl.

Preferred heterocyclo groups in compounds of formula (I) include

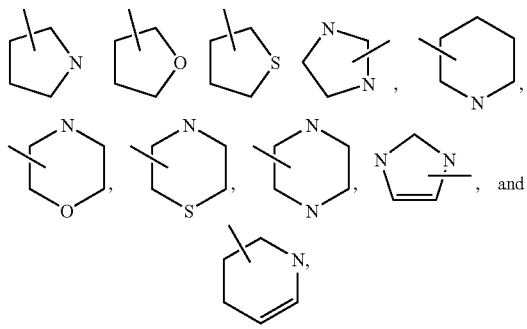

which optionally may be substituted.

The term "heteroaryl" refers to substituted and unsubstituted aromatic 5- or 6-membered monocyclic groups, 9- or 10-membered bicyclic groups, and 11- to 14-membered tricyclic groups which have at least one heteroatom (O, S or N) in at least one of the rings, said heteroatom-containing ring preferably having 1, 2, or 3 heteroatoms selected from O, S, and N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents selected from the group consisting of halogen, trifluoromethyl, trifluoromethoxy, alkyl, substituted alkyl, alkenyl, substituted alkenyl, alkynyl, nitro, cyano, $OR_a$, $SR_a$, (=S), $-NR_aR_b$, $-N(alkyl)_3{}^+$, $-NR_aSO_2$, $-NR_aSO_2R_c$, $-SO_2R_c$, $-SO_2NR_aR_b$, $-SO_2NR_aC(\!=\!O)R_b$, $SO_3H$, $-PO(OH)_2$, $-C(\!=\!O)R_a$, $-CO_2R_a$, $-C(\!=\!O)NR_aR_b$, $-C(\!=\!O)(C_{1-4}alkylene)NR_aR_b$, $-C(\!=\!O)NR_a$ $(SO_2)R_b$, $-CO_2(C_{1-4}alkylene)NR_aR_b$, $-NR_aC(\!=\!O)R_b$, $-NR_aCO_2R_b$, $-NR_a(C_{1-4}alkylene)CO_2R_b$, aryl, cycloalkyl, heterocyclo, and/or heteroaryl, wherein $R_a$, $R_b$ and $R_c$ are as defined above for substituted alkyl groups, and are also in turn optionally substituted as recited above. When a heteroaryl is substituted with a further ring, said ring in turn is optionally substituted with one to two of $(C_{1-4})$alkyl, $(C_{2-4})$alkenyl, $(C_{2-4})$alkynyl, halogen, hydroxy, cyano, nitro, $CF_3$, $O(C_{1-4}alkyl)$, $OCF_3$, $C(\!=\!O)H$, $C(\!=\!O)(C_{1-4}alkyl)$, $CO_2H$, $CO_2(C_{1-4}alkyl)$, $NHCO_2(C_{1-4}alkyl)$, $-S(C_{1-4}alkyl)$, $-NH_2$, $NH(C_{1-4}alkyl)$, $N(C_{1-4}alkyl)_2$, $N(C_{1-4}alkyl)_3{}^+$, $SO_2$ $(C_{1-4}alkyl)$, $C(\!=\!O)(C_{1-4}alkylene)NH_2$, $C(\!=\!O)(C_{1-4}alkylene)NH(alkyl)$, $C(\!=\!O)(C_{1-4}alkylene)N(C_{1-4}alkyl)_2$ and/or phenyl optionally substituted with any of the preceeding groups. As valence allows, if said further ring is cycloalkyl or heterocyclo it is additionally optionally substituted with =O (oxo).

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

In compounds of formula (I), preferred heteroaryl groups include

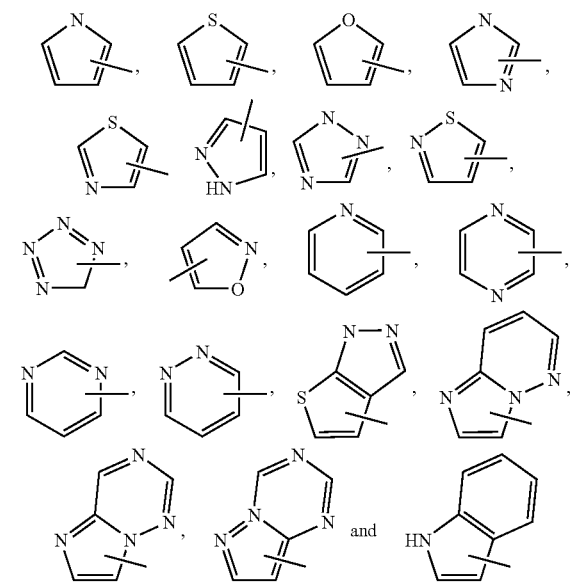

and the like, which optionally may be substituted at any available carbon or nitrogen atom. Aromatic rings may also be designated by an unbroken circle in the ring. For example the core ring of formula (I),

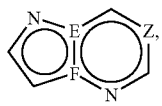

represents a bicyclic heteroaryl group.

Unless otherwise indicated, when reference is made to a specifically-named aryl (e.g., phenyl), cycloalkyl (e.g., cyclohexyl), heterocyclo (e.g., pyrrolidinyl, piperidinyl, and morpholinyl) or heteroaryl (e.g., tetrazolyl, imidazolyl, pyrazolyl, triazolyl, thiazolyl, and furyl) unless otherwise specifically indicated the reference is intended to include rings having 0 to 3, preferably 0-2, substituents selected from those recited above for the aryl, cycloalkyl, heterocyclo and/or heteroaryl groups, as appropriate.

Generally, for a non-formula substituent listing a combination of groups, unless specifically designated otherwise, the last group of the combination is the point of attachment with adjacent groups attached sequentially. Accordingly, for example, the term "aminocyclohexylmethyl is intended" to mean

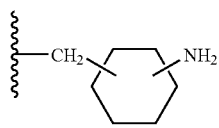

and N-(n-propyl)sulfonamido is intended to mean

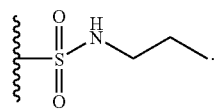

The term "heteroatoms" shall include oxygen, sulfur and nitrogen.

The term "carbocyclic" means a saturated or unsaturated monocyclic or bicyclic ring in which all atoms of all rings are carbon. Thus, the term includes cycloalkyl and aryl rings. The carbocyclic ring may be substituted in which case the substituents are selected from those recited above for cycloalkyl and aryl groups.

When the term "unsaturated" is used herein to refer to a ring or group, the ring or group may be fully unsaturated or partially unsaturated.

When the term "optionally substituted" is used herein to refer to a ring or group, the ring or group may be substituted or unsubstituted.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

According to the foregoing definitions, the instant invention provides compounds within the scope of formula (I) having the formulae (Ia), (Ib), or (Ic):

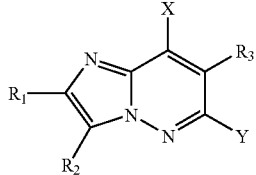

(Ia)

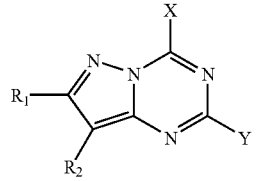

(Ib)

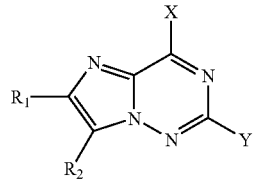

(Ic)

wherein the groups $R_1$, $R_2$, $R_3$, X and Y, are as defined herein.

The compounds of formula (I) can form salts which are also within the scope of this invention. Unless otherwise indicated, reference to an inventive compound is understood to include reference to salts thereof. The term "salt(s)" denotes acidic and/or basic salts formed with inorganic and/or organic acids and bases. In addition, the term "salt(s) may include zwitterions (inner salts), e.g., when a compound of formula (I) contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g. in isolation or purification steps which may be employed during preparation, and thus, are contemplated within the scope of the invention. Salts of the compounds of the formula (I) may be formed, for example, by reacting a compound of the formula (I) with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylene-diamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate salts.

Prodrugs and solvates of the inventive compounds are also contemplated. The term "prodrug" denotes a compound which, upon administration to a subject, undergoes chemical conversion by metabolic or chemical processes to yield a compound of the formula (I), and/or a salt and/or solvate thereof. Any compound that will be converted in vivo to provide the bioactive agent (i.e., the compound for formula I) is a prodrug within the scope and spirit of the invention. For example, compounds containing a carboxy group can form physiologically hydrolyzable esters which serve as prodrugs by being hydrolyzed in the body to yield formula (I) compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula (I) include $C_{1-6}$alkylbenzyl, 4-methoxybenzyl, indanyl, phthalyl, methoxymethyl, $C_{1-6}$alkanoyloxy-$C_{1-6}$alkyl, e.g. acetoxymethyl, pivaloyloxymethyl or propionyloxymethyl, $C_{1-6}$alkoxycarbonyloxy-$C_{1-6}$alkyl, e.g. methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Various forms of prodrugs are well known in the art. For examples of such prodrug derivatives, see:
a) *Design of prodrugs*, edited by H. Bundgaard, (Elsevier, 1985) and *Methods in Enzymology*, Vol. 112, pp. 309-396, edited by K. Widder, et al. (Academic Press, 1985);
b) *A Textbook of Drug Design and Development*, edited by Krosgaard-Larsen and H. Bundgaard, Chapter 5, "Design and Application of Prodrugs," by H. Bundgaard, pp. 113-191 (1991); and
c) H. Bundgaard, *Advanced Drug Delivery Reviews*, Vol. 8, pp. 1-38 (1992), each of which is incorporated herein by reference.

Compounds of the formula (I) and salts thereof may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention.

Additionally, inventive compounds may have trans and cis isomers and may contain one or more chiral centers, therefore existing in enantiomeric and diastereomeric forms. The invention includes all such isomers, as well as mixtures of cis and trans isomers, mixtures of diastereomers and racemic mixtures of enantiomers (optical isomers). When no specific mention is made of the configuration (cis, trans or R or S) of a compound (or of an asymmetric carbon), then any one of the isomers or a mixture of more than one isomer is intended. The processes for preparation can use racemates, enantiomers or diastereomers as starting materials. When enantiomeric or diastereomeric products are prepared, they can be separated by conventional methods for example, chromatographic or fractional crystallization. The inventive compounds may be in the free or hydrate form.

It should further be understood that solvates (e.g., hydrates) of the compounds of Formula (I) are also with the scope of the present invention. Methods of solvation are generally known in the art.

Preferred Compounds

Preferred compounds are those within the scope of formula (I) (above) have the following formulae (Ia), (Ib) or (Ic),

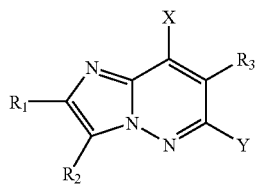

(Ia)

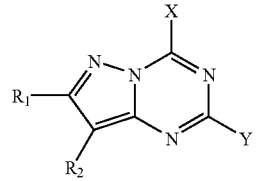

(Ib)

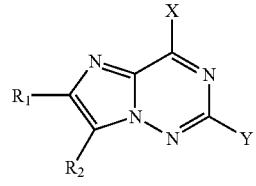

(Ic)

their enantiomers, diastereomers, a pharmaceutically-acceptable salt, or hydrate, thereof. Compounds of each formula, (Ia), (Ib), or (Ic), are alternatively preferred.

Other preferred compounds, including enantiomers, diastereomers, a pharmaceutically-acceptable salt, or hydrate, thereof, within the scope of each of formulae (Ia), (Ib) or (Ic) are those in which:

X is $NR_4R_5$;
$R_4$ is -AM;
$R_5$ is hydrogen or $C_{1-4}$alkyl (more preferably $R_5$ is hydrogen or methyl);
or $R_4$ and $R_5$ together with the nitrogen atom to which they are attached form a 5-, 6- or 7-membered monocyclic heteroaryl or heterocyclo ring, or a 7- to 11-membered bicyclic heteroaryl or heterocyclo ring, each ring optionally substituted with one to three groups, $T_1$, $T_2$; and/or $T_3$;

A is a bond, $C_{1-3}$alkylene, $C_{2-4}$alkenylene, $C_{2-4}$alkynylene, —C(O)—, or —SO$_2$—;

M is (i) hydrogen, NR$_{15}$R$_{16}$, alkyl, alkoxy, or alkenyl; or (ii) cycloalkyl, heterocyclo, aryl, or heteroaryl, each group optionally substituted by one to three groups, T$_1$, T$_2$, and/or T$_3$;

T$_1$, T$_2$, and T$_3$ are independently selected from (i) halogen, alkyl, substituted alkyl, alkenyl, substituted alkenyl, alkynyl, substituted alkynyl, nitro, cyano, SO$_3$H SR$_{19}$, S(O)$_p$R$_{21}$, S(O)$_p$NR$_{19}$R$_{20}$, NR$_{19}$S(O)$_p$R$_{21}$, OR$_{19}$, NR$_{19}$R$_{20}$, NR$_{19}$C(=O)R$_{20}$, NR$_{19}$C(=O)NR$_{19}$R$_{20}$, CO$_2$R$_{19}$, C(=O)R$_{19}$, —O—C(=O)R$_{19}$, —C(=O)NR$_{19}$R$_{20}$, cycloalkyl, heterocyclo, aryl, and heteroaryl, wherein p is one or 2; and/or (ii) two groups, T$_1$ and T$_2$, located on adjacent ring atoms are taken together with the ring atoms to which they are attached to form a fused cycloalkyl, aryl, heteroaryl, or heterocyclo;

R$_{19}$, R$_{20}$, and R$_{21}$ at each occurrence, are selected independently from (i) hydrogen, alkyl, substituted alkyl, alkenyl, substituted alkenyl, cycloalkyl, aryl, heteroaryl, and heterocyclo; or (ii) R$_{19}$ and R$_{20}$ together with the nitrogen atom to which they are both attached form a heteroaryl or heterocyclo; and R$_{21}$ at each occurrence, is selected from alkyl, substituted alkyl, alkenyl, substituted alkenyl, alkynyl, substituted alkynyl, cycloalkyl, aryl, heteroaryl, and heterocyclo.

More preferred compounds, including enantiomers, diastereomers, a pharmaceutically-acceptable salt, or hydrate, thereof, within the scope of formula (I) are those in which X is NR$_4$R$_5$;

R$_4$ is -AM;

A is a bond, —C(O)—, or —S(O)$_2$—, or $C_{1-3}$alkylene (A is more preferably a bond; methylene, or ethylene, especially a bond);

M is (i) hydrogen, —NH(aryl), $C_{1-6}$alkyl, $C_{2-4}$alkenyl, or —OC$_{1-4}$alkyl or (ii) $C_{3-6}$cycloalkyl, phenyl, fluorenyl, 1-naphthyl, or 2-naphthyl, each group optionally substituted by one to three groups, T$_1$, T$_2$, and/or T$_3$; or (iii) a 5-, 6- or 7-membered monocyclic or a 7- to 11-membered bicyclic heteroaryl or heterocyclo ring, each ring optionally substituted by one to three groups, T$_1$, T$_2$, and/or T$_3$ (is more preferably a $C_{3-6}$cycloalkyl, or a 5-, 6-, or 7-membered aryl, heteroaryl, or heteroaryl ring, each ring optionally substituted by 1 to 3 groups, T$_1$, T$_2$, and/or T$_3$, especially a 5-, 6-, or 7-membered aryl, heteroaryl, or heteroaryl ring, each ring optionally substituted by 1 to 2 groups, T$_1$ and/or T$_2$); and T$_1$, T$_2$, and T$_3$ are independently selected from (i) $C_{1-4}$alkyl, substituted $C_{1-4}$alkyl, $C_{1-4}$alkyloxy, substituted $C_{1-4}$alkyloxy, $C_{1-4}$alkylthio, phenoxy, —NR$_{19}$R$_{20}$, halogen, hydroxy, cyano, SO$_3$H, COOH, —C(O)(R$_{19}$), C(O)NR$_{19}$R$_{20}$, NR$_{19}$C(O)R$_{20}$, S(O)$_2$R$_{21}$, S(O)$_2$NR$_{19}$R$_{20}$ and NR$_{19}$(C(O)NR$_{19}$R$_{20}$; and/or (ii) phenyl, cyclopropyl, cyclohexyl, tetrazolyl, imidazolyl, pyrazolyl, triazolyl, thiazolyl, furyl, and morpholinyl, each group of which is optionally substituted as valence allows from one to three groups, R$_{22}$, R$_{23}$ and/or R$_{24}$; and/or (iii) two groups, T$_1$ and T$_2$, substituted on adjacent ring atoms are taken together with the ring atoms to which they are attached to form, a fused five- to seven-membered cycloalkyl, a fused phenyl or a fused 5- or 6-membered heterocyclo or heteroaryl, each group of which is optionally substituted as valence allows from one to three groups, R$_{22}$, R$_{23}$ and/or R$_{24}$; and R$_{19}$ and R$_{20}$ at each occurrence are selected independently from (i) hydrogen, —(CH$_2$)$_v$OH, and $C_{1-4}$alkyl; or (ii) —(CH$_2$)$_v$cyclohexyl, —(CH$_2$)$_v$phenyl, —(CH$_2$)$_v$morpholinyl, —(CH$_2$)$_v$pyridyl, —(CH$_2$)$_v$pyrazolyl, —(CH$_2$)$_v$cyclopropyl, —(CH$_2$)$_v$pyrrolidinyl, —(CH$_2$)$_v$piperidinyl, —(CH$_2$)$_v$furyl, —(CH$_2$)$_v$imidazolyl, —(CH$_2$)$_v$pyrimidinyl, —(CH$_2$)$_v$piperazinyl, and —(CH$_2$)$_v$pyradizinyl, each group of which is optionally substituted as valence allows from one to three groups, R$_{22}$, R$_{23}$ and/or R$_{24}$; or R$_{19}$ and R$_{20}$ are taken together with the nitrogen atom to which they are both attached to form a pyrrolindyl, morpholinyl, piperidinyl, pyradazinyl, or piperazinyl, each group of which is optionally substituted as valence allows from one to three groups, R$_{22}$, R$_{23}$ and/or R$_{24}$;

R$_{21}$ at each occurrence is selected from (i) —(CH$_2$)$_v$OH, and $C_{1-4}$alkyl; or (ii) —(CH$_2$)$_v$cyclohexyl, —(CH$_2$)$_v$phenyl, —(CH$_2$)$_v$morpholinyl, —(CH$_2$)$_v$pyridyl, —(CH$_2$)$_v$pyrazolyl, —(CH$_2$)$_v$cyclopropyl, —(CH$_2$)$_v$pyrrolidinyl, —(CH$_2$)$_v$piperidinyl, —(CH$_2$)$_v$furyl, —(CH$_2$)$_v$imidazolyl, —(CH$_2$)$_v$pyrimidinyl, —(CH$_2$)$_v$piperazinyl, and —(CH$_2$)$_v$pyradizinyl, each group of which is optionally substituted as valence allows from one to three groups, R$_{22}$, R$_{23}$ and/or R$_{24}$; R$_{22}$, R$_{23}$, and R$_{24}$ at each occurrence, are selected independently from ($C_{1-4}$)alkyl, ($C_{2-4}$)alkenyl, halogen, hydroxy, cyano, nitro, CF$_3$, =O, O($C_{1-4}$alkyl), OCF$_3$, C(=O)H, C(=O)($C_{1-4}$alkyl), CO$_2$H, CO$_2$($C_{1-4}$alkyl), NHCO$_2$($C_{1-4}$alkyl), —S($C_{1-4}$alkyl), —NH$_2$, NH($C_{1-4}$alkyl), N($C_{1-4}$alkyl)$_2$, N($C_{1-4}$alkyl)$_3^+$, SO$_2$($C_{1-4}$alkyl), C(=O)($C_{1-4}$alkylene)NH$_2$, C(=O)($C_{1-4}$alkylene)NH(alkyl), C(=O)($C_{1-4}$alkylene)N($C_{1-4}$alkyl)$_2$, and optionally substituted phenyl; and v is 0, 1, 2, or 3.

Other more preferred compounds, including enantiomers, diastereomers, a pharmaceutically-acceptable salt, or hydrate, thereof, within the scope of formula (I) are those in which:

X is NR$_4$R$_5$;

R$_4$ is -AM;

A is a bond, methylene, or ethylene;

M is hydrogen, methoxy, phenyl, fluorenyl, pyridyl, cyclopropyl, cyclohexyl, isopropyl, ethyl, n-propenyl, isopentyl, n-propyl, n-butyl, pyrazolyl, or pyrimidinyl, each group optionally substituted by one to two groups selected from T$_1$ and T$_2$; and T$_1$ and T$_2$ are independently selected from ethoxy, methoxy, methyl, n-butoxy, phenyl, benzyloxy, dimethylamino, chloro, iodo, trifluoromethyl, fluoro, hydroxyl, cyano, carboxylic acid, N-methyl-N-(pyridinylethyl)amido, ethyltetrazole, phenoxy, chlorophenyl, methylphenyl, benzyl, morpholinyl, isopropyl, n-propyl, n-butyl, ethyl, isopropoxy, n-propoxy, methylthio, cyclohexyl, t-butyl, trifluoromethoxy, amino, triazolyl, dichloroimidazolyl, dimethylpyrazolyl, methyltriazolyl, methylimidazolyl, methylthiazolyl, methylfuryl, N,N-dimethylamido, phenylsulfonyl, morpholinylsulfonyl, pyrrolidinylsulfonyl, N,N-diethylamido, N-methylamido, N-methylsulfonamido, N-methylsulfonamido, methanesulfonamido, N,N-dimethylsulfonamido, N,N-diethylsulfonamido, N-propylsulfonamido, N-ethylsulfonamido, N-methylsulfonamido, sulfonamido, aminomethyl, amido, N-(furylmethyl)amido, N-(imidazolylmethyl)amido; N-(pyridylmethyl)amido, (phenylpiperidinyl)carbonyl, piperidinylcarbonyl, N-benzylamido, N-methoxyphenylamido, N-phenylamido, N-(hydroxyethyl)amido, 1-morpholinylcarbonyl, N-(pyridinyl)amido, N-(pyridinylmethyl)amido, N-(pyridinylethyl)amido, N,N-diethylamido, N-cyclopropylamido, N-(cyclohexylmethyl)amido, N-(cyclohexyl)amido N-(methylpyrazolyl)amido, N-((oxopyrrolidinyl)propyl)amido, 3-phenylurea, and 1-(fluorophenyl)-N-methyl-oxo-dihydropyridine-3-carboxamido;

or T$_1$ and T$_2$ substituted on adjacent atoms of M combine with the atoms to which they are attached to form a fused ring thereby forming a ring system selected from indolyl, methylbenzothiazolyl, napthyl, methylindolyl, tetrahydroquinolinyl, fluorenyl, quinolinyl, and dihydroindazol-one-yl.

Other preferred compounds, including enantiomers, diastereomers, a pharmaceutically-acceptable salt, or hydrate, thereof, within the scope of formula (I) are those in which Y is hydrogen, halogen, OR$_8$, NR$_6$R$_7$, —(CH$_2$)heterocyclo, or aryl; (more preferably Y is hydrogen, halogen, OR$_8$, NR$_6$R$_7$, even more preferably Y is NR$_6$R$_7$);

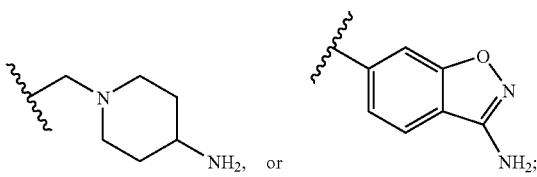

R$_6$ is selected from hydrogen or C$_{1-4}$alkyl optionally substituted by one to three groups selected from halogen, C$_{1-4}$alkyl, nitro, cyano, amino, C$_{1-4}$alkoxy, and OH(R$_6$ is more preferably hydrogen or C$_{1-4}$alkyl);

R$_7$ and R$_8$ are independently selected from alkyl, cycloalkyl, heterocyclo, aryl, and heteroaryl, each group of which is optionally substituted by one to three groups, T$_4$, T$_5$, and/or T$_6$ (R$_7$ is more preferably C$_{1-4}$alkyl, C$_{3-6}$cycloalkyl, or a 5-, 6-, or 7-membered heterocyclo, each group optionally substituted by one to three groups T$_4$, T$_5$, and/or T$_6$; R$_8$ is more preferably C$_{3-6}$cycloalkyl, especially cyclohexyl substituted by C$_{1-4}$alkyl, amino, amino substituted with C$_{1-4}$alkyl, substituted C$_{1-4}$alkyl, furyl, or piperidinyl);

or R$_6$ and R$_7$ together with the nitrogen atom to which they are attached form a heteroaryl or heterocyclo ring (more preferably 5-, 6-, or 7-membered rings), each ring is optionally substituted by one to three groups, T$_4$, T$_5$, and/or T$_6$;

T$_4$, T$_5$ and T$_6$ are independently selected from (i) halogen, alkyl, substituted alkyl, alkenyl, substituted alkenyl, alkynyl, substituted alkynyl, nitro, cyano, SR$_{19}$, OR$_{19}$, NR$_{19}$R$_{20}$, NR$_{19}$C(=O)R$_{20}$, CO$_2$R$_{19}$, C(=O)R$_{19}$, —O—C(=O)R$_{19}$, —C(=O)NR$_{19}$R$_{20}$, cycloalkyl, heterocyclo, aryl, and heteroaryl; and/or (ii) two groups, T$_4$ and T$_5$, substituted on adjacent ring atoms are taken together with the ring atoms to which they are attached to form a fused cycloalkyl, heterocyclo, aryl, or heteroaryl (T$_4$, T$_5$ and T$_6$ are more preferably C$_{1-4}$alkyl, and NR$_{19}$R$_{20}$); and R$_{19}$ and R$_{20}$, at each occurrence are selected independently from (i) hydrogen, alkyl, substituted alkyl, alkenyl, substituted alkenyl, cycloalkyl, aryl, heteroaryl, and heterocyclo; or (ii) R$_{19}$ with R$_{20}$ together with the nitrogen atom to which they are both attached combine to form a heteroaryl or heterocyclo.

Other more preferred compounds, including enantiomers, diastereomers, a pharmaceutically-acceptable salt, or hydrate, thereof, within the scope of formula (I) are those in which Y is NR$_6$R$_7$;

R$_6$ is selected from hydrogen or C$_{1-4}$alkyl (R$_6$ is more preferably hydrogen);

R$_7$ is selected from C$_{1-4}$alkyl, cyclopentyl, cyclohexyl, bicyclo[2.2.2]octyl, pyrrolidinyl, and piperidinyl, each group of which is optionally substituted by one to three groups, T$_4$, T$_5$, and/or T$_6$ (R$_7$ is more preferably cyclohexyl and bicycle {222}octyl, each group substituted by one group, T$_4$);

or R$_6$ and R$_7$ together with the nitrogen atom to which they are attached form piperazinyl, piperidinyl, pyrrolidinyl, or diazepanyl, each group of which is optionally substituted by one to three groups, T$_4$, T$_5$, and/or T$_6$ (more preferably R$_6$ and R$_7$ are taken together with the nitrogen atom to which they are both attached form an unsubstituted piperidinyl ring); and T$_4$, T$_5$, and T$_6$ are independently selected from (i) C$_{1-4}$alkyl, OH, NH$_2$, NH(C$_{1-4}$alkyl), furyl, and N(C$_{1-4}$alkyl)$_2$, and NH(pyrimidinyl) wherein the pyrimidinyl is substituted by halogen; or (ii) C$_{1-4}$alkyl substituted by cyclohexyl or OH, wherein the cyclohexyl is substituted by NH$_2$. (More preferably T$_4$, T$_5$, and T$_6$ are selected from NH$_2$, NH(C$_{1-4}$alkyl), and (4-NH$_2$-cyclohexyl)methyl).

Yet other preferred compounds, including enantiomers, diastereomers, a pharmaceutically-acceptable salt, or hydrate, thereof, within the scope of formula (I) are those in which R$_6$ is hydrogen;

R$_7$ is methyl, ethyl, n-propyl, n-butyl, cyclopentyl, cyclohexyl, bicyclo[2.2.2]octane, pyrrolidinyl, or piperidinyl, each group of which is optionally substituted by T$_4$ selected from amino, methyl, aminocyclohexylmethyl, dimethylamino, furyl, ethylamino, methylamino, piperidinyl, and (chloropyrimidinyl)amino; or R$_6$ and R$_7$ together with the nitrogen atom to which they are attached form a piperazinyl, piperidinyl, pyrrolidinyl, and diazepanyl ring, each ring optionally substituted by T$_4$ selected from amino, hydroxyethyl, aminopyrrolidinyl, and methyl.

Other preferred compounds, including enantiomers, diastereomers, a pharmaceutically-acceptable salt, or hydrate, thereof, are those within the scope of formula (I) (above) having the formula (Ia), (Ib) or (Ic), in which:

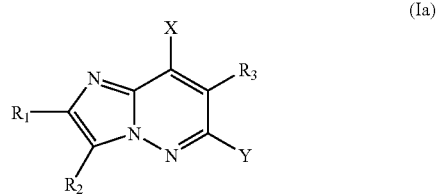
(Ia)

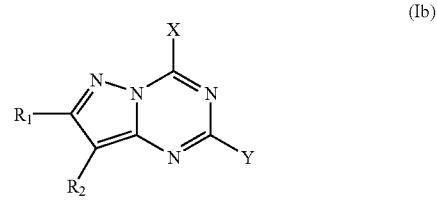
(Ib)

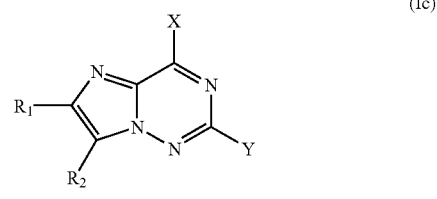
(Ic)

or an enantiomer, diastereomer, or a pharmaceutically-acceptable salt, thereof, wherein:

X is $NR_4R_5$;

Y is hydrogen, halogen, $OR_8$, or $NR_6R_7$ (Y is more preferably $NR_6R_7$);

$R_1$ and $R_2$ are independently selected from hydrogen, halogen, $OR_{10}$, cyano, $C_{1-4}$alkyl, $CO_2R_{10}$, and $C(O)NR_{10}R_{11}$;

$R_3$ is selected from (i) hydrogen, halogen, nitro, cyano, $OR_{10}$, $NR_{10}R_{11}$, $CO_2R_{10}$, and $C(=O)R_{10}$, (ii) $C_{1-4}$alkyl, substituted $C_{1-4}$alkyl, cycloalkyl, aryl, and heteroaryl;

$R_4$ is -AM;

$R_5$ is hydrogen or $C_{1-4}$alkyl;

or $R_4$ and $R_5$ together with the nitrogen atom to which they are attached form a 5-, 6- or 7-membered monocyclic heteroaryl or heterocyclo ring, or a 7- to 11-membered bicyclic heteroaryl or heterocyclo ring, each ring optionally substituted with one to three groups, $T_1$, $T_2$, and/or $T_3$;

A is a bond, $C_{1-3}$alkylene, $C_{2-4}$alkenylene, $C_{2-4}$alkynylene, —C(O)—, or —$SO_2$—;

M is (i) hydrogen, $NR_{15}R_{16}$, alkyl, alkoxy, or alkenyl; or (ii) cycloalkyl, heterocyclo, aryl, or heteroaryl, each ring optionally substituted by one to three groups, $T_1$, $T_2$, and/or $T_3$;

$R_6$ is selected from hydrogen or $C_{1-4}$alkyl optionally substituted by one to three groups selected from halogen, $C_{1-4}$alkyl, nitro, cyano, amino, $C_{1-4}$alkoxy, and OH;

$R_7$ and $R_8$ are independently selected from alkyl, cycloalkyl, heterocyclo, aryl, and heteroaryl, each group of which is optionally substituted by one to three groups, $T_4$, $T_5$, and/or $T_6$ ($R_8$ is preferably $C_{3-6}$cycloalkyl, especially cyclohexyl optionally substituted by $NH_2$, $NH(C_{1-4}$alkyl), and (4-$NH_2$-cyclohexyl)methyl);

or $R_6$ and $R_7$ together with the nitrogen atom to which they are attached form a heteroaryl or heterocyclo ring, each ring is optionally substituted by one to three groups, $T_4$, $T_5$, and/or $T_6$;

$R_{10}$ and $R_{11}$ at each occurrence are independently selected from (i) hydrogen, $C_{1-4}$alkyl, and substituted $C_{1-4}$alkyl; or (ii) $R_{10}$ and $R_{11}$ together with the nitrogen atom they are both attached combine to form an optionally substituted 5-, 6-, or 7-membered heteroaryl or heterocyclo;

$R_{15}$ and $R_{16}$ are independently selected from (i) hydrogen, alkyl, substituted alkyl, alkenyl, substituted alkenyl, alkynyl, substituted alkynyl, cycloalkyl, aryl, heteroaryl, and heterocyclo; or (ii) together with the nitrogen atom to which they are attached $R_{15}$ is taken together with $R_{16}$ to form a heteroaryl or heterocyclo;

$T_1$, $T_2$, and $T_3$ are independently selected from (i) halogen, alkyl, substituted alkyl, alkenyl, substituted alkenyl, alkynyl, substituted alkynyl, nitro, cyano, $SO_3H$ $SR_{19}$, $S(O)_pR_{21}$, $S(O)_pNR_{19}R_{20}$, $NR_{19}S(O)_pR_{21}$, $OR_{19}$, $NR_{19}R_{20}$, $NR_{19}C(=O)R_{20}$, $NR_{19}C(=O)NR_{19}R_{20}$, $CO_2R_{19}$, $C(=O)R_{19}$, —O—$C(=O)R_{19}$, —$C(=O)NR_{19}R_{20}$, cycloalkyl, heterocyclo, aryl, and heteroaryl, wherein p is one or 2; and/or (ii) two groups, $T_1$ and $T_2$, located on adjacent ring atoms are taken together with the ring atoms to which they are attached to form a fused cycloalkyl, aryl, heteroaryl, or heterocyclo;

$T_4$, $T_5$ and $T_6$ are independently selected from (i) halogen, alkyl, substituted alkyl, alkenyl, substituted alkenyl, alkynyl, substituted alkynyl, nitro, cyano, $SR_{19}$, $OR_{19}$, $NR_{19}R_{20}$, $NR_{19}C(=O)R_{20}$, $CO_2R_{19}$, $C(=O)R_{19}$, —O—C$(=O)R_{19}$, —$C(=O)NR_{19}R_{20}$, cycloalkyl, heterocyclo, aryl, and heteroaryl; and/or (ii) two groups, $T_4$ and $T_5$, substituted on adjacent ring atoms are taken together with the ring atoms to which they are attached to form a fused cycloalkyl, heterocyclo, aryl, or heteroaryl; and $R_{19}$ and $R_{20}$ at each occurrence are selected independently from (i) hydrogen, alkyl, substituted alkyl, alkenyl, substituted alkenyl, cycloalkyl, aryl, heteroaryl, and heterocyclo; or (ii) $R_{19}$ and $R_{20}$ together with the nitrogen atom to which they are both attached form a heteroaryl or heterocyclo ring; and $R_{21}$ at each occurrence, is selected from alkyl, substituted alkyl, alkenyl, substituted alkenyl, alkynyl, substituted alkynyl, cycloalkyl, aryl, heteroaryl, and heterocyclo;

with the following provisos:

(1) if E is C, F is N, Z is $CR_3$, and X is NH(Me), $NH(Me)_2$, NH(unsubstituted phenyl), or $NHNH_2$, then Y is other than hydrogen or halogen; and (2) if E is N, F is C, Z is N, and Y is $NR_6R_7$;

(a) then X is other than NH($C_{1-4}$alkyl), N($C_{1-4}$alkyl)$_2$, NH($C_{1-4}$alkenyl), NH(—$CH_2$-furyl), NHNH2, NH(C-methoxyalkylene), and NHAc;

(b) and if X is NH(—$CH_2$— (substituted or unsubstituted) pyridyl) or NH(—$CH_2$— (substituted or unsubstituted) phenyl), then Y is other than

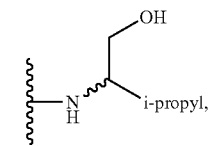

NH(substituted piperidine), or NH(—$CH_2$-pyridine);

(c) and if X is NH(cyclopentyl), then Y is other than NH(cyclopentyl);

(d) and if X is $N(CH_3)$(substituted phenyl) or $N(CH_3)$(pyridyl), then Y is other than

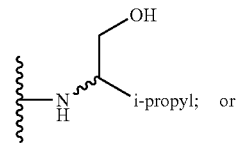

(e) and if X is NH(substituted phenyl), then Y is other than

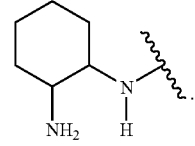

Particularly preferred compounds, including enantiomers, diastereomers, a pharmaceutically-acceptable salt, or hydrate, thereof, are those within the scope of formula (I) (above) having the formula (Ia), (Ib) or (Ic), in which:

$R_1$ and $R_2$ are independently selected from (i) hydrogen, halogen, $OR_{10}$, cyano, $CO_2R_{10}$, and $C(O)NR_{10}R_{11}$, or (ii) $C_{1-4}$alkyl, $C_{3-6}$cycloalkyl, $C_2$-$C_4$ alkenyl, or $C_2$-$C_4$ alkynyl, each group of which is optionally substituted;

$R_3$ is selected from (i) hydrogen, halogen, nitro, cyano, $OR_{13}$, $NR_{13}R_{14}$, $CO_2R_{13}$, $C(=O)R_{13}$, $C_{1-4}$alkyl, substituted $C_{1-4}$alkyl, cycloalkyl, aryl, and heteroaryl; and $R_{10}$, $R_{11}$, $R_{13}$, and $R_{14}$ at each occurrence are independently selected from (i) hydrogen, $C_{1-4}$alkyl, substituted $C_{1-4}$alkyl, and an optionally substituted phenyl or 5-, 6-, or 7-membered heteroaryl or heterocyclo; or (ii) $R_{10}$ and $R_{11}$ and/or $R_{13}$, and $R_{14}$ together with the nitrogen atom they are both attached combine to form an optionally substituted 5-, 6-, or 7-membered heteroaryl or heterocyclo.

Even more preferred compounds, including enantiomers, diastereomers, a pharmaceutically-acceptable salt, or hydrate, thereof, are those within the scope of formula (I) (above) having the formula (Ia), (Ib) or (Ic), in which:

$R_1$ is hydrogen, fluoro, or $C_{1-4}$alkyl (more preferably $R_1$ is hydrogen, fluoro, or methyl);

$R_2$ is cyano, halogen, $C_{1-4}$alkyl, $C_{2-4}$alkenyl(phenyl), $C_{2-4}$alkenyl(heteroaryl), cyclopropyl, propynyl, or $C(O)NR_{10}R_{11}$ (more preferably $R_2$ is hydrogen, cyano, halogen, $C(O)NH_2$, $C(O)NH$(4-pyridinyl), cyclopropyl, —CH=CH(4-pyridinyl), or $C(O)NH$(4-pyridinyl));

$R_3$ is hydrogen, halogen, $C_{1-4}$alkyl, substituted $C_{1-4}$alkyl, or aryl (more preferably $R_3$ is hydrogen, halogen, $C_{1-4}$alkyl, substituted methylene, or optionally substituted phenyl, even more preferably $R_3$ is hydrogen, methyl, ethyl, isopropyl, benzyl, unsubstituted phenyl, 3-chlorophenyl, or 4-chlorophenyl), $R_{10}$ and $R_{11}$ at each occurrence are independently selected from hydrogen, $C_{1-4}$alkyl, substituted $C_{1-4}$alkyl, an optionally substituted phenyl, and an optionally substituted heteroaryl wherein the heteroaryl is selected from pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl, indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl, carbazolyl, benzidolyl, phenanthrollinyl, acridinyl, phenanthridinyl, and xanthenyl.

Even more particularly preferred compounds, including enantiomers, diastereomers, a pharmaceutically-acceptable salt, or hydrate, thereof, are those within the scope of formula (I) (above) having the formula (Ia), (Ib) or (Ic), in which $NR_4R_5$ is selected from:

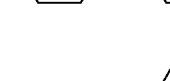
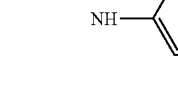
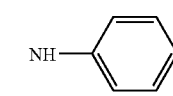
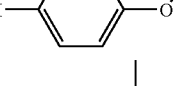
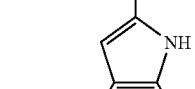
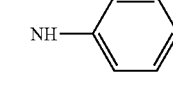

-continued

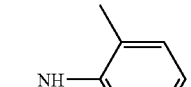
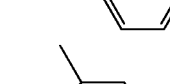
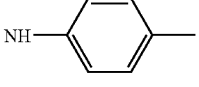
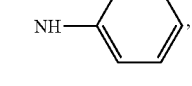
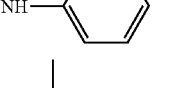
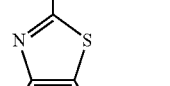
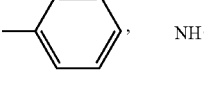
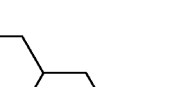

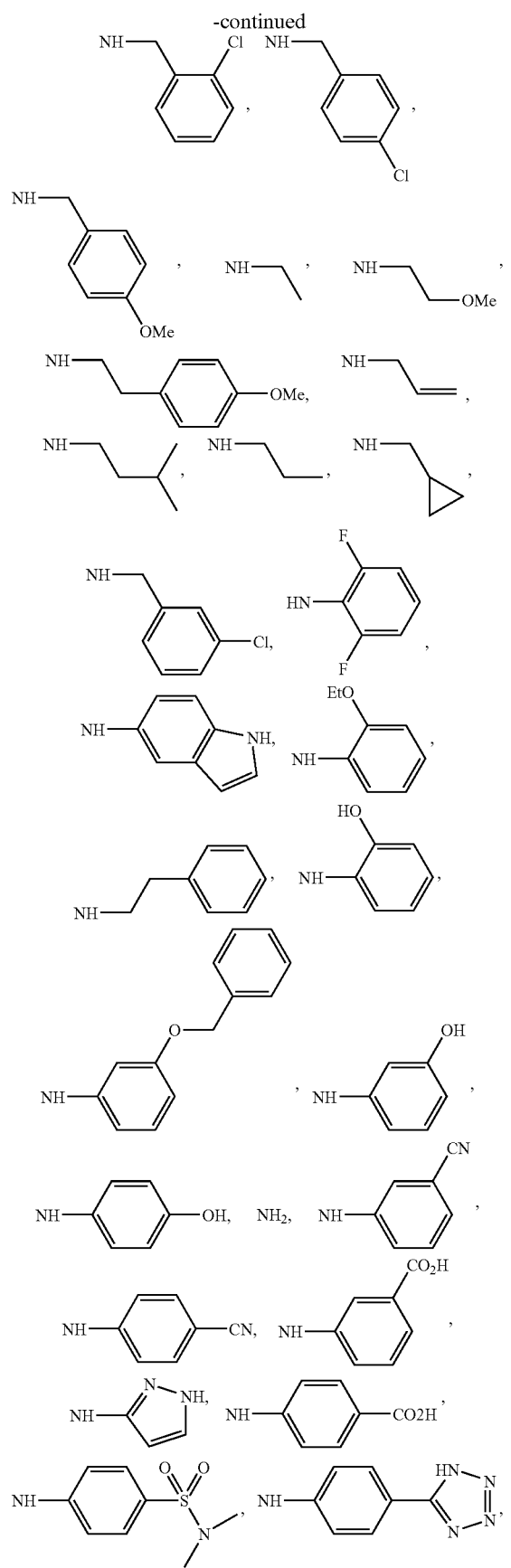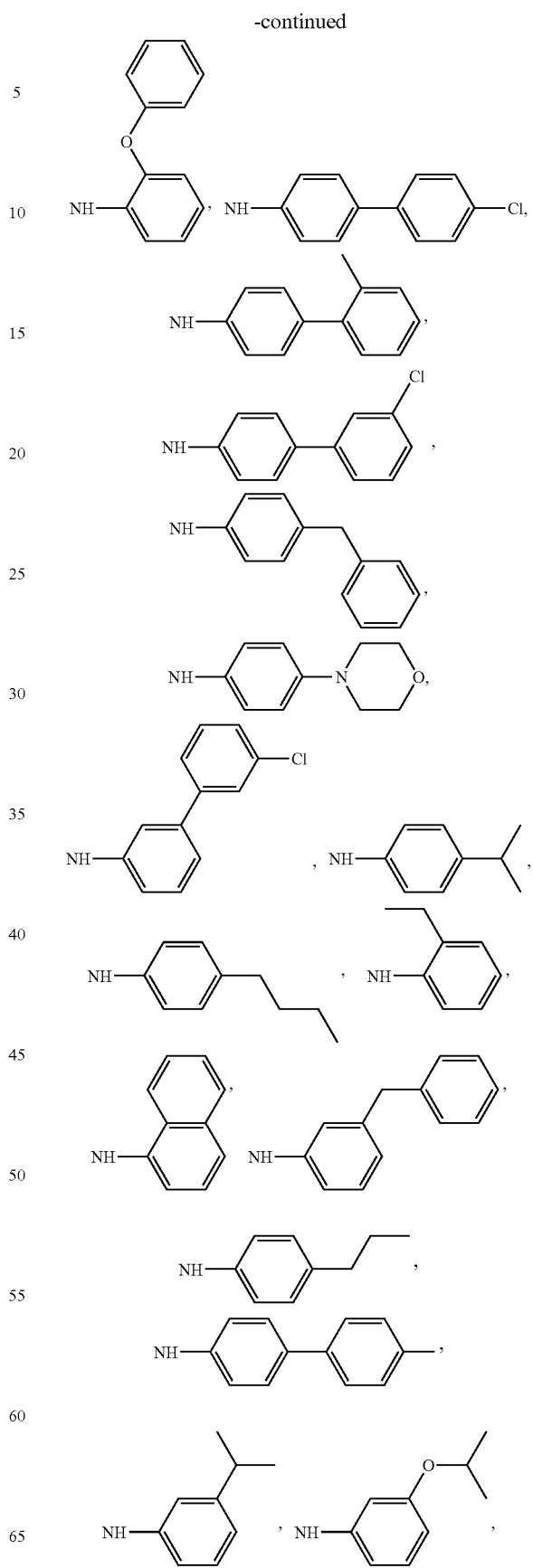

-continued
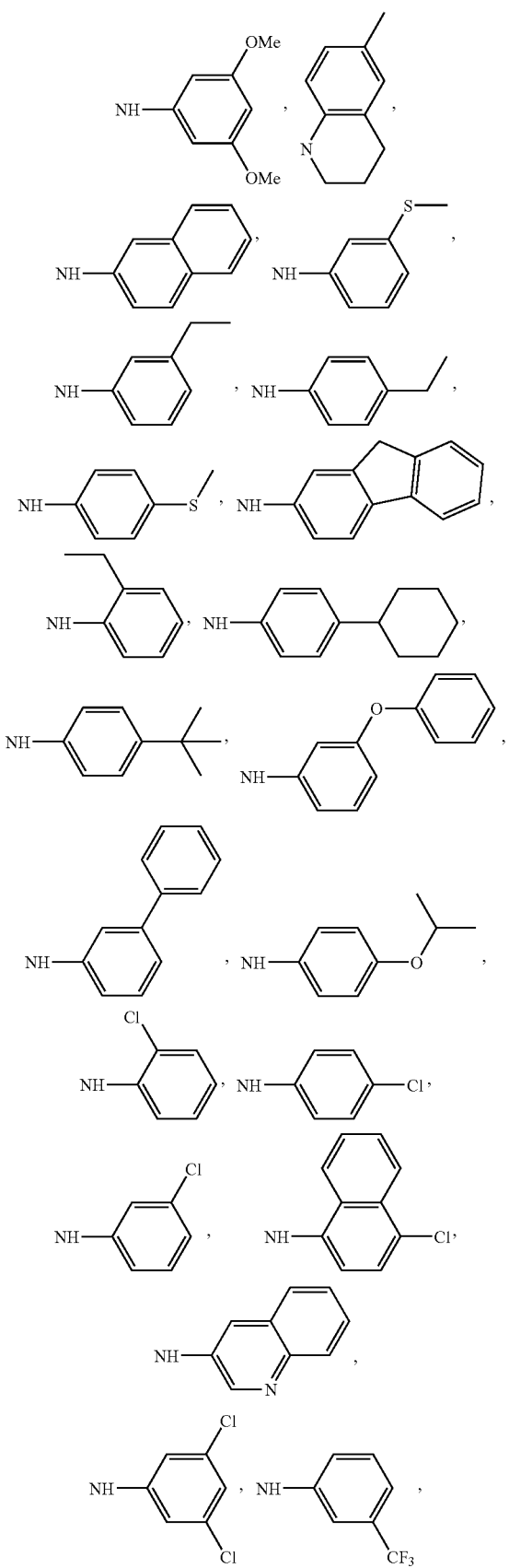
-continued
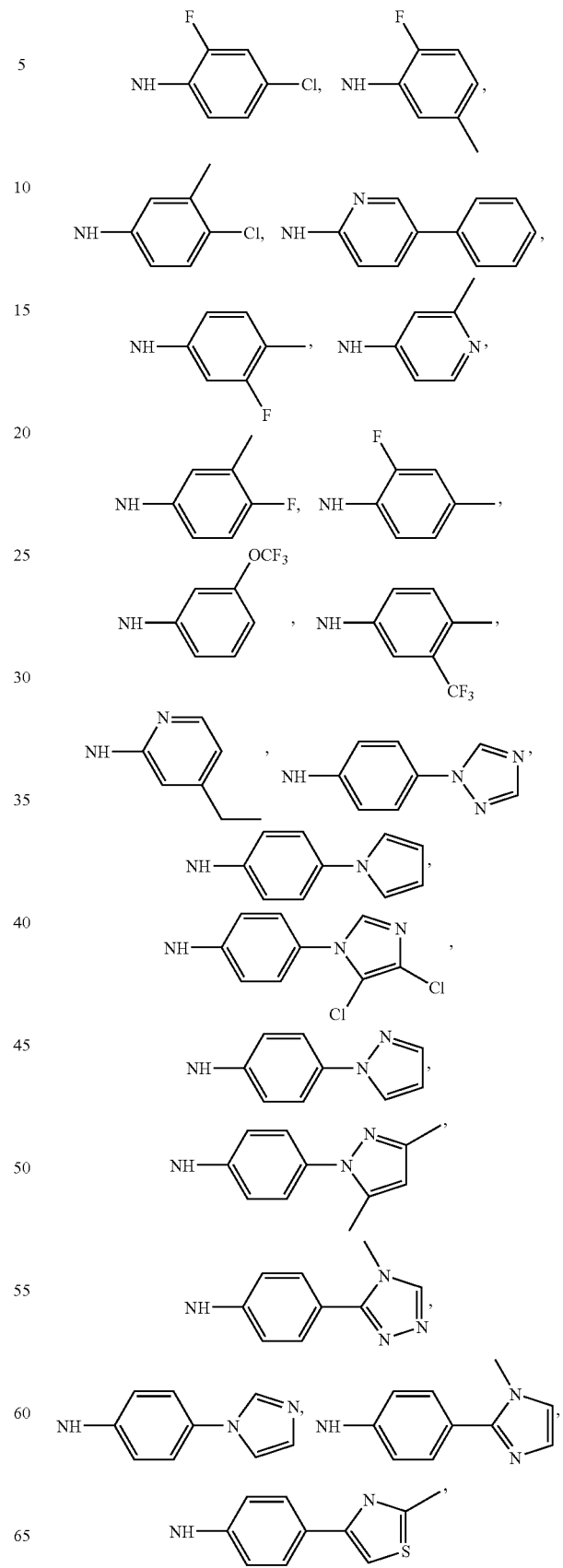

-continued
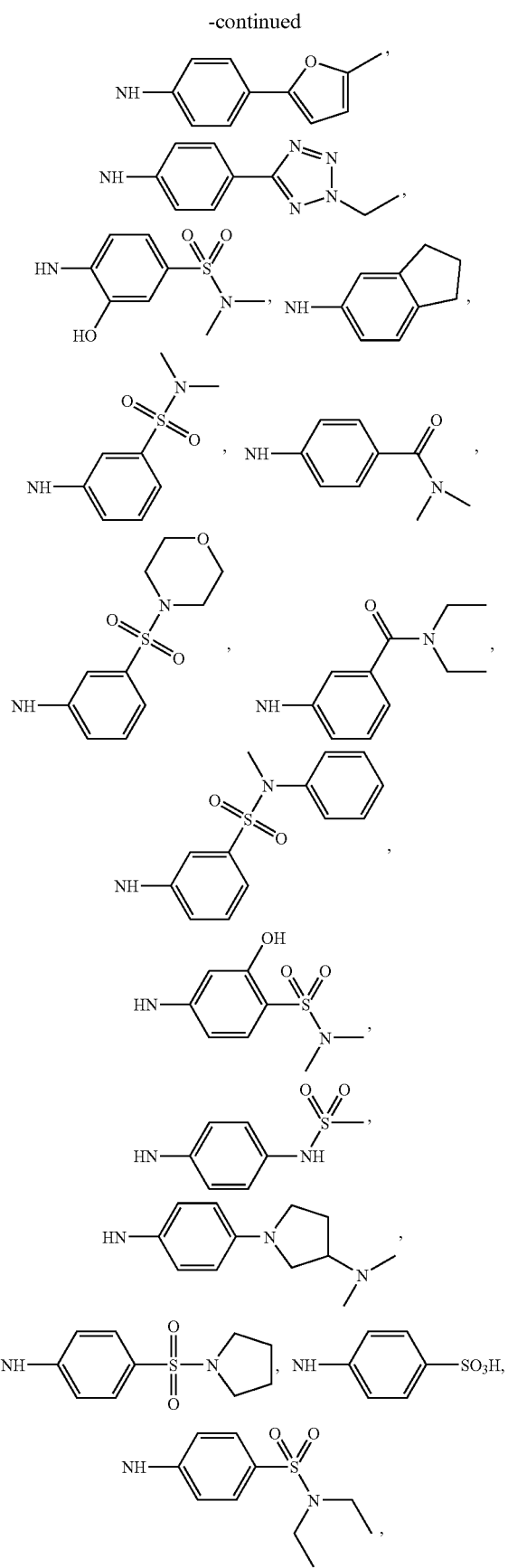
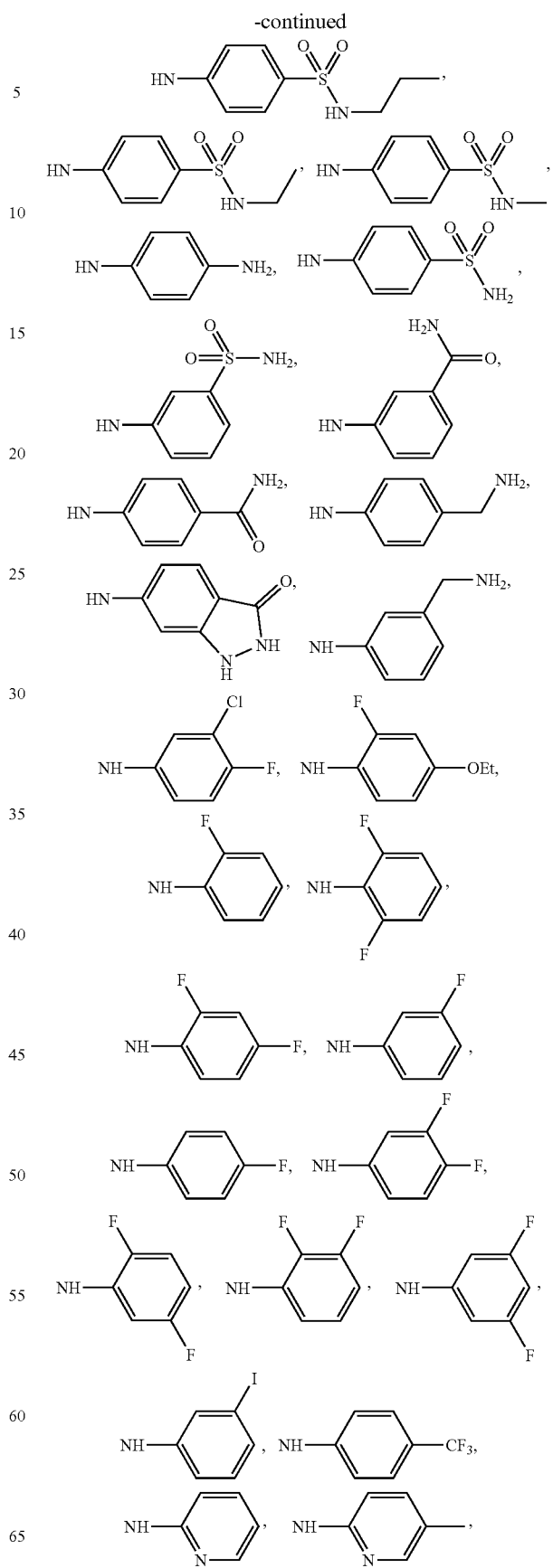

-continued
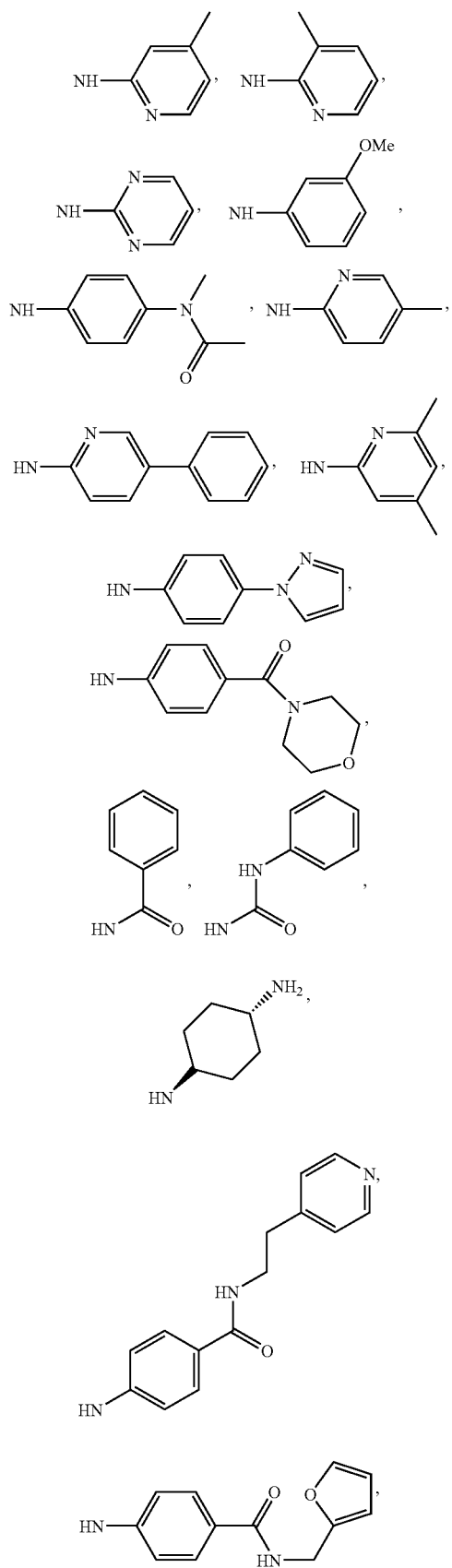
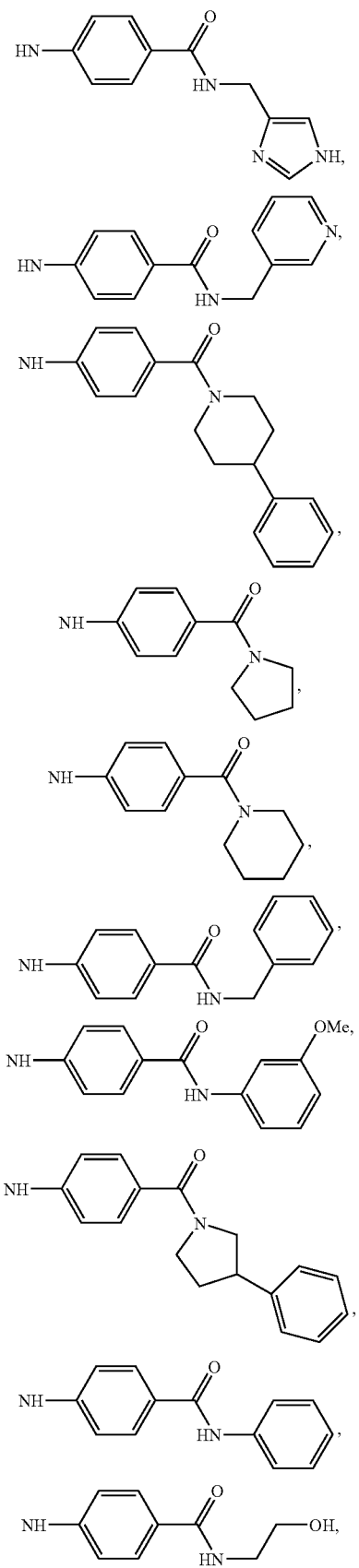

-continued
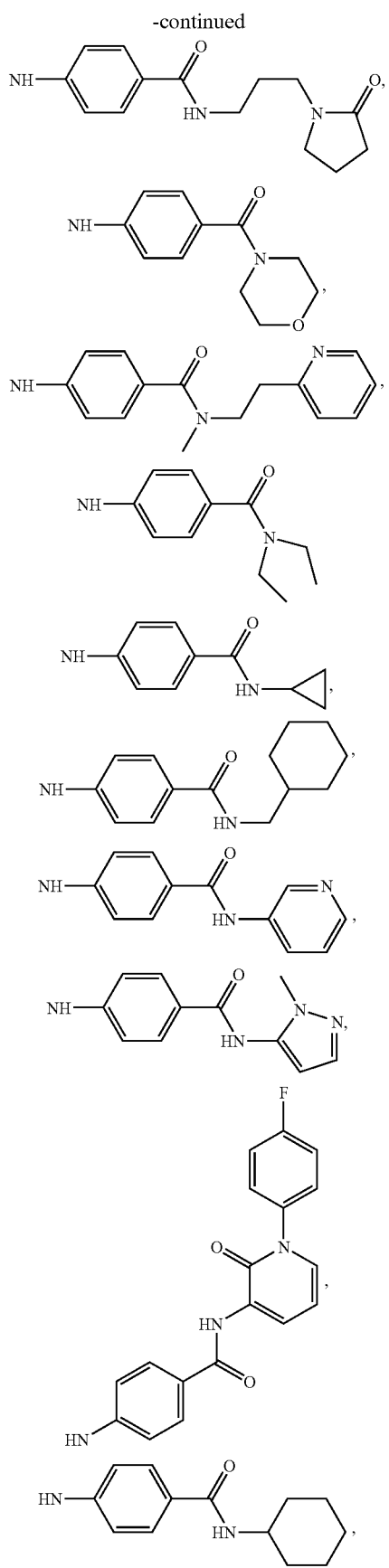
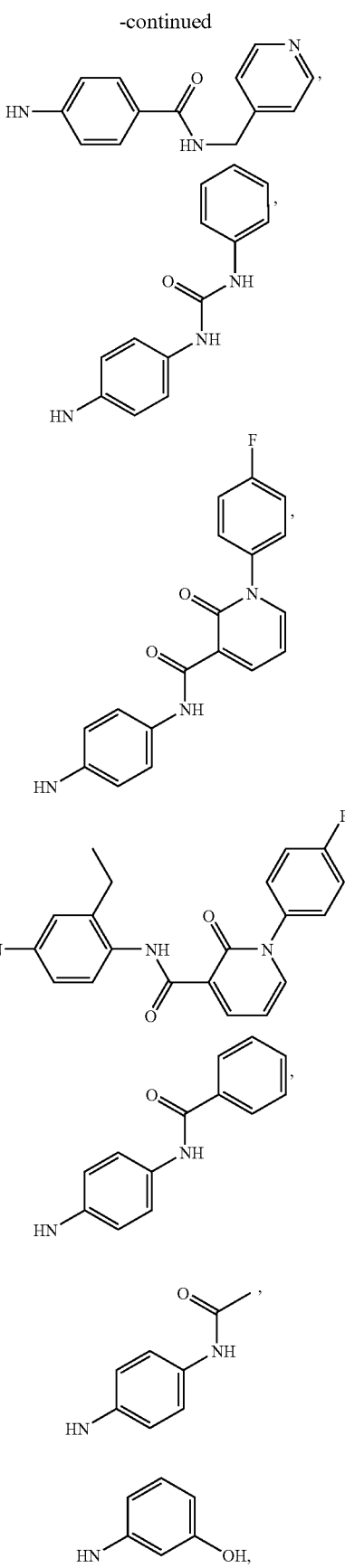

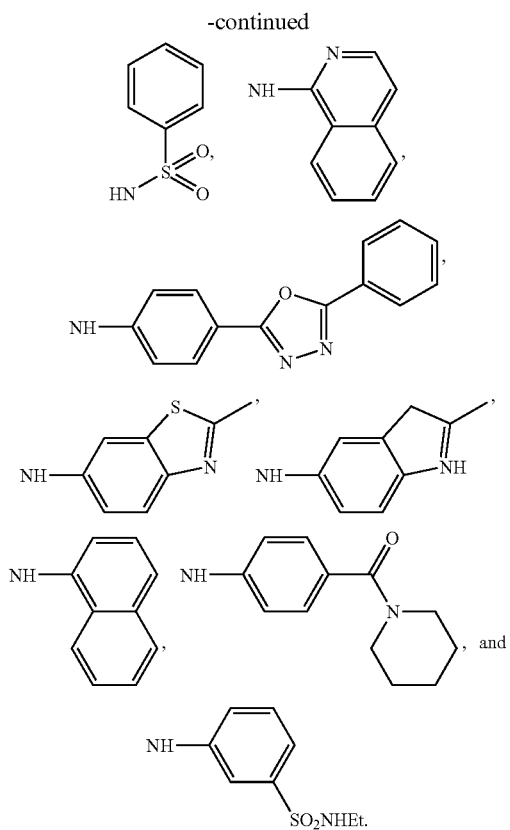
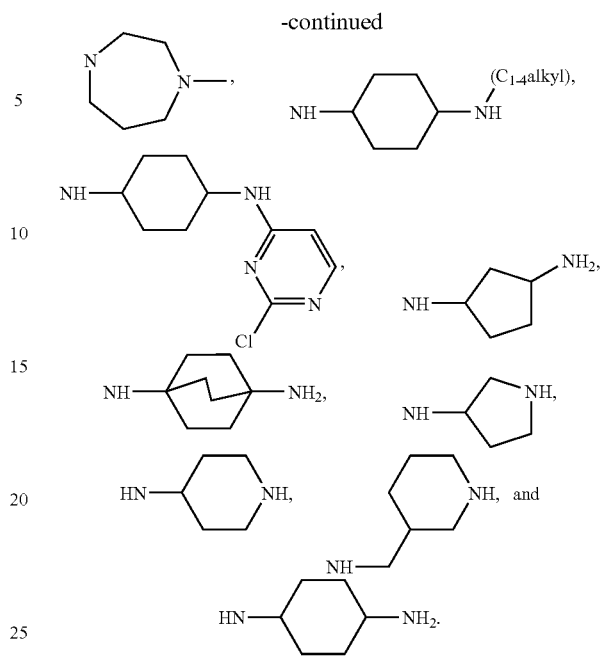

Alternative even more particularly preferred compounds, including enantiomers, diastereomers, a pharmaceutically-acceptable salt, or hydrate, thereof, are those within the scope of formula (I) in which NR$_6$R$_7$ is selected from:

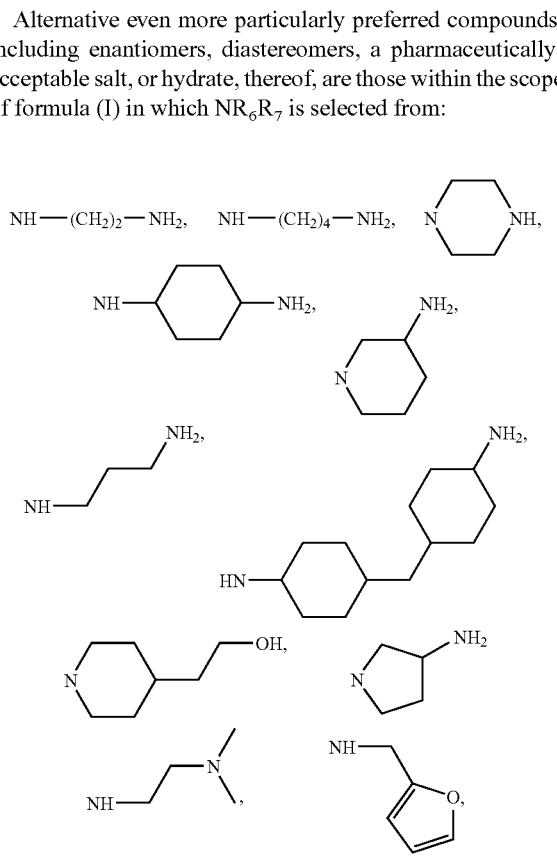

Other preferred compounds within the scope of formula (I), or an enantiomer, diastereomer, or a pharmaceutically-acceptable salt, thereof wherein:

R$_4$ is selected from a C$_{3-6}$cycloalkyl, a 5-, 6-, or 7-membered aryl, heteroaryl, or a heteroaryl ring optionally substituted by 1 to 3 groups selected from T$_1$, T$_2$, and T$_3$. (More preferably, R$_4$ is selected from phenyl, pyridyl, pyrimidinyl, cyclohexyl, and piperidinyl, each group optionally substituted by 1 to 2 groups, T$_1$ and/or T$_2$. T$_1$ and/or T$_2$ are preferably selected from ethoxy, methoxy, methyl, ethyl, n-butoxy, phenyl, benzyloxy, dimethylamino, chloro, iodo, trifluoromethyl, fluoro, hydroxyl, cyano, carboxylic acid, N-methyl-N-(pyridinylethyl)amido, ethyltetrazole, phenoxy, chlorophenyl, methylphenyl, benzyl, morpholinyl, isopropyl, n-propyl, n-butyl, ethyl, isopropoxy, n-propoxy, methylthio, cyclohexyl, t-butyl, chloro, trifluoromethoxy, amino, triazolyl, dichloroimidazolyl, dimethylpyrazolyl, methyltriazolyl, methylimidazolyl, methylthiazolyl, methylfuryl, N,N-dimethylamido, morpholinylsulfonyl, pyrrolidinylsulfonyl, N,N-diethylamido, N-methylamido, N-methylsulfonamido, N-methylsulfonamido, methanesulfonamido, N,N-dimethylsulfonamido, N,N-diethylsulfonamido, N-propylsulfonamido, N-ethylsulfonamido, N-methylsulfonamido, sulfonamido, aminomethyl, amido, N-(furylmethyl)amido, N-(imidazolylmethyl)amido; N-(pyridylmethyl)amido, (phenylpiperidinyl)carbonyl, piperidinylcarbonyl, N-benzylamido, N-methoxyphenylamido, N-phenylamido, N-(hydroxyethyl)amido, 1-morpholinylcarbonyl, N-(pyridinyl)amido, N-(pyridinylmethyl)amido, N-(pyridinylethyl)amido, N,N-diethylamido, N-cyclopropylamido, N-(cyclohexylmethyl)amido, N-(cyclohexyl)amido N-(methylpyrazolyl)amido, N-((oxopyrrolidinyl)propyl)amido, phenylurea, and 1-(fluorophenyl)-N-methyl-oxo-dihydropyridine-3-carboxamido);

or T$_1$ and T$_2$ located on adjacent atoms of M together with the atoms to which they are attached combine to form a fused ring thereby forming a fused ring system selected from indolyl, methylbenzothiazolyl, napthyl, methylindolyl, tetrahydroquinolinyl, fluorenyl, quinolinyl, and dihydroindazol-one-yl.

Yet other preferred compounds, including enantiomers, diastereomers, a pharmaceutically-acceptable salt, or hydrate, thereof, are those within the scope of formula (I) in which $NR_6R_7$ is selected from:

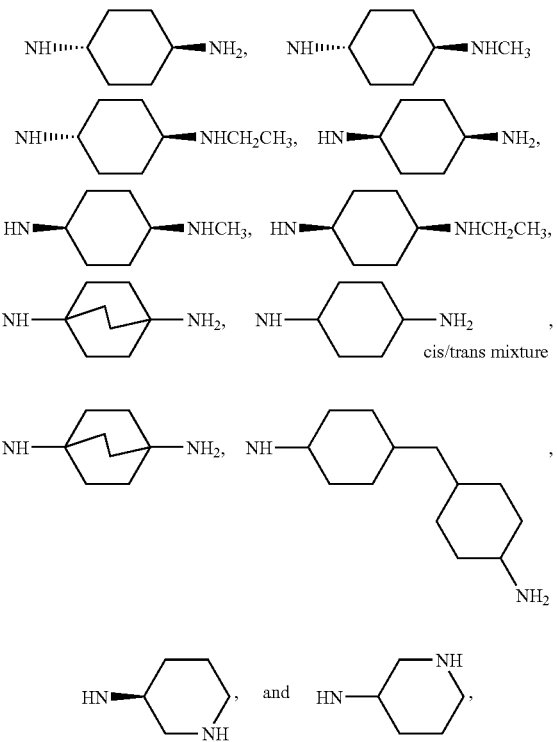

All aspects of the preferred compounds, including individual variable definitions, may be combined with other aspects to form other preferred compounds.

Methods of Preparation

Compounds of the present invention may be prepared by the exemplary processes described in the following reaction schemes, A to E. Exemplary reagents and procedures for these reactions appear hereinafter. Starting materials are commercially available or can be readily prepared by one of ordinary skill in the art. Modifications can be made to the methods of schemes by one skilled in the art using known methods. For all of the schemes, the groups $R_1$, $R_2$, are as described herein for a compound of formula (I), unless otherwise indicated. Groups designated generally as R', R", Z, P' and P''' as well as appropriate solvents, temperatures, pressures, starting materials (having the desired substituents), and other reaction conditions, may be readily selected by one of ordinary skill in the art. It is anticipated that, where possible, the products of the reaction schemes described below may be further elaborated by one of ordinary skill in the art

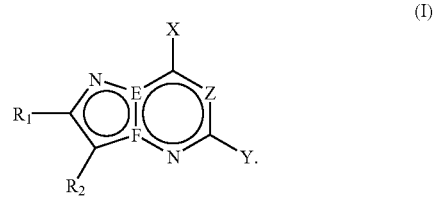

Compounds of general formula (I) where E=C and F=N, and Z=CR3 (i.e. formula (Ia)) may be prepared as described below in Schemes A, B and C.

Scheme A

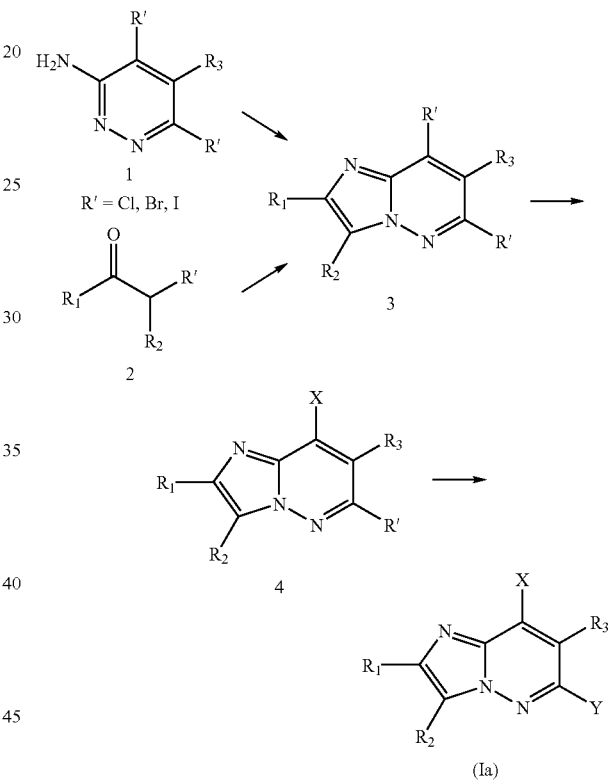

Readily prepared 3-amino-4,6-dihalopyridazines 1 are condensed with commercially available or readily prepared 2-haloaldehydes or 2-haloketones 2 or their equivalents to provide 6,8-dihaloimidazo[1,2-b]pyridazines 3 in an alcoholic solvent (such as ethanol). The reaction of 3 with an amine in a suitable solvent (such as N-methylpyrrolidinone or alcohols) in the presence of a suitable base (such as triethylamine or cesium carbonate) provides 6-haloimidazo[1,2-b]pyridazines 4. Alternatively, the reaction of 3 with non-reactive nucleophiles (such as electron deficient anilines) in a suitable solvent (such as dimethylformamide or tetrahydrofuran) with a suitable base (such as sodium hydride) may provide compounds having the formula 4. Reaction of 6-haloimidazo[1,2-b]pyridazines 4 with nucleophiles (such as amines) provides imidazo[1,2-b]pyridazines (Ia) under either neat conditions or in a solvent (such as N-methylpyrrolidinone) in the presence of a suitable base (such as cesium carbonate).

Scheme B

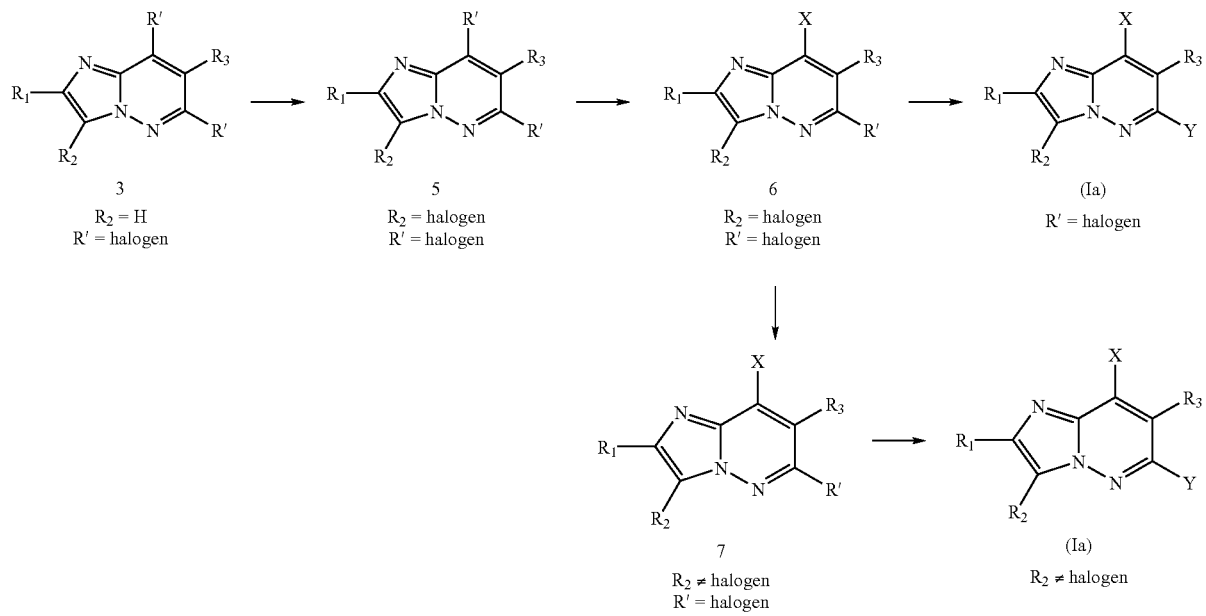

Compounds having the formula (Ia) can also be obtained via treatment of 6,8-dihaloimidazo[1,2-b]pyridazines 3 prepared as described in Scheme A with halogenating agents (such as NBS, NCS, NIS, selectfluor) in a suitable solvent (such as chloroform or acetonitrile) to provide the corresponding 3,6,8-trihaloimidazo[1,2-b]pyridazines 5. The reaction of 5 with an amine in a suitable solvent (such as N-methylpyrrolidinone or alcohols) in the presence of a suitable base (such as triethylamine or cesium carbonate) provides 3,6-dihaloimidazo[1,2-b]pyridazines 6. Alternatively, the reaction of 5 with non-reactive nucleophiles (such as electron deficient anilines) in a suitable solvent (such as dimethylformamide or tetrahydrofuran) with a suitable base (such as sodium hydride) may provide compounds having the formula 6. The reaction of 6-haloimidazo[1,2-b]pyridazines such as 6 with amines provides imidazo[1,2-b]pyridazines (Ia) under either neat conditions or in a solvent (such as N-methylpyrrolidinone, dioxane) in the presence of a suitable base (such as cesium carbonate) with or without a catalyst (such as palladium acetate). Alternately, the 3-position of 3,6-dihaloimidazo[1,2-b]pyridazines 6 may be readily converted by one skilled in the art employing one of the many procedures of converting aryl halides into other functional groups to provide of 6-haloimidazo[1,2-b]pyridazines such as 7 where $R_2$ is other than halogen. The newly introduced functionality at $R_2$ can be further elaborated by known methods to prepare additional analogs. The reaction of 6-haloimidazo[1,2-b]pyridazines such as 7 with nucleophiles (such as amines or alcohols) provides imidazo[1,2-b]pyridazines (Ia) under either neat conditions or in a solvent (such as N-methylpyrrolidinone, dioxane) in the presence of a suitable base (such as cesium carbonate) with or without a catalyst (such as palladium acetate).

Scheme C

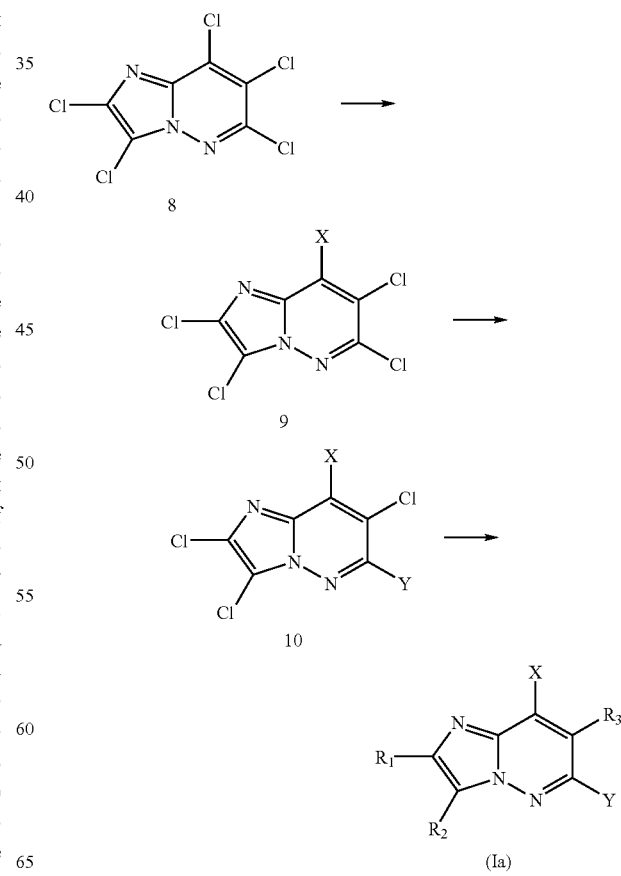

Compounds having the formula (Ia) can also be obtained via treatment of imidazo[1,2-b]pyridazine 8 with nucleophiles (such as amines) in a suitable solvent (such as ethanol) with a suitable base (such as triethylamine) to provide imidazo[1,2-b]pyridazines 9. See e.g. *Synthesis* Vol. 8 (1971) at pp 424. Reaction of imidazo[1,2-b]pyridazines 9 with nucleophiles (such as amines) provides imidazo[1,2-b]pyridazines 10. Treatment of imidazo[1,2-b]pyridazines 10 with a suitable catalyst (such as platinum oxide) in a suitable solvent (such as ethanol) under hydrogen pressure (such as 55 psi) provides imidazo[1,2-b]pyridazines (Ia) where $R_1$, $R_2$, and $R_3$ are independently selected from H and Cl.

Compounds of general formula (I) where E=N, F=C, Z=N (i.e. formula (Ib)) may be prepared by as described in Scheme D.

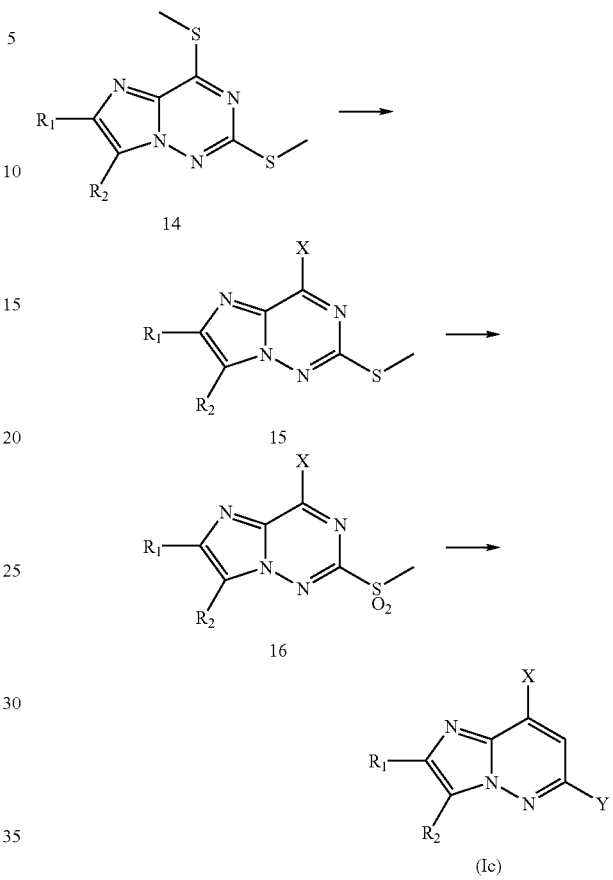

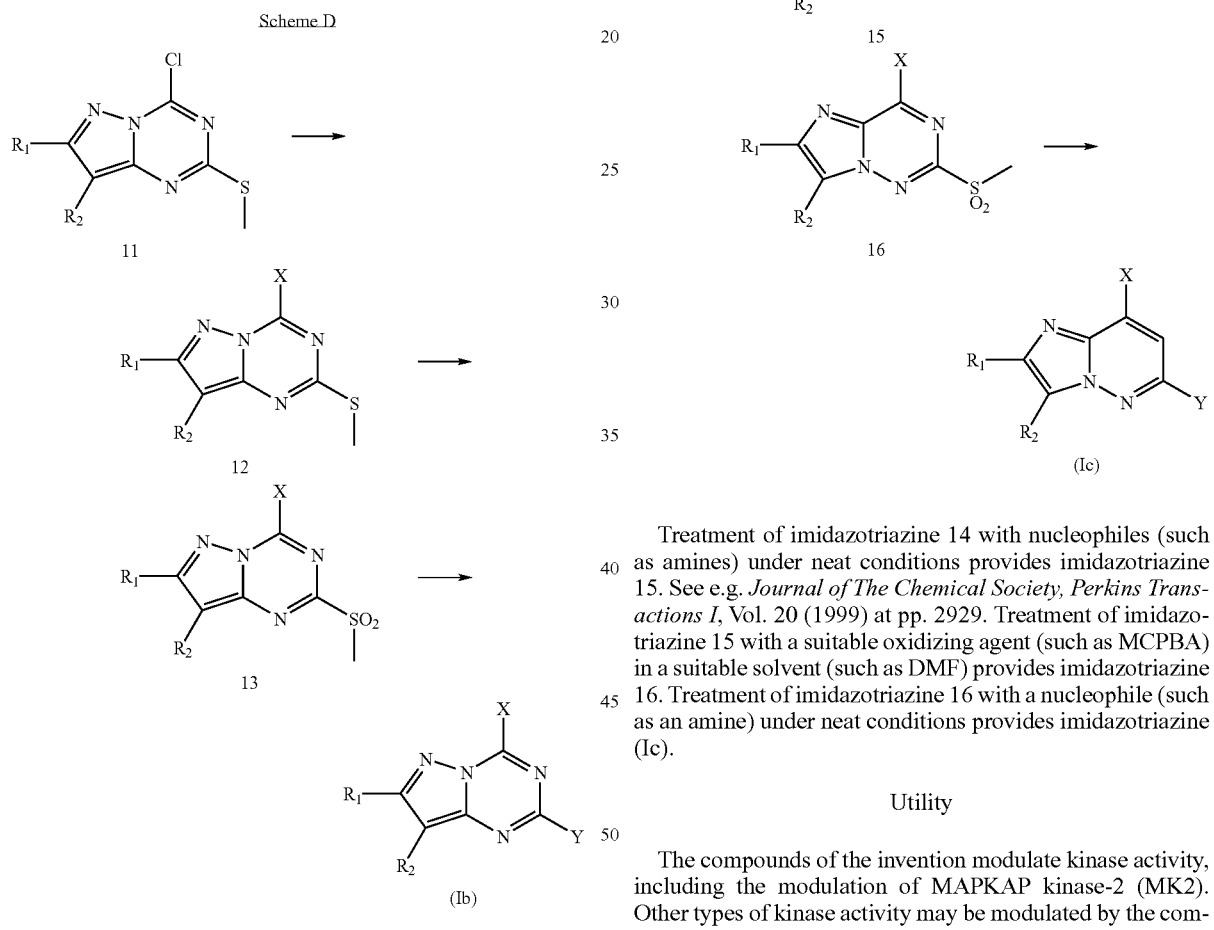

Treatment of pyrazolotriazines 11 with nucleophiles (such as amines) in a suitable solvent (such as dioxane) provides pyrazolotriazines 12. See e.g. *Journal of Heterocyclic Chemistry* Vol. 11(2) (1974) at pp. 199. Treatment of pyrazolotriazine 12 with a suitable oxidizing agent (such as MCPBA) in a suitable solvent (such as DMF) provides pyrazolotriazine 13 Treatment of pyrazolotriazine 13 with a nucleophile (such as an amine) under neat conditions provides pyrazolotriazines (Ib).

Compounds of general formula (I) where E=C, F=N, Z=N (i.e. formula (Ic)) may be prepared by as described in Scheme E Treatment of imidazotriazine 14 with nucleophiles (such as amines) under neat conditions provides imidazotriazine 15. See e.g. *Journal of The Chemical Society, Perkins Transactions I*, Vol. 20 (1999) at pp. 2929. Treatment of imidazotriazine 15 with a suitable oxidizing agent (such as MCPBA) in a suitable solvent (such as DMF) provides imidazotriazine 16. Treatment of imidazotriazine 16 with a nucleophile (such as an amine) under neat conditions provides imidazotriazine (Ic).

Utility

The compounds of the invention modulate kinase activity, including the modulation of MAPKAP kinase-2 (MK2). Other types of kinase activity may be modulated by the compounds of the invention including, but not limited to AKT1, AKT2, AKT3, DMPK1, MRCKA, GPRK4, GPRK5, GPRK6, NDR2, PKACA, PKACB, PRKX, PKACA, PDK1, PKCA, PKCD, PKCT, PKCH, PKCI, PKCZ, PKG1, PKG2, PKN2, MSK1, MSK2, RSK1, RSK2, RSK4, YANK2, YANK3, ADCK3, ADCK4, CAMK1A, CAMK1D, CAMK1G, CAMK2A, CAMK2B, CAMK2D, CAMK2G, AMPKA1, AMPKA2, BRSK2, LKB1, MARK1, MARK2, MARK4, QIK, STK33, DAPK2, DAPK3, DRAK1, DRAK2, DCAMKL3, MNK2, SKMLCK, PHKG1, PHKG2, PIM1, PIM2, CK1A2, CK1D, CK1E, CK1G1, CK1G2, CDK2, CDK2, CDK5, CDK5, PCTAIRE1, CLK1, CLK2, CLK3, CLK4, GSK3A, GSK3B, GSK3B, ERK1, ERK2, JNK1, JNK2, JNK3, NLK, P38A, P38B, P38G, SRPK1, AURA, AURB, AURC, CAMKK1, CAMKK2, CK2A1, CK2A2, IKKB, AAK1, BIKE, GAK, MPSK1, NEK2, NEK6, NEK7, NEK9, GCN2, PLK1, PLK3, PLK4, TLK1, TLK2, TTK, FUSED, ULK3, MYT1, MAP3K4, MAP3K5, HPK1, KHS1, KHS2, ZC1/HGK, ZC2/TNIK, MST1, MST2, PAK1, PAK2, PAK3, PAK4, PAK5, PAK6, LOK, SLK, MST3, MST4, YSK1, ABL, ARG, ACK, TNK1, ALK, LTK, AXL, MER, TYRO3, CSK, DDR2, EGFR, HER2/ERBB2, HER4/ERBB4, EPHA1, EPHA2, EPHA3, EPHA4, EPHA5, EPHA6, EPHA7, EPHA8, EPHB1, EPHB2, EPHB3, EPHB4, FAK, PYK2, FER, FES, FGFR1, FGFR2, FGFR3, FGFR4, IGF1R, INSR, IRR, IGF1R, INSR, JAK1, JAK2, TYK2, JAK2, MET, MUSK, FLT3, FMS, KIT, PDGFRA, PDGFRB, FLT3, RET, ROS, BLK, BRK, FGR, FRK, FYN, HCK, LCK, LYN, SRC, YES, LCK, SYK, ZAP70, BMX, BTK, ITK, TXK, TIE2, TRKA, TRKB, TRKC, TRKA, TRKB, FLT1, FLT4, KDR, LIMK1, LIMK2, TESK1, HH498, MLK3, BRAF, BRAF, RAF1, RIPK2, ALK1, ALK2, ALK4, BMPR1A, TGFBR1, ACTR2, ACTR2B, and mutants thereof.

Accordingly, compounds of formula (I) have utility in treating conditions associated with the modulation of kinase activity, and particularly the selective inhibition of MK2 activity. Such conditions include diseases in which cytokine levels are modulated as a consequence of intracellular signaling via the p38 pathway, with MK2 as the downstream kinase substrate, and in particular, diseases that are associated with an overproduction of cytokines IL-1, IL-6, IL-8, IFNγ and TNF-α. As used herein, the terms "treating" or "treatment" encompass either or both responsive and prophylaxis measures, e.g. measures designed to inhibit or delay the onset of the disease or disorder, achieve a full or partial reduction of the symptoms or disease state, and/or to alleviate, ameliorate, lessen, or cure the disease or disorder and/or its symptoms.

In view of their activity as selective inhibitors of MK2, compounds of Formula (I) are useful in treating cytokine-associated conditions including, but not limited to, inflammatory diseases such as Crohn's and ulcerative colitis, asthma, graft versus host disease, chronic obstructive pulmonary disease; autoimmune diseases such as Grave's disease, rheumatoid arthritis, systemic lupus erythematosis, psoriasis; destructive bone disorders such as bone resorption disease, osteoarthritis, osteoporosis, multiple myeloma-related bone disorder; proliferative disorders such as acute myelogenous leukemia, chronic myelogenous leukemia; angiogenic disorders such as angiogenic disorders including solid tumors, ocular neovasculization, and infantile haemangiomas; infectious diseases such as sepsis, septic shock, and Shigellosis; neurodegenerative diseases such as Alzheimer's disease, Parkinson's disease, cerebral ischemias or neurodegenerative disease caused by traumatic injury, oncologic and viral diseases such as metastatic melanoma, Kaposi's sarcoma, multiple myeloma, and HIV infection and CMV retinitis, AIDS, respectively.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosis, scleroderma, chronic thyroiditis, Grave's disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoisosis, bone resorption disease, allograft rejections, fever and myalgias due to infection, cachexia secondary to infection, meloid formation, scar tissue formation, ulcerative colitis, pyresis, influenza, osteoporosis, osteoarthritis, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovasculization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hyposia, vascular hyperplasia, cardiac and renal reperfusion injury, thrombosis, cardiac hypertrophy, thrombin-induced platelet aggregation, endotoxemia and/or toxic shock syndrome, conditions associated with prostaglandin endoperoxidase syndase-2, and pemphigus vulgaris. Preferred methods of treatment are those wherein the condition is selected from Crohns and ulcerative colitis, allograft rejection, rheumatoid arthritis, psoriasis, ankylosing spondylitis, psoriatic arthritis, and pemphigus vulgaris. Alternatively preferred methods of treatment are those wherein the condition is selected from ischemia reperfusion injury, including cerebral ischemia reperfusions injury arising from stroke and cardiac ischemia reperfusion injury arising from myocardial infarction. Another preferred method of treatment is one in which the condition is multiple myeloma.

In addition, the MK2 inhibitors of the present invention inhibit the expression of inducible pro-inflammatory proteins such as prostaglandin endoperoxide synthase-2 (PGHS-2), also referred to as cyclooxygenase-2 (COX-2). Accordingly, additional MK2-associated conditions include edema, analgesia, fever and pain, such as neuromuscular pain, headache, pain caused by cancer, dental pain and arthritis pain. The inventive compounds also may be used to treat veterinary viral infections, such as lentivirus infections, including, but not limited to equine infectious anemia virus; or retro virus infections, including feline immunodeficiency virus, bovine immunodeficiency virus, and canine immunodeficiency virus.

When the terms "MK2-associated condition" or "MK2-associated disease or disorder" are used herein, each is intended to encompass all of the conditions identified above as if repeated at length, as well as any other condition that is affected by MK2 kinase activity.

The present invention thus provides methods for treating such conditions, comprising administering to a subject in need thereof a therapeutically-effective amount of at least one compound of Formula (I) or a salt thereof. Therapeutically effective amount" is intended to include an amount of a compound of the present invention that is effective when administered alone or in combination to inhibit MK2.

The methods of treating MK2 kinase-associated conditions may comprise administering compounds of Formula (I) alone or in combination with each other and/or other suitable therapeutic agents useful in treating such conditions. Accordingly, "therapeutically effective amount" is also intended to include an amount of the combination of compounds claimed that is effective to inhibit MK2. The combination of compounds is preferably a synergistic combination. Synergy, as described, for example, by Chou and Talalay, *Adv. Enzyme Regul.* 1984, 22:27-55, occurs when the effect (in this case, inhibition of P2Y$_1$) of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased antithrombotic effect, or some other beneficial effect of the combination compared with the individual components.

Exemplary of such other therapeutic agents include corticosteroids, rolipram, calphostin, cytokine-suppressive anti-inflammatory drugs (CSAIDs), 4-substituted imidazo[1,2-A] quinoxalines as disclosed in U.S. Pat. No. 4,200,750; Interleukin-10, glucocorticoids, salicylates, nitric oxide, and other immunosuppressants; nuclear translocation inhibitors, such as deoxyspergualin (DSG); non-steroidal antiinflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, Prograf); cytotoxic drugs such as azathiprine and cyclophosphamide; TNF-α inhibitors such as tenidap, anti-TNF antibodies or soluble TNF receptor, and rapamycin (sirolimus or Rapamune) or derivatives thereof.

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds. The present invention also provides pharmaceutical compositions capable of treating MK2 kinase-associated conditions, including IL-1, IL-6, IL-8, IFNγ and TNF-α-mediated conditions, as described above.

The inventive compositions may contain other therapeutic agents as described above and may be formulated, for example, by employing conventional solid or liquid vehicles or diluents, as well as pharmaceutical additives of a type appropriate to the mode of desired administration (e.g. excipients, binders, preservatives, stabilizers, flavors, etc.) according to techniques such as those well known in the art of pharmaceutical formulation.

Accordingly, the present invention further includes compositions comprising one or more compounds of Formula I and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 17th ed., 1985, which is incorporated herein by reference in its entirety.

The compounds of Formula (I) may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g. with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The therapeutically-effective amount of a compound of the present invention may be determined by one of ordinary skill in the art, and includes exemplary dosage amounts for a mammal of from about 0.05 to 1000 mg/kg; 1-1000 mg/kg; 1-50 mg/kg; 5-250 mg/kg; 250-1000 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species, that are affected by mediation of MK2 enzyme levels.

Examples of formula (I) as specified in the "Examples" section below, have been tested in one or more of the assays described below and have activity as inhibitors of MK2 enzymes at an $IC_{50}$ of less than 30 uM and preferably less than 10 uM; and inhibit TNF-α at an $IC_{50}$ of less than 100 uM and preferably less than 30 uM.

Biological Assays

Generation of Activated MK2 Kinase

DNA oligonucleotide PCR primers were synthesized and used to amplify from template DNA the MK2 DNA sequence (NCBI Refseq NM_032960.2) encoding native amino acid residues 47-400. The PCR primers were designed such that the amplified DNA also encoded an N-terminal $(His)_6$-affinity purification tag followed by a thrombin-cleavable linker. This amplified product was inserted into the pET28N vector. *E. coli* strain BL21(DE3) was transformed with the MK2(47-400)-pET28N plasmid and cultured at 37° C. in a defined medium. IPTG (0.5 mM) was added to the medium to induce recombinant protein expression at 20° C. for 18 hours. The cell paste was harvested by sedimentation and frozen at −80° C.

Frozen cell paste was thawed and lysed in buffer at 4° C. using a microfluidizer. The MK2 protein was purified by sequential chromatography on columns of SP-Sepharose Fast Flow and Ni-NTA Superflow. The N-terminal $(His)_6$-tag was removed from the purified MK2 protein by digestion with thrombin followed by sequential benzamidine-Sepharose and Superdex 200 size exclusion chromatography.

MK2(47-400) was dialyzed and diluted into a final reaction buffer of 0.5 mg/ml MK2(47-400) in 20 mM HEPES pH 7.5, 5% glycerol, 2 mM DTT, 20 mM $MgCl_2$, 1 mM ATP, and 8 µg/ml activated $(His)_5$-p38alpha. The reaction was incubated at 25° C. for 1 hour, after which an additional 1 mM fresh ATP was added. After an additional 30 minute incubation at 25° C. the reaction was stopped by placing it on ice and adding NaCl and EDTA to 200 mM and 30 mM, respectively.

The protein in the activation reaction was concentrated, filtered, and buffer exchanged into 25 mM HEPES pH 7.2, 400 mM NaCl, 20 mM imidazole, 5% glycerol, 10 mM 2-mercaptoethanol, 0.5 mM TCEP. The void volume peak from this column was concentrated and loaded onto a Ni-NTA column to capture the $(His)_5$-p38 protein. The activated MK2(47-400) protein was not retained and eluted in the flow-through fractions. Fractions containing activated MK2(47-400) were pooled, supplemented with 10 mM EDTA, concentrated, and loaded onto a Superdex 200 column equilibrated with 20 mM HEPES pH 7.5, 100 mM NaCl, 10% (v/v) glycerol, 0.1 mM EDTA, 2 mM DTT). The activated MK2(47-400) protein eluted as a single, large peak, and fractions from the center of this peak were pooled, divided into aliquots, and frozen at −80° C.

MK2 Assay

The MK2 radioactive assay was performed in a 96 well round bottom non-binding polystyrene plates (Corning 3605). The final assay volume was 30 µl prepared from three 10 µl additions of enzyme, substrates (HSP-27 and ATP) and test compounds in assay buffer (20 mM HEPES pH 7.5, 25 mM β-glycerolphosphate, 15 mM $MgCl_2$, 1 mM DTT). The reaction was incubated at RT for 30 min. and terminated by adding 20 µl of 0.5 M EDTA to each sample. Then 40 µl of the reaction mixture was transferred onto a pre-wet (2% phosphoric acid) Millipore Multiscreen phosphocellulose filter plate (MAPHNOB50). This reaction mixture was filtered through a Millipore multiscreen resist vacuum manifold. The filterplate was washed 3× with 2% phosphoric acid and air dried. The filterplate is put into a Packard multiscreen adapter plate. 50 µl of Microscint 20 was added to each well and sealed with a plate sealer and counted on the Packard Top Count NXT. Inhibition data were analyzed in ABASE using excel fit. The final concentration of reagents in the assay are 5 µM ATP; 10 µCi/µl [γ-$^{33}$P]ATP, 5 ng MK2 enzyme, 30 µM HSP-27 and DMSO, 0.3% for screening.

The Molecular Devices IMAP MAPKAP K2 Assay Kit is performed in a HE black microplate (Molecular Devices 75-000-005). The final assay volume is 10 µl prepared from 2.5 µl compound, 5 µl ATP/Peptide and 2.5 µl MK2 enzyme. The final concentration of reagents in the assay are 1 µM ATP, 200 n Peptide and 0.070 nM MK2 enzyme (note: The MK2 enzyme concentration should produce approximately 70% of the maximal signal of 380 mP=/−40 mP). Prepare a 1× complete reaction buffer (CRB) using distilled water from a 5× stock and add DTT to a 1 mM final concentration. The CRB is used for the initial reaction preparation. Incubate the reaction covered in foil at room temperature for 30 minutes. Prepare 1× Buffer A using distilled water from the 5× Buffer A stock. Add IMAP reagent by diluting 400 times into Buffer A. Add 30 uL of IMAP reagent in buffer to each well. Incubate for 30 minutes at RT covered in foil. Read on LJL analyst using 485 excitation 530 emission.

Caliper LabChip 3000 Assay is performed in U-bottom 384-well plates. The final assay volume is 30 µl prepared from 15 µl additions of enzyme and substrates (MK2 peptide and ATP) and test compounds in assay buffer (100 mM HEPES pH 7.4, 10 mM $MgCl_2$, 0.015% Brij35 and 4 mM DTT). The reaction is initiated by the combination of MapKapK2 with substrates and test compounds. The reaction is incubated at room temperature for 60 min. and terminated by adding 30 µl of 35 mM EDTA to each sample. The reaction mixture is analyzed on the Caliper LabChip 3000 by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays are ATP, 1 µM; MK2 peptide, 1.5 uM; MapKapK2, 0.08 nM; Brij35, 0.015% and DMSO, 1.6%. Dose response curves are generated to determine the concentration required inhibiting 50% of kinase activity ($IC_{50}$). Compounds are dissolved at 10 mM in dimethylsulfoxide (DMSO) and evaluated at eleven concentrations, each in duplicate. $IC_{50}$ values are derived by non-linear regression analysis.

TNF-α Production by LPS-Stimulated PBMCs

EDTA-treated human whole blood was obtained from healthy volunteers. Peripheral blood mononuclear cells (PBMCs) were purified from human whole blood by Ficoll-Hypaque density gradient centrifugation (Lympho Separation Media Cellgro #25-072-CV) and resuspended at a concentration of $2.5 \times 10^6$/ml in assay medium (RPMI medium containing 10% fetal bovine serum). 100 ul of cell suspension was incubated with 50 ul of test compound (4× concentration in assay medium containing 0.3% DMSO) in 96-well tissue culture plates for 1 hour at 37° C. 50 ul of LPS (400 ng/ml stock) was then added to the cell suspension yielding a 100 ng/ml final concentration of LPS and the plate was incubated for 5 hours at 37° C. Following incubation, the culture medium was collected and assayed. TNF-α concentration in the medium was quantified using a standard ELISA kit (R&D Systems Cat#DY210). Concentrations of TNF-α and $IC_{50}$ values for test compounds (concentration of compound that inhibited LPS-stimulated TNF-α production by 50%) were calculated using softmax software using a 4-parameter curve fit.

EXAMPLES

The following Examples illustrate embodiments of the inventive compounds and starting materials, and are not intended to limit the scope of the claims. For ease of reference, the following abbreviations are used herein:

Abbreviations

BOC=tert-butoxycarbonyl bp=boiling point

Bu=butyl

DMAP=4-dimethylaminopyridine

DIPEA or DIEA=N,N-diisopropylethylamine

DME=1,2-dimethoxyethane

DMF=dimethyl formamide

EDCI=1-3-dimethylaminopropyl)-3-ethylcarbodiimide

Et=ethyl $Et_2O$=diethyl ether

HOBT=1-hydroxybenzotriazole

EtOAc=ethyl acetate

EtOH=ethanol g=gram(s)

H=hydrogen l=liter mCPBA—meta chloro perbenzoic acid

Me=methyl

MeCN=acetonitrile

MeOH=methanol

NMP=1-methyl-2-pyrrolidinone

Ph=phenyl

Pr=propyl

PS=polystyrene

TEA=triethylamine

TFA=trifluoroacetic acid mg=milligram(s)

ml or mL=milliliter

µl=microliter mmol=millimole

µmol=micromole mol=mole mp=melting point

RT=room temperature

HPLC=high pressure liquid chromatography

LC/MS=liquid chromatography/mass spectrometry

Example I(1)

$N^6$-(trans-4-aminocyclohexyl)-$N^8$-[4-(ethyloxy)phenyl]imidazo[1,2-b]pyridazine-6,8-diamine

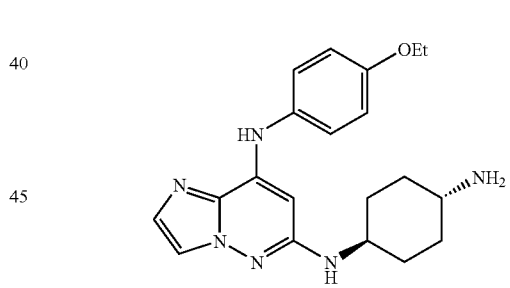

(1a) Bromine (9.71 g, 3.15 mL, 60.75 mmol) was added dropwise to a mixture of 3-amino-6-chloropyridazine (7.87 g, 60.75 mmol) in methanol (115 mL) and sodium bicarbonate (10.22 g, 121.67 mmol). The resultant mixture was stirred at room temperature for 16 hours and then filtered. Water (500 mL) was added to the filtrate and the solution was extracted with ethyl acetate (3×500 mL). The organic layers were combined and concentrated in vacuo. The resulting residue was purified by flash chromatography eluting with 1/1 hexane/ethyl acetate to give 5.40 g (43%) 3-amino-4-bromo-6-chloropyridazine.

(1b) Chloroacetaldehyde solution (50% in water, 13.2 mL, 16.32 g, 104.6 mmol) was added to 3-amino-4-bromo-6-chloropyridazine (4.2 g, 20.2 mmol) from 1a in ethanol (28 mL). The solution was heated to 50° C. for 16 hours and then concentrated in vacuo. Acetone (22 mL) was added to the residue and the solid was collected by vacuum filtration and washed with cold acetone. Upon air drying 4.3 g (79%) of 8-bromo-6-chloroimidazo[1,2-b]pyridazine was obtained as a hydrochloride salt.

(1c variation 1) To a mixture of 8-bromo-6-chloroimidazo [1,2-b]pyridazine (257 mg, 0.956 mmol) from 1b in THF (2.0 ml) was added p-phenetidine (131 mg, 0.956 mmol) and a 1.0 M solution of KOt-Bu in THF (2.5 eq, 2.4 ml, 2.39 mmol). The mixture was allowed to heat at 50° C. for 1 hour. The solution was then concentrated in vacuo to provide crude 6-chloro-N-(4-ethoxyphenyl)imidazo[1,2-b]pyridazin-8-amine as a solid. The solid was then used as is in the following step.

(1c variation 2) p-Phenetidine (1.0 eq, 0.149 mmol) and triethyamine (33 mg, 0.327 mmol) were added to a mixture of 8-bromo-6-chloroimidazo[1,2-b]pyridazine hydrochloride (40 mg, 0.149 mmol) from 1b in EtOH (1.5 mL). The mixture was heated to 90° C. and stirred for 24-48 hours. The solution was then concentrated in vacuo to give crude 6-chloro-N-(4-ethoxyphenyl)imidazo[1,2-b]pyridazin-8-amine.

(1d) trans-1,4-Diaminocyclohexane (1000 mg, 8.77 mmol) was added to the crude 6-chloro-N-(4-ethoxyphenyl) imidazo[1,2-b]pyridazin-8-amine (0.149 mmol) from 1c. The mixture was heated to 160° C. and allowed to melt. After stirring at 160° C. for 24-48 hrs, the liquid mixture was cooled to room temperature. Water was added, followed by extraction with dichloromethane. The organic layer was concentrated in vacuo. The resulting residue was purified by reverse phase preparative HPLC to provide the above titled compound as a TFA salt in approximately 35% yield. $^1$H NMR (400 MHz, MeOH) δ ppm 7.59 (1H, s), 7.29 (1H, s), 7.23 (2H, d, J=8.8 Hz), 6.95 (2H, d, J=8.8 Hz), 5.85 (1H, s), 4.04 (2H, q, J=7 Hz), 3.51-3.61 (1H, m), 2.65-2.73 (1H, m), 2.10 (2H, d, J=12.30 Hz), 1.92 (2H, d, J=12.30 Hz), 1.38 (3H, t, J=7 Hz), 1.20-1.33 (4H, m). LC/MS, m/e 367 (M+1). HPLC Rt, 2.11 min. YMC ODSC18 column (4.6×50 mm). 0%-100% B. Solvent B: (90% MeOH, 10% H$_2$O, 0.1% TFA). Solvent A: (10% MeOH, 90% H$_2$O, 0.1% TFA). Gradient, start % B=0, final % B=100, gradient time 4 min, hold at 100% B 1 min, flow rate 4 mL/min.

Examples prepared in a similar manner are indicated in Table 1

Alternatively, Example I(1) may also be prepared by the following method.

(1e) To perchloroimidazo[1,2-b]pyridazine (Synthesis 1971, 8, 424) (213 mg, 0.731 mmol) in EtOH (5 mL) was added p-phenetidine (100 mg, 0.731 mmol) and triethyamine (86 mg, 0.804 mmol). The mixture was allowed to heat at 90° C. for 5 hours. The solution was then cooled to 0° C. The resulting solid was collected by vacuum filtration and washed with cold EtOH. Upon air drying 191 mg (67%) of crude 2,3,6,7-tetrachloro-N-(4-ethoxyphenyl)imidazo[1,2-b]pyridazin-8-amine was isolated.

(1f) To 2,3,6,7-tetrachloro-N-(4-ethoxyphenyl)imidazo[1,2-b]pyridazin-8-amine (184 mg, 0.47 mmol) from 1e was added trans-1,4-diaminocyclohexane (360 mg, 3.16 mmol). The mixture was allowed to melt at 120° C. for 1½ hours. The melt was then cooled, diluted with water and extracted with ethyl acetate. The organic layer was then concentrated in vacuo to give 200 mg (91%) of crude product. 20 mg of this product was then purified by preparative HPLC. This gave 8.0 mg of N$^6$-(4-aminocyclohexyl)-2,3,7-trichloro-N$^8$-(4-ethoxyphenyl)imidazo[1,2-b]pyridazine-6,8-diamine as a TFA salt.

(1g) To a mixture of crude N$^6$-(4-aminocyclohexyl)-2,3,7-trichloro-N$^8$-(4-ethoxyphenyl)imidazo[1,2-b]pyridazine-6,8-diamine from if as a free base (140 mg, 0.300 mmol) in EtOH (10 ml) in a 500 ml PARR bottle was added 10% Palladium on carbon (175 mg). The PARR bottle was then charged with H$_2$ at 55 psi and allow to shake at room temperature for 24 hours. The catalyst was then filtered and the filtrate was concentrated in vacuo to give a crude mixture of 3 compounds. This mixture was purified by preparative HPLC to give 4.7 mg of Example I(1), N$^6$-(4-aminocyclohexyl)-N$^8$-(4-ethoxyphenyl)imidazo[1,2-b]pyridazine-6,8-diamine as a TFA salt, LC/MS, m/e 367 (M+1). 9.0 mg of N$^6$-(4-aminocyclohexyl)-3-chloro-N$^8$-(4-ethoxyphenyl)imidazo[1,2-b]pyridazine-6,8-diamine, LC/MS, m/e 401 (M+1) and 18.5 mg of N$^6$-(4-aminocyclohexyl)-2,3-dichloro-N$^8$-(4-ethoxyphenyl)imidazo[1,2-b]pyridazine-6,8-diamine, LC/MS, m/e 435 (M+1).

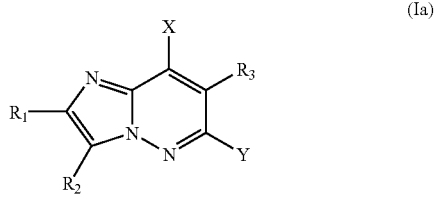

(Ia)

Compounds having the formula (Ia) were prepared according to procedures similar to Example I(1), where in R$_1$, R$_2$, R$_3$, X and Y have the values listed in Table 1, using the appropriate starting materials and substantially the same procedures as indicated.

TABLE 1

| Exp | Name | R$_1$ | R$_2$ | R$_3$ | X | Y | LC/MS m/z (M + 1) |
|---|---|---|---|---|---|---|---|
| I(2) | N$^6$-(2-aminoethyl)-N$^8$-(4-(ethyloxy)phenyl)imidazo[1,2-b]pyridazine-6,8-diamine | H | H | H | NH—⟨C$_6$H$_4$⟩—OEt | NH—(CH$_2$)$_2$—NH$_2$ | 313 |
| I(3) | N$^6$-(4-aminobutyl)-N$^8$-(4-(ethyloxy)phenyl)imidazo[1,2-b]pyridazine-6,8-diamine | H | H | H | NH—⟨C$_6$H$_4$⟩—OEt | NH—(CH$_2$)$_4$—NH$_2$ | 341 |
| I(4) | 7-chloro-N-(4-(ethyloxy)phenyl)-6-(1-piperazinyl)imidazo[1,2-b]pyridazin-8-amine | H | H | Cl | NH—⟨C$_6$H$_4$⟩—OEt | piperazinyl | 373 |

TABLE 1-continued

| Exp | Name | R₁ | R₂ | R₃ | X | Y | LC/MS m/z (M + 1) |
|---|---|---|---|---|---|---|---|
| I(5) | $N^6$-(trans-4-aminocyclohexyl)-$N^8$-(4-(methyloxy)phenyl)imidazo[1,2-b]pyridazine-6,8-diamine | H | H | H | NH–C₆H₄–OMe (4-) | trans-NH–C₆H₁₀–NH₂ | 353 |
| I(6) | $N^6$-(trans-4-aminocyclohexyl)-$N^8$-(3-(ethyloxy)phenyl)imidazo[1,2-b]pyridazine-6,8-diamine | H | H | H | NH–C₆H₄–OEt (3-) | trans-NH–C₆H₁₀–NH₂ | 367 |
| I(7) | $N^6$-(trans-4-aminocyclohexyl)-$N^8$-phenylimidazo[1,2-b]pyridazine-6,8-diamine | H | H | H | NH–C₆H₅ | trans-NH–C₆H₁₀–NH₂ | 323 |
| I(8) | $N^6$-(trans-4-aminocyclohexyl)-$N^8$-(3-(methyloxy)phenyl)imidazo[1,2-b]pyridazine-6,8-diamine | H | H | H | NH–C₆H₄–OMe (3-) | trans-NH–C₆H₁₀–NH₂ | 353 |
| I(9) | $N^6$-(trans-4-aminocyclohexyl)-$N^8$-(3,4-dimethylphenyl)imidazo[1,2-b]pyridazine-6,8-diamine | H | H | H | NH–C₆H₃(3,4-diMe) | trans-NH–C₆H₁₀–NH₂ | 351 |
| I(10) | $N^6$-(trans-4-aminocyclohexyl)-$N^8$-(4-(phenyloxy)phenyl)imidazo[1,2-b]pyridazine-6,8-diamine | H | H | H | NH–C₆H₄–O–C₆H₅ (4-) | trans-NH–C₆H₁₀–NH₂ | 415 |
| I(11) | $N^6$-(trans-4-aminocyclohexyl)-$N^8$-(4-(butyloxy)phenyl)imidazo[1,2-b]pyridazine-6,8-diamine | H | H | H | NH–C₆H₄–O–C₄H₉ (4-) | trans-NH–C₆H₁₀–NH₂ | 395 |
| I(12) | $N^6$-(trans-4-aminocyclohexyl)-$N^8$-4-biphenylylimidazo[1,2-b]pyridazine-6,8-diamine | H | H | H | NH–C₆H₄–C₆H₅ (4-) | trans-NH–C₆H₁₀–NH₂ | 399 |
| I(13) | $N^6$-(trans-4-aminocyclohexyl)-$N^8$-(4-methylphenyl)imidazo[1,2-b]pyridazine-6,8-diamine | H | H | H | NH–C₆H₄–Me (4-) | trans-NH–C₆H₁₀–NH₂ | 339 |
| I(14) | $N^6$-(trans-4-aminocyclohexyl)-$N^8$-(3,4-bis(methyloxy)phenyl)imidazo[1,2-b]pyridazine-6,8-diamine | H | H | H | NH–C₆H₃(3,4-diOMe) | trans-NH–C₆H₁₀–NH₂ | 383 |
| I(15) | $N^6$-(trans-4-aminocyclohexyl)-$N^8$-(4-((phenylmethyl)oxy)phenyl)imidazo[1,2-b]pyridazine-6,8-diamine | H | H | H | NH–C₆H₄–O–CH₂–C₆H₅ (4-) | trans-NH–C₆H₁₀–NH₂ | 429 |
| I(16) | $N^6$-(trans-4-aminocyclohexyl)-$N^8$-(4-(propyloxy)phenyl)imidazo[1,2-b]pyridazine-6,8-diamine | H | H | H | NH–C₆H₄–O–C₃H₇ (4-) | trans-NH–C₆H₁₀–NH₂ | 387 |

TABLE 1-continued

| Exp | Name | R₁ | R₂ | R₃ | X | Y | LC/MS m/z (M + 1) |
|---|---|---|---|---|---|---|---|
| I(17) | N⁶-(trans-4-aminocyclohexyl)-N⁸-pyridin-3-ylimidazo[1,2-b]pyridazine-6,8-diamine | H | H | H | 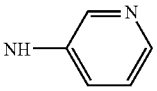 |  | 324 |
| I(18) | N⁶-(trans-4-aminocyclohexyl)-N⁸-(2-methyl-1H-indol-5-yl)imidazo[1,2-b]pyridazine-6,8-diamine | H | H | H | 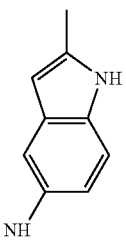 |  | 376 |
| I(19) | N⁶-(trans-4-aminocyclohexyl)-N⁸-methyl-N⁸-phenylimidazo[1,2-b]pyridazine-6,8-diamine | H | H | H | 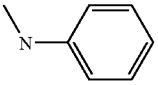 |  | 337 |
| I(19a) | N⁶-(trans-4-aminocyclohexyl)-N⁸-[2-(methyloxy)phenyl]imidazo[1,2-b]pyridazine-6,8-diamine | H | H | H | 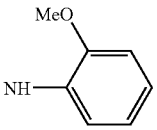 |  | 353 |
| I(20) | N⁶-(trans-4-aminocyclohexyl)-N⁸-(2-methylphenyl)imidazo[1,2-b]pyridazine-6,8-diamine | H | H | H | 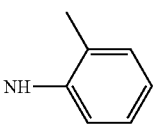 |  | 337 |
| I(21) | N⁶-(trans-4-aminocyclohexyl)-N⁸-(2,3-dimethylphenyl)imidazo[1,2-b]pyridazine-6,8-diamine | H | H | H | 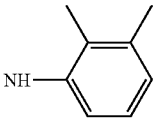 |  | 351 |
| I(22) | N⁶-(trans-4-aminocyclohexyl)-N⁸-(2,4-dimethylphenyl)imidazo[1,2-b]pyridazine-6,8-diamine | H | H | H | 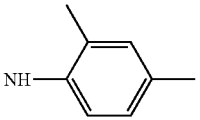 | 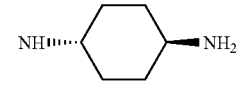 | 351 |
| I(23) | N⁶-(trans-4-aminocyclohexyl)-N⁸-(2,5-dimethylphenyl)imidazo[1,2-b]pyridazine-6,8-diamine | H | H | H | 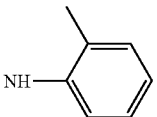 |  | 351 |
| I(24) | N⁶-(trans-4-aminocyclohexyl)-N⁸-(3-methylphenyl)imidazo[1,2-b]pyridazine-6,8-diamine | H | H | H | 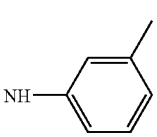 |  | 337 |
| I(25) | N⁶-(trans-4-aminocyclohexyl)-N⁸-(3,5-dimethylphenyl)imidazo[1,2-b]pyridazine-6,8-diamine | H | H | H | 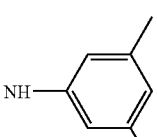 |  | 351 |

TABLE 1-continued

| Exp | Name | R₁ | R₂ | R₃ | X | Y | LC/MS m/z (M + 1) |
|---|---|---|---|---|---|---|---|
| I(26) | N⁶-(trans-4-aminocyclohexyl)-N⁸-[3-(dimethylamino)phenyl]imidazo[1,2-b]pyridazine-6,8-diamine | H | H | H | 3-(dimethylamino)phenyl-NH- | trans-4-aminocyclohexyl-NH- | 366 |
| I(27) | N⁶-(trans-4-aminocyclohexyl)-N⁸-(2-methyl-1,3-benzothiazol-6-yl)imidazo[1,2-b]pyridazine-6,8-diamine | H | H | H | 2-methyl-1,3-benzothiazol-6-yl-NH- | trans-4-aminocyclohexyl-NH- | 394 |
| I(28) | N⁶-(trans-4-aminocyclohexyl)-N⁸-(2-methyl-1,3-benzothiazol-5-yl)imidazo[1,2-b]pyridazine-6,8-diamine | H | H | H | 2-methyl-1,3-benzothiazol-5-yl-NH- | trans-4-aminocyclohexyl-NH- | 394 |
| I(29) | N⁶-(trans-4-aminocyclohexyl)-N⁸-cyclopropylimidazo[1,2-b]pyridazine-6,8-diamine | H | H | H | cyclopropyl-NH- | trans-4-aminocyclohexyl-NH- | 287 |
| I(30) | N⁶-(trans-4-aminocyclohexyl)-N⁸-cyclohexylimidazo[1,2-b]pyridazine-6,8-diamine | H | H | H | cyclohexyl-NH- | trans-4-aminocyclohexyl-NH- | 329 |
| I(31) | N⁶-(trans-4-aminocyclohexyl)-N⁸-(cyclohexylmethyl)imidazo[1,2-b]pyridazine-6,8-diamine | H | H | H | cyclohexylmethyl-NH- | trans-4-aminocyclohexyl-NH- | 393 |
| I(32) | N⁶-(trans-4-aminocyclohexyl)-N⁸-(1-methylethyl)imidazo[1,2-b]pyridazine-6,8-diamine | H | H | H | isopropyl-NH- | trans-4-aminocyclohexyl-NH- | 289 |
| I(33) | N⁶-(trans-4-aminocyclohexyl)-N⁸-(phenylmethyl)imidazo[1,2-b]pyridazine-6,8-diamine | H | H | H | benzyl-NH- | trans-4-aminocyclohexyl-NH- | 337 |
| I(34) | N⁶-(trans-4-aminocyclohexyl)-N⁸-[(2-chlorophenyl)methyl]imidazo[1,2-b]pyridazine-6,8-diamine | H | H | H | (2-chlorophenyl)methyl-NH- | trans-4-aminocyclohexyl-NH- | 371 |

TABLE 1-continued

| Exp | Name | R₁ | R₂ | R₃ | X | Y | LC/MS m/z (M + 1) |
|---|---|---|---|---|---|---|---|
| I(35) | $N^6$-(trans-4-aminocyclohexyl)-$N^8$-((4-chlorophenyl)methyl)imidazo[1,2-b]pyridazine-6,8-diamine | H | H | H | 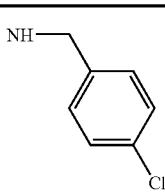 |  | 371 |
| I(36) | $N^6$-(trans-4-aminocyclohexyl)-$N^8$-((4-(methyloxy)phenyl)methyl)imidazo[1,2-b]pyridazine-6,8-diamine | H | H | H | 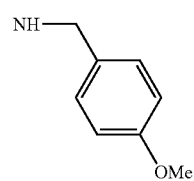 |  | 367 |
| I(37) | $N^6$-(trans-4-aminocyclohexyl)-$N^8$-ethylimidazo[1,2-b]pyridazine-6,8-diamine | H | H | H |  |  | 275 |
| I(38) | $N^6$-(trans-4-aminocyclohexyl)-$N^8$-(2-(methyloxy)ethyl)imidazo[1,2-b]pyridazine-6,8-diamine | H | H | H |  |  | 305 |
| I(39) | $N^6$-(trans-4-aminocyclohexyl)-$N^8$-(2-(4-(methyloxy)phenyl)ethyl)imidazo[1,2-b]pyridazine-6,8-diamine | H | H | H | 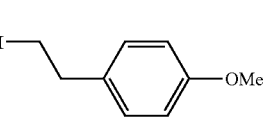 |  | 381 |
| I(40) | $N^6$-(trans-4-aminocyclohexyl)-$N^8$-2-propen-1-ylimidazo[1,2-b]pyridazine-6,8-diamine | H | H | H | 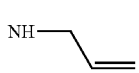 |  | 287 |
| I(41) | $N^6$-(trans-4-aminocyclohexyl)-$N^8$-(3-methylbutyl)imidazo[1,2-b]pyridazine-6,8-diamine | H | H | H | 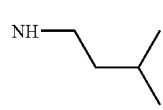 |  | 317 |
| I(42) | $N^6$-(trans-4-aminocyclohexyl)-$N^8$-propylimidazo[1,2-b]pyridazine-6,8-diamine | H | H | H | 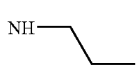 |  | 289 |
| I(43) | $N^6$-(trans-4-aminocyclohexyl)-$N^8$-(cyclopropylmethyl)imidazo[1,2-b]pyridazine-6,8-diamine | H | H | H | 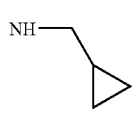 |  | 301 |
| I(44) | $N^6$-(trans-4-aminocyclohexyl)-$N^8$-((3-chlorophenyl)methyl)imidazo[1,2-b]pyridazine-6,8-diamine | H | H | H | 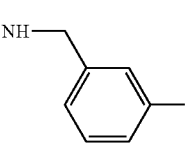 |  | 371 |
| I(46) | $N^6$-(3-aminopropyl)-$N^8$-(4-(ethyloxy)phenyl)imidazo[1,2-b]pyridazine-6,8-diamine | H | H | H | 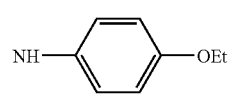 | 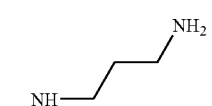 | 327 |

TABLE 1-continued

| Exp | Name | R₁ | R₂ | R₃ | X | Y | LC/MS m/z (M + 1) |
|---|---|---|---|---|---|---|---|
| I(48) | N⁶-(4-((4-aminocyclohexyl)methyl)cyclohexyl)-N⁸-(4-(ethyloxy)phenyl)imidazo[1,2-b]pyridazine-6,8-diamine | H | H | H | NH–C₆H₄–OEt | HN-cyclohexyl-CH₂-cyclohexyl-NH₂ | 463 |
| I(49) | 2-(1-(8-((4-(ethyloxy)phenyl)amino)imidazo[1,2-b]pyridazin-6-yl)-4-piperidinyl)ethanol | H | H | H | NH–C₆H₄–OEt | N-piperidinyl-CH₂CH₂OH | 382 |
| I(50) | N⁶-(trans-4-aminocyclohexyl)-N⁸-1H-indol-5-ylimidazo[1,2-b]pyridazine-6,8-diamine | H | H | H | NH-indole | NH-trans-cyclohexyl-NH₂ | 363 |
| I(51) | N⁶-(trans-4-aminocyclohexyl)-N⁸-(2-(ethyloxy)phenyl)imidazo[1,2-b]pyridazine-6,8-diamine | H | H | H | 2-EtO-C₆H₄-NH | NH-trans-cyclohexyl-NH₂ | 368 |
| I(52) | 6-(3-amino-1-pyrrolidinyl)-N-(4-(ethyloxy)phenyl)imidazo[1,2-b]pyridazine-8-amine | H | H | H | NH–C₆H₄–OEt | N-pyrrolidinyl-NH₂ | 339 |
| I(53) | N⁶-(trans-4-aminocyclohexyl)-N⁸-(2-phenylethyl)imidazo[1,2-b]pyridazine-6,8-diamine | H | H | H | NH-CH₂CH₂-C₆H₅ | NH-trans-cyclohexyl-NH₂ | 351 |
| I(54) | N-(4-(ethyloxy)phenyl)-6-(1-piperazinyl)imidazo[1,2-b]pyridazin-8-amine | H | H | H | NH–C₆H₄–OEt | piperazinyl | 339 |
| I(55) | N⁶-(2-(dimethylamino)ethyl)-N⁸-(4-(ethyloxy)phenyl)imidazo[1,2-b]pyridazine-6,8-diamine | H | H | H | NH–C₆H₄–OEt | NH-CH₂CH₂-N(CH₃)₂ | 341 |
| I(56) | N⁸-(4-(ethyloxy)phenyl)-N⁶-(2-furanylmethyl)imidazo[1,2-b]pyridazine-6,8-diamine | H | H | H | NH–C₆H₄–OEt | NH-CH₂-furan | 350 |
| I(57) | N-(4-(ethyloxy)phenyl)-6-(4-methyl-1,4-diazepan-1-yl)imidazo[1,2-b]pyridazin-8-amine | H | H | H | NH–C₆H₄–OEt | 4-methyl-1,4-diazepan-1-yl | 368 |
| I(58) | 2-((6-((trans-4-aminocyclohexyl)amino)imidazo[1,2-b]pyridazin-8-yl)amino)phenol | H | H | H | 2-HO-C₆H₄-NH | NH-trans-cyclohexyl-NH₂ | 339 |

TABLE 1-continued

| Exp | Name | R₁ | R₂ | R₃ | X | Y | LC/MS m/z (M + 1) |
|---|---|---|---|---|---|---|---|
| I(59) | N⁶-(trans-4-aminocyclohexyl)-N⁸-(3-((phenylmethyl)oxy)phenyl)imidazo[1,2-b]pyridazine-6,8-diamine | H | H | H | 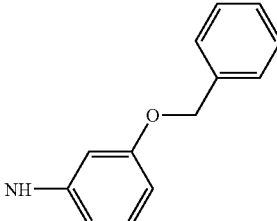 |  | 430 |
| I(60) | 3-((6-((trans-4-aminocyclohexyl)amino)imidazo[1,2-b]pyridazin-8-yl)amino)phenol | H | H | H | 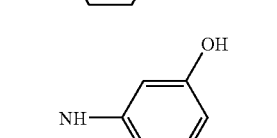 |  | 339 |
| I(61) | 4-((6-((trans-4-aminocyclohexyl)amino)imidazo[1,2-b]pyridazin-8-yl)amino)phenol | H | H | H | 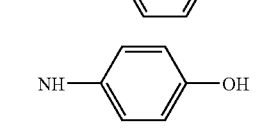 | 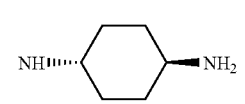 | 339 |
| I(62) | N⁶-(trans-4-aminocyclohexyl)imidazo[1,2-b]pyridazine-6,8-diamine | H | H | H | NH2 |  | 247 |
| I(63) | 3-((6-((trans-4-aminocyclohexyl)amino)imidazo[1,2-b]pyridazin-8-yl)amino)benzonitrile | H | H | H | 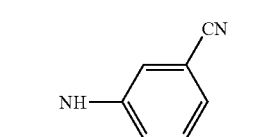 | 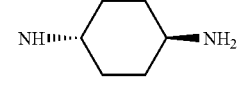 | 348 |
| I(64) | 4-((6-((trans-4-aminocyclohexyl)amino)imidazo[1,2-b]pyridazin-8-yl)amino)benzonitrile | H | H | H | 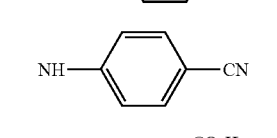 |  | 348 |
| I(65) | 3-((6-((trans-4-aminocyclohexyl)amino)imidazo[1,2-b]pyridazin-8-yl)amino)benzoic acid | H | H | H | 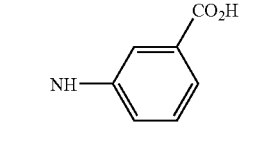 | 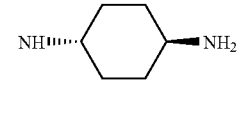 | 367 |
| I(66) | N⁶-(trans-4-aminocyclohexyl)-N⁸-1H-pyrazol-3-ylimidazo[1,2-b]pyridazine-6,8-diamine | H | H | H | 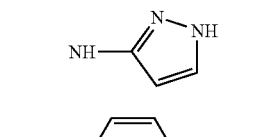 | 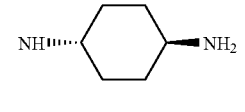 | 313 |
| I(67) | 4-((6-((trans-4-aminocyclohexyl)amino)imidazo[1,2-b]pyridazin-8-yl)amino)benzoic acid | H | H | H | 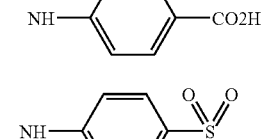 | 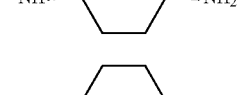 | 367 |
| I(68) | 4-((6-((trans-4-aminocyclohexyl)amino)imidazo[1,2-b]pyridazin-8-yl)amino)-N,N-dimethylbenzenesulfonamide | H | H | H |  | 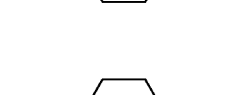 | 431 |
| I(69) | N⁶-(trans-4-aminocyclohexyl)-N⁸-(4-(1H-tetrazol-5-yl)phenyl)imidazo[1,2-b]pyridazine-6,8-diamine | H | H | H | 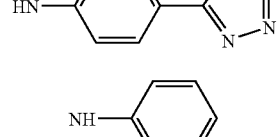 | 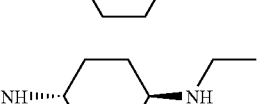 | 391 |
| I(70) | N⁶-(trans-4-(ethylamino)cyclohexyl)-N⁸-phenylimidazo[1,2-b]pyridazine-6,8-diamine | H | H | H | 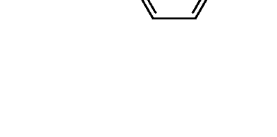 |  | 351 |

TABLE 1-continued

| Exp | Name | R₁ | R₂ | R₃ | X | Y | LC/MS m/z (M + 1) |
|---|---|---|---|---|---|---|---|
| I(71) | N⁶-(trans-4-(methylamino)cyclohexyl)-N⁸-phenylimidazo[1,2-b]pyridazine-6,8-diamine | H | H | H | NH-phenyl | NH-(trans-cyclohexyl)-NHMe | 337 |
| I(72) | N⁶-(trans-4-aminocyclohexyl)-N⁸-(2-(phenyloxy)phenyl)imidazo[1,2-b]pyridazine-6,8-diamine | H | H | H | 2-(phenyloxy)phenyl-NH | NH-(trans-cyclohexyl)-NH₂ | 416 |
| I(73) | N⁶-(trans-4-aminocyclohexyl)-N⁸-(4'-chloro-4-biphenylyl)imidazo[1,2-b]pyridazine-6,8-diamine | H | H | H | 4'-chloro-4-biphenylyl-NH | NH-(trans-cyclohexyl)-NH₂ | 434 |
| I(74) | N⁶-(trans-4-aminocyclohexyl)-N⁸-(2'-methyl-4-biphenylyl)imidazo[1,2-b]pyridazine-6,8-diamine | H | H | H | 2'-methyl-4-biphenylyl-NH | NH-(trans-cyclohexyl)-NH₂ | 414 |
| I(75) | N⁶-(trans-4-aminocyclohexyl)-N⁸-(3'-chloro-4-biphenylyl)imidazo[1,2-b]pyridazine-6,8-diamine | H | H | H | 3'-chloro-4-biphenylyl-NH | NH-(trans-cyclohexyl)-NH₂ | 434 |
| I(76) | N⁶-(trans-4-aminocyclohexyl)-N⁸-(4-(phenylmethyl)phenyl)imidazo[1,2-b]pyridazine-6,8-diamine | H | H | H | 4-(phenylmethyl)phenyl-NH | NH-(trans-cyclohexyl)-NH₂ | 414 |
| I(77) | N⁶-(trans-4-aminocyclohexyl)-N⁸-(4-(4-morpholinyl)phenyl)imidazo[1,2-b]pyridazine-6,8-diamine | H | H | H | 4-(4-morpholinyl)phenyl-NH | NH-(trans-cyclohexyl)-NH₂ | 409 |
| I(78) | N⁶-(trans-4-aminocyclohexyl)-N⁸-(3'-chloro-3-biphenylyl)imidazo[1,2-b]pyridazine-6,8-diamine | H | H | H | 3'-chloro-3-biphenylyl-NH | NH-(trans-cyclohexyl)-NH₂ | 434 |
| I(79) | N⁶-(trans-4-aminocyclohexyl)-N⁸-(4-(1-methylethyl)phenyl)imidazo[1,2-b]pyridazine-6,8-diamine | H | H | H | 4-isopropylphenyl-NH | NH-(trans-cyclohexyl)-NH₂ | 366 |
| I(80) | N⁶-(trans-4-aminocyclohexyl)-N⁸-(4-butylphenyl)imidazo[1,2-b]pyridazine-6,8-diamine | H | H | H | 4-butylphenyl-NH | NH-(trans-cyclohexyl)-NH₂ | 380 |

TABLE 1-continued

| Exp | Name | R₁ | R₂ | R₃ | X | Y | LC/MS m/z (M + 1) |
|---|---|---|---|---|---|---|---|
| I(81) | N⁶-(trans-4-aminocyclohexyl)-N⁸-(5,6,7,8-tetrahydro-1-naphthalenyl)imidazo[1,2-b]pyridazine-6,8-diamine | H | H | H | (5,6,7,8-tetrahydronaphthalen-1-yl)amino | trans-4-aminocyclohexylamino | 378 |
| I(82) | N⁶-(trans-4-aminocyclohexyl)-N⁸-1-naphthalenylimidazo[1,2-b]pyridazine-6,8-diamine | H | H | H | naphthalen-1-ylamino | trans-4-aminocyclohexylamino | 374 |
| I(83) | N⁶-(trans-4-aminocyclohexyl)-N⁸-(3-(phenylmethyl)phenyl)imidazo[1,2-b]pyridazine-6,8-diamine | H | H | H | 3-benzylphenylamino | trans-4-aminocyclohexylamino | 414 |
| I(84) | N⁶-(trans-4-aminocyclohexyl)-N⁸-(4-propylphenyl)imidazo[1,2-b]pyridazine-6,8-diamine | H | H | H | 4-propylphenylamino | trans-4-aminocyclohexylamino | 366 |
| I(85) | N⁶-(trans-4-aminocyclohexyl)-N⁸-(4'-methyl-4-biphenylyl)imidazo[1,2-b]pyridazine-6,8-diamine | H | H | H | 4'-methylbiphenyl-4-ylamino | trans-4-aminocyclohexylamino | 414 |
| I(86) | N⁶-(trans-4-aminocyclohexyl)-N⁸-(3-(1-methylethyl)phenyl)imidazo[1,2-b]pyridazine-6,8-diamine | H | H | H | 3-isopropylphenylamino | trans-4-aminocyclohexylamino | 366 |
| I(87) | N⁶-(trans-4-aminocyclohexyl)-N⁸-(3-((1-methylethyl)oxy)phenyl)imidazo[1,2-b]pyridazine-6,8-diamine | H | H | H | 3-isopropoxyphenylamino | trans-4-aminocyclohexylamino | 382 |
| I(88) | N⁶-(trans-4-aminocyclohexyl)-N⁸-(3,5-bis(methyloxy)phenyl)imidazo[1,2-b]pyridazine-6,8-diamine | H | H | H | 3,5-dimethoxyphenylamino | trans-4-aminocyclohexylamino | 384 |
| I(89) | trans-N-(8-(6-methyl-3,4-dihydro-1(2H)-quinolinyl)imidazo[1,2-b]pyridazin-6-yl)-1,4-cyclohexanediamine | H | H | H | 6-methyl-3,4-dihydroquinolin-1(2H)-yl | trans-4-aminocyclohexylamino | 378 |

TABLE 1-continued

| Exp | Name | R₁ | R₂ | R₃ | X | Y | LC/MS m/z (M + 1) |
|---|---|---|---|---|---|---|---|
| I(90) | N⁶-(trans-4-aminocyclohexyl)-N⁸-2-naphthalenylimidazo[1,2-b]pyridazine-6,8-diamine | H | H | H | 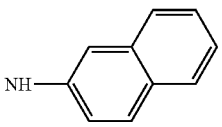 |  | 374 |
| I(91) | N⁶-(trans-4-aminocyclohexyl)-N⁸-(3-(methylsulfanyl)phenyl)imidazo[1,2-b]pyridazine-6,8-diamine | H | H | H | 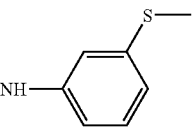 |  | 370 |
| I(92) | N⁶-(trans-4-aminocyclohexyl)-N⁸-(3-ethylphenyl)imidazo[1,2-b]pyridazine-6,8-diamine | H | H | H | 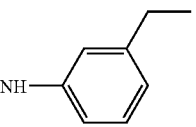 |  | 352 |
| I(93) | N⁶-(trans-4-aminocyclohexyl)-N⁸-(4-ethylphenyl)imidazo[1,2-b]pyridazine-6,8-diamine | H | H | H | 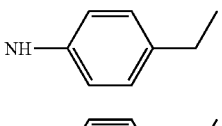 |  | 352 |
| I(94) | N⁶-(trans-4-aminocyclohexyl)-N⁸-(4-(methylsulfanyl)phenyl)imidazo[1,2-b]pyridazine-6,8-diamine | H | H | H | 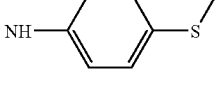 | 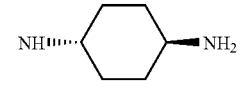 | 370 |
| I(95) | N⁶-(trans-4-aminocyclohexyl)-N⁸-9H-fluoren-2-ylimidazo[1,2-b]pyridazine-6,8-diamine | H | H | H | 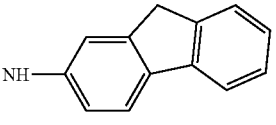 |  | 412 |
| I(96) | N⁶-(trans-4-aminocyclohexyl)-N⁸-(2-ethylphenyl)imidazo[1,2-b]pyridazine-6,8-diamine | H | H | H | 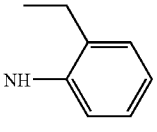 | 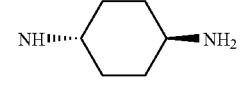 | 352 |
| I(97) | N⁶-(trans-4-aminocyclohexyl)-N⁸-(4-cyclohexylphenyl)imidazo[1,2-b]pyridazine-6,8-diamine | H | H | H | 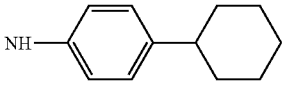 | 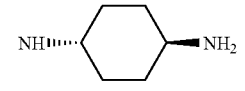 | 406 |
| I(98) | N⁶-(trans-4-aminocyclohexyl)-N⁸-(4-(1,1-dimethylethyl)phenyl)imidazo[1,2-b]pyridazine-6,8-diamine | H | H | H |  |  | 380 |
| I(99) | N⁶-(trans-4-aminocyclohexyl)-N⁸-(3-(phenyloxy)phenyl)imidazo[1,2-b]pyridazine-6,8-diamine | H | H | H | 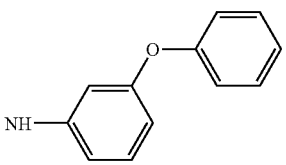 |  | 416 |
| I(100) | N⁶-(trans-4-aminocyclohexyl)-N⁸-3-biphenylylimidazo[1,2-b]pyridazine-6,8-diamine | H | H | H | 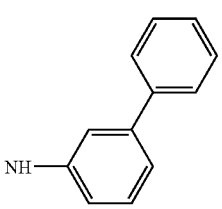 |  | 400 |

TABLE 1-continued

| Exp | Name | R₁ | R₂ | R₃ | X | Y | LC/MS m/z (M + 1) |
|---|---|---|---|---|---|---|---|
| I(101) | $N^6$-(trans-4-aminocyclohexyl)-$N^8$-(4-((1-methylethyl)oxy)phenyl)imidazo[1,2-b]pyridazine-6,8-diamine | H | H | H | 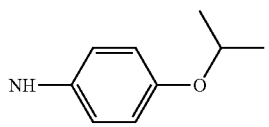 | 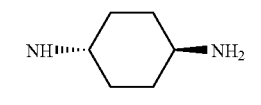 | 382 |
| I(102) | $N^6$-(trans-4-aminocyclohexyl)-$N^8$-(2-chlorophenyl)imidazo[1,2-b]pyridazine-6,8-diamine | H | H | H | 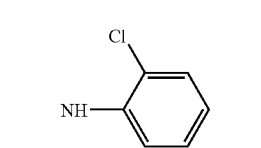 | 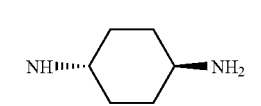 | 358 |
| I(103) | $N^6$-(trans-4-aminocyclohexyl)-$N^8$-(4-chlorophenyl)imidazo[1,2-b]pyridazine-6,8-diamine | H | H | H | 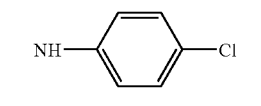 | 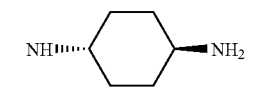 | 358 |
| I(104) | $N^6$-(trans-4-aminocyclohexyl)-$N^8$-(3-chlorophenyl)imidazo[1,2-b]pyridazine-6,8-diamine | H | H | H | 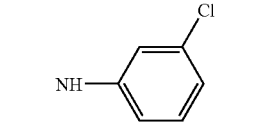 | 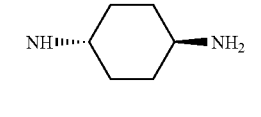 | 358 |
| I(105) | $N^6$-(trans-4-aminocyclohexyl)-$N^8$-(4-chloro-1-naphthalenyl)imidazo[1,2-b]pyridazine-6,8-diamine | H | H | H | 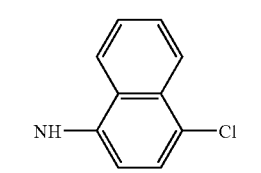 | 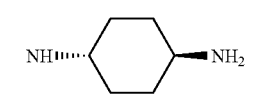 | 408 |
| I(106) | $N^6$-(trans-4-aminocyclohexyl)-$N^8$-3-quinolinylimidazo[1,2-b]pyridazine-6,8-diamine | H | H | H | 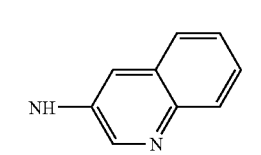 | 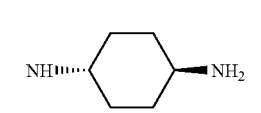 | 375 |
| I(107) | $N^6$-(trans-4-aminocyclohexyl)-$N^8$-(3,5-dichlorophenyl)imidazo[1,2-b]pyridazine-6,8-diamine | H | H | H | 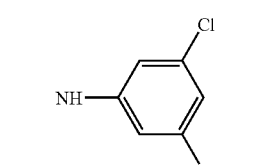 | 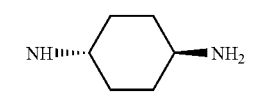 | 392 |
| I(108) | $N^6$-(trans-4-aminocyclohexyl)-$N^8$-(3-(trifluoromethyl)phenyl)imidazo[1,2-b]pyridazine-6,8-diamine | H | H | H | 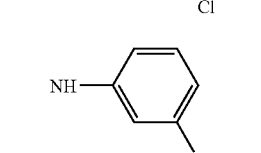 | 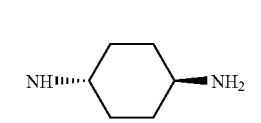 | 391 |
| I(109) | $N^6$-(trans-4-aminocyclohexyl)-$N^8$-(4-chloro-2-fluorophenyl)imidazo[1,2-b]pyridazine-6,8-diamine | H | H | H | 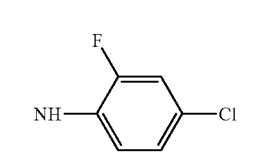 | 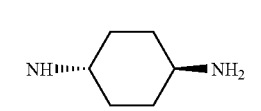 | 376 |
| I(110) | $N^6$-(trans-4-aminocyclohexyl)-$N^8$-(2-fluoro-5-methylphenyl)imidazo[1,2-b]pyridazine-6,8-diamine | H | H | H | 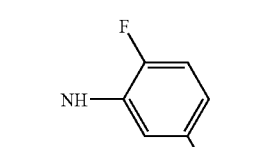 | 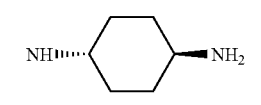 | 355 |

TABLE 1-continued

| Exp | Name | $R_1$ | $R_2$ | $R_3$ | X | Y | LC/MS m/z (M + 1) |
|---|---|---|---|---|---|---|---|
| I(111) | $N^6$-(trans-4-aminocyclohexyl)-$N^8$-(4-chloro-3-methylphenyl)imidazo[1,2-b]pyridazine-6,8-diamine | H | H | H | NH–(3-methyl-4-chlorophenyl) | NH–cyclohexyl–$NH_2$ (trans) | 372 |
| I(112) | $N^6$-(trans-4-aminocyclohexyl)-$N^8$-(5-phenyl-2-pyridinyl)imidazo[1,2-b]pyridazine-6,8-diamine | H | H | H | NH–(5-phenylpyridin-2-yl) | NH–cyclohexyl–$NH_2$ (trans) | 401 |
| I(113) | $N^6$-(trans-4-aminocyclohexyl)-$N^8$-(3-fluoro-4-methylphenyl)imidazo[1,2-b]pyridazine-6,8-diamine | H | H | H | NH–(3-fluoro-4-methylphenyl) | NH–cyclohexyl–$NH_2$ (trans) | 355 |
| I(114) | $N^6$-(trans-4-aminocyclohexyl)-$N^8$-(2-methyl-4-pyridinyl)imidazo[1,2-b]pyridazine-6,8-diamine | H | H | H | NH–(2-methylpyridin-4-yl) | NH–cyclohexyl–$NH_2$ (trans) | 338 |
| I(115) | $N^6$-(trans-4-aminocyclohexyl)-$N^8$-(4-fluoro-3-methylphenyl)imidazo[1,2-b]pyridazine-6,8-diamine | H | H | H | NH–(4-fluoro-3-methylphenyl) | NH–cyclohexyl–$NH_2$ (trans) | 355 |
| I(116) | $N^6$-(trans-4-aminocyclohexyl)-$N^8$-(2-fluoro-4-methylphenyl)imidazo[1,2-b]pyridazine-6,8-diamine | H | H | H | NH–(2-fluoro-4-methylphenyl) | NH–cyclohexyl–$NH_2$ (trans) | 355 |
| I(117) | $N^6$-(trans-4-aminocyclohexyl)-$N^8$-(3-((trifluoromethyl)oxy)phenyl)imidazo[1,2-b]pyridazine-6,8-diamine | H | H | H | NH–(3-$OCF_3$-phenyl) | NH–cyclohexyl–$NH_2$ (trans) | 407 |
| I(118) | $N^6$-(trans-4-aminocyclohexyl)-$N^8$-(4-methyl-3-(trifluoromethyl)phenyl)imidazo[1,2-b]pyridazine-6,8-diamine | H | H | H | NH–(4-methyl-3-$CF_3$-phenyl) | NH–cyclohexyl–$NH_2$ (trans) | 405 |
| I(119) | $N^6$-(trans-4-aminocyclohexyl)-$N^8$-(4-ethyl-2-pyridinyl)imidazo[1,2-b]pyridazine-6,8-diamine | H | H | H | NH–(4-ethylpyridin-2-yl) | NH–cyclohexyl–$NH_2$ (trans) | 353 |
| I(120) | $N^6$-(trans-4-aminocyclohexyl)-$N^8$-(4-(1H-1,2,4-triazol-1-yl)phenyl)imidazo[1,2-b]pyridazine-6,8-diamine | H | H | H | NH–(4-(1H-1,2,4-triazol-1-yl)phenyl) | NH–cyclohexyl–$NH_2$ (trans) | 390 |
| I(121) | $N^6$-(trans-4-aminocyclohexyl)-$N^8$-(4-(1H-pyrrol-1-yl)phenyl)imidazo[1,2-b]pyridazine-6,8-diamine | H | H | H | NH–(4-(1H-pyrrol-1-yl)phenyl) | NH–cyclohexyl–$NH_2$ (trans) | 389 |

TABLE 1-continued

| Exp | Name | R₁ | R₂ | R₃ | X | Y | LC/MS m/z (M + 1) |
|---|---|---|---|---|---|---|---|
| I(122) | $N^6$-(trans-4-aminocyclohexyl)-$N^8$-(4-(4,5-dichloro-1H-imidazol-1-yl)phenyl)imidazo[1,2-b]pyridazine-6,8-diamine | H | H | H | NH–C₆H₄–(4,5-dichloroimidazol-1-yl) | NH–trans-cyclohexyl–NH₂ | 458 |
| I(123) | $N^6$-(trans-4-aminocyclohexyl)-$N^8$-(4-(1H-pyrazol-1-yl)phenyl)imidazo[1,2-b]pyridazine-6,8-diamine | H | H | H | NH–C₆H₄–(pyrazol-1-yl) | NH–trans-cyclohexyl–NH₂ | 390 |
| I(124) | $N^6$-(trans-4-aminocyclohexyl)-$N^8$-(4-(3,5-dimethyl-1H-pyrazol-1-yl)phenyl)imidazo[1,2-b]pyridazine-6,8-diamine | H | H | H | NH–C₆H₄–(3,5-dimethylpyrazol-1-yl) | NH–trans-cyclohexyl–NH₂ | 418 |
| I(125) | $N^6$-(trans-4-aminocyclohexyl)-$N^8$-(4-(4-methyl-4H-1,2,4-triazol-3-yl)phenyl)imidazo[1,2-b]pyridazine-6,8-diamine | H | H | H | NH–C₆H₄–(4-methyl-4H-1,2,4-triazol-3-yl) | NH–trans-cyclohexyl–NH₂ | 405 |
| I(126) | $N^6$-(trans-4-aminocyclohexyl)-$N^8$-(4-(1H-imidazol-1-yl)phenyl)imidazo[1,2-b]pyridazine-6,8-diamine | H | H | H | NH–C₆H₄–(imidazol-1-yl) | NH–trans-cyclohexyl–NH₂ | 390 |
| I(127) | $N^6$-(trans-4-aminocyclohexyl)-$N^8$-(4-(1-methyl-1H-imidazol-2-yl)phenyl)imidazo[1,2-b]pyridazine-6,8-diamine | H | H | H | NH–C₆H₄–(1-methyl-1H-imidazol-2-yl) | NH–trans-cyclohexyl–NH₂ | 404 |
| I(128) | $N^6$-(trans-4-aminocyclohexyl)-$N^8$-(4-(2-methyl-1,3-thiazol-4-yl)phenyl)imidazo[1,2-b]pyridazine-6,8-diamine | H | H | H | NH–C₆H₄–(2-methylthiazol-4-yl) | NH–trans-cyclohexyl–NH₂ | 421 |
| I(129) | $N^6$-(trans-4-aminocyclohexyl)-$N^8$-(4-(5-methyl-2-furanyl)phenyl)imidazo[1,2-b]pyridazine-6,8-diamine | H | H | H | NH–C₆H₄–(5-methylfuran-2-yl) | NH–trans-cyclohexyl–NH₂ | 404 |
| I(130) | $N^6$-(trans-4-aminocyclohexyl)-$N^8$-(4-(2-ethyl-2H-tetrazol-5-yl)phenyl)imidazo[1,2-b]pyridazine-6,8-diamine | H | H | H | NH–C₆H₄–(2-ethyl-2H-tetrazol-5-yl) | NH–trans-cyclohexyl–NH₂ | 420 |
| I(131) | 4-((6-((trans-4-aminocyclohexyl)amino)imidazo[1,2-b]pyridazin-8-yl)amino)-3-hydroxy-N,N-dimethylbenzenesulfonamide | H | H | H | HN–C₆H₃(3-OH)–SO₂N(CH₃)₂ | NH–trans-cyclohexyl–NH₂ | 447 |
| I(132) | $N^6$-(trans-4-aminocyclohexyl)-$N^8$-(2,3-dihydro-1H-inden-5-yl)imidazo[1,2-b]pyridazine-6,8-diamine | H | H | H | NH–(2,3-dihydro-1H-inden-5-yl) | NH–trans-cyclohexyl–NH₂ | 364 |

TABLE 1-continued

| Exp | Name | R₁ | R₂ | R₃ | X | Y | LC/MS m/z (M + 1) |
|---|---|---|---|---|---|---|---|
| I(133) | 3-((6-((trans-4-aminocyclohexyl)amino)imidazo[1,2-b]pyridazin-8-yl)amino)-N,N-dimethylbenzenesulfonamide | H | H | H | | | 431 |
| I(134) | 4-((6-((trans-4-aminocyclohexyl)amino)imidazo[1,2-b]pyridazin-8-yl)amino)-N,N-dimethylbenzamide | H | H | H | | | 395 |
| I(135) | N⁶-(trans-4-((2-chloro-4-pyrimidinyl)amino)cyclohexyl)-N⁸-phenylimidazo[1,2-b]pyridazine-6,8-diamine | H | H | H | | | 436 |
| I(136) | N⁶-(3-aminocyclopentyl)-N⁸-phenylimidazo[1,2-b]pyridazine-6,8-diamine | H | H | H | | | 309 |
| I(137) | N⁶-(trans-4-aminocyclohexyl)-N⁸-(3-(4-morpholinylsulfonyl)phenyl)imidazo[1,2-b]pyridazine-6,8-diamine | H | H | H | | | 473 |
| I(138) | 3-((6-((trans-4-aminocyclohexyl)amino)imidazo[1,2-b]pyridazin-8-yl)amino)-N,N-diethylbenzamide | H | H | H | | | 423 |
| I(139) | 3-((6-((trans-4-aminocyclohexyl)amino)imidazo[1,2-b]pyridazin-8-yl)amino)-N-methyl-N-phenylbenzensulfonamide | H | H | H | | | 493 |
| I(140) | 4-((6-((trans-4-aminocyclohexyl)amino)imidazo[1,2-b]pyridazin-8-yl)amino)-2-hydroxy-N,N-dimethylbenzenesulfonamide | H | H | H | | | 447 |

TABLE 1-continued

| Exp | Name | R₁ | R₂ | R₃ | X | Y | LC/MS m/z (M + 1) |
|---|---|---|---|---|---|---|---|
| I(141) | N⁶-(4-aminobicyclo[2.2.2.]oct-1-yl)-N⁸-phenylimidazo[1,2-b]pyridazine-6,8-diamine | H | H | H | 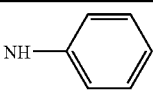 |  | 349 |
| I(42) | N-(4-((6-((trans-4-aminocyclohexyl)amino)imidazo[1,2-b]pyridazin-8-yl)amino)phenyl)methanesulfonamide | H | H | H | 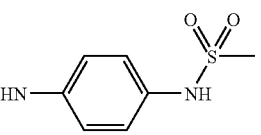 | 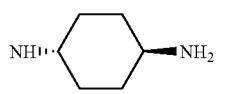 | 417 |
| I(143) | N⁶-(trans-4-aminocyclohexyl)-N⁸-(4-(3-(dimethylamino)-1-pyrrolidinyl)phenyl)imidazo[1,2-b]pyridazine-6,8-diamine | H | H | H | 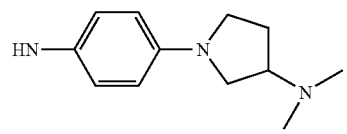 | 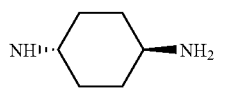 | 436 |
| I(144) | N⁶-(trans-4-aminocyclohexyl)-N⁸-(4-(1-pyrrolidinylsulfonyl)phenyl)imidazo[1,2-b]pyridazine-6,8-diamine | H | H | H | 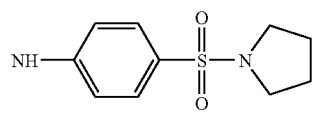 | 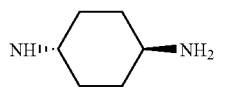 | 457 |
| I(145) | 4-((6-((trans-4-aminocyclohexyl)amino)imidazo[1,2-b]pyridazin-8-yl)amino)benzenesulfonic acid | H | H | H | 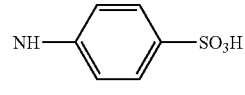 | 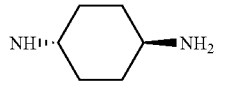 | 403 |
| I(146) | 4-((6-((trans-4-aminocyclohexyl)amino)imidazo[1,2-b]pyridazin-8-yl)amino)-N,N-diethylbenzenesulfonamide | H | H | H | 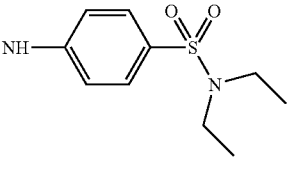 | 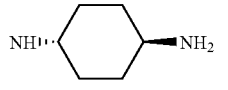 | 459 |
| I(147) | 4-((6-((trans-4-aminocyclohexyl)amino)imidazo[1,2-b]pyridazin-8-yl)amino)-N-propylbenzensulfonamide | H | H | H | 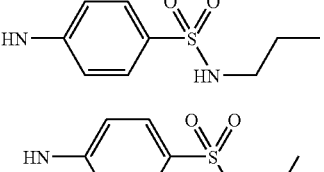 | 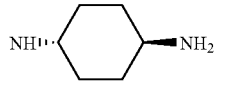 | 445 |
| I(148) | 4-((6-((trans-4-aminocyclohexyl)amino)imidazo[1,2-b]pyridazin-8-yl)amino)-N-ethylbenzenesulfonamide | H | H | H |  |  | 431 |
| I(149) | 4-((6-((trans-4-aminocyclohexyl)amino)imidazo[1,2-b]pyridazin-8-yl)amino)-N-methylbenzenesulfonamide | H | H | H | 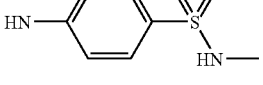 | 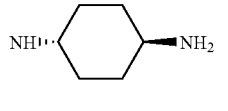 | 417 |
| I(150) | N⁶-(trans-4-aminocyclohexyl)-N⁸-(4-aminophenyl)imidazo[1,2-b]pyridazine-6,8-diamine | H | H | H | 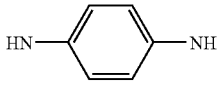 | 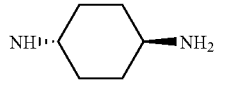 | 338 |
| I(151) | 4-((6-((trans-4-aminocyclohexyl)amino)imidazo[1,2-b]pyridazin-8-yl)amino)benzenesulfonamide | H | H | H | 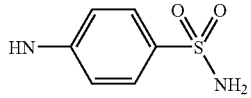 | 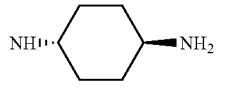 | 402 |
| I(152) | 3-((6-((trans-4-aminocyclohexyl)amino)imidazo[1,2-b]pyridazin-8-yl)amino)benzenesulfonamide | H | H | H | 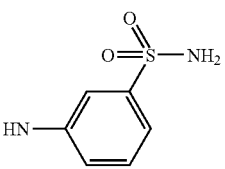 | 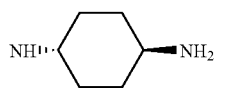 | 402 |

TABLE 1-continued

| Exp | Name | R₁ | R₂ | R₃ | X | Y | LC/MS m/z (M + 1) |
|---|---|---|---|---|---|---|---|
| I(153) | 3-((6-((trans-4-aminocyclohexyl)amino)imidazo[1,2-b]pyridazin-8-yl)amino)benzamide | H | H | H | (3-carbamoylphenyl)amino | trans-4-aminocyclohexylamino | 366 |
| I(154) | 4-((6-((trans-4-aminocyclohexyl)amino)imidazo[1,2-b]pyridazin-8-yl)amino)benzamide | H | H | H | (4-carbamoylphenyl)amino | trans-4-aminocyclohexylamino | 366 |
| I(155) | $N^6$-(trans-4-aminocyclohexyl)-$N^8$-(4-(aminomethyl)phenyl)imidazo[1,2-b]pyridazine-6,8-diamine | H | H | H | (4-(aminomethyl)phenyl)amino | trans-4-aminocyclohexylamino | 352 |
| I(156) | 6-((6-((trans-4-aminocyclohexyl)amino)imidazo[1,2-b]pyridazin-8-yl)amino)-1,2-dihydro-3H-indazol-3-one | H | H | H | (3-oxo-2,3-dihydro-1H-indazol-6-yl)amino | trans-4-aminocyclohexylamino | 379 |
| I(157) | $N^6$-(trans-4-aminocyclohexyl)-$N^8$-(3-(aminomethyl)phenyl)imidazo[1,2-b]pyridazine-6,8-diamine | H | H | H | (3-(aminomethyl)phenyl)amino | trans-4-aminocyclohexylamino | 352 |
| I(158) | $N^6$-(4-Aminocyclohexyl)-$N^8$-phenylimidazo[1,2-b]pyridazine-6,8-diamine(3:1 cis:trans mixture) | H | H | H | phenylamino | 4-aminocyclohexylamino | 323 |
| I(159) | $N^6$-(trans-4-Aminocyclohexyl)-$N^8$-2-quinolinylimidazo[1,2-b]pyridazine-6,8-diamine | H | H | H | quinolin-2-ylamino | trans-4-aminocyclohexylamino | 374 |
| I(160) | $N^6$-(trans-4-Aminocyclohexyl)-$N^8$-1-isoquinolinylimidazo[1,2-b]pyridazine-6,8-diamine | H | H | H | isoquinolin-1-ylamino | trans-4-aminocyclohexylamino | 374 |

Example II(1)

$N^6$-(trans-4-aminocyclohexyl)-$N^8$-(2,6-difluorophenyl)imidazo[1,2-b]pyridazine-6,8-diamine

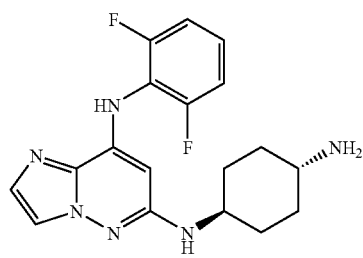

(1a) To 60% NaH (22.5 mg, 0.563 mmol) in DMF (400 µl) was added 2,6-difluoroaniline (24 mg, 0.186 mmol). After stirring at RT for 5 minutes THF (1000 µl) was added followed by 8-bromo-6-chloroimidazo[1,2-b]pyridazine (50 mg, 0.186 mmol, prepared as described in Example 1, step (1b). The reaction was heated at 50° C. for 3 hours. The reaction was quenched with a few drops of water and methanol. The solution was then concentrated in vacuo to give crude 6-chloro-N-(2,6-difluorophenyl)imidazo[1,2-b]pyridazin-8-amine.

(1b) To crude 6-chloro-N-(2,6-difluorophenyl)imidazo[1,2-b]pyridazin-8-amine (0.186 mmol) from 1a was added trans-1,4-diaminocyclohexane (1000 mg, 8.77 mmol). The mixture was allowed to melt at 160° C. for 24 hrs. The melt was then cooled, water was added, followed by extraction with dichloromethane. The organic layer was then concentrated in vacuo and the resulting residue purified by reverse phase preparative HPLC to provide 50.6 mg (46%) of the titled compound as a TFA salt. LC/MS, m/e 359 (M+1). HPLC Rt, 1.7 min. YMC ODSC18 column (4.6×50 mm). 0%-100% B. Solvent B: (90% MeOH, 10% H$_2$O, 0.1% TFA). Solvent A: (10% MeOH, 90% H$_2$O, 0.1% TFA). Gradient, start % B=0, final % B=100, gradient time 4 min, hold at 100% B 1 min, flow rate 4 mL/min. Examples prepared in a similar manner are indicated in Table 2.

Compounds having the formula (Ia) were prepared according to procedures similar to Example II(1), where in $R_1$, $R_2$, $R_3$, X and Y have the values listed in Table 2, using the appropriate starting materials and substantially the same procedures as indicated.

TABLE 2

| Exp | Name | $R_1$ | $R_2$ | $R_3$ | X | Y | LC/MS m/z (M + 1) |
|---|---|---|---|---|---|---|---|
| II(2) | N$^6$-(trans-4-aminocyclohexyl)-7-chloro-N$^8$-[4-(ethyloxy)phenyl]imidazo[1,2-b]pyridazine-6,8-diamine | H | H | H | 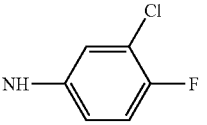 | 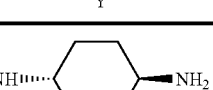 | 375 |
| II(3) | N$^6$-(3-aminopropyl)-N$^8$-[4-(ethyloxy)phenyl]imidazol[1,2-b]pyridazine-6,8-diamine | H | H | H | 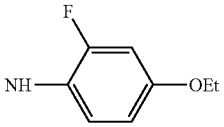 | 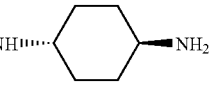 | 385 |
| II(4) | N$^6$-(trans-4-aminocyclohexyl)-N$^8$-(2-fluorophenyl)imidazo[1,2-b]pyridazine-6,8-diamine | H | H | H | 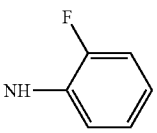 | 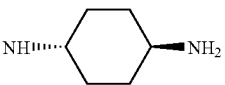 | 341 |
| II(6) | N$^6$-(trans-4-aminocyclohexyl)-N$^8$-(2,4-difluorophenyl)imidazo[1,2-b]pyridazine-6,8-diamine | H | H | H | 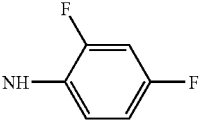 | 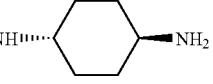 | 359 |
| II(7) | N$^6$-(trans-4-aminocyclohexyl)-N$^8$-(3-fluorophenyl)imidazo[1,2-b]pyridazine-6,8-diamine | H | H | H | 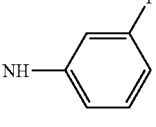 | 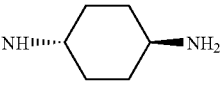 | 341 |
| II(8) | N$^6$-(trans-4-aminocyclohexyl)-N$^8$-(4-fluorophenyl)imidazo[1,2-b]pyridazine-6,8-diamine | H | H | H | 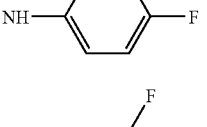 | 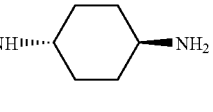 | 341 |
| II(9) | N$^6$-(trans-4-aminocyclohexyl)-N$^8$-(3,4-difluorophenyl)imidazo[1,2-b]pyridazine-6,8-diamine | H | H | H | 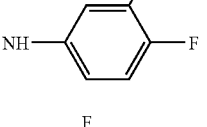 | 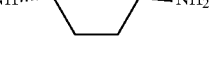 | 359 |
| II(10) | N$^6$-(trans-4-aminocyclohexyl)-N$^8$-(2,5-difluorophenyl)imidazo[1,2-b]pyridazine-6,8-diamine | H | H | H | 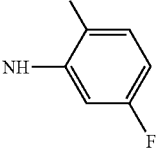 | 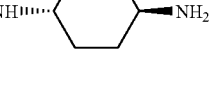 | 359 |
| II(11) | N$^6$-(trans-4-aminocyclohexyl)-N$^8$-(2,3-difluorophenyl)imidazo[1,2-b]pyridazine-6,8-diamine | H | H | H | 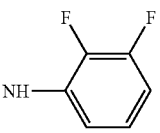 | 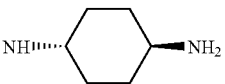 | 359 |

TABLE 2-continued

| Exp | Name | R₁ | R₂ | R₃ | X | Y | LC/MS m/z (M + 1) |
|---|---|---|---|---|---|---|---|
| II(12) | N⁶-(trans-4-aminocyclohexyl)-N⁸-(3,5-difluorophenyl)imidazo[1,2-b]pyridazine-6,8-diamine | H | H | H | NH—(3,5-difluorophenyl) | NH''''—cyclohexyl—NH₂ | 359 |
| II(13) | N⁶-(trans-4-aminocyclohexyl)-N⁸-(3-iodophenyl)imidazo[1,2-b]pyridazine-6,8-diamine | H | H | H | NH—(3-iodophenyl) | NH''''—cyclohexyl—NH₂ | 449 |
| II(14) | N⁶-(trans-4-aminocyclohexyl)-N⁸-[4-(trifluoromethyl)phenyl]imidazo[1,2-b]pyridazine-6,8-diamine | H | H | H | NH—phenyl—CF₃ | NH''''—cyclohexyl—NH₂ | 391 |
| II(15) | N⁶-(trans-4-aminocyclohexyl)-N⁸-pyridin-2-ylimidazo[1,2-b]pyridazine-6,8-diamine | H | H | H | NH—pyridin-2-yl | NH''''—cyclohexyl—NH₂ | 324 |
| II(16) | N⁶-(trans-4-aminocyclohexyl)-N⁸-(4-methylpyridin-2-yl)imidazo[1,2-b]pyridazine-6,8-diamine | H | H | H | NH—(4-methylpyridin-2-yl) | NH''''—cyclohexyl—NH₂ | 338 |
| II(17) | N⁶-(trans-4-aminocyclohexyl)-N⁸-(5-methylpyridin-2-yl)imidazo[1,2-b]pyridazine-6,8-diamine | H | H | H | NH—(5-methylpyridin-2-yl) | NH''''—cyclohexyl—NH₂ | 338 |
| II(18) | N⁶-(trans-4-aminocyclohexyl)-N⁸-(4,6-dimethylpyridin-2-yl)imidazo[1,2-b]pyridazine-6,8-diamine | H | H | H | NH—(4,6-dimethylpyridin-2-yl) | NH''''—cyclohexyl—NH₂ | 352 |
| II(19) | N⁶-(trans-4-aminocyclohexyl)-N⁸-pyrimidin-2-ylimidazo[1,2-b]pyridazine-6,8-diamine | H | H | H | NH—pyrimidin-2-yl | NH''''—cyclohexyl—NH₂ | 325 |

Example III(1)

N⁶-(trans-4-aminocyclohexyl)-N⁸-[4-(ethyloxy)phenyl]-7-methylimidazo[1,2-b]pyridazine-6,8-diamine

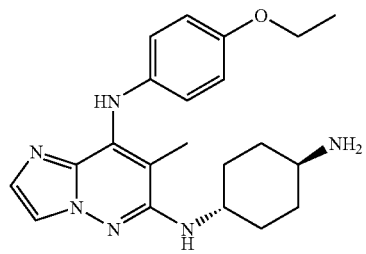

(1a) 3,6-Dichloro-4-methylpyridizine (4.2 g, 26 mmol, Alfa) was suspended in aqueous 28% NH₄OH (14 mL) in a sealed microwave tube and heated at 155° C. for 1.5 h. The microwave tube was uncapped and allowed to stir at room temperature for 30 min and in an ice bath for 30 min. The solid that crashed out was filtered, washed with ice water, and dried to give a mixture of 6-chloro-5-methylpyridazin-3-amine and 3-chloro-5-methylpyridazin-6-amine (3.4 g, 91%).

(1b) The mixture of 6-chloro-5-methylpyridazin-3-amine and 3-chloro-5-methylpyridazin-6-amine (1.45 g, 10 mmol) from 1a and NaHCO₃ (2.1 g, 25 mmol) were suspended in MeOH (20 mL) and treated with Br₂ (0.57 mL, 11 mmol). The mixture was stirred at room temperature for 4 h, then filtered. The filtrate was condensed in vacuo. The resulting residue was resuspended in EtOAc (100 mL) and washed sequentially with sat. aqueous NaHCO₃ solution (2×20 mL) and aqueous NaCl solution (1×20 mL). The solution was dried over MgSO₄. The solvent was removed in vacuo to give crude 4-bromo-6-chloro-5-methylpyridazin-3-amine (1 g).

(1c) Chloroacetaldehyde (1.6 ml, 10 mmol, 50% in H₂O) was added to a solution of crude 4-bromo-6-chloro-5-methylpyridazin-3-amine (0.5 g, 2 mmol) from 1b in EtOH (5 mL). The mixture was heated in a sealed vial at 110° C. for 2 h. Solvent was removed in vacuo and the resulting solid was suspended in acetone/Et₂O (1/1, 5 mL), filtered, and then washed with Et₂O to give 8-bromo-6-chloro-7-methylimidazo[1,2-b]pyridazine HCl salt (0.5 g, >90% pure).

(1d variation 1) A mixture of 8-bromo-6-chloro-7-methylimidazo[1,2-b]pyridazine HCl salt (30 mg, 0.1 mmol) from 1c, p-methoxyaniline (20 μL, 0.15 mmol) and K₂CO₃ (75 mg) were suspended in NMP (600 μL) and heated in a microwave at 225° C. for 15 min. The mixture was cooled to room temperature and then treated with H₂O (5 mL). The solid that precipitated out was filtered, washed with water and dried to provide 6-chloro-N-(4-ethoxyphenyl)-7-methylimidazo[1,2-b]pyridazin-8-amine (21 mg, >90% pure by HPLC).

(1d variation 2) To a mixture of bromo-6-chloro-7-methylimidazo[1,2-b]pyridazine HCl salt (102 mg, 0.36 mmol) from 1c, in THF (1.5 ml) was added p-Phenetidine (49 mg, 0.36 mmol) and a 1.0 M solution of KOt-Bu in THF (3.0 eq, 1.08 ml, 1.08 mmol). The mixture was allowed to heat at 50 C for 1 hour. The solution was then concentrated in vacuo to dryness to provide 6-chloro-N-(4-ethoxyphenyl)-7-methylimidazo[1,2-b]pyridazin-8-amine as a solid. m/e 303 (MH+).

(1e) 6-chloro-N-(4-ethoxyphenyl)-7-methylimidazo[1,2-b]pyridazin-8-amine (20 mg, 0.067 mmol) from 1d and trans-1,4-diaminocyclohexane (150 mg) were combined and heated at 165° C. for 70 h. The mixture was cooled to room temperature, then diluted with water (10 mL) and extracted with EtOAc (4×5 mL). The organic layers were combined and concentrated in vacuo. The resulting residue was purified using preparative HPLC to give the above titled compound as a TFA salt (4.5 mg, 11%). ¹H NMR (400 MHz, CD₃OD) δ 7.97 (d, J=2.4 Hz, 1H), 7.67 (d, J=2.4 Hz, 1H), 6.90 (m, 4H), 4.05 (q, 2H, J=7.2 Hz), 4.00 (m, 1H), 3.20 (m, 1H), 2.30 (m, 2H), 2.20 (m, 2H), 2.15 (s, 3H), 1.60 (m, 4H), 1.40 (t, J=7.2 Hz, 3H). LC/MS, m/e 381 (M+1). HPLC Rt, 2.1 min. YMC ODSC18 column (4.6×50 mm). 0%-100% B. Solvent B: (90% MeOH, 10% H₂O, 0.1% TFA). Solvent A: (10% MeOH, 90% H₂O, 0.1% TFA). Gradient, start % B=0, final % B=100, gradient time 4 min, hold at 100% B 1 min, flow rate 4 mL/min.

Compounds having the formula (Ia) were prepared according to procedures similar to Example III(1), where in R₁, R₂, R₃, X and Y have the values listed in Table 3, using the appropriate starting materials and substantially the same procedures as indicated.

TABLE 3

| Exp | Name | R₁ | R₂ | R₃ | X | Y | LC/MS m/z (M + 1) |
|---|---|---|---|---|---|---|---|
| III(2) | N⁶-(trans-4-aminocyclohexyl)-7-ethyl-N⁸-[4-(ethyloxy)phenyl]imidazo[1,2-b]pyridazine-6,8-diamine | H | H | Et | NH—C₆H₄—OEt | NH‴—C₆H₁₀—NH₂ | 395 |
| III(3) | N⁶-(trans-4-aminocyclohexyl)-7-methyl-N⁸-phenylimidazo[1,2-b]pyridazine-6,8-diamine | H | H | Me | NH—C₆H₅ | NH‴—C₆H₁₀—NH₂ | 337 |
| III(4) | N⁶-(trans-4-aminocyclohexyl)-N⁸-(3,4-dimethylphenyl)-7-methylimidazo[1,2-b]pyridazine-6,8-diamine | H | H | Me | NH—C₆H₃(CH₃)₂ | NH‴—C₆H₁₀—NH₂ | 365 |
| III(5) | N⁶-(trans-4-aminocyclohexyl)-7-methyl-N⁸-(4-methylphenyl)imidazo[1,2-b]pyridazine-6,8-diamine | H | H | Me | NH—C₆H₄—CH₃ | NH‴—C₆H₁₀—NH₂ | 351 |
| III(6) | N⁶-(trans-4-aminocyclohexyl)-7-methyl-N⁸-[3-(methyloxy)phenyl]imidazo[1,2-b]pyridazine-6,8-diamine | H | H | Me | NH—C₆H₄—OMe | NH‴—C₆H₁₀—NH₂ | 367 |
| III(7) | N⁶-(trans-4-aminocyclohexyl)-N⁸-biphenyl-4-yl-7-methylimidazo[1,2-b]pyridazine-6,8-diamine | H | H | Me | NH—C₆H₄—C₆H₅ | NH‴—C₆H₁₀—NH₂ | 413 |
| III(8) | N⁶-(trans-4-aminocyclohexyl)-7-methyl-N⁸-[4-(propyloxy)phenyl]imidazo[1,2-b]pyridazine-6,8-diamine | H | H | Me | NH—C₆H₄—O—C₃H₇ | NH‴—C₆H₁₀—NH₂ | 395 |

TABLE 3-continued

| Exp | Name | R₁ | R₂ | R₃ | X | Y | LC/MS m/z (M + 1) |
|---|---|---|---|---|---|---|---|
| III(9) | 4-((6-((trans-4-aminocyclohexyl)amino)-7-methylimidazo[1,2-b]pyridazin-8-yl)amino)benzoic acid | H | H | Me | HN-C₆H₄-COOH | NH-cyclohexyl-NH₂ (trans) | 381 |
| III(10) | 4-((6-((4-aminocyclohexyl)amino)-7-methylimidazo[1,2-b]pyridazin-8-yl)amino)-N,N-dimethylbenzenesulfonamide | H | H | Me | HN-C₆H₄-SO₂N(CH₃)₂ | NH-cyclohexyl-NH₂ (trans) | 444 |
| III(11)1 | N-(4-((6-((trans-4-aminocyclohexyl)amino)-7-methylimidazo[1,2-b]pyridazin-8-yl)amino)phenyl)-N-methylacetamide | H | H | Me | NH-C₆H₄-N(CH₃)C(O)CH₃ | NH-cyclohexyl-NH₂ (trans) | 408 |
| III(12) | $N^6$-(trans-4-aminocyclohexyl)-7-ethyl-$N^8$-phenylimidazo[1,2-b]pyridazine-6,8-diamine[6] | H | H | Et | NH-C₆H₅ | NH-cyclohexyl-NH₂ (trans) | 351 |
| III(13) | $N^6$-(4-Aminocyclohexyl)-7-methyl-$N^8$-phenylimidazo[1,2-b]pyridazine-6,8-diamine (3:1 cis:trans mixture) | H | H | Me | NH-C₆H₅ | NH-cyclohexyl-NH₂ | 337 |
| III(14) | $N^6$-(trans-4-Aminocyclohexyl)-7-methyl-$N^8$-(4-phenoxyphenyl)imidazo[1,2-b]pyridazine-6,8-diamine | H | H | Me | NH-C₆H₄-O-C₆H₅ | NH-cyclohexyl-NH₂ (trans) | 429 |
| III(15) | $N^6$-(trans-4-Aminocyclohexyl)-7-methyl-$N^8$-(4-(1-piperidinylcarbonyl)phenyl)imidazo[1,2-b]pyridazine-6,8-diamine | H | H | Me | NH-C₆H₄-C(O)-piperidinyl | NH-cyclohexyl-NH₂ (trans) | 448 |
| III(16) | 4-((6-((trans-4-Aminocyclohexyl)amino)-7-methylimidazo[1,2-b]pyridazin-8-yl)amino)-2-hydroxy-N,N-dimethylbenzenesulfonamide | H | H | Me | HN-C₆H₃(OH)-SO₂N(CH₃)₂ | NH-cyclohexyl-NH₂ (trans) | 460 |
| III(17) | $N^6$-(trans-4-Aminocyclohexyl)-7-methyl-$N^8$-(4-(5-phenyl-1,3,4-oxadiazol-2-yl)phenyl)imidazo[1,2-b]pyridazine-6,8-diamine | H | H | Me | NH-C₆H₄-(1,3,4-oxadiazol-2-yl)-C₆H₅ | NH-cyclohexyl-NH₂ (trans) | 481 |
| III(18) | $N^6$-(trans-4-Aminocyclohexyl)-7-methyl-$N^8$-(4-(4-morpholinylcarbonyl)phenyl)imidazo[1,2-b]pyridazine-6,8-diamine | H | H | Me | NH-C₆H₄-C(O)-morpholinyl | NH-cyclohexyl-NH₂ (trans) | 450 |
| III(19) | 4-((6-((trans-4-Aminocyclohexyl)amino)-7-methylimidazo[1,2-b]pyridazin-8-yl)amino)-N-phenylbenzamide | H | H | Me | NH-C₆H₄-C(O)NH-C₆H₅ | NH-cyclohexyl-NH₂ (trans) | 456 |

TABLE 3-continued

| Exp | Name | R₁ | R₂ | R₃ | X | Y | LC/MS m/z (M + 1) |
|---|---|---|---|---|---|---|---|
| III(20) | $N^6$-(trans-4-Aminocyclohexyl)-7-methyl-$N^8$-(2-methyl-1,3-benxothiazol-6-yl)imidazo[1,2-b]pyridazine-6,8-diamine | H | H | Me | 2-methylbenzothiazol-6-ylamino | trans-4-aminocyclohexylamino | 408 |
| III(21) | $N^6$-(trans-4-Aminocyclohexyl)-7-methyl-$N^8$-(2-methyl-1H-indol-5-yl)imidazo[1,2-b]pyridazine-6,8-diamine | H | H | Me | 2-methyl-1H-indol-5-ylamino | trans-4-aminocyclohexylamino | 390 |
| III(22) | 4-((6-((trans-4-Aminocyclohexyl)amino)-7-methylimidazo[1,2-b]pyridazin-8-yl)amino)-N-methylbenzenesulfonamide | H | H | Me | 4-(N-methylsulfamoyl)phenylamino | trans-4-aminocyclohexylamino | 430 |
| III(23) | 4-((6-((trans-4-Aminocyclohexyl)amino)-7-methylimidazo[1,2-b]pyridazin-8-yl)amino)-N-cyclohexylbenzamide | H | H | Me | 4-(cyclohexylcarbamoyl)phenylamino | trans-4-aminocyclohexylamino | 462 |
| III(24) | $N^6$-(trans-4-aminocyclohexyl)-7-methyl-$N^8$-(2-methylphenyl)imidazo[1,2-b]pyridazine-6,8-diamine | H | H | Me | 2-methylphenylamino | trans-4-aminocyclohexylamino | 351 |
| III(25) | $N^6$-(trans-4-aminocyclohexyl)-$N^8$-(2-fluorophenyl)-7-methylimidazo[1,2-b]pyridazine-6,8-diamine | H | H | Me | 2-fluorophenylamino | trans-4-aminocyclohexylamino | 355 |

*For substituents X and Y, substitution on the core (formula Ia) occurs at the available nitrogen atom Example IV(1)

$N^6$-(trans-4-aminocyclohexyl)-7-chloro-$N^8$-[4-(ethyloxy)phenyl]imidazo[1,2-b]pyridazine-6,8-diamine

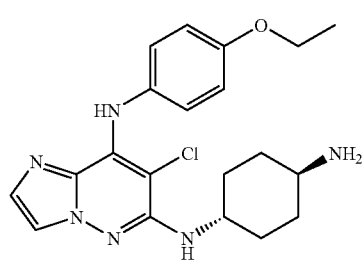

(1a) 3-Hydroxy-4,5-dichloropyridizine (5.34 g, 32.5 mmol) was added to a stirred solution of fuming $H_2SO_4$ (14.0 mL, 273 mmol) and conc. $H_2SO_4$ (7.3 mL, 137 mmol). $KNO_3$ (9.0 g, 88 mmol) was subsequently added slowly at room temperature. The reaction mixture was heated to 90° C. and the temperature was maintained at 90° C. for 18 hrs. The solution was cooled and poured over ice water. After stirring for one hour, the solid suspension was filtered to give 3-hydroxy-4,5-dichloro-6-nitropyridizine as a white solid (4.2 g, 62%).

(1b) $Na_2S_2O_4$ (0.65 g, 3.6 mmol) was added to a stirred solution of 3-hydroxy-4,5-dichloro-6-nitropyridizine (0.26 g, 1.2 mmol) from 1a in THF (4.0 mL, 0.3 M) and $H_2O$ (4.0 mL, 0.3 M). The reaction mixture was warmed to reflux, after 1 hr ethyl acetate was added. The layers were allowed to separate and the organic layer was washed with $H_2O$ (10 mL), followed by brine (10 mL). The organic layer was dried over $Na_2SO_4$ and then concentrated in vacuo. The resulting residue was triturated with diethyl ether and filtered to give 3-hydroxy-4,5-dichloro-6-aminopyridizine as a white solid (0.165 g, 67%).

(1c) Chloroacetaldehyde (0.57 ml, 4.6 mmol, 50% in $H_2O$) was added to a solution of 3-hydroxy-4,5-dichloro-6-aminopyridizine (0.165 g, 0.92 mmol) from 1b in EtOH (1.3 mL, 0.7 M). The reaction was heated in a sealed vial at 150° C. for 15 minutes in the microwave. The solvent was removed in vacuo and the solid was re-suspended in diethyl ether (10 mL), filtered and rinsed with diethyl ether to give 6-hydroxy-7,8-dichloroimidazo[1,2-b]pyridazine as an HCl salt (0.3 g, 60%).

(1d) 6-Hydroxy-7,8-dichloroimidazo[1,2-b]pyridazine (0.1 g, 0.5 mmol) from 1c was added to POCl$_3$ (0.4 mL, 1.4 M) in a 1 dram vial. The mixture was heated to 120° C. for 2 days. Upon cooling CH$_2$Cl$_2$ was added and the mixture was poured onto ice water. The layers were separated and the aqueous layer was extracted with CH$_2$Cl$_2$ (15 mL). The organic layers were combined and washed with H$_2$O (5 mL), followed by brine (5 mL). The solution was dried over Na$_2$SO$_4$ and concentrated in vacuo to give 6,7,8-trichloroimidazo[1,2-b]pyridazine as a tan solid (0.04 g, 37%).

(1e) A mixture of 6,7,8-trichloroimidazo[1,2-b]pyridazine (0.04 g, 0.18 mmol) from 1d, p-ethoxyaniline (0.025 g, 0.18 mmol) and triethylamine (0.055 mL, 0.4 mmol) were suspended in EtOH (1.0 mL) and heated to 90° C. for 2.5 hours. The reaction mixture was then cooled to room temperature and concentrated in vacuo to provide crude 6,7-dichloro-N-(4-ethoxyphenyl)imidazo[1,2-b]pyridazin-8-amine (0.05 g, 86%).

(1f) Crude 6,7-dichloro-N-(4-ethoxyphenyl)imidazo[1,2-b]pyridazin-8-amine (0.03 g, 0.09 mmol) from 1e was mixed with trans-1,4-diaminocyclohexane (0.07 g, 0.6 mmol). The resulting mixture was heated to 120° C. for 1.5 days. Upon cooling, CH$_2$Cl$_2$ (10 mL) and H$_2$O (10 mL) were added and the layers separated. The organic layer was washed with brine (5 mL), dried over Na$_2$SO$_4$, and concentrated in vacuo. The resulting oil was purified by preparative HPLC to give the above titled compound as a TFA salt (0.010 g, 29%); $^1$H NMR (MeOH) δ 8.00 (s, 1H), 7.70 (s, 1H), 7.13 (d, J=8.8 Hz, 2H), 6.98 (d, J=8.8 Hz, 2H), 4.09 (q, J=7.0 Hz, 2H), 4.00-3.90 (m, 1H), 3.24-3.15 (m, 1H), 2.30-2.23 (m, 2H), 2.20-2.10 (m, 2H), 1.65 1.57 (m, 4H), 1.50 (t, 3H). LC/MS, m/e 402 (M+1). HPLC Rt, 1.95 min. YMC ODSC18 column (4.6×100 mm). 20%-100% B. Solvent B: (90% MeOH, 10% H$_2$O, 0.1% TFA). Solvent A: (10% MeOH, 90% H$_2$O, 0.1% TFA). Gradient, start % B=20, final % B=100, gradient time 10 min, hold at 100% B, 2 min, flow rate 4 mL/min.

Example V(1)

N$^8$-[4-(ethyloxy)phenyl]-N$^6$-piperidin-3-ylimidazo[1,2-b]pyridazine-6,8-diamine

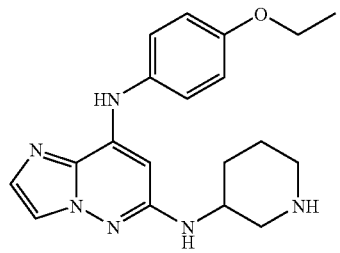

To a mixture of a N-(1-benzylpiperidin-3-yl)-N$^8$-(4-ethoxyphenyl)imidazo[1,2-b]pyridazine-6,8-diamine TFA salt (14 mg, 0.021 mmol), prepared by the method of example I(1) using 1-benzylpiperidin-3-amine in place of trans-1,4-diaminocyclohexane in step (1d), and MeOH (5 mL) in a 500 ml PARR bottle was added 10% Pd/C (20 mg) and 3 drops of glacial acetic acid. The PARR bottle was then charged with H$_2$ at 55 psi and allow to shake at room temperature for hours. The reaction mixture was then filtered and the filtrate concentrated in vacuo. The residue was purified by preparative HPLC followed by neutralization with ion exchange resin to furnish 0.5 mg (7%) of the title compound $^1$H NMR (500 MHz, MeOH) δ ppm 7.57 (1H, s), 7.31 (1H, s), 7.24 (2H, d, J=8.7 Hz), 6.97 (2H, d, J=8.7 Hz), 5.89 (1H, s), 4.05 (2H, q, J=6.9 Hz), 3.85 (1H, m), 3.45 (1H, m), 3.10 (1H, m), 2.85 (1H, m), 2.75 (1H, m), 2.05 (1H, m), 1.90 (1H, m), 1.70 (1H, m), 1.55 (1H, m), 1.39 (3H, t, J=6.9 Hz), LC/MS, m/e 353 (M+1). HPLC Rt, 2.04 min. YMC ODSC18 column (4.6×50 mm). 0%-100% B. Solvent B: (90% MeOH, 10% H$_2$O, 0.1% TFA). Solvent A: (10% MeOH, 90% H$_2$O, 0.1% TFA). Gradient, start % B=0, final % B=100, gradient time 4 min, hold at 100% B 1 min, flow rate 4 mL/min.

Compounds having the formula (Ia) were prepared according to procedures similar to Example V(1), where in R$_1$, R$_2$, R$_3$, X and Y have the values listed in Table 4, using the appropriate starting materials and substantially the same procedures as indicated.

TABLE 4

| Exp | Name | R$_1$ | R$_2$ | R$_3$ | X | Y | LC/MS m/z (M + 1) |
|---|---|---|---|---|---|---|---|
| V(2) | N$^8$-[4-(ethyloxy)phenyl]-N$^6$-pyrrolidin-3-ylimidazo[1,2-b]pyridazine-6,8-diamine | H | H | H | NH—⟨phenyl⟩—OEt | NH—⟨pyrrolidine⟩—NH | 339 |
| V(3) | N$^8$-[4-(ethyloxy)phenyl]-N$^6$-piperidin-4-ylimidazo[1,2-b]pyridazine-6,8-diamine | H | H | H | NH—⟨phenyl⟩—OEt | HN—⟨piperidine⟩—NH | 353 |

TABLE 4-continued

| Exp | Name | $R_1$ | $R_2$ | $R_3$ | X | Y | LC/MS m/z (M + 1) |
|---|---|---|---|---|---|---|---|
| V(4) | 6-(3-amino-1-piperidinyl)-N-(4-(ethyloxy)phenyl)imidazo[1,2-b]pyridazin-8-amine | H | H | H | NH—C₆H₄—OEt | 3-amino-1-piperidinyl | 323 |
| V(5) | $N^8$-[4-(ethyloxy)phenyl]-7-methyl-$N^6$-3-piperidinylimidazo[1,2-b]pyridazine-6,8-diamine | H | H | Me | NH—C₆H₄—OEt | 3-piperidinylamino | 367 |
| V(6) | $N^8$-phenyl-$N^6$-3-piperidinylimidazo[1,2-b]pyridazine-6,8-diamine | H | H | H | NH—Ph | 3-piperidinylamino | 309 |
| V(7) | $N^8$-Phenyl-$N^6$-((3S)-3-piperidinyl)imidazo[1,2-b]pyridazine-6,8-diamine | H | H | H | NH—Ph | (3S)-3-piperidinylamino | 309 |
| V(8) | $N^8$-(4-Phenoxyphenyl)-$N^6$-((3S)-3-piperidinyl)imidazo[1,2-b]pyridazine-6,8-diamine | H | H | H | NH—C₆H₄—O—Ph | (3S)-3-piperidinylamino | 401 |
| V(9) | 7-Methyl-$N^8$-phenyl-$N^6$-((3S)-3-piperidinyl)imidazo[1,2-b]pyridazine-6,8-diamine | H | H | Me | NH—Ph | (3S)-3-piperidinylamino | 323 |
| V(10) | $N^8$-(4-(4-Morpholinylcarbonyl)phenyl)-$N^6$-((3S)-3-piperidinyl)imidazo[1,2-b]pyridazine-6,8-diamine | H | H | H | NH—C₆H₄—C(O)—morpholine | (3S)-3-piperidinylamino | 422 |
| V(11) | 3-((6-((3S)-3-Piperidinylamino)imidazo[1,2-b]pyridazin-8-yl)amino)phenol | H | H | H | NH—C₆H₄—OH | (3S)-3-piperidinylamino | 325 |
| V(12) | N-Cyclohexyl-4-((6-((3S)-3-piperidinylamino)imidazo[1,2-b]pyridazin-8-yl)amino)benzamide | H | H | H | NH—C₆H₄—C(O)NH—cyclohexyl | (3S)-3-piperidinylamino | 434 |
| V(13) | $N^8$-1-Naphthyl-$N^6$-((3S)-3-piperidinyl)imidazo[12-b]pyridazine-6,8-diamine | H | H | H | NH—1-naphthyl | (3S)-3-piperidinylamino | 359 |
| V(14) | $N^8$-(5-Methyl-2-pyridinyl)-$N^6$-((3S)-3-piperidinyl)imidazo[1,2-b]pyridazine-6,8-diamine | H | H | H | NH—(5-methyl-2-pyridinyl) | (3S)-3-piperidinylamino | 324 |

TABLE 4-continued

| Exp | Name | $R_1$ | $R_2$ | $R_3$ | X | Y | LC/MS m/z (M + 1) |
|---|---|---|---|---|---|---|---|
| V(15) | $N^6$-((3S)-3-Piperidinyl)-$N^8$-(4-(1-pyrrolidinylcarbonyl)phenyl)imidazo[1,2-b]pyridazine-6,8-diamine | H | H | H | 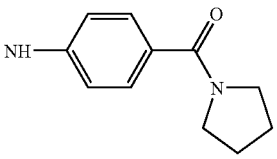 | 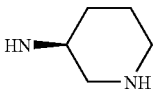 | 406 |
| V(16) | N-Methyl-4-((6-((3S)-3-piperidinylamino)imidazo[1,2-b]pyridazin-8-yl)amino)benzenesulfonamide | H | H | H | 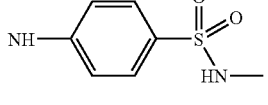 | 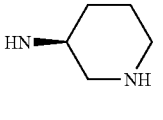 | 402 |
| V(17) | $N^6$-((3S)-3-Piperidinyl)-$N^8$-(4-(trifluoromethyl)phenyl)imidazo[1,2-b]pyridazine-6,8-diamine | H | H | H | 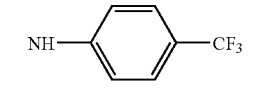 | 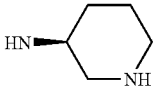 | 377 |
| V(18) | N,N-Diethyl-4-((6-((3S)-3-piperidinylamino)imidazo[1,2-b]pyridazin-8-yl)amino)benzamide | H | H | H | 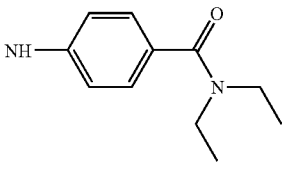 | 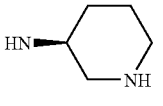 | 408 |
| V(19) | $N^8$-(4-Ethoxyphenyl)-$N^6$-((3S)-3-piperidinyl)imidazo[1,2-b]pyridazine-6,8-diamine | H | H | H | 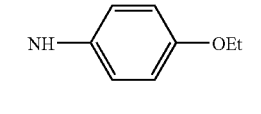 | 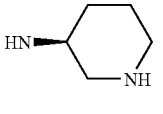 | 353 |
| V(20) | $N^8$-(2-Methyl-1,3-benzothiazol-6-yl)-$N^6$-((3S)-3-piperidinyl)imidazo[1,2-b]pyridazine-6,8-diamine | H | H | H | 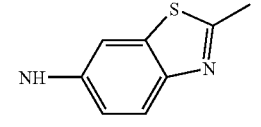 | 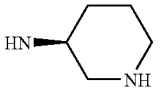 | 380 |
| V(21) | 4-((6-((3S)-3-Piperidinylamino)imidazo[1,2-b]pyridazin-8-yl)amino)-N-propylbenzenesulfonamide | H | H | H | 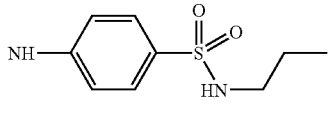 | 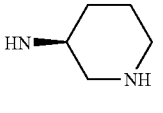 | 430 |
| V(22) | $N^8$-(4-Ethoxyphenyl)-7-methyl-$N^6$-((3S)-3-piperidinyl)imidazo[1,2-b]pyridazine-6,8-diamine | H | H | Me | 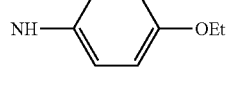 | 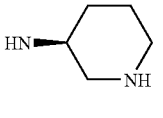 | 367 |
| V(23) | 7-Ethyl-$N^8$-phenyl-$N^6$-((3S)-3-piperidinyl)imidazo[1,2-b]pyridazine-6,8-diamine | H | H | Et | 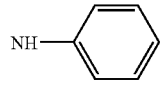 | 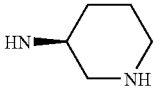 | 337 |
| V(24) | 7-Isopropyl-$N^8$-phenyl-$N^6$-((3S)-3-piperidinyl)imidazo[1,2-b]pyridazine-6,8-diamine | H | H | i-Pr | 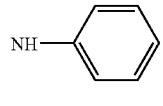 | 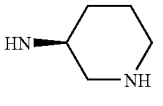 | 351 |

*For substituents X and Y, substitution on the core (formula Ia) occurs at the available nitrogen atom

Example VI(1)

6-[(3S)-3-aminopyrrolidin-1-yl]-N-[4-(ethyloxy)phenyl]imidazo[1,2-b]pyridazin-8-amine

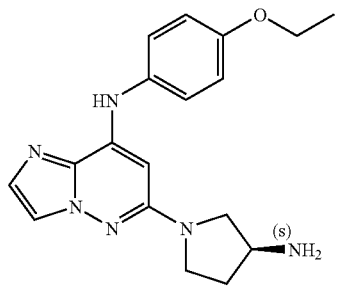

To 6-chloro-N-(4-ethoxyphenyl)imidazo[1,2-b]pyridazin-8-amine (26 mg, 0.090 mmol), prepared as described in example 1, step (1c) was added (S)-3-amino-1-N-boc-pyrrolidine (180 mg, 0.96 mmol). The mixture was microwaved at 225° C. for one hour. The melt was then cooled, water was added followed by extraction with dichloromethane. The organic layer was then concentrated in vacuo and purified by preparative HPLC to give 0.9 mg (2%) of the title compound as a TFA salt, (Note that during the reaction the Boc cleaves and the 1-nitrogen of the pyrrolidine adds). $^1$H NMR (500 MHz, MeOH) δ ppm 7.99 (1H, s), 7.88 (1H, s), 7.31 (2H, d, J=7.7 Hz), 7.03 (2H, d, J=7.7 Hz), 6.18 (1H, s), 4.07 (2H, q, J=6.9 Hz), 4.0 (1H, m), 3.80 (1H, m), 3.55 (3H, m), 2.50 (1H, m), 2.15 (1H, m), 1.40 (3H, t, J=6.9 Hz). LC/MS, m/e 339 (M+1). HPLC Rt, 1.83 min. YMC ODSC18 column (4.6×50 mm). 0%-100% B. Solvent B: (90% MeOH, 10% H$_2$O, 0.1% TFA). Solvent A: (10% MeOH, 90% H$_2$O, 0.1% TFA). Gradient, start % B=0, final % B=100, gradient time 4 min, hold at 100% B 1 min, flow rate 4 mL/min.

Example VII(1)

$N^2$-(trans-4-aminocyclohexyl)-$N^4$-[4-(ethyloxy)phenyl]pyrazolo[1,5-a][1,3,5]triazine-2,4-diamine

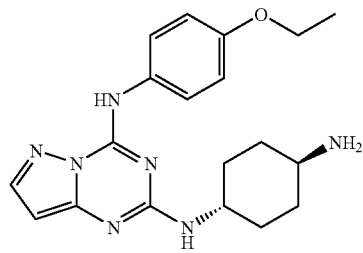

(1a) Ethoxycarbonyl isothiocyanate (3.16 g, 24.07 mmol) was added to 3-aminopyrazole (Aldrich) (2.0 g, 24.07 mmol) in acetone (20 mL). The reaction mixture was stirred at room temperature for 1 hour. Then cold water (100 mL) was added to the reaction mixture. The solid precipitate was collected through filtration, washed with water (50 mL), and then air dried to give 4.64 g (90%) of ethyl 1H-pyrazol-5-ylcarbamothioylcarbamate.

(1b) Ethyl 1H-pyrazol-5-ylcarbamothioylcarbamate (4.64 g, 21.68 mmol) from 1a was added to 2N NaOH solution (51 mL). The reaction mixture was stirred at room temperature for 2½ hours and then acidified with 2NH$_2$SO$_4$. The resulting precipitate was collected by vacuum filtration, washed with water followed by diethyl ether, and then air dried to give 3.32 g (82%) of 2-thioxo-2,3-dihydropyrazolo[1,5-a][1,3,5]triazin-4(1H)-one as a pale yellow solid.

(1c) A 1.75N NaOH solution (39.52 mmol, 22.58 ml) was added to a suspension of 2-thioxo-2,3-dihydropyrazolo[1,5-a][1,3,5]triazin-4(1H)-one (3.32 g, 19.76 mmol) from 1b in absolute EtOH (80 mL). Methyl iodide (2.80 g, 19.76 mmol) was then added and the reaction mixture was allowed to stir for 2 hours at room temperature. The resulting precipitate was collected by vacuum filtration, suspended in water (110 mL) and acidified with 2NH$_2$SO$_4$. The solution was stirred at 0° C. for 5 minutes and the new precipitate was collected by vacuum filtration, washed with cold water, and then air dried to give 1.88 g (52%) of 2-(methylthio)pyrazolo[1,5-a][1,3,5]triazin-4(3H)-one.

(1d) N,N-Dimethylaniline (601 mg, 4.96 mmol) was added to a suspension of 2-(methylthio)pyrazolo[1,5-a][1,3,5]triazin-4(3H)-one (1.88 g, 10.33 mmol) from 1c in POCl$_3$ (29 mL). The reaction mixture was heated to reflux for 7 hours, and then cooled to room temperature, concentrated in vacuo, and diluted with cold water (110 mL). The resulting solid was collected by vacuum filtration, washed with cold water and hexane, and then air dried to give 1.68 g (81%) of 4-chloro-2-(methylthio)pyrazolo[1,5-a][1,3,5]triazine.

(1e) p-Phenetidine (3.09 g, 22.51 mmol) was added to a mixture of 4-chloro-2-(methylthio)pyrazolo[1,5-a][1,3,5]triazine (300 mg, 1.5 mmol) from 1d in 1,4-dioxane (6 mL). The mixture was heated to 100° C. for ½ hour. Water (15 mL) was then added to the reaction mixture and the resulting precipitate was collected by vacuum filtration, washed with cold water and hexane, and then air dried to give 360 mg (80%) of N-(4-ethoxyphenyl)-2-(methylthio)pyrazolo[1,5-a][1,3,5]triazin-4-amine.

(1f) mCPBA (702 mg, 4.06 mmol) was added to N-(4-ethoxyphenyl)-2-(methylthio)pyrazolo[1,5-a][1,3,5]triazin-4-amine (360 mg, 1.19 mmol) from 1e in DMF (10 mL) at room temperature. After 1 hour the reaction mixture was concentrated in vacuo, followed by the addition of saturated sodium bicarbonate. The aqueous solution was then extracted with ethyl acetate and the organic layer was dried to give 250 mg (63%) of N-(4-ethoxyphenyl)-2-(methylsulfonyl)pyrazolo[1,5-a][1,3,5]triazin-4-amine.

(1g) trans-1,4-Diaminocyclohexane (200 mg, 1.75 mmol) was added to N-(4-ethoxyphenyl)-2-(methylsulfonyl)pyrazolo[1,5-a][1,3,5]triazin-4-amine (50 mg, 0.15 mmol) from 1f. The reaction mixture was melted at 100° C. for 1 hour. The melt was then cooled to room temperature. Water was added, followed by extraction with ethyl acetate. The organic layer was then concentrated in vacuo and the residue was purified by preparative HPLC to gave 35.3 mg (20%) of above titled compound as a TFA salt. $^1$H NMR (500 MHz, DMSO) δ ppm 7.90 (3H, m), 7.63 (2H, m), 6.88 (2H, m), 3.98 (2H, m), 3.60 (1H, m), 2.95 (1H, m), 1.92 (4H, m), 1.30 (7H, m). LC/MS, m/e 368 (M+1). HPLC Rt, 2.05 min. YMC ODSC18 column (4.6×50 mm). 0%-100% B. Solvent B: (90% MeOH, 10% H$_2$O, 0.1% TFA). Solvent A: (10% MeOH, 90% H$_2$O, 0.1% TFA). Gradient, start % B=0, final % B=100, gradient time 4 min, hold at 100% B 1 min, flow rate 4 mL/min.

Example XIII(1)

Imidazo[2,1-f][1,2,4]triazine-2,4-diamine, $N^2$-(trans-4-aminocyclohexyl)-$N^4$-(4-ethoxyphenyl)

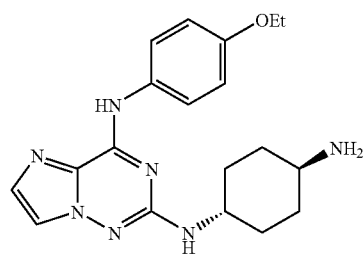

(1a) 2,4-bis(Methylthio)imidazo[1,2-j][1,2,4]triazine (0.077 g, 0.36 mmol), prepared as described in Journal of The Chemical Society, Perkins Transactions 1 1999, 20, 2929, and p-phenetidine (0.75 g, 5.46 mmol) were melted together in a vial at 90° C. for 6 hrs. The mixture was cooled and diluted with HCl (1N). The brown precipitate that formed was filtered and dried under vacuum to provide 0.103 g, (95%) of N-(4-ethoxyphenyl)-2-(methylthio)imidazo[1,2-f][1,2,4]triazin-4-amine.

(1b) A vial was charged with N-(4-ethoxyphenyl)-2-(methylthio)imidazo[1,2-j][1,2,4]triazin-4-amine (0.103 g, 0.34 mmol) from 1a, meta-chloroperbenzoic acid. (0.286 g, 1.16 mmol) and dimethylformamide (5 mL) and stirred at room temperature for 2 hrs. The mixture was quenched with aqueous saturated sodium bicarbonate, extracted with ethyl acetate, concentrated and dried under vacuum to provide 0.105 g, of crude N-(4-ethoxyphenyl)-2-(methylsulfonyl)imidazo[1,2-j][1,2,4]triazin-4-amine.

(1c) A vial was charged with N-(4-ethoxyphenyl)-2-(methylsulfonyl)imidazo[1,2-j][1,2,4]triazin-4-amine (0.105 g, 0.32 mmol) from 1b, trans-1,4-cyclohexyldiamine. (0.54 g, 4.7 mmol) and melted at 100° C. for 6 hrs. The mixture was cooled to room temperature, diluted with methanol, and purified by preparative HPLC to provide 0.006 g (11%) of the titled compound as a TFA salt. $^1$H NMR (500 MHz, CD$_3$OD) δ ppm 7.75 (4H, m), 6.95 (2H, m), 4.03 (2H, m), 3.68 (1H, m), 3.11 (1H, m), 2.22 (2H, m), 2.10 (2H, m), 1.4 (7H, m). LC/MS, m/e 368 (M+1). HPLC Rt, 2.18 min. Waters Sunfire C18 column (4.6×50 mm). 0%-100% B. Solvent B: (90% MeOH, 10% H$_2$O, 0.1% TFA). Solvent A: (10% MeOH, 90% H$_2$O, 0.1% TFA). Gradient, start % B=0, final % B=100, gradient time 4 min, hold at 100% B 1 min, flow rate 4 mL/min.

Example IX(1)

$N^6$-(cis-4-aminocyclohexyl)-$N^8$-[4-(ethyloxy)phenyl]-7-methylimidazo[1,2-b]pyridazine-6,8-diamine

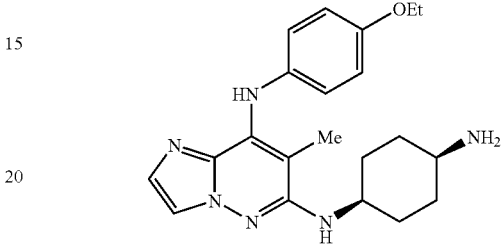

To 6-chloro-N-(4-ethoxyphenyl)-7-methylimidazo[1,2-b]pyridazin-8-amine (40 mg, 0.14 mmol) from Example III(1), step 1d was added cis-1,4-diaminocyclohexane (250 mg, 2.19 mmol). The mixture was allowed to heat at 165° C. for 48 hrs. The reaction mixture then cooled, diluted with methanol and purified by preparative HPLC. The eluent was then concentrated in vacuo, diluted with methanol (2 mL), purified and neutralized by passing through a 500 mg SCX (Cation exchange column). The eluent was concentrated to give 6.0 mg (11.3%) of the titled compound. $^1$H NMR (500 MHz, MeOH) δ ppm 7.65 (1H, s), 7.25 (1H, s), 6.85 (4 H, m), 3.95 (2H, d, J=7.2 Hz), 3.95 (1H, m), 3.05 (1H, m), 1.95 (2H, m), 1.85 (3H, s), 1.80 (4H, m), 1.65 (2H, m), 1.35 (3H, t, J=7.2 Hz). LC/MS m/e 381 (M+1). HPLC, 1.91 min. Waters Sunfire C18 4.6×50.0%-100% B. B: 90% MeOH, 10% H$_2$O, 0.1% TFA. A: 10% MeOH, 90% H$_2$O, 0.1% TFA, gradient time 4 min, hold at 100% B 1 min, flow rate 4 mL/min.

Compounds having the formula (Ia) were prepared according to procedures similar to Example IX(1), where in R$_1$, R$_2$, R$_3$, X and Y have the values listed in Table 5 using the appropriate starting materials and substantially the same procedures as indicated.

TABLE 5

| Exp | Name | R$_1$ | R$_2$ | R$_3$ | X | Y | LC/MS m/z (M + 1) |
|---|---|---|---|---|---|---|---|
| IX(2) | $N^6$-(cis-4-aminocyclohexyl)-$N^8$-(5-methyl-2-pyridinyl)imidazo[1,2-b]pyridazine-6,8-diamine | H | H | H | NH—(5-methyl-2-pyridinyl) | H$_2$N—cyclohexyl—NH$_2$ | 338 |
| IX(3) | $N^6$-(cis-4-aminocyclohexyl)-$N^8$-phenylimidazo[1,2-b]pyridazine-6,8-diamine | H | H | H | NH—phenyl | H$_2$N—cyclohexyl—NH$_2$ | 323 |
| IX(4) | $N^6$-(cis-4-aminocyclohexyl)-7-methyl-$N^8$-phenylimidazo[1,2-b]pyridazine-6,8-diamine | H | H | Me | NH—phenyl | H$_2$N—cyclohexyl—NH$_2$ | 337 |

TABLE 5-continued

| Exp | Name | $R_1$ | $R_2$ | $R_3$ | X | Y | LC/MS m/z (M + 1) |
|---|---|---|---|---|---|---|---|
| IX(5) | $N^6$-(cis-4-aminocyclohexyl)-$N^8$-(4-(ethyloxy)phenyl)imidazo[1,2-b]pyridazine-6,8-diamine | H | H | H | HN–C6H4–OEt | H2N–cyclohexyl–NH2 | 367 |
| IX(6) | $N^6$-(cis-4-aminocyclohexyl)-$N^8$-(3,4-dimethylphenyl)imidazo[1,2-b]pyridazine-6,8-diamine | H | H | H | HN–(3,4-dimethylphenyl) | HN–cyclohexyl–NH2 | 351 |
| IX(7) | $N^6$-(cis-4-aminocyclohexyl)-$N^8$-(5-phenyl-2-pyridinyl)imidazo[1,2-b]pyridazine-6,8-diamine | H | H | H | HN–(5-phenyl-2-pyridinyl) | HN–cyclohexyl–NH2 | 400 |
| IX(8) | 4-((6-((cis-4-aminocyclohexyl)amino)imidazo[1,2-b]pyridazin-8-yl)amino)-N,N-dimethylbenzenesulfonamide | H | H | H | HN–C6H4–SO2N(CH3)2 | HN–cyclohexyl–NH2 | 430 |
| IX(9) | $N^6$-(cis-4-aminocyclohexyl)-$N^8$-(4-methylphenyl)imidazo[1,2-b]pyridazine-6,8-diamine | H | H | H | HN–C6H4–CH3 | HN–cyclohexyl–NH2 | 336 |
| IX(10) | $N^6$-(cis-4-aminocyclohexyl)-$N^8$-(4,6-dimethyl-2-pyridinyl)imidazo[1,2-b]pyridazine-6,8-diamine | H | H | H | HN–(4,6-dimethyl-2-pyridinyl) | HN–cyclohexyl–NH2 | 352 |
| IX(11) | $N^6$-(cis-4-aminocyclohexyl)-$N^8$-(4-(1H-pyrazol-1-yl)phenyl)imidazo[1,2-b]pyridazine-6,8-diamine | H | H | H | HN–C6H4–(1H-pyrazol-1-yl) | HN–cyclohexyl–NH2 | 389 |
| IX(12) | $N^6$-(cis-4-aminocyclohexyl)-$N^8$-(4-(4-morpholinylcarbonyl)phenyl)imidazo[1,2-b]pyridazine-6,8-diamine | H | H | H | HN–C6H4–C(O)–morpholinyl | HN–cyclohexyl–NH2 | 436 |
| IX(13) | $N^6$-(cis-4-aminocyclohexyl)-7-methyl-$N^8$-(2-methylphenyl)imidazo[1,2-b]pyridazine-6,8-diamine | H | H | Me | HN–(2-methylphenyl) | HN–cyclohexyl–NH2 | 351 |
| IX(14) | $N^6$-(cis-4-aminocyclohexyl)-$N^8$-(2-fluorophenyl)-7-methylimidazo[1,2-b]pyridazine-6,8-diamine | H | H | Me | HN–(2-fluorophenyl) | HN–cyclohexyl–NH2 | 355 |
| IX(15) | $N^6$-(cis-4-Aminocyclohexyl)-$N^8$-(4-phenoxyphenyl)imidazo[1,2-b]pyridazine-6,8-diamine | H | H | H | HN–C6H4–O–C6H5 | H2N–cyclohexyl–NH2 | 415 |

TABLE 5-continued

| Exp | Name | R₁ | R₂ | R₃ | X | Y | LC/MS m/z (M + 1) |
|---|---|---|---|---|---|---|---|
| IX(15a) | 4-((6-((cis-4-Aminocyclohexyl)amino)imidazo[1,2-b]pyridazin-8-yl)amino)-2-hydroxy-N,N-dimethylbenzenesulfonamide | H | H | H | | | 446 |
| IX(16) | N⁶-(cis-4-Aminocyclohexyl)-N⁸-4-biphenylylimidazo[1,2-b]pyridazine-6,8-diamine | H | H | H | | | 399 |
| IX(17) | N⁶-(cis-4-Aminocyclohexyl)-N⁸-2-pyridinylimidazo[1,2-b]pyridazine-6,8-diamine | H | H | H | | | 324 |
| IX(18) | N⁶-(cis-4-Aminocyclohexyl)-N⁸-(4-(1H-pyrrol-1-yl)phenyl)imidazo[1,2-b]pyridazine-6,8-diamine | H | H | H | | | 388 |
| IX(19) | N⁶-(cis-4-Aminocyclohexyl)-N⁸-(4-methyl-2-pyridinyl)imidazo[1,2-b]pyridazine-6,8-diamine | H | H | H | | | 338 |
| IX(20) | N⁶-(cis-4-Aminocyclohexyl)-N⁸-(4-(1-piperidinylcarbonyl)phenyl)imidazo[1,2-b]pyridazine-6,8-diamine | H | H | H | | | 434 |
| IX(21) | N⁶-(cis-4-Aminocyclohexyl)-7-methyl-N⁸-(4-phenoxyphenyl)imidazo[1,2-b]pyridazine-6,8-diamine | H | H | Me | | | 429 |
| IX(22) | N⁶-(cis-4-Aminocyclohexyl)-7-methyl-N⁸-(4-(1-piperidinylcarbonyl)phenyl)imidazo[1,2-b]pyridazine-6,8-diamine | H | H | Me | | | 448 |
| IX(23) | 4-((6-((cis-4-Aminocyclohexyl)amino-7-methylimidazo[1,2-b]pyridazin-8-yl)amino)-2-hydroxy-N,N-dimethylbenzenesulfonamide | H | H | Me | | | 460 |

*For substituents X and Y, substitution on the core (formula Ia) occurs at the available nitrogen atom

Example X(1)

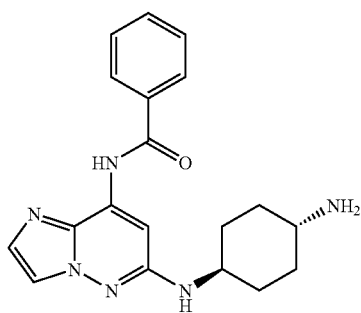

(1a) p-Methoxybenzyl amine (1.0 eq, 1.49 mmol) and triethylamine (330 mg, 3.27 mmol) were added to a mixture of 8-bromo-6-chloroimidazo[1,2-b]pyridazine hydrochloride (40 mg, 1.49 mmol) from Example 1, step 1b in EtOH (15 mL). The mixture was heated to 90° C. and stirred for 24 hours. The solution was then concentrated in vacuo. The resulting residue was purified by reverse phase preparative HPLC to provide 6-chloro-N-(4-methoxybenzyl)imidazo[1,2-b]pyridazin-8-amine as a TFA salt. LC/MS, m/e 288.97 (M+1). HPLC Rt, 2.84 min. Waters Sunfire C18 column (4.6×50 mm). 0%-100% B. Solvent B: (90% MeOH, 10% $H_2O$, 0.1% TFA). Solvent A: (10% MeOH, 90% $H_2O$, 0.1% TFA). Gradient, start % B=0, final % B=100, gradient time 4 min, hold at 100% B 1 min, flow rate 4 mL/min.

(1b) trans-1,4-Diaminocyclohexane (1000 mg, 8.77 mmol) was added to 6-chloro-N-(4-methoxybenzyl)imidazo[1,2-b]pyridazin-8-amine (426 mg, 1.475 mmol) from 1a. The mixture was heated to 160° C. and allowed to melt. After stirring at 160° C. for 7 days, the liquid mixture was cooled to room temperature. Water was added, followed by extraction with dichloromethane. The organic layer was concentrated in vacuo. The resulting residue was purified by reverse phase preparative HPLC to provide the $N^6$-(trans-4-aminocyclohexyl)-$N^8$-(4-methoxybenzyl)imidazo[1,2-b]pyridazine-6,8-diamine as a TFA salt in approximately 44% yield (0.335 g). LC/MS, m/e 367.27 (M+1). HPLC Rt, 1.81 min. Waters Sunfire C18 column (4.6×50 mm). 0%-100% B. Solvent B: (90% MeOH, 10% $H_2O$, 0.1% TFA). Solvent A: (10% MeOH, 90% $H_2O$, 0.1% TFA). Gradient, start % B=0, final % B=100, gradient time 4 min, hold at 100% B 1 min, flow rate 4 mL/min.

(1c) To $N^6$-(trans-4-aminocyclohexyl)-$N^8$-(4-methoxybenzyl)imidazo[1,2-b]pyridazine-6,8-diamine from 1b in dichloromethane (5 mL) was added TFA (2 mL). After stirring at RT for 2 hours, the reaction solution was concentrated in vacuo To provide crude $N^6$-(trans-4-aminocyclohexyl)imidazo[1,2-b]pyridazine-6,8-diamine that was used without further purification. LC/MS, m/e 247.16 (M+1). HPLC Rt, 0.73 min. Waters Sunfire C18 column (4.6×50 mm). 0%-100% B. Solvent B: (90% MeOH, 10% $H_2O$, 0.1% TFA). Solvent A: (10% MeOH, 90% $H_2O$, 0.1% TFA). Gradient, start % B=0, final % B=100, gradient time 4 min, hold at 100% B 1 min, flow rate 4 mL/min.

(1d) To $N^6$-(trans-4-aminocyclohexyl)imidazo[1,2-b]pyridazine-6,8-diamine (70 mg, 0.284 mml, 1.0 eq.) from 1c in THF (3 mL) was added triethylamine (31.6 mg, 0.313 mmol, 1.1 eq.) and boc anhydride (68.2 mg, 0.313 mmol, 1.1 eq). The reaction solution was stirred at RT for 2 hours. The solution was then concentrated in vacuo to give crude tert-butyl(trans)-4-(8-aminoimidazo[1,2-b]pyridazin-6-ylamino) cyclohexylcarbamate which was used as is in the next reaction. LC/MS, m/e 347.23 (M+1). HPLC Rt, 2.50 min. Waters Sunfire C18 column (4.6×50 mm). 0%-100% B. Solvent B: (90% MeOH, 10% $H_2O$, 0.1% TFA). Solvent A: (10% MeOH, 90% $H_2O$, 0.1% TFA). Gradient, start % B=0, final % B=100, gradient time 4 min, hold at 100% B 1 min, flow rate 4 mL/min.

(1e) To 60% NaH (2.9 mg, 0.072 mmol) in THF (2 ml) was added tert-butyl (trans)-4-(8-aminoimidazo[1,2-b]pyridazin-6-ylamino)cyclohexylcarbamate (25 mg, 0.072 mmol) from 1d. After stirring at RT for 1 hour, benzoyl chloride (20.3 mg, 0.144 mg, 2.0 eq.) was added and the reaction solution was heated at 60° C. for 3 days. The reaction was quenched with a few drops of water and methanol. The solution was then concentrated in vacuo. The resulting residue was purified by reverse phase preparative HPLC to provide tert-butyl(trans)-4-(8-benzamidoimidazo[1,2-b]pyridazin-6-ylamino)cyclohexylcarbamate as a TFA salt in approximately 10% yield (9.1 mg). LC/MS, m/e 451.26 (M+1). HPLC Rt, 2.99 min. Waters Sunfire C18 column (4.6×50 mm). 0%-100% B. Solvent B: (90% MeOH, 10% $H_2O$, 0.1% TFA). Solvent A: (10% MeOH, 90% $H_2O$, 0.1% TFA). Gradient, start % B=0, final % B=100, gradient time 4 min, hold at 100% B 1 min, flow rate 4 mL/min.

(1f) To tert-butyl(trans)-4-(8-benzamidoimidazo[1,2-b]pyridazin-6-ylamino)cyclohexylcarbamate from 1e in dichloromethane (2 mL) was added TFA (1 mL). After stirring at RT for 2 hours, the reaction solution was concentrated in vacuo. The residue was purified by SCX column (300 mg, eluting with 2M ammonia in methanol) to give the titled compound as a TFA salt in approximately 50% yield. $^1$H NMR (500 MHz, MeOH) δ ppm 8.07 (2H, d, J=7.7 Hz), 7.69 (2H, s), 7.65 (1H, t), 7.55 (2H, t), 7.36 (1H, s), 3.65 (1H, m), 2.72 (1H, m), 2.17 (2H, m), 1.95 (2H, m), 1.31 (4H, t). LC/MS, m/e 351.21 (M+1). HPLC Rt, 1.70 min. Waters Sunfire C18 column (4.6×50 mm). 0%-100% B. Solvent B: (90% MeOH, 10% $H_2O$, 0.1% TFA). Solvent A: (10% MeOH, 90% $H_2O$, 0.1% TFA). Gradient, start % B=0, final % B=100, gradient time 4 min, hold at 100% B 1 min, flow rate 4 mL/min.

Example XI(1)

1-(6-((trans-4-aminocyclohexyl)amino)imidazo[1,2-b]pyridazin-8-yl)-3-phenylurea

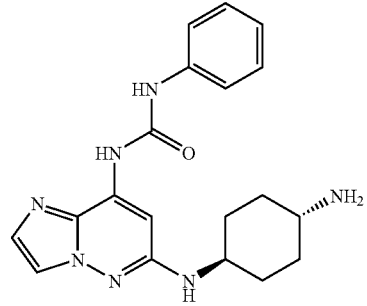

(1a) To 60% NaH (2.9 mg, 0.072 mmol) in THF (2 ml) was added tert-butyl(trans)-4-(8-benzamidoimidazo[1,2-b]pyridazin-6-ylamino)cyclohexylcarbamate (25 mg, 0.072 mmol, prepared in Example X step 1d). After stirring at RT for 1 hour, phenyl isocyanate (17 mg, 0.144 mmol, 2.0 eq.) was added and the reaction solution was heated at 60° C. for 3 days. The reaction was quenched with a few drops of water and methanol. The solution was then concentrated in vacuo. The resulting residue was purified by reverse phase preparative HPLC to provide tert-butyl(trans)-4-(8-(3-phenylureido)imidazo[1,2-b]pyridazin-6-ylamino)cyclohexylcarbamate as a TFA salt (6.5 mg). LC/MS, m/e 466.29 (M+1). HPLC Rt, 3.39 min. Waters Sunfire C18 column (4.6×50 mm). 0%-100% B. Solvent B: (90% MeOH, 10% $H_2O$, 0.1% TFA). Solvent A: (10% MeOH, 90% $H_2O$, 0.1% TFA). Gradient, start % B=0, final % B=100, gradient time 4 min, hold at 100% B 1 min, flow rate 4 mL/min.

(1b) To tert-butyl(trans)-4-(8-(3-phenylureido)imidazo[1,2-b]pyridazin-6-ylamino)cyclohexylcarbamate (6.3 mg, 0.135 mmol) from 1a in dichloromethane (2 mL) was added TFA (1 mL). After stirring at RT for 2 hours, the reaction solution was concentrated in vacuo. The residue was purified by SCX column (300 mg, eluting with 2M ammonia in methanol) to give the title compound as a TFA salt 3.2 mgs (64%). $^1$H NMR (500 MHz, MeOH) δ ppm 7.64 (1H, s), 7.47 (2H, m), 7.31 (2H, m), 7.06 (2H, m), 6.71 (2H, m), 3.63 (1H, m), 2.71 (1H, m), 2.15 (2H, m), 1.91 (2H, m), 1.28-1.33 (4H, t). LC/MS, m/e 366.27 (M+1). HPLC Rt, 2.18 min. Waters Sunfire C18 column (4.6×50 mm). 0%-100% B. Solvent B: (90% MeOH, 10% $H_2O$, 0.1% TFA). Solvent A: (10% MeOH, 90% $H_2O$, 0.1% TFA). Gradient, start % B=0, final % B=100, gradient time 4 min, hold at 100% B 1 min, flow rate 4 mL/min.

Example XII(1)

N,N'-bis(4-trans-aminocyclohexyl)imidazo[1,2-b]pyridazine-6,8-diamine

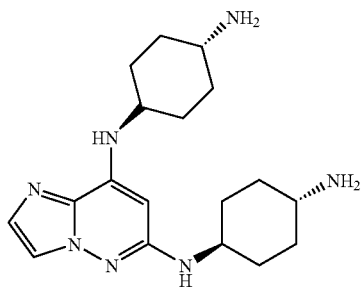

To 8-bromo-6-chloroimidazo[1,2-b]pyridazine (50 mg, 0.19 mmol) from Example 1, step 1b was added trans-1,4-diaminocyclohexane (430 mg, 3.8 mmol). The mixture heated at 180° C. for 48 h. The reaction vessel was cooled to rt. and diluted with water (10 mL) and extracted with DCM (3×10 mL). The organic extracts were combined, concentrated in vacuo and purified using preparative HPLC to provide the title compound (40 mg, 30%) as a TFA salt. $^1$H NMR (400 MHz, MeOH) δ ppm 7.90 (1H, d, J=2 Hz), 7.81 (1H, d, J=2 Hz), 6.06 (1H, s), 3.75 (1H, m), 3.50 (1H, m), 3.20 (2H, m), 2.28 (4H, M), 2.16 (4H, m), 1.70-1.48 (6H, m), 1.42 (2H, m). LC/MS, m/e 344 (M+1). HPLC Rt, 1.01 min. Waters Sunfire C18 column (4.6×50 mm). 0%-100% B. Solvent B: (90% MeOH, 10% $H_2O$, 0.1% TFA). Solvent A: (10% MeOH, 90% $H_2O$, 0.1% TFA). Gradient, start % B=0, final % B=100, gradient time 4 min, hold at 100% B 1 min, flow rate 4 mL/min.

Example XIII(1)

$N^6$-(trans-4-aminocyclohexyl)-$N^8$-(4-ethyloxyphenyl)-7-phenylimidazo[1,2-b]pyridazine-6,8-diamine

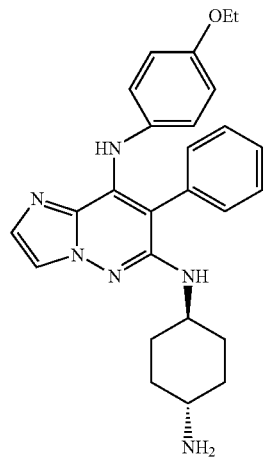

(1a) 3,6-dichloro-4-phenylpyridazine (*J. Med. Chem.* 2005, 48, 7089; 5.93 g, 26.3 mmol) was divided into 6 microwave tubes, and concentrated $NH_4OH$ (7 mL) was added to each. After sealing, each was heated at 140° C. for 1 h. The microwave tubes were uncapped, the precipitates were filtered and washed with cold water. The precipitates from all reactions were combined, and $Et_2O$ (150 mL) was added. After stirring overnight, the remaining solid was filtered, rinsed with $Et_2O$ and dried to give 6-chloro-5-phenylpyridazin-3-amine (3.06 g, 56%)

(1b) To a suspension of 6-chloro-5-phenylpyridazin-3-amine (1.01 g, 4.9 mmol) from 1a in methanol (25 mL) under nitrogen was added $NaHCO_3$ (1.09 g, 13.0 mmol). At 0° C., bromine (0.55 M in methanol, 10 mL, 5.5 mmol) was added over 5 min. After 1 h, the cold bath was removed, and the reaction mixture was stirred at room temperature for 6 h. After concentrating in vacuo, the residue was taken up in $CH_2Cl_2$ and saturated aqueous $Na_2S_2O_5$, and the layers were separated. The organic layer was washed with saturated aqueous $NaHCO_3$ and brine, dried over $Na_2SO_4$, filtered, and concentrated in vacuo to give crude 4-bromo-6-chloro-5-phenylpyridazin-3-amine (1.28 g).

(1c) Chloroacetaldehyde (2.0 mL, 31.5 mmol) was added to a solution of crude 4-bromo-6-chloro-5-phenylpyridazin-3-amine (0.193 g, 0.676 mmol) from 1b in EtOH (5.0 mL). The mixture was heated in a sealed tube at 118° C. for 5 h. After cooling to room temperature, the reaction mixture was concentrated in vacuo, and suspended in acetone/$Et_2O$ (1:1, 3 mL), filtered, and washed with $Et_2O$ to give 8-bromo-6-chloro-7-phenylimidazo[1,2-b]pyridazine HCl salt (0.147 g, >94% purity).

(1d) To a solution of 8-bromo-6-chloro-7-phenylimidazo[1,2-b]pyridazine HCl salt (0.0431 g, 0.125 mmol) from 1c and 4-ethoxyaniline (0.31 M in THF, 0.40 mL) under nitrogen at 0° C. was added KOtBu (1 N in THF, 0.32 mL, 0.32 mmol). After 1 min, the cold bath was removed, and the reaction mixture was stirred to room temperature for 1 h. After concentrating in vacuo, the residue was taken up in $CH_2Cl_2$ and water, and the layers were separated. The aqueous layer was extracted with $CH_2Cl_2$ (2×). The organic layers were combined, dried over $Na_2SO_4$, filtered, and concentrated in vacuo. Trituration with hexanes provided 6-chloro-N-(4-ethoxyphenyl)-7-phenylimidazo[1,2-b]pyridazin-8-amine (0.0334 g).

(1e) 6-chloro-N-(4-ethoxyphenyl)-7-phenylimidazo[1,2-b]pyridazin-8-amine (0.0201 g, 0.058 mmol) from 1d and (trans)-cyclohexane-1,4-diamine (0.1702 g, 1.49 mmol) were heated at 165° C. for 6 d. After cooling to room temperature, the mixture was taken up in $CH_2Cl_2$ and water, and the layers were separated. The aqueous layer was extracted with $CH_2Cl_2$ (2×). The organic layers were combined, dried over $Na_2SO_4$, filtered, and concentrated in vacuo. The residue was purified using preparative HPLC. The appropriate fraction was collected, and $NaHCO_3$ (solid) was added to it. It was concentrated in vacuo not to dryness, and extracted with $CH_2Cl_2$ (2×). The organic layers were combined, dried over $Na_2SO_4$, filtered, and concentrated in vacuo to give the above titled compound (1.5 mg, 4.0% yield). LC/MS, m/e 443.40 (M+1). HPLC RT, 2.29 min. YMC ODSC18 column (4.6×50 mm). 0%-100% B. Solvent B: (90% MeOH, 10% $H_2O$, 0.1% TFA). Solvent A: (10% MeOH, 90% $H_2O$, 0.1% TFA). Gradient, start % B=0, final % B=100, gradient time 4 min, hold at 100% B 1 min, flow rate 4 mL/min.

Compounds having the formula (Ia) were prepared according to procedures similar to Example XIII(1), where in $R_1$, $R_2$, $R_3$, X and Y have the values listed in Table 6 using the appropriate starting materials and substantially the same procedures as indicated.

(1a) In a 250 ml round bottom flask, under a nitrogen atmosphere, was added 8-bromo-6-chloroimidazo[1,2-b]pyridazine (5.0 g, 18.6 mmol) from Example I(1), step 1b, tert-butyl 4-aminobenzoate (3.95 g, 20.5 mmol), and DMF (30 ml). The solution was cooled to 0° C. and 1.0 M potassium tert-butoxide in THF (46 ml) was added dropwise via syringe over 30 minutes. The reaction was allowed to stir at room temperature for 30 minutes and then warmed to 50° C. for 2 hrs and then concentrated in vacuo to remove THF. The resulting solution was taken up in ethyl acetate, washed with $H_2O$ (3×300 ml) and then brine (1×50 ml). The organic layers were combined, dried over $Na_2SO_4$ and filtered. Following solvent evaporation, 6.0 g of crude product was obtained. Further purification was done via triteration with 3:1 diethyl ether/heptane to give 2.2 g of tert-butyl 4-(6-chloroimidazo[1,2-b]pyridazin-8-ylamino)benzoate as a brown solid after filtration.

(1b) In a 50 ml round bottom flask was added tert-butyl 4-(6-chloroimidazo[1,2-b]pyridazin-8-ylamino)benzoate (1.07 g, 3.1 mmol) from 1a and 4M HCl in 1,4 Dioxane (8.0 ml, 31.0 mmol). The reaction was stirred at room temperature

TABLE 6

| Exp | Name | $R_1$ | $R_2$ | $R_3$ | X | Y | LC/MS m/z (M + 1) |
|---|---|---|---|---|---|---|---|
| XIII(2) | $N^6$-(trans-4-aminocyclohexyl)-$N^8$-(phenyl)-7-phenylimidazo[1,2-b]pyridazine-6,8-diamine | H | H | Ph | HN—Ph | NH⋯⟨cyclohexyl⟩—$NH_2$ | 399 |
| XIII(3) | $N^6$-(trans-4-aminocyclohexyl)-$N^8$-(phenyl)-7-phenylimidazo[1,2-b]pyridazine-6,8-diamine | H | H | Ph | HN—Ph | NH—⟨cyclohexyl⟩—$NH_2$ | 399 |
| XII(4) | $N^6$-(cis-4-aminocyclohexyl)-$N^8$-(4-ethoxyphenyl)-7-phenylimidazo[1,2-b]pyridazine-6,8-diamine | H | H | Ph | HN—Ph—OEt | NH—⟨cyclohexyl⟩—$NH_2$ | 443 |

*For substituents X and Y, substitution on the core (formula Ia) occurs at the available nitrogen atom Example XIV(1)

4-((6-((trans-4-aminocyclohexyl)amino)imidazo[1,2-b]pyridazin-8-yl)amino)-N-(2-(4-pyridinyl)ethyl)benzamide

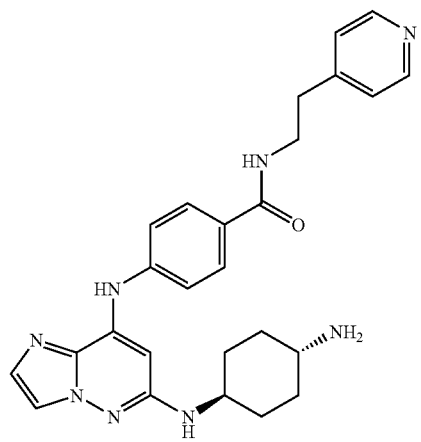

for 18 hrs and then concentrated in vacuo. The resulting 4-(6-chloroimidazo[1,2-b]pyridazin-8-ylamino)benzoic acid HCl salt (1.05 g) was used crude.

(1c) In a 50 ml round bottom flask was added 4-(6-chloroimidazo[1,2-b]pyridazin-8-ylamino)benzoic acid HCl salt (0.53 g, 1.6 mmol) from 1b, dichloromethane (10 ml) and DMF (20 ul). To this solution, neat oxalyl chloride (0.71 ml 8.2 mmol) was added dropwise. The solution was allowed to stir for 1 hr then concentrated in vacuo. This gave 0.5 g of 4-(6-chloroimidazo[1,2-b]pyridazin-8-ylamino)benzoyl chloride as a yellowish solid.

(1d) To a one dram concave vial was added 4-(6-chloroimidazo[1,2-b]pyridazin-8-ylamino)benzoyl chloride (0.024 g, 0.070 mmol) from 1c, dichloromethane (0.7 ml, 0.1M), 2-(pyridine-4-yl)ethanamine (0.017 ml, 0.13 mmol) and diisopropylethylamine. (0.012 ml, 0.18 mmol) The reaction was capped and allowed to stir at room temperature for 2 hours. The solvent was removed in vacuo and trans-1,4-cyclohexyldiamine was added. The reaction was sealed and allowed to stir at 165° C. for 18 hrs. Upon cooling, the sample was dissolved in a methanol (25%)/water (75%) mixture with 4 drops of trifluoroacetic acid. The solution was purified by HPLC (5-60% methanol gradient), which provided the TFA salt of the title compound as a brown solid 0.128 g (21%). $^1$H NMR (400 MHz, MeOH) δ ppm 8.75 (2H, d, 6.6 Hz), 8.04-

8.06 (2H, dd, 6.5 Hz), 8.01 (1H, d, 2 Hz), 7.88-7.90 (3H, m), 7.43 (2H, d, J=8.6 Hz), 6.74 (1H, s), 3.81-3.83 (3H, m), 3.30-3.34 (2H, m), 3.10-3.20 (1H, m), 2.30 (2H, m), 2.10 (2H, m), 1.55-1.58 (2H, m), 1.35-1.45 (2H, m). LC/MS, m/e 471 (M+1). HPLC Rt, 1.39 min. YMC ODSC18 column (4.6×50 mm). 0%-100% B. Solvent B: (90% MeOH, 10% H₂O, 0.1% TFA). Solvent A: (10% MeOH, 90% H₂O, 0.1% TFA). Gradient, start % B=0, final % B=100, gradient time 4 min, hold at 100% B 1 min, flow rate 4 mL/min.

Compounds having the formula (Ia) were prepared according to procedures similar to Example XIV(1), where in $R_1$, $R_2$, $R_3$, X and Y have the values listed in Table 7 using the appropriate starting materials and substantially the same procedures as indicated.

TABLE 7

| Exp | Name | $R_1$ | $R_2$ | $R_3$ | X | Y | LC/MS m/z (M + 1) |
|---|---|---|---|---|---|---|---|
| XIV(2) | 4-((6-((trans-4-aminocyclohexyl)amino)imidazo[1,2-b]pyridazin-8-yl)amino)-N-(2-furanylmethyl)benzamide | H | H | H | | | 446 |
| XIV(3) | 4-((6-((trans-4-aminocyclohexyl)amino)imidazo[1,2-b]pyridazin-8-yl)amino)-N-(1H-imidazol-4-ylmethyl)benzmide | H | H | H | | | 446 |
| XIV(4) | 4-((6-((trans-4-aminocyclohexyl)amino)imidazo[1,2-b]pyridazin-8-yl)amino)-N-(3-pyridinylmethyl)benzamide | H | H | H | | | 457 |
| XIV(5) | N⁶-(trans-4-aminocyclohexyl)-N⁸-(4-((4-phenyl-1-piperidinyl)carbonyl)phenyl)imidazo[1,2-b]pyridazine-6,8-diamine | H | H | H | | | 510 |
| XIV(6) | N⁶-(trans-4-aminocyclohexyl)-N⁸-(4-(1-pyrrolidinylcarbonyl)phenyl)imidazo[1,2-b]pyridazine-6,8-diamine | H | H | H | | | 420 |
| XIV(7) | N⁶-(trans-4-aminocyclohexyl)-N⁸-(4-(1-piperidinylcarbonyl)phenyl)imidazo[1,2-b]pyridazine-6,8-diamine | H | H | H | | | 434 |
| XIV(8) | 4-((6-((trans-4-aminocyclohexyl)amino)imidazo[1,2-b]pyridazin-8-yl)amino)-N-(phenylmethyl)benzamide | H | H | H | | | 456 |

TABLE 7-continued

| Exp | Name | R₁ | R₂ | R₃ | X | Y | LC/MS m/z (M + 1) |
|---|---|---|---|---|---|---|---|
| XIV(9) | 4-((6-((trans-4-aminocyclohexyl)amino)imidazo[1,2-b]pyridazin-8-yl)amino)-N-(3-(methyloxy)phenyl)benzamide | H | H | H | (structure) | (trans-4-aminocyclohexyl) | 472 |
| XIV(10) | N⁶-(trans-4-aminocyclohexyl)-N⁸-(4-((3-phenyl-1-pyrrolidinyl)carbonyl)phenyl)imidazo[1,2-b]pyridazine-6,8-diamine | H | H | H | (structure) | (trans-4-aminocyclohexyl) | 496 |
| XVI(11) | 3-(6-((trans-4-aminocyclohexyl)amino)imidazo[1,2-b]pyridazin-8-yl)amino)-N-phenylbenzamide | H | H | H | (structure) | (trans-4-aminocyclohexyl) | 442 |
| XIV(12) | 4-((6-((trans-4-aminocyclohexyl)amino)imidazo[1,2-b]pyridazin-8-yl)amino)-N-(2-hydroxyethyl)benzamide | H | H | H | (structure) | (trans-4-aminocyclohexyl) | 410 |
| XIV(13) | 4-((6-((trans-4-aminocyclohexyl)amino)imidazo[1,2-b]pyridazin-8-yl)amino)-N-(3-(2-oxo-1-pyrrolidinyl)propyl)benzamide | H | H | H | (structure) | (trans-4-aminocyclohexyl) | 491 |
| XIV(14) | N⁶-(trans-4-aminocyclohexyl)-N⁸-(4-(4-morpholinylcaronyl)phenyl)imidazo[1,2-b]pyridazine-6,8-diamine | H | H | H | (structure) | (trans-4-aminocyclohexyl) | 436 |
| XIV(15) | 4-((6-((trans-4-aminocyclohexyl)amino)imidazo[1,2-b]pyridazin-8-yl)amino)-N-methyl-N-(2-(2-pyridinyl)ethyl)benzamide | H | H | H | (structure) | (trans-4-aminocyclohexyl) | 485 |
| XIV(16) | 4-((6-((trans-4-aminocyclohexyl)amino)imidazo[1,2-b]pyridazin-8-yl)amino)-N,N-diethylbenzamide | H | H | H | (structure) | (trans-4-aminocyclohexyl) | 423 |
| XIV(17) | 4-((6-((trans-4-aminocyclohexyl)amino)imidazo[1,2-b]pyridazin-8-yl)amino)-N-cyclopropylbenzamide | H | H | H | (structure) | (trans-4-aminocyclohexyl) | 406 |

TABLE 7-continued

| Exp | Name | R₁ | R₂ | R₃ | X | Y | LC/MS m/z (M + 1) |
|---|---|---|---|---|---|---|---|
| XIV(18) | 4-((6-((trans-4-aminocyclohexyl)amino)imidazo[1,2-b]pyridazin-8-yl)amino)-N-(cyclohexylmethyl)benzamide | H | H | H | NH—C₆H₄—C(O)NH—CH₂—cyclohexyl | NH'''—cyclohexyl—NH₂ | 462 |
| XIV(19) | 4-((6-((trans-4-aminocyclohexyl)amino)imidazo[1,2-b]pyridazin-8-yl)amino)-N-3-pyridinylbenzamide | H | H | H | NH—C₆H₄—C(O)NH-(3-pyridinyl) | NH'''—cyclohexyl—NH₂ | 443 |
| XIV(20) | 4-((6-((trans-4-aminocyclohexyl)amino)imidazo[1,2-b]pyridazin-8-yl)amino)-N-(1-methyl-1H-pyrazol-5-yl)benzamide | H | H | H | NH—C₆H₄—C(O)NH-(1-methyl-1H-pyrazol-5-yl) | NH'''—cyclohexyl—NH₂ | 446 |

Example XV(1)

4-((6-((trans-4-aminocyclohexyl)amino)imidazo[1,2-b]pyridazin-8-yl)amino)-N-(1-(4-fluorophenyl)-2-oxo-1,2-dihydro-3-pyridinyl)benzamide

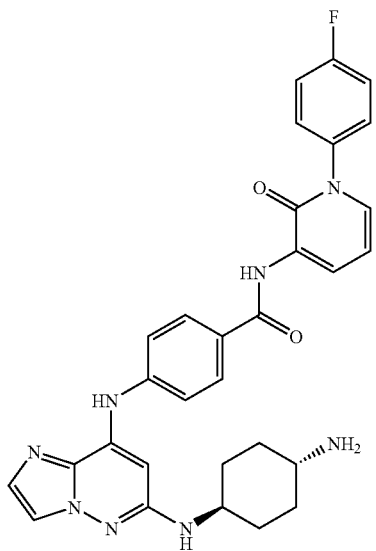

(1a) To a 2 dram vial was added 4-(6-chloroimidazo[1,2-b]pyridazin-8-ylamino)benzoic acid (0.050 g, 0.17 mmol, prepared as described in Example XIV, step 1b), 3-amino-1-(4-fluorophenyl)pyridin-2(1H)-one (0.053 g, 0.26) from 1a-1 and 1a-2 described below, EDCI (0.050 g, 0.26 mmol), HOBt (0.035 g, 0.26 mmol), TEA (0.07 ml, 0.51 mmol), DMF (0.8 ml) and CH₃CN (0.8 ml). the reaction was allowed to stir at 50° C. for 12 hrs. Upon cooling, the solvent was removed in vacuo and diluted with methanol (2 ml). The solution was purified by HPLC (20-100% methanol gradient), which yielded 0.0.12 g of 4-(6-chloroimidazo[1,2-b]pyridazin-8-ylamino)-N-(1-(4-fluorophenyl)-2-oxo-1,2-dihydropyridin-3-yl)benzamide.

(1a-1) To a solution of 2-hydroxy-3-nitropyridine (Aldrich, 3.0 mmol, 420 mg) in 1,4-dioxane (20 mL), were added 4-fluorophenyl boronic acid (Combi-block, 6.0 mmol, 840 mg), copper(II) acetate (Aldrich, 4.5 mmol, 815 mg) and pyridine (2 mL). The reaction was heated at 80° C. for 20 h. After cooling to room temperature, 30 mL of cold water was added. The solid formed was collected by filtration, washed with ammonium hydroxide and water, and dried under vacuum to give 1-(4-fluorophenyl)-3-nitropyridin-2(1H)-one (610 mg, 87% yield) as a solid.

(1a-2) To a solution of 1-(4-fluorophenyl)-3-nitropyridin-2(1H)-one (610 mg, 2.6 mmol) from 1a-1 in THF (50 mL) and MeOH (50 mL), were added ammonium chloride (695 mg, 13.0 mmol, EMD) and Zn dust (850 mg, 13.0 mmol, Aldrich). The reaction mixture was stirred at room temperature for 3 h, diluted with 200 mL of EtOAc and filtered through a pad of Celite. The filtrate was concentrated in vacuo to give 3-Amino-1-(4-fluorophenyl)pyridin-2(1H)-one (530 mg, 100% yield) as a brown solid.

(1b) To 4-(6-chloroimidazo[1,2-b]pyridazin-8-ylamino)-N-(1-(4-fluorophenyl)-2-oxo-1,2-dihydropyridin-3-yl)benzamide (0.011 g, 0.023 mmol) from 1a was added trans-1,4-diaminocyclohexane (0.5 g, 57.0 mmol). The mixture was allowed to melt at 160° C. for 12 hours. The melt was then cooled, diluted with water and extracted with dichloromethane. The organic layer was then concentrated in vacuo to give 0.020 g of crude product. Purification was done via preparative HPLC providing 0.006 g of the title compound as a TFA salt. 1H NMR (400 MHz, MeOD) δ ppm 8.56 (1H, dd, J=7.38, 1.78 Hz), 7.92-8.10 (3H, m), 7.88 (1H, d, J=2.03 Hz), 7.42-7.61 (3H, m), 7.39 (1H, dd, J=7.12, 1.53 Hz), 7.30 (2H, t, J=8.65 Hz), 6.77 (1H, s), 6.54 (1H, t, J=7.12 Hz), 3.97 (1H, s), 3.66-3.84 (1H, m), 3.03-3.24 (1H, m), 2.26 (2H, m), 2.00-2.20 (2H, m), 1.44-1.68 (2H, m), 1.22-1.46 (2H, m). LC/MS, m/e 533 (M+1). HPLC Rt, 2.14 min. YMC ODSC18 column (4.6×50 mm). 0%-100% B. Solvent B: (90% MeOH, 10% H₂O, 0.1% TFA). Solvent A: (10% MeOH, 90% H₂O, 0.1% TFA). Gradient, start % B=0, final % B=100, gradient time 4 min, hold at 100% B 1 min, flow rate 4 mL/min.

Compounds having the formula (Ia) were prepared according to procedures similar to Example XV(1), where in R₁, R₂, R₃, X and Y have the values listed in Table 8 using the appropriate starting materials and substantially the same procedures as indicated.

TABLE 8

| Exp | Name | R₁ | R₂ | R₃ | X | Y | LC/MS m/z (M + 1) |
|---|---|---|---|---|---|---|---|
| XV(2) | 4-((6-((trans-4-aminocyclohexyl)amino)imidazo[1,2-b]pyridazin-8-yl)amino)-N-phenylbenzamide | H | H | H | HN—⟨benzamide with NH-phenyl⟩ | NH⋯⟨cyclohexyl⟩⋯NH₂ | 442 |
| XV(3) | 4-((6-((trans-4-aminocyclohexyl)amino)imidazo[1,2-b]pyridazin-8-yl)amino)-N-cyclohexylbenzamide | H | H | H | HN—⟨benzamide with NH-cyclohexyl⟩ | NH⋯⟨cyclohexyl⟩⋯NH₂ | 448 |
| XV(4) | 4-((6-((trans-4-aminocyclohexyl)amino)imidazo[1,2-b]pyridazin-8-yl)amino)-N-(4-pyridinylmethyl)benzamide | H | H | H | HN—⟨benzamide with NH-CH₂-pyridyl⟩ | NH⋯⟨cyclohexyl⟩⋯NH₂ | 457 |

*For substituents X and Y, substitution on the core (formula Ia) occurs at the available nitrogen atom

Example XVI(1)

1-(4-((6-((trans-4-aminocyclohexyl)amino)imidazo[1,2-b]pyridazin-8-yl)amino)phenyl)-3-phenylurea

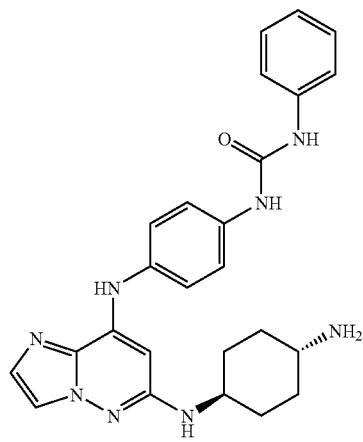

(1a) p-Aminoaniline (0.48 g, 4.4 mmol) and triethylamine (1.3 ml, 9.2 mmol) were added to 8-bromo-6-chloroimidazo[1,2-b]pyridazine HCl (1.0 g, 4.2 mmol) from Example I(1), step 1b in EtOH (20 mL). The mixture was heated to 90° C. and stirred for 1 hr. The solution was then concentrated in vacuo to give crude N1-(6-chloroimidazo[1,2-b]pyridazin-8-yl)benzene-1,4-diamine. Cold ethanol was then added and the crude solid rinsed 3×. Following filtration, collected 0.45 g of the desired material.

(1b) To N1-(6-chloroimidazo[1,2-b]pyridazin-8-yl)benzene-1,4-diamine (0.2 g, 0.77 mmol) from 1a was added trans-1,4-diaminocyclohexane (1.7 g, 15.0 mmol). The mixture was allowed to melt at 160° C. for 3 days. The melt was then cooled, diluted with water and extracted with dichloromethane. The organic layer was then concentrated in vacuo to give 0.4 g of crude N6-(trans-4-aminocyclohexyl)-N8-(4-aminophenyl)imidazo[1,2-b]pyridazine-6,8-diamine.

(1c) In a 200 ml round bottom flask charged with $N^6$-(trans-4-aminocyclohexyl)-$N^8$-(4-aminophenyl)imidazo[1,2-b]pyridazine-6,8-diamine (0.39 g, 1.1 mmol) from 1b and dichloromethane (10 ml) was added di-tert-butyl dicarbonate (0.25 g, 1.1 mmol) in dichloromethane (2 ml). The reaction was stirred at room temperature for 30 min, then concentrated and purified on silica gel (ethyl acetate/heptane, 20 min gradient: 15-100% ethyl acetate). tert-butyl(trans)-4-(8-(4-aminophenylamino)imidazo[1,2-b]pyridazin-6-ylamino)cyclohexylcarbamate (0.050 g) was obtained as a white solid.

(1d) In a 2 dram vial was added tert-butyl(trans)-4-(8-(4-aminophenylamino)imidazo[1,2-b]pyridazin-6-ylamino)cyclohexylcarbamate (0.04 g, 0.09 mmol) from 1c, dichloroethane (1.0 ml) and phenylisocyanate (0.05 ml, 0.5 mmol). The reaction was allowed to stir for 2 hrs and then concentrated to dryness. Diethyl ether was added and the resulting suspension was stirred for 30 min. Upon filtration, tert-butyl(trans)-4-(8-(4-(3-phenylureido)phenylamino)imidazo[1,2-b]pyridazin-6-ylamino)cyclohexylcarbamate (0.035 g) was collected and used with no further purification.

(1e) In a 2 dram vial was added tert-butyl(trans)-4-(8-(4-(3-phenylureido)phenylamino)imidazo[1,2-b]pyridazin-6-ylamino)cyclohexylcarbamate (0.035 g, 0.06 mmol) from 1d and 4.0M HCl in 1,4 Dioxane (2.0 ml). The reaction was stirred for 1 hr at 25° C., concentrated and then triturated with diethyl ether. The titled compound was filtered off as an HCl salt (0.018 g). 1H NMR (400 MHz, DMSO-D6) δ ppm 9.36 (1H, s), 9.00 (1H, s), 8.88 (1H, s), 8.67 (1H, s), 8.60 (1H, s), 8.10 (1H, s), 7.87 (2H, d, J=5.09 Hz), 7.54 (1H, d, J=9.16 Hz), 7.44 (2H, t, J=7.63 Hz), 7.34 (1H, s), 7.20-7.31 (2H, m), 6.85-7.04 (2H, m), 6.27 (1H, s), 3.38 (1H, s), 3.02 (1H, s), 2.04 (2H, m), 1.95 (2H, m), 1.31-1.53 (2H, m), 1.11-1.29 (2H, m). LC/MS, m/e 457 (M+1). HPLC Rt, 1.93 min. YMC ODSC18 column (4.6×50 mm). 0%-100% B. Solvent B: (90% MeOH, 10% H₂O, 0.1% TFA). Solvent A: (10% MeOH, 90% H₂O, 0.1% TFA). Gradient, start % B=0, final % B=100, gradient time 4 min, hold at 100% B 1 min, flow rate 4 mL/min.

Compounds having the formula (Ia) were prepared according to procedures similar to Example XVI(1), where in R₁, R$_2$, R$_3$, X and Y have the values listed in Table 9, using the appropriate starting materials and substantially the same procedures as indicated.

TABLE 9

| Exp | Name | R$_1$ | R$_2$ | R$_3$ | X | Y | LC/MS m/z (M + 1) |
|---|---|---|---|---|---|---|---|
| XVI(2) | 1-(4-((6-((cis-4-aminocyclohexyl)amino)-7-methylimidazo[1,2-b]pyridazin-8-yl)amino)phenyl)-3-phenylurea | H | H | Me | | | 471 |
| XVI(3) | 1-(4-((6-((trans-4-aminocyclohexyl)amino)-7-methylimidazo[1,2-b]pyridazin-8-yl)amino)phenyl)-3-phenylurea | H | H | Me | | | 471 |

For substituents X and Y, substituion on the core (formula Ia) occurs at the available nitrogen atom

Example XVII(1)

N-(4-((6-((trans-4-aminocyclohexyl)amino)imidazo[1,2-b]pyridazin-8-yl)amino)-phenyl)-1-(4-fluorophenyl)-2-oxo-1,2-dihydro-3-pyridinecarboxamide

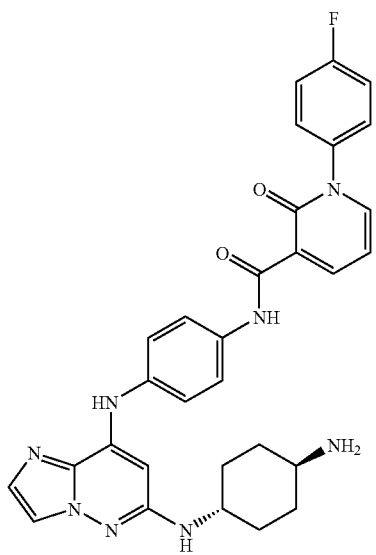

(1a) In a 2 dram reaction vial was added 8-bromo-6-chloroimidazo[1,2-b]pyridazine hydrochloric acid salt (0.5 g, 1.9 mmol) from Example I(1), step 1b, 4-nitroaniline (0.27 g, 1.9 mmol), 1.0 M potassium tert-butoxide in THF (7.6 ml, 7.6 mmol) and DMF (1.4 ml). Under N$_2$, the reaction was stirred for 16 hr at 50° C. and the concentrated in vacuo. The resulting material was taken up in ethyl acetate and washed with H$_2$O (2×50 ml) and then brine (1×20 ml). the organic layers were combined and dried over Na$_2$SO$_4$ and filtered. Following solvent evaporation, 0.42 g of crude 6-chloro-N-(4-nitrophenyl)imidazo[1,2-b]pyridazin-8-amine was obtained.

(1b) In a 2 dram reaction vial was added crude 6-chloro-N-(4-nitrophenyl)imidazo[1,2-b]pyridazin-8-amine (0.42 g, 1.4 mmol) from 1a and trans-1,4-diaminocyclohexane (1.0 g, 8.0 mmol). The mixture was allowed to melt at 160° C. for 8 hrs. The melt was then cooled, diluted with water and extracted with dichloromethane. The organic layer was concentrated to provide crude N6-((trans)-4-aminocyclohexyl)-N8-(4-nitrophenyl)imidazo[1,2-b]pyridazine-6,8-diamine which was used without further purification.

(1c) In a 100 ml round bottom flask charged with N6-((trans)-4-aminocyclohexyl)-N8-(4-nitrophenyl)imidazo[1,2-b]pyridazine-6,8-diamine (0.31 g, 0.85 mmol) from from 1b, triethylamine (0.13 ml, 0.93 mmol) add dichloromethane (10 ml) was added di-tert-butyl dicarbonate (0.3 ml, 1.3 mmol). The reaction was stirred at 25° C. for 0.5 hrs, then concentrated and purified on silica gel (ethyl acetate/heptane, 20 min gradient: 25-100% ethyl acetate) to give tert-butyl (trans)-4-(8-(4-nitrophenylamino)imidazo[1,2-b]pyridazin-6-ylamino)cyclohexylcarbamate (0.090 g) as a white solid.

(1d) In a 50 ml round bottom flask was added tert-butyl (trans)-4-(8-(4-nitrophenylamino)imidazo[1,2-b]pyridazin-6-ylamino)cyclohexylcarbamate (0.090 g, 0.19 mmol) from 1c, chloroform (2.0 ml), methanol (2.0 ml), ammonium chloride (0.12 g, 0.19 mmol) and zinc dust (0.13 g, 0.19 mmol). The reaction was allowed to stir for 30 min at room temperature. The reaction was then filtered through a plug of celite and rinsed with dichloromethane to afford 0.1 g of crude tert-butyl(trans)-4-(8-(4-aminophenylamino)imidazo[1,2-b]pyridazin-6-ylamino)cyclohexylcarbamate.

(1e) To a 2 dram vial was added crude tert-butyl(trans)-4-(8-(4-aminophenylamino)imidazo[1,2-b]pyridazin-6-ylamino)cyclohexylcarbamate (0.064 g, 0.15 mmol) from 1d, 1-(4-fluorophenyl)-2-oxo-1,2-dihydropyridine-3-carboxylic acid (0.051 g, 0.22 mmol) prepared as described in steps 1e-1, 1e-2 below, EDCI (0.043 g, 0.22 mmol), HOBt (0.030 g, 0.22 mmol), TEA (0.06 ml, 0.45 mmol), and CH$_3$CN (1 ml). The reaction was allowed to stir around 25° C. for 16 hrs. The solvent was then removed in vacuo and the sample was diluted with MeOH (4 ml). The solution was purified by HPLC (20-100% methanol gradient), which yielded 0.025 g of tert-butyl(trans)-4-(8-(4-(5-(4-fluorophenyl)-6-oxocyclohexa-1,3-dienecarboxamido)phenylamino)imidazo[1,2-b]pyridazin-6-ylamino)cyclohexylcarbamate as a TFA salt.

(1e-1) In a 200 ml round bottom flask added methyl 2-oxo-2H-pyran-3-carboxylate (5.45 g, 35.0 mmol), 4-floroaniline (3.35 ml, 35.0 mmol) and DMF (63 ml). The reaction was stirred for 3 hrs at room temperature. EDCI (9.4 g, 50.0 mmol) and DMAP (0.3 g, 2.0 mmol) were then added and the reaction was allowed to stir at room temperature overnight.

Compounds having the formula (Ia) were prepared according to procedures similar to Example XVII(1), where in $R_1$, $R_2$, $R_3$, X and Y have the values listed in Table 10, using the appropriate starting materials and substantially the same procedures as indicated.

TABLE 10

| Exp | Name | $R_1$ | $R_2$ | $R_3$ | X | Y | LC/MS m/z (M + 1) |
|---|---|---|---|---|---|---|---|
| XVII(2) | N-(4-((6-((trans-4-aminocyclohexyl)amino)imidazo[1,2-b]pyridazin-8-yl)amino)-2-ethylphenyl)-1-(4-fluorophenyl)-2-oxo-1,2-dihydro-3-pyridinecarboxamide | H | H | H | (structure) | (structure) | 581 |

*For substituents X and Y, substitution on the core (formula Ia) occurs at the available nitrogen atom The reaction was quenched with 50 ml of 1N HCl and ethyl acetate was added. The layers were separated and the resulting aqueous phase was extracted 2× with ethyl acetate. The combined organics were washed 2× with 10% lithium chloride solution and dried over $Na_2SO_4$. Following filtration of the solids and concentration in vacuo, the product was obtained as a yellow solid.

(1e-2) In a 200 ml round bottom flask added methyl 5-(4-fluorophenyl)-6-oxocyclohexa-1,3-dienecarboxylate (1.1 g, 4.3 mmol), THF (8 ml), MeOH (8 ml) and 1N NaOH solution (13 ml). The reaction was allowed to stir overnight at room temperature. Upon concentration of the volatiles, the basic solution was extracted 2× with diethyl ether. The aqueous phase was then acidified to pH 3 with 1N HCl amd subsequently extracted 2× with dichloromethane. The organics were collected and washed with saturated NaCl and the layers separated. The organic solution was dried over $Na_2SO_4$, filtered and concentrated in vacuo. This resulted in 0.7 g of product, 1-(4-fluorophenyl)-2-oxo-1,2-dihydropyridine-3-carboxylic acid.

(1f) In a 50 ml round bottom flask added tert-butyl(trans)-4-(8-(4-(5-(4-fluorophenyl)-6-oxocyclohexa-1,3-dienecarboxamido)phenylamino)imidazo[1,2-b]pyridazin-6-ylamino)cyclohexylcarbamate (0.025 g, 0.04 mmol) from 1e and 20% trifloroacetic acid in methylene chloride (4 ml). The reaction was allowed to stir at room temperature for 5 min. The reaction was then concentrated in vacuo and diluted with methanol and purified via HPLC (20-100% methanol gradient), which provided the titled compound as a TFA salt (0.007 g). 1H NMR (400 MHz, MeOD) δ ppm 12.11 (1H, s), 8.68 (1H, dd, J=7.38, 2.29 Hz), 7.87-8.13 (2H, m), 7.71-7.88 (3H, m), 7.41-7.63 (2H, m), 7.33 (4H, t, J=8.65 Hz), 6.65-6.82 (1H, m), 6.43 (1H, s), 3.54-3.88 (1H, m), 2.96-3.17 (1H, m), 2.23 (2H, m), 2.08 (2H, m), 1.44-1.68 (2H, m), 1.17-1.43 (2H, m). LC/MS, m/e 553 (M+1). HPLC Rt, 2.14 min. YMC ODSC18 column (4.6×50 mm). 0%-100% B. Solvent B: (90% MeOH, 10% $H_2O$, 0.1% TFA). Solvent A: (10% MeOH, 90% $H_2O$, 0.1% TFA). Gradient, start % B=0, final % B=100, gradient time 4 min, hold at 100% B 1 min, flow rate 4 mL/min.

Example XVIII(1)

N-(4-((6-((trans-4-aminocyclohexyl)amino)imidazo[1,2-b]pyridazin-8-yl)amino)phenyl)benzamide

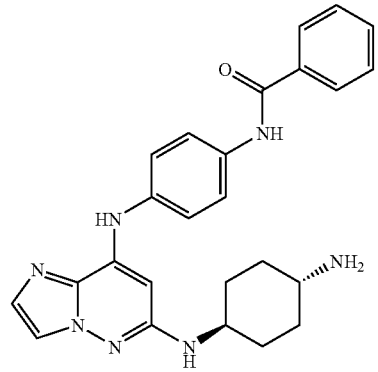

In a 2 dram reaction vial was added N-1-(6-chloroimidazo[1,2-b]pyridazin-8-yl)benzene-1,4-diamine (0.050 g, 0.19 mmol, prepared in Example XVI, step 1a), dichloromethane (1.0 ml) and triethylamine (0.040 ml, 0.29 mmol). To this solution benzoyl chloride (0.025 ml, 0.21 mmol) was added dropwise. The reaction was stirred for 30 min at 25° C. and then concentrated in vacuo. To this was added trans-1,4-diaminocyclohexane (0.5 g, 23.0 mmol). The mixture was allowed to melt at 160° C. for 24 hrs. The melt was then cooled, diluted with water and extracted with dichloromethane. The organic layer was then concentrated in vacuo to give 0.036 g of crude product. The crude material was then purified by preparative HPLC to provide 0.018 g of the title compound as a TFA salt. 1H NMR (400 MHz, MeOD) δ ppm 7.94 (3H, m), 7.76-7.88 (3H, m), 7.45-7.67 (3H, m), 7.36 (2H, d, 8.8 Hz), 6.45 (1H, s), 3.59-3.87 (1H, m), 3.01-3.21 (1H, m), 2.24 (2H, m), 2.09 (2H, m), 1.46-1.65 (2H, m), 1.24-1.42 (2H, m). LC/MS, m/e 442 (M+1). HPLC Rt, 1.80 min. YMC ODSC18 column (4.6×50 mm). 0%-100% B. Solvent B: (90% MeOH, 10% $H_2O$, 0.1% TFA). Solvent A: (10%

MeOH, 90% H₂O, 0.1% TFA). Gradient, start % B=0, final % B=100, gradient time 4 min, hold at 100% B 1 min, flow rate 4 mL/min.

Example XIX(1)

N-(4-((6-((trans-4-aminocyclohexyl)amino)imidazo[1,2-b]pyridazin-8-yl)amino)phenyl)acetamide

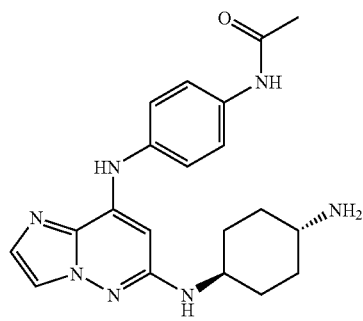

In a 2 dram reaction vial was added N-1-(6-chloroimidazo[1,2-b]pyridazin-8-yl)benzene-1,4-diamine (0.050 g, 0.19 mmol, prepared as described in Example XVI, step 1a), dichloromethane (1.0 ml) and triethylamine (0.040 ml, 0.29 mmol). To this solution acetic anhydride (0.022 ml, 0.23 mmol) was added dropwise. The reaction was stirred for 30 min at 25° C. and then concentrated in vacuo. To this was added trans-1,4-diaminocyclohexane (0.5 g, 4.3 mmol). The mixture was allowed to melt at 160° C. for 24 hrs. The melt was then cooled, diluted with water and extracted with dichloromethane. The organic layer was then concentrated in vacuo to give 0.030 g of crude product. The crude material was then purified by preparative HPLC. This gave 0.008 g of the title compound as a TFA salt. 1H NMR (400 MHz, MeOD) δ ppm 7.95 (1H, d, J=2.03 Hz), 7.86 (1H, d, J=2.03 Hz), 7.65 (2H, d, J=8.65 Hz), 7.29 (2H, d, J=9.16 Hz), 6.40 (1H, s), 3.60-3.81 (1H, m), 3.02-3.24 (1H, m), 2.17-2.30 (2H, m), 2.13 (3H, s), 2.04-2.12 (2H, m), 1.43-1.64 (2H, m), 1.24-1.42 (2H, m). LC/MS, m/e 380 (M+1). HPLC Rt, 1.62 min. YMC ODSC18 column (4.6×50 mm). 0%-100% B. Solvent B: (90% MeOH, 10% H₂O, 0.1% TFA). Solvent A: (10% MeOH, 90% H₂O, 0.1% TFA). Gradient, start % B=0, final % B=100, gradient time 4 min, hold at 100% B 1 min, flow rate 4 mL/min.

Example XX(1)

3-((6-((trans-4-aminocyclohexyl)amino)-7-methylimidazo[1,2-b]pyridazin-8-yl)amino)phenol

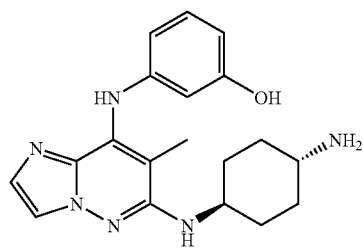

(1a) In a microwave vial was added 8-bromo-6-chloro-7-methylimidazo[1,2-b]pyridazine (0.070 g, 0.24 mmol, prepared as described in Example III, step 1c), NMP (1.4 ml), K₂CO₃ (0.17 g, 1.2 mmol) and 3-(benzyloxy)aniline (0.050 g, 0.24 mmol). The reaction was heated via microwave at 225° C. for 15 min. Upon cooling, the solution was diluted with MeOH (2 ml) and purified by preparative HPLC. This gave 0.011 g of 3-(6-chloro-7-methylimidazo[1,2-b]pyridazin-8-ylamino)phenol. m/z=275. (Note: the benzyl ether was cleaved during the reaction)

(1b) In a 2 dram reaction vial was added 3-(6-chloro-7-methylimidazo[1,2-b]pyridazin-8-ylamino)phenol (0.011 g, 0.028 mmol) from 1a and trans-1,4-diaminocyclohexane (1.0 g, 8.0 mmol). The mixture was allowed to melt at 160° C. for 24 hrs. The melt was then cooled, diluted with water and MeOH, and then purified by preparative HPLC to give 0.005 g of the title compound as a TFA salt. 1H NMR (400 MHz, MeOD) δ ppm 8.01 (1H, s), 7.73 (1H, s), 7.11 (1H, t, J=8.14 Hz), 6.48 (1H, d, J=7.63 Hz), 6.28 (1H, s), 3.88-4.10 (1H, m), 3.05-3.27 (1H, m), 2.24-2.37 (2H, m, J=8.65 Hz), 2.11-2.23 (5H, m), 1.45-1.70 (4H, m). LC/MS, m/e 353 (M+1). HPLC Rt, 1.20 min. YMC ODSC18 column (4.6×50 mm). 0%-100% B. Solvent B: (90% MeOH, 10% H₂O, 0.1% TFA). Solvent A: (10% MeOH, 90% H₂O, 0.1% TFA). Gradient, start % B=0, final % B=100, gradient time 4 min, hold at 100% B 1 min, flow rate 4 mL/min.

Example XXI(1)

N-(4-((6-chloroimidazo[1,2-b]pyridazin-8-yl)amino)phenyl)-1-(4-fluorophenyl)-2-oxo-1,2-dihydro-3-pyridinecarboxamide

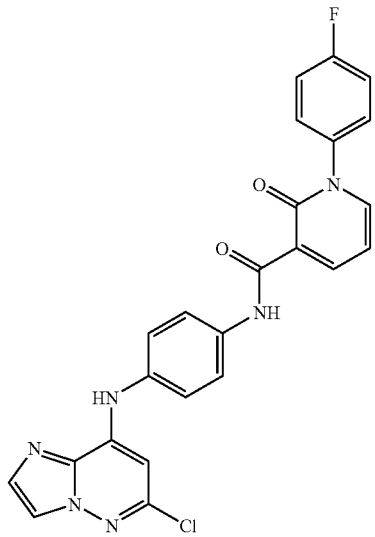

To a 2 dram vial was added N1-(6-chloroimidazo[1,2-b]pyridazin-8-yl)benzene-1,4-diamine (0.078 g, 0.3 mmol, prepared as described in Example XV1, step 1a), 1-(4-fluorophenyl)-2-oxo-1,2-dihydropyridine-3-carboxylic acid (0.10 g, 0.45 mmol, prepared as described in Example XVII, step 1e2), EDCI (0.086 g, 0.45 mmol), HOBt (0.061 g, 0.45 mmol), TEA (0.12 ml, 0.9 mmol), DMF (0.8 ml) and CH₃CN (1.5 ml). The reaction was allowed to stir around 50° C. for 12 hrs. Upon cooling, the solvent was removed in vacuo and diluted with methanol (2 ml). The solution was purified by HPLC (20-100% methanol gradient), which yielded 0.014 g of the title compound as a TFA salt. 1H NMR (400 MHz, CHLOROFORM-D) δ ppm 11.88 (1H, s), 8.70 (1H, dd, J=7.12, 2.03 Hz), 7.71-7.91 (3H, m), 7.67 (1H, s), 7.50-7.63 (1H, m), 7.10-7.43 (5H, m), 6.64 (1H, s), 6.56 (1H, t, J=7.12 Hz). LC/MS, m/e 475 (M+1). HPLC Rt, 2.82 min. YMC ODSC18 column (4.6×50 mm). 0%-100% B. Solvent B: (90% MeOH, 10% H$_2$O, 0.1% TFA). Solvent A: (10% MeOH, 90% H$_2$O, 0.1% TFA). Gradient, start % B=0, final % B=100, gradient time 4 min, hold at 100% B 1 min, flow rate 4 mL/min.

Example XXII(1)

1-(4-fluorophenyl)-N-(4-(imidazo[1,2-b]pyridazin-8-ylamino)phenyl)-2-oxo-3-piperidinecarboxamide

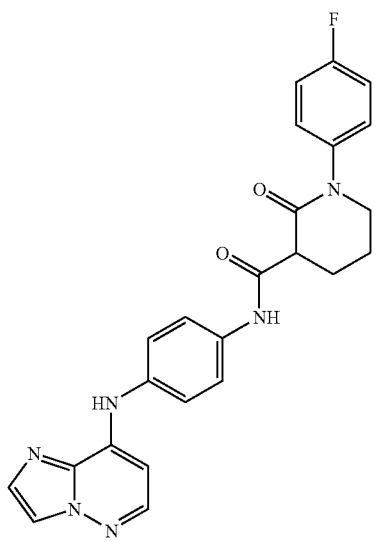

To a suspension of N-(4-((6-chloroimidazo[1,2-b]pyridazin-8-yl)amino)phenyl)-1-(4-fluorophenyl)-2-oxo-1,2-dihydro-3-pyridinecarboxamide TFA salt (0.013 g, 0.027 mmol) from Example XXI(i) and EtOH (4 mL) in a 500 ml PARR bottle was added 10% Pd/C (20 mg) and 2 drops of triethylamine. The PARR bottle was then charged with Hydrogen gas at 55 psi and allow to shake at room temperature for 12 hours. The reaction mixture was then filtered and the filtrate concentrated in vacuo. The residue was purified by preparative HPLC to furnish 0.008 g of the title compound as a TFA salt. LC/MS, m/e 445 (M+1). HPLC Rt, 1.81 mm. YMC ODSC18 column (4.6×50 mm). 0%-100% B. Solvent B: (90% MeOH, 10% H$_2$O, 0.1% TFA). Solvent A: (10% MeOH, 90% H$_2$O, 0.1% TFA). Gradient, start % B=0, final % B=100, gradient time 4 mm, hold at 100% B 1 mm, flow rate 4 mL/min.

Example XXIII(1)

1-(4-fluorophenyl)-N-(4-(imidazo[1,2-b]pyridazin-8-ylamino)phenyl)-2-oxo-1,2-dihydro-3-pyridinecarboxamide

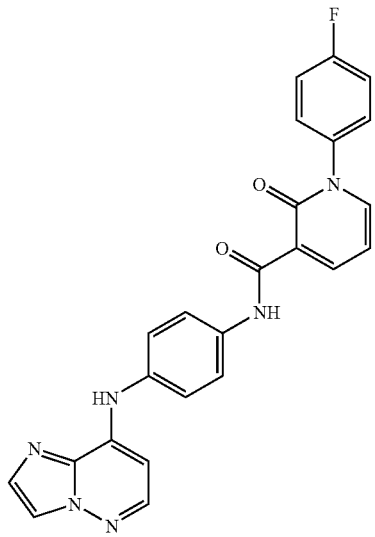

(1a) In a 100 ml round bottom flask charged with N1-(6-chloroimidazo[1,2-b]pyridazin-8-yl)benzene-1,4-diamine (0.5 g, 1.9 mmol, prepared as described in Example XVI, step 1a) and tetrahydrofuran (10 ml) was added di-tert-butyl dicarbonate (0.44 g, 1.9 mmol). The reaction was stirred at 50° C. for 5 hrs, then concentrated and purified on silica gel (ethyl acetate/heptane, 20 min gradient: 5-50% ethyl acetate) to give tert-butyl 4-(6-chloroimidazo[1,2-b]pyridazin-8-ylamino) phenylcarbamate (0.050 g) as a white solid.

(1b) To a mixture of tert-butyl 4-(6-chloroimidazo[1,2-b]pyridazin-8-ylamino)phenylcarbamate (0.1 g, 0.28 mmol) from 1a and EtOH (4 mL) in a 500 ml PARR bottle was added 10% Pd/C (0.02 g) and 2 drops of triethyl amine. The PARR bottle was then charged with H$_2$ at 55 psi and allow to shake at room temperature for 12 hours. The reaction mixture was then filtered and the filtrate concentrated in vacuo to give 0.085 g of crude tert-butyl 4-(imidazo[1,2-b]pyridazin-8-ylamino)phenylcarbamate.

(1c) In a 2 dram vial was added tert-butyl 4-(imidazo[1,2-b]pyridazin-8-ylamino)phenylcarbamate. (0.085 g, 0.26 mmol) from 1b and 4.0M HCl in 1,4 dioxane (5.0 ml). The reaction was stirred for 2 hr at 25° C., concentrated. N$^1$-(imidazo[1,2-b]pyridazin-8-yl)benzene-1,4-diamine resulted as a di-HCl salt (0.085 g). The product was used with no further purification.

(1d) To a 2 dram vial was added N$^1$-(imidazo[1,2-b]pyridazin-8-yl)benzene-1,4-diamine di-HCl salt (0.080 g, 0.3 mmol) from 1c, 1-(4-fluorophenyl)-2-oxo-1,2-dihydropyridine-3-carboxylic acid (0.13 g, 0.57 mmol), EDCI (0.11 g, 0.57 mmol), HOBt (0.077 g, 0.57 mmol), TEA (0.16 ml, 1.1 mmol), and CH$_3$CN (4 ml). The reaction was allowed to stir around 25° C. for 12 hrs. The solvent was then removed in vacuo and the sample was diluted with MeOH (4 ml). The solution was purified by HPLC (20-100% methanol gradient), which yielded 0.015 g of the title compound as a TFA salt. 1H NMR (400 MHz, DMSO-D6) δ ppm 11.96 (1H, s), 9.47 (1H, s), 8.59 (1H, dd, J=7.38, 2.29 Hz), 7.99-8.27 (3H, m), 7.67-7.85 (3H, m), 7.55-7.67 (2H, m, J=9.16, 5.09 Hz), 7.33-7.49 (3H, m), 6.66-6.82 (1H, m), 6.55 (1H, d, J=6.10 Hz) LC/MS, m/e 441 (M+1). HPLC Rt, 2.64 min. YMC ODSC18 column (4.6×50 mm). 0%-100% B. Solvent B: (90% MeOH, 10% $H_2O$, 0.1% TFA). Solvent A: (10% MeOH, 90% $H_2O$, 0.1% TFA). Gradient, start % B=0, final % B=100, gradient time 4 min, hold at 100% B 1 min, flow rate 4 mL/min.

Example XXIV(1)

6-((trans-4-aminocyclohexyl)amino)-8-((4-(ethyloxy)phenyl)amino)imidazo[1,2-b]pyridazine-3-carbonitrile

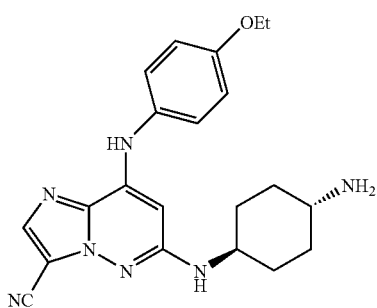

(1a) In a 200 ml round bottom flask was added 8-bromo-6-chloroimidazo[1,2-b]pyridazine hydrochloride (3.0 g, 11.2 mmol) from Example I(1), step 1b, chloroform (55 ml) and NBS (3.0 g, 16.8 mmol). The reaction was heated at 80° C. for 1 hr, cooled to room temperature and the volatiles removed under reduced pressure. Ethyl acetate was added and the mixture was washed with $Na_2CO_3$ (2×100 ml), $H_2O$ (2×100 ml) and then brine (1×25 ml). The organic layers were combined and dried over $Na_2SO_4$ and then concentrated. This gave 1.8 g of crude 3,8-dibromo-6-chloroimidazo[1,2-b]pyridazine.

(1b) p-Phenetidine (0.38 ml, 2.9 mmol) and triethylamine (0.8 ml, 5.8 mmol) were added to a mixture of 3,8-dibromo-6-chloroimidazo[1,2-b]pyridazine (0.83 g, 2.67 mmol) from 1a in EtOH (10 mL). The mixture was heated to 80° C. and stirred for 16 hrs. The solution was then concentrated in vacuo to give crude 3-bromo-6-chloro-N-(4-ethoxyphenyl)imidazo[1,2-b]pyridazin-8-amine.

(1c) In a 5 ml microwave vial was added 3-bromo-6-chloro-N-(4-ethoxyphenyl)imidazo[1,2-b]pyridazin-8-amine (0.3 g, 0.8 mmol) from 1b, Pd(PPh$_3$)$_4$ (0.18 g, 0.16 mmol), Zn(CN)$_2$ (0.47 g, 4.0 mmol) and DMF (3 ml). The reaction was heated via microwave for 25 min at 200° C. Upon cooling, the reaction mixture was diluted with ethyl acetate and filtered through a plug of celite. The solvent was removed in vacuo and the resulting material was purified by silica gel chromatography (ethyl acetate/heptane, 25 min gradient: 5-50% ethyl acetate) to give 0.11 g of 6-chloro-8-(4-ethoxyphenylamino)imidazo[1,2-b]pyridazine-3-carbonitrile.

(1d) In a 2 dram reaction vial was added 6-chloro-8-(4-ethoxyphenylamino)imidazo[1,2-b]pyridazine-3-carbonitrile (0.055 g, 0.017 mmol) from 1c and trans-1,4-diaminocyclohexane (1.0 g, 8.0 mmol). The mixture was allowed to melt at 160° C. for 1.5 hrs. The melt was then cooled, diluted with water and extracted with dichloromethane. The organic layer was concentrated and then diluted with MeOH, and then purified by preparative HPLC to give 0.039 g of the title compound as a TFA salt. 1H NMR (500 MHz, Solvent) δ ppm 7.91 (1H, s), 7.23 (2H, d, J=8.80 Hz), 6.96 (2H, d, J=8.80 Hz), 5.96 (1H, s), 4.04 (4H, q, J=6.78 Hz), 3.61-3.80 (1H, m), 2.99-3.19 (1H, m), 2.16-2.35 (2H, m, J=11.55 Hz), 2.01-2.16 (2H, m, J=12.65 Hz), 1.47-1.65 (2H, m), 1.39 (3H, t, J=7.15 Hz), 1.24-1.36 (2H, m). LC/MS, m/e 392 (M+1). HPLC Rt, 2.69 min. YMC ODSC18 column (4.6×50 mm). 0%-100% B. Solvent B: (90% MeOH, 10% $H_2O$, 0.1% TFA). Solvent A: (10% MeOH, 90% $H_2O$, 0.1% TFA). Gradient, start % B=0, final % B=100, gradient time 4 min, hold at 100% B 1 min, flow rate 4 mL/min.

Compounds having the formula (Ia) were prepared according to procedures similar to Example XXIV(1), where in $R_1$, $R_2$, $R_3$, X and Y have the values listed in Table 11, using the appropriate starting materials and substantially the same procedures as indicated.

TABLE 11

| Exp) | Name | $R_1$ | $R_2$ | $R_3$ | X | Y | LC/MS m/z (M + 1) |
|---|---|---|---|---|---|---|---|
| XXIV(2) | 6-((trans-4-aminocyclohexyl)amino)-8-(phenylamino)imidazo[1,2-b]pyridazine-3-carbonitrile | H | CN | H | NH—⟨phenyl⟩— | NH⋯⟨cyclohexyl⟩—NH$_2$ | 348 |

*For substituents X and Y, substitution on the core (formula Ia) occurs at the available nitrogen atom Example XXV(1)

6-((4-trans-aminocyclohexyl)amino)-7-methyl-8-(phenylamino)imidazo[1,2-b]pyridazine-3-carbonitrile

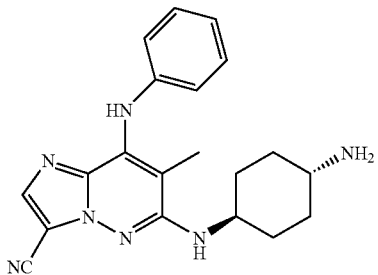

(1a) In a 200 ml round bottom flask was added 8-bromo-6-chloro-7-methylimidazo[1,2-b]pyridazine hydrochloride (0.52 g, 1.8 mmol) from Example III, step 1c, chloroform (10 ml) and NBS (0.5 g, 2.7 mmol). The reaction was heated at 80° C. for 1 hr, cooled to room temperature and the volatiles removed under reduced pressure. Ethyl acetate was added and the mixture was washed with $Na_2CO_3$ (2×100 ml), $H_2O$ (2×100 ml) and then brine (1×25 ml). The organic layers were combined and dried over $Na_2SO_4$ and then concentrated. This gave 1.8 g of crude product that was then dry loaded onto silica gel and purified via column chromatography using 30% ethyl acetate as the mobile phase. This resulted in 0.14 g of pure 3,8-dibromo-6-chloro-7-methylimidazo[1,2-b]pyridazine.

(1b) In a 2 dram reaction vial was added 3,8-dibromo-6-chloro-7-methylimidazo[1,2-b]pyridazine (0.14 g, 0.43 mmol) from 1a, 11.0M potassium tert-butoxide in THF (1.0 ml) and THF (1.4 ml). Under $N_2$, the reaction was stirred for 1 hr at room temperature and then concentrated in vacuo. The resulting material was taken up in ethyl acetate, washed with $H_2O$ (2×50 ml) and then brine (1×20 ml). the organic layers were combined and dried over $Na_2SO_4$ and filtered. Following solvent evaporation, 0.14 g of crude product was obtained. Further purification was done via silica gel chromatography (ethyl acetate/heptane, 25 min gradient: 5-50% ethyl acetate) to give 0.053 g of 3-bromo-6-chloro-7-methyl-N-phenylimidazo[1,2-b]pyridazin-8-amine.

(1c) In a 5 ml microwave vial was added 3-bromo-6-chloro-7-methyl-N-phenylimidazo[1,2-b]pyridazin-8-amine (0.053 g, 0.16 mmol) from 1a, $Pd(PPh_3)_4$ (0.036 g, 0.032 mmol), $Zn(CN)_2$ (0.088 g, 0.78 mmol) and DMF (3 ml). The reaction was heated via microwave for 30 min at 180° C. Upon cooling, the reaction mixture was diluted with ethyl acetate and filtered through a plug of celite. The solvent was removed in vacuo and the resulting material was purified by preparative HPLC to give 0.013 g of 3-bromo-6-chloro-7-methyl-N-phenylimidazo[1,2-b]pyridazin-8-amine.

(1d) In a 2 dram reaction vial was added 3-bromo-6-chloro-7-methyl-N-phenylimidazo[1,2-b]pyridazin-8-amine (0.013 g, 0.045 mmol) from 1b and trans-1,4-diaminocyclohexane (1.0 g, 8.0 mmol). The mixture was allowed to melt at 160° C. for 45 min. The melt was then cooled, diluted with water and extracted with dichloromethane. The organic layer was concentrated and then diluted with MeOH and then purified by preparative HPLC to give the title compound as a TFA salt. 1H NMR (400 MHz, MeOD) δ ppm 7.99 (1H, s), 7.19-7.33 (2H, m), 6.97 (1H, t, J=7.38 Hz), 6.87 (2H, d, J=7.63 Hz), 3.88-4.02 (1H, m), 3.07-3.25 (1H, m), 2.25-2.40 (2H, m, J=12.21 Hz), 2.07-2.22 (2H, m, J=12.21 Hz), 1.94 (3H, s), 1.41-1.72 (4H, m). LC/MS, m/e 362 (M+1). HPLC Rt, 2.58 min. YMC ODSC18 column (4.6×50 mm). 0%-100% B. Solvent B: (90% MeOH, 10% $H_2O$, 0.1% TFA). Solvent A: (10% MeOH, 90% $H_2O$, 0.1% TFA). Gradient, start % B=0, final % B=100, gradient time 4 min, hold at 100% B 1 min, flow rate 4 mL/min.

Compounds having the formula (Ia) were prepared according to procedures similar to Example XXV(1), where in $R_1$, $R_2$, $R_3$, X and Y have the values listed in Table 12 using the appropriate starting materials and substantially the same procedures as indicated.

TABLE 12

| Exp | Name | $R_1$ | $R_2$ | $R_3$ | X | Y | LC/MS m/z (M + 1) |
|---|---|---|---|---|---|---|---|
| XXV(2) | 6-((trans)-4-aminocyclohexylamino)-7-ethyl-8-(phenylamino)imidazo[1,2-b]pyridazine-3-carbonitrile | H | CN | Et | HN—phenyl | NH⋯cyclohexyl—$NH_2$ | 376 |
| XXV(3) | 6-((trans-4-aminocyclohexyl)amino)-8-anilino-7-isopropylimidazo[1,2-b]pyridazine-3-carbonitrile | H | CN | i-Pr | HN—phenyl | NH⋯cyclohexyl—$NH_2$ | 390 |
| XXV(4) | 6-((trans-4-Aminocyclohexyl)amino)-8-anilino-7-benzylimidazo[1,2-b]pyridazine-3-carbonitrile | H | CN | $CH_2Ph$ | HN—phenyl | NH⋯cyclohexyl—$NH_2$ | 438 |
| XXV(5) | 6-((trans-4-Aminocyclohexyl)amino)-8-anilino-7-(4-chlorophenyl)imidazo[1,2-b]pyridazine-3-carbonitrile | H | CN | Ph(4-Cl) | HN—phenyl | NH⋯cyclohexyl—$NH_2$ | 459 |
| XXV(6) | 6-((trans-4-Aminocyclohexyl)amino)-8-((4-ethoxyphenyl)amino)-7-phenylimidazo[1,2-b]pyridazine-3-carbonitrile | H | CN | Ph | NH—phenyl—OEt | NH⋯cyclohexyl—$NH_2$ | 468 |

*For substituents X and Y, substitution on the core (formula Ia) occurs at the available nitrogen atom

Example XXVI(1)

$N^6$-(trans-4-aminocyclohexyl)-$N^8$-(4-(ethyloxy)phenyl)-3-fluoroimidazo[1,2-b]pyridazine-6,8-diamine

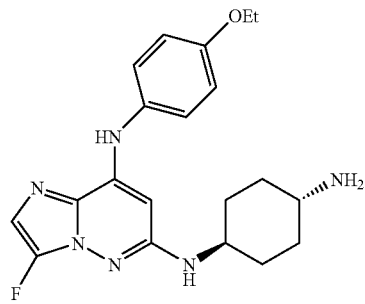

(1a) In a 20 ml reaction vial was added 8-bromo-6-chloroimidazo[1,2-b]pyridazine hydrochloride salt (0.33 g, 1.4 mmol) from Example I(1), step 1b, CH₃CN (7.0 ml) and selectflor (0.5 g, 1.4 mmol). The reaction was stirred at 50 C for 6 hrs, then concentrated to dryness. Purification was done by silica gel chromatography (ethyl acetate/heptane, 25 min gradient: 5-50% ethyl acetate) to give 0.085 g of 8-bromo-6-chloro-3-fluoroimidazo[1,2-b]pyridazine.

(1b) p-Phenetidine (0.044 ml, 0.34 mmol) and triethylamine (0.1 ml, 0.75 mmol) were added to a mixture of 8-bromo-6-chloro-3-fluoroimidazo[1,2-b]pyridazine (0.085 g, 0.34 mmol) from 1a in EtOH (1.7 mL). The mixture was heated to 80° C. and stirred for 16 hors. The solution was then concentrated in vacuo to give crude 6-chloro-N-(4-ethoxyphenyl)-3-fluoroimidazo[1,2-b]pyridazin-8-amine.

(1c) In a 2 dram reaction vial was added 6-chloro-N-(4-ethoxyphenyl)-3-fluoroimidazo[1,2-b]pyridazin-8-amine (0.080 g, 0.26 mmol) from 1b and trans-1,4-diaminocyclohexane (1.0 g, 8.0 mmol). The mixture was allowed to melt at 160° C. for 5 hrs. The melt was then cooled, diluted with water and extracted with dichloromethane. The organic layer was concentrated and then diluted with MeOH, and then purified by preparative HPLC to give the titled compound as a TFA salt. 1H NMR (500 MHz, Solvent) δ ppm 7.32 (1H, d, J=6.05 Hz), 7.24 (2H, d, J=8.80 Hz), 6.98 (2H, d, J=8.80 Hz), 5.99 (1H, s), 4.05 (2H, q, J=7.15 Hz), 3.66-3.79 (1H, m), 3.04-3.18 (1H, m), 2.16-2.28 (2H, m, J=1.55 Hz), 1.99-2.12 (2H, m, J=12.10 Hz), 1.46-1.62 (2H, m), 1.39 (3H, t, J=6.87 Hz), 1.25-1.36 (2H, m). LC/MS, m/e 385 (M+1). HPLC Rt, 2.25 min. YMC ODSC18 column (4.6×50 mm). 0%-100% B. Solvent B: (90% MeOH, 10% H₂O, 0.1% TFA). Solvent A: (10% MeOH, 90% H₂O, 0.1% TFA). Gradient, start % B=0, final % B=100, gradient time 4 min, hold at 100% B 1 min, flow rate 4 mL/min.

Example XXVII(1)

$N^6$-(trans-4-aminocyclohexyl)-$N^8$-(4-(ethyloxy)phenyl)-3-methylimidazo[1,2-b]pyridazine-6,8-diamine

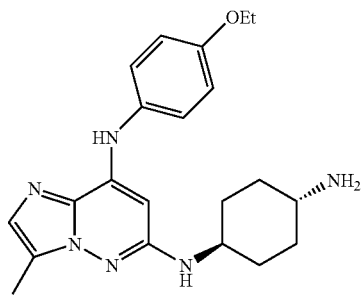

(1a) To a mixture of crude 4-bromo-6-chloro-2,3-dihydropyridazin-3-amine (0.5 g, 2.3 mmol) from Example I(1), step 1b, 2-chloro-1,1-dimethoxypropane (1.6 ml), EtOH (5 ml) and H₂O (2 ml) was added 4 drops of 35% HBr in acetic acid. The reaction was stirred at 100° C. for 16 hrs. The reaction was then concentrated to dryness and triturated from diethyl ether. Upon filtration a mixture of 8-bromo-6-chloro-3-methylimidazo[1,2-b]pyridazine and 6,8-dichloro-3-methylimidazo[1,2-b]pyridazine were obtained as HCl salts.

(1b) p-Phenetidine (0.068 g, 0.5 mmol) and triethylamine (0.15 ml, 1.1 mmol) were added to a mixture of 8-bromo-6-chloro-3-methylimidazo[1,2-b]pyridazine and 6,8-dichloro-3-methylimidazo[1,2-b]pyridazine (0.011 g, 0.5 mmol) both from 1a in EtOH (10 mL). The mixture was heated to 90° C. and stirred for 30 hrs. The solution was then concentrated in vacuo to give crude 6-chloro-N-(4-ethoxyphenyl)-3-methylimidazo[1,2-b]pyridazin-8-amine.

(1c) In a 2 dram reaction vial was added crude 6-chloro-N-(4-ethoxyphenyl)-3-methylimidazo[1,2-b]pyridazin-8-amine (0.15 g, 0.5 mmol) from 1b and trans-1,4-diaminocyclohexane (1.0 g, 8.0 mmol). The mixture was allowed to melt at 160° C. for 48 hrs. The melt was then cooled, diluted with water and extracted with dichloromethane. The organic layer was concentrated and then diluted with MeOH and then purified by preparative HPLC to give the title compound as a TFA salt. 1H NMR (400 MHz, MeOD) δ ppm 7.62 (1H, s), 7.25 (2H, d, J=9.16 Hz), 6.99 (2H, d, J=9.16 Hz), 6.21 (1H, s), 4.05 (2H, q, J=7.12 Hz), 3.64-3.89 (1H, m), 3.00-3.22 (1H, m), 2.48 (3H, s), 2.17-2.38 (2H, m, J=11.19 Hz), 1.99-2.18 (2H, m, J=12.21 Hz), 1.45-1.71 (2H, m), 1.22-1.46 (5H, m). LC/MS, m/e 381 (M+1). HPLC Rt, 1.91 min. YMC ODSC18 column (4.6×50 mm). 0%-100% B. Solvent B: (90% MeOH, 10% H₂O, 0.1% TFA). Solvent A: (10% MeOH, 90% H₂O, 0.1% TFA). Gradient, start % B=0, final % B=100, gradient time 4 min, hold at 100% B 1 min, flow rate 4 mL/min

Example XXVIII(1)

$N^6$-(trans-4-aminocyclohexyl)-$N^8$-(4-(ethyloxy)phenyl)-2,3-dimethylimidazo[1,2-b]pyridazine-6,8-diamine

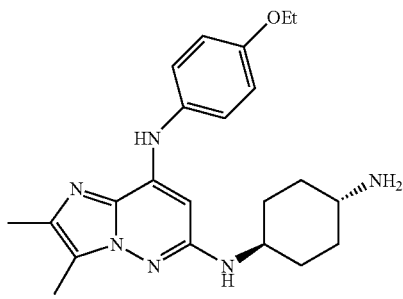

(1a) A mixture of 4-bromo-6-chloro-2,3-dihydropyridazin-3-amine (0.1 g, 0.48 mmol) from Example I(1), step 1a, 3-chlorobutane-2-one (0.42 g, 3.3 mmol) and EtOH (1 ml) was stirred at 90° C. for 48 hrs. The reaction was then concentrated to dryness and triturated from diethyl ether. Upon filtration, an oily material resulted. The frit containing the oily solid was rinsed with methanol and the material collected as a mixture of 8-bromo-6-chloro-2,3-dimethylimidazo[1,2-b]pyridazine and 6,8-dichloro-2,3-dimethylimidazo[1,2-b]pyridazine (HCl salt).

(1b) p-Phenetidine (0.04 g, 0.29 mmol) and potassium carbonate (0.12 g, 0.87 mmol) were added to a mixture of 8-bromo-6-chloro-2,3-dimethylimidazo[1,2-b]pyridazine and 6,8-dichloro-2,3-dimethylimidazo[1,2-b]pyridazine (HCl salt) (0.063 g, 0.29 mmol) both from 1a, in EtOH (1.0 mL). The mixture was heated to 90° C. and stirred for 48 hrs. The solution was then concentrated in vacuo and purified by preparative HPLC (20-100% Methanol/Water gradient). This gave 0.013 g of 6-chloro-N-(4-ethoxyphenyl)-3-methylimidazo[1,2-b]pyridazin-8-amine.

(1c) In a 2 dram reaction vial was added crude 6-chloro-N-(4-ethoxyphenyl)-2,3-dimethylimidazo[1,2-b]pyridazin-8-amine (0.013 g, 0.04 mmol) from 1b and trans-1,4-diaminocyclohexane (1.0 g, 8.0 mmol). The mixture was allowed to melt at 160° C. for 4 days. The melt was then cooled, diluted with water and extracted with dichloromethane. The organic layer was concentrated and then diluted with MeOH and then purified by preparative HPLC. This gave 0.005 g of the titled compound as a TFA salt. 1H NMR (500 MHz, MeOD) δ ppm 7.24 (2H, d, J=8.25 Hz), 7.00 (2H, d, J=8.80 Hz), 6.17 (1H, s), 4.05 (2H, q, J=6.96 Hz), 3.62-3.83 (1H, m), 3.02-3.21 (1H, m), 2.47 (3H, s), 2.42 (3H, s), 2.18-2.29 (2H, m, J=11.55 Hz), 2.03-2.14 (2H, m, J=12.65 Hz), 1.45-1.62 (2H, m), 1.39 (3H, t, J=6.87 Hz), 1.26-1.36 (2H, m). LC/MS, m/e 395 (M+1). HPLC Rt, 2.49 min. YMC ODSC18 column (4.6×50 mm). 0%-100% B. Solvent B: (90% MeOH, 10% $H_2O$, 0.1% TFA). Solvent A: (10% MeOH, 90% $H_2O$, 0.1% TFA). Gradient, start % B=0, final % B=100, gradient time 4 min, hold at 100% B 1 min, flow rate 4 mL/min.

Example XXIX(1)

N-(6-((trans-4-aminocyclohexyl)amino)imidazo[1,2-b]pyridazin-8-yl)benzenesulfonamide

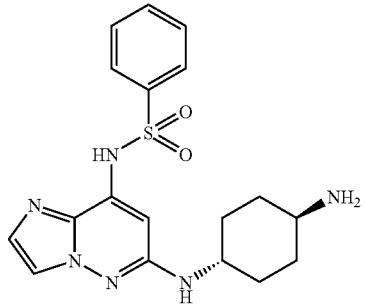

(1a) To a 16×100 mm tube was added benzenesulfonamide (58 mg, 0.37 mmol), tris(dibenzylideneacetone)dipalladium (0) (2 mg, 0.0022 mmol), 4,5-bis(diphenylphosphino)-9,9-dimethylxanthene (4 mg 0.0077 mmol) and cesium carbonate (240 mg, 1.25 mmol). The tube was evacuated and back filled with nitrogen. 8-Bromo-6-chloroimidazo[1,2-b]pyridazine (120 mg, 0.447 mmol) from Example I(1), step 1b and 1,4-dioxane (1.0 ml) was then added. The mixture was allowed to heat at 100° C. for 16 hours. The solution was then diluted with dichloromethane, filtered and concentrated in vacuo to afford crude N-(6-chloroimidazo[1,2-b]pyridazin-8-yl)benzenesulfonamide 100 mg (73%).

(1b) To N-(6-chloroimidazo[1,2-b]pyridazin-8-yl)benzenesulfonamide (100 mg, 0.325 mmol) from 1a was added trans-1,4-diaminocyclohexane (1000 mg, 8.77 mmol). The mixture was allowed to melt at 165° C. for 3 days. The melt was then cooled, water was added followed by extraction with dichloromethane. The organic layer was then concentrated in vacuo and purified by preparative HPLC. This gave 4.5 mg (2%) of the title compound as a TFA salt. $^1$H NMR (500 MHz, MeOH-$D_3$) δ ppm 7.97 (2H, d, J=5 Hz), 7.85 (1H, s), 7.71 (1H, s), 7.63 (1H, m), 7.56 (2H, m), 6.63 (1H, s), 3.64 (1H, m), 3.12 (1H, m), 2.23-2.04 (4H, m), 1.51 (2H, m), 1.34 (2H, m). LC/MS m/e 387 (MH+). HPLC, 1.60 min. Waters Sunfire C18 4.6×50. 0%-100% B. B: 90% MeOH, 10% $H_2O$, 0.1% TFA. A: 10% MeOH, 90% $H_2O$, 0.1% TFA.

Example XXXI(1)

6-((trans-4-aminocyclohexyl)oxy)-8-anilinoimidazo[1,2-b]pyridazine-3-carbonitrile

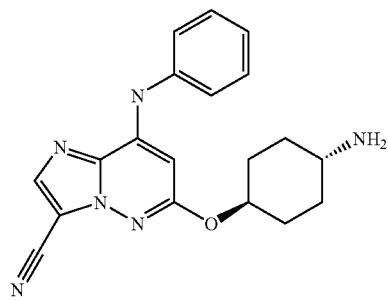

(1a) N-(4-Methoxybenzyl)aniline (215 mg, 1 mmol) was dissolved in dry DMF (4 mL), placed under a nitrogen atmosphere, and cooled to 0° C. in an ice bath. Potassium t-butoxide (1 mL, 1 mmol, 1M THF solution) was added and the mixture was allowed to stir for 10 min at 0° C. and room temperature for 30 min. The resulting mixture was cool to 0° C. Solid 3,8-dibromo-6-chloroimidazo[1,2-b]pyridazine (310 mg, 1 mmol) from Example XXIV, step 1a was added. The mixture was allowed to stir for 30 min at 0° C. and overnight at room temperature. The mixture was diluted with ethyl acetate (100 mL), washed sequentially with 10% LiCl, water and brine, and dried over anhydrous magnesium sulfate. The solvent was removed in vacuo and the resulting material was purified by silica gel chromatography (ethyl acetate/heptane, 25 min gradient: 5-50% ethyl acetate) to provide 0.27 g of 3-bromo-6-chloro-N-(4-methoxybenzyl)-N-phenylimidazo[1,2-b]pyridazin-8-amine.

(1b) A microwave vial was charged with 3-bromo-6-chloro-N-(4-methoxybenzyl)-N-phenylimidazo[1,2-b]pyridazin-8-amine (220 mg, 0.49 mmol) from step 1a, zinc cyanide (34.8 mg, 0.3 mmol), Tris(dibenzylideneaceton)dipalladium(0) (22.7 mg, 0.025 mmol), 1,1'-Bis(diphenylphosphino)ferrocene (19.8 mg, 0.036 mmol) and DMF (2 mL). The resulting mixture was heated in a microwave for 15 min at 150° C. The solution was cooled, diluted with ethyl acetate, washed with saturated LiCl solution, dried over anhydrous magnesium sulfate and concentrated in vacuo. The resulting residue was purified silica gel chromatography (5% ethyl acetate/heptane) to provide 91 mg of 6-chloro-3-cyano-N-(4-methoxybenzyl)-N-phenylimidazo[1,2-b]pyridazin-8-amine (1c) A mixture of 6-chloro-3-cyano-N-(4-methoxybenzyl)-N-phenylimidazo[1,2-b]pyridazin-8-amine (20 mg, 0.05 mmol) from 1b, tert-butyl(trans)-4-hydroxycyclohexylcarbamate (22 mg, 0.1 mmol), palladium(II) acetate (1.1 mg, 0.005 mmol), 1,2,3,4,5-Pentaphenyl-1'-(di-tert-butylphosphino)ferrocene (7.5, 0.01 mmol) and cesium carbonate (100 mg) was suspended in anhydrous dioxane (1 mL) in a Teflon lined septum capped vial. The vessel was purged with argon and heated at 105° C. for 48 h. LCMS shows that product (m/z, M+1, 569.4) is present (~25% conversion) along with starting materials. The reaction is cooled and filtered thru a plug of celite and the celite pad rinsed with ~5 ml of ethyl acetate. The solvents are removed in vacuo and the resulting oil suspended in 1 mL of TFA and heated at 50° C. of 2 h. The reaction showed complete removal of the p-methoxybenzyl protecting group. TFA is removed under a stream of air and the resulting mixture taken up in MeOH (2 mL) and purified by preparative HPLC to yield 2.2 mg of the titled compound as a TFA salt. MS m/e 349 (M+1); 1H NMR (MeOH, δ) 8.1 (1H, s), 7.48 (2H, t, J=8 Hz), 7.39 (2H, d, J=8 Hz), 7.27 (1H, t, J=8 Hz), 6.21 (1H, s), 5.00 1H, m), 3.21 (1H, m), 2.38 (2H, m), 2.15, 2H, m), 1.62 (4H, m).

Example XXXII(1)

6-((trans-4-aminocyclohexyl)amino)-8-anilinoimidazo[1,2-b]pyridazine-3-carboxamide

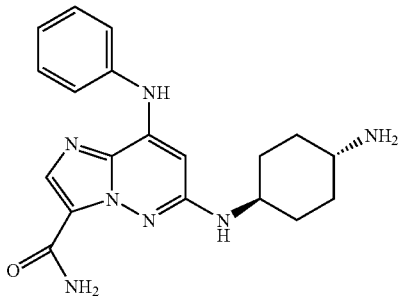

(1a) A mixture of 6-chloro-3-cyano-N-(4-methoxybenzyl)-N-phenylimidazo[1,2-b]pyridazin-8-amine (25 mgs) from Example XXXI(1) step 1b, 6N NaOH (0.1 mL), MeOH (0.1 mL) and dioxane (1 mL) in a vial was heated to 100° C. for 16 h. The mixture was cooled to room temperature and concentrated in vacuo. Upon addition of 1M HCl a precipitate forms. The precipitate was collected by filtration and dried to provide 35 mgs of crude 6-chloro-8-((4-methoxybenzyl)(phenyl)amino)imidazo[1,2-b]pyridazine-3-carboxamide.

(1b) To a vial containing crude 6-chloro-8-((4-methoxybenzyl)(phenyl)amino)imidazo[1,2-b]pyridazine-3-carboxamide 35 mgs from 1a was added trans-1,4-cyclohexyldiamine (250 mgs, mmol). The resulting mixture was heated to 160° C. for 4 h. The mixture was cooled to room temperature and diluted with water causing a precipitate to form. The precipitate was collected, washed with water and dried to give crude 6-((trans)-4-aminocyclohexylamino)-8-((4-methoxybenzyl)(phenyl)amino)imidazo[1,2-b]pyridazine-3-carboxamide.

(1c) Crude 6-((trans)-4-aminocyclohexylamino)-8-((4-methoxybenzyl)(phenyl)amino)imidazo[1,2-b]pyridazine-3-carboxamide from 1b was suspended in trifluoracetic acid (1 mL) and heated to 50° C. for 2 h. The mixture was cooled to room temperature and the trifluoractic acid was evaporated under a stream of nitrogen. The residue was suspended in methanol, filtered to remove solids and purified by prep HPLC to provide 2.1 mg of the titled compound as a TFA salt. MS m/e 366 (M+1); 1H NMR (MeOH, δ) 8.1 (1H, s), 7.46 (2H, t, J=8 Hz), 7.39 (2H, d, J=8 Hz), 7.23 (1H, t, J=8 Hz), 6.31 (1H, s), 3.62 (1H, m), 3.17 (1H, m), 2.30 (2H, m), 2.13, (2H, m), 1.55 (2H, m), 1.42 (2H, m).

Example XXXIII(1)

$N^6$-(trans-4-aminocyclohexyl)-7-ethyl-$N^8$-phenylimidazo[1,2-b]pyridazine-6,8-diamine

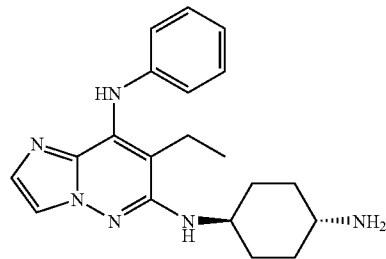

(1a) To a suspension of 3,6-dichloropyridazine (11.25 g, 0.076 mol, 1.0 eq), silver nitrate (6.41 g, 0.038 mol, 0.5 eq), propionic acid (8.39 g, 0.113 mol, 1.5 eq) in water (125 mL) at 50° C. was added a solution of sulfuric acid (11.54 mL, 0.227 ml. 3.0 eq) in water (125 mL). The solution was heated to 60° C. and then a solution of ammonium persulfate (51.7 g, 0.227 mol, 3.0 eq) was added in slowly in 20 minutes. The solution was then heated to 75° C. for 30 minutes. The reaction solution was poured into ice water and adjusted to pH 7 with 30% ammonium hydroxide solution. The mixture was extracted with dichloromethane (3×), and the extracts washed with water, brine, dried with sodium sulfate and concentrated in vacuo. The resulting residue was purified using an ISCO chromatography system (120 g silica cartridge, 5% ethyl acetate in heptane) to provide the compound 3,6-dichloro-4-ethylpyridazine (7.3 g, 54% yield). LC/MS, m/e 177.15 (M+1). HPLC Rt, 2.03 min. Waters Sunfire C18 column (4.6×50 mm). 0%-100% B. Solvent B: (90% MeOH, 10% H$_2$O, 0.1% TFA). Solvent A: (10% MeOH, 90% H$_2$O, 0.1%

TFA). Gradient, start % B=0, final % B=100, gradient time 4 min, hold at 100% B 1 min, flow rate 4 mL/min.

(1b) 3,6-Dichloro-4-ethylpyridazine (3.5 g, 0.020 mol) from 1a was suspended in aqueous 28% NH₄OH (12 mL) in a sealed microwave tube and heated at 145° C. for 1 h. The reaction solution was cooled and then heated once more at 145° C. for 1 h. The microwave tube was uncapped and allowed to stir at room temperature for 30 min and in an ice bath for 30 min. The solid that crashed out was filtered and then washed with ice water and dried to give 3.5 g of a mixture of the desired 6-chloro-5-ethylpyridazin-3-amine and the 6-chloro-4-ethylpyridazin-3-amine regioisomer LC/MS, m/e 158.19 (M+1). HPLC Rt, 0.78 min. Waters Sunfire C18 column (4.6×50 mm). 0%-100% B. Solvent B: (90% MeOH, 10% H₂O, 0.1% TFA). Solvent A: (10% MeOH, 90% H₂O, 0.1% TFA). Gradient, start % B=0, final % B=100, gradient time 4 min, hold at 100% B 1 min, flow rate 4 mL/min.

(1c) The mixture of 6-Chloro-5-ethylpyridazin-3-amine and chloro-4-ethylpyridazin-3-amine (3.50 g, 0.022 mol) from 1b and NaHCO₃ (3.73 g, 0.044 mol, 2 eq) were suspended in MeOH (20 mL) and treated with Br₂ (1.25 mL, 0.024 mol). The mixture was stirred at room temperature for 24 h, then filtered. The filtrate was condensed in vacuo. The resulting residue was resuspended in EtOAc (100 mL) and washed sequentially with sat. aqueous NaHCO₃ solution (2×20 mL) and aqueous NaCl solution (1×20 mL). The solution was dried over sodium sulfate. The solvent was removed in vacuo to give crude 4-bromo-6-chloro-5-ethylpyridazin-3-amine. LC/MS, m/e 236 (M+1). HPLC Rt, 2.15 min. Waters Sunfire C18 column (4.6×50 mm). 0%-100% B. Solvent B: (90% MeOH, 10% H₂O, 0.1% TFA). Solvent A: (10% MeOH, 90% H₂O, 0.1% TFA). Gradient, start % B=0, final % B=100, gradient time 4 min, hold at 100% B 1 min, flow rate 4 mL/min.

(1d) Chloroacetaldehyde (17.26 ml, 0.111 mol, 50% in H₂O) was added to a solution of crude 4-bromo-6-chloro-5-ethylpyridazin-3-amine (5.23 g, 0.022 mol) from 1c in EtOH (30 mL). The mixture was heated in a sealed vial at 50° C. for 24 h. Solvent was removed in vacuo and the solid was resuspended in acetone/Et₂O (1/1, 5 mL), filtered, and then washed with Et₂O to give 8-bromo-6-chloro-7-ethylimidazo[1,2-b]pyridazine as an HCl salt (3.02 g, >80% pure). LC/MS, m/e 260 (M+1). HPLC Rt, 2.68 min. Waters Sunfire C18 column (4.6×50 mm). 0%-100% B. Solvent B: (90% MeOH, 10% H₂O, 0.1% TFA). Solvent A: (10% MeOH, 90% H₂O, 0.1% TFA). Gradient, start % B=0, final % B=100, gradient time 4 min, hold at 100% B 1 min, flow rate 4 mL/min.

(1e) A mixture of 8-bromo-6-chloro-7-ethylimidazo[1,2-b]pyridazine (60 mg, 0.2 mmol, 1 eq) from 1d, aniline (20.3 µL, 0.22 mmol, 1.1 eq) and potassium tert-butoxide (0.51 mL, 0.51 mmol, 2.5 eq) were suspended in DMF (3 mL) and stirred at RT for 1 h. The mixture was quenched with ethyl acetate and washed with lithium chloride saturated solution, dried with sodium sulfate and concentrated in vacuo. The residue was purified using an ISCO chromatography system (4 g silica cartridge, 5% ethyl acetate in heptane) to provide 6-chloro-N-phenyl-7-ethylimidazo[1,2-b]pyridazin-8-amine (22 mg). LC/MS, m/e 273.14 (M+1). HPLC Rt, 2.24 min. Waters Sunfire C18 column (4.6×50 mm). 0%-100% B. Solvent B: (90% MeOH, 10% H₂O, 0.1% TFA). Solvent A: (10% MeOH, 90% H₂O, 0.1% TFA). Gradient, start % B=0, final % B=100, gradient time 4 min, hold at 100% B 1 min, flow rate 4 mL/min.

(1f) 6-Chloro-N-phenyl-7-ethylimidazo[1,2-b]pyridazin-8-amine (22 mg, 0.08 mmol) from 1e and trans-1,4-diaminohexane (230 mg) were combined and heated at 165° C. for 4 days. The mixture was cooled to room temperature, then diluted with methanol. The resulting residue was purified using preparative HPLC to give the titled compound as a TFA salt (18.9 mg, 66%). ¹H NMR (500 MHz, CD₃OD) δ 7.95 (d, 1H), 7.62 (d, 1H), 7.27 (t, J=7.4 Hz, 2H), 7.0 (t, J=7.4 Hz, 1H), 6.85 (d, J=8.2 Hz, 2H), 4.0 (m, 1H), 3.20 (m, 1H), 2.79 (m, 2H), 2.25 (m, 2H), 2.14 (m, 2H), 1.58 (m, 4H), 1.13 (t, J=7.2 Hz, 3H). LC/MS, m/e 351 (M+1). HPLC Rt, 1.67 min. Waters Sunfire C18 column (4.6×50 mm). 0%-100% B. Solvent B: (90% MeOH, 10% H₂O, 0.1% TFA). Solvent A: (10% MeOH, 90% H₂O, 0.1% TFA). Gradient, start % B=0, final % B=100, gradient time 4 min, hold at 100% B 1 min, flow rate 4 mL/min.

Compounds having the formula (Ia) were prepared according to procedures similar to Example XXXIII(1), where in $R_1$, $R_2$, $R_3$, X and Y have the values listed in Table 13, using the appropriate starting materials and substantially the same procedures as indicated.

TABLE 13

| Exp | Name | $R_1$ | $R_2$ | $R_3$ | X | Y | LC/MS m/z (M + 1) |
|---|---|---|---|---|---|---|---|
| XXXIII(2) | N⁶-(trans-4-aminocyclohexyl)-7-isopropyl-N⁸-phenylimidazo[1,2-b]pyridazine-6,8-diamine | H | H | i-Pr | NH—phenyl | NH⋯cyclohexyl—NH₂ | 365 |
| XXXIII(3) | N⁶-(trans-4-Aminocyclohexyl)-7-benzyl-N⁸-phenylimidazo[1,2-b]pyridazine-6,8-diamine | H | H | CH₂Ph | NH—phenyl | NH⋯cyclohexyl—NH₂ | 365 |
| XXXIII(4) | 3-((6-((trans-4-Aminocyclohexyl)amino)-7-isopropylimidazo[1,2-b]pyridazin-8-yl)amino)-N-ethylbenzenesulfonamide | H | H | i-Pr | NH—phenyl-SO₂NHEt | NH⋯cyclohexyl—NH₂ | 472 |

TABLE 13-continued

| Exp | Name | R1 | R2 | R3 | X | Y | LC/MS m/z (M + 1) |
|---|---|---|---|---|---|---|---|
| XXXIII(5) | 4-((6-((trans-4-Aminocyclohexyl)amino)-7-isopropylimidazo[1,2-b]pyridazin-8-yl)amino)-N-ethylbenzenesulfonamide | H | H | i-Pr | NH—C6H4—SO2NHEt | NH—cyclohexyl—NH2 | 472 |
| XXXIII(6) | 4-((6-((trans-4-Aminocyclohexyl)amino)-7-isopropylimidazo[1,2-b]pyridazin-8-yl)amino)-N-phenylbenzamide | H | H | i-Pr | NH—C6H4—C(O)NH-Ph | NH—cyclohexyl—NH2 | 484 |
| XXXIII(7) | $N^6$-(trans-4-Aminocyclohexyl)-7-isopropyl-$N^8$-3-pyridinylimidazo[1,2-b]pyridazine-6,8-diamine | H | H | i-Pr | NH—(3-pyridinyl) | NH—cyclohexyl—NH2 | 366 |
| XXXIII(8) | $N^6$-(trans-4-Aminocyclohexyl)-$N^8$-(3-ethoxyphenyl)-7-isopropylimidazo[1,2-b]pyridazine-6,8-diamine | H | H | i-Pr | NH—C6H4—OMe (3-) | NH—cyclohexyl—NH2 | 409 |
| XXXIII(9) | $N^6$-(trans-4-Aminocyclohexyl)-$N^8$-(4-ethoxyphenyl)-7-isopropylimidazo[1,2-b]pyridazine-6,8-diamine | H | H | i-Pr | NH—C6H4—OMe (4-) | NH—cyclohexyl—NH2 | 409 |
| XXXIII(10) | 4-((6-((trans-4-Aminocyclohexyl)amino)-7-isopropylimidazo[1,2-b]pyridazin-8-yl)amino)phenol | H | H | i-Pr | NH—C6H4—OH | NH—cyclohexyl—NH2 | 381 |

Example XXXV(1)

$N^6$-(trans-4-Aminocyclohexyl)-$N^8$-(4-(aminomethyl)phenyl)-7-methylimidazo[1,2-b]pyridazine-6,8-diamine

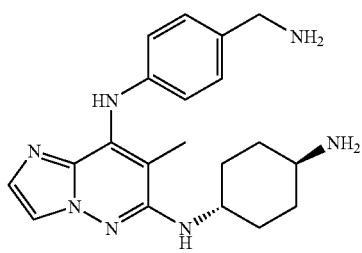

(1a) To a mixture of free based 8-bromo-6-chloroimidazo[1,2-b]pyridazine from Example 1, step 1b (100 mg, 0.35 mmol) in THF (1.0 ml) was added p-cyanoaniline (42 mg, 0.35 mmol) and a 1.0 M solution of KOt-Bu in THF (3.0 eq, 1.05 ml, 1.05 mmol). The mixture was allowed to heat at 50° C. for 1 hour. The solution was then concentrated in vacuo to dryness to provide 4-(6-chloro-7-methylimidazo[1,2-b]pyridazin-8-ylamino)benzonitrile as a solid m/e 284 (MH+)

(1b) To 4-(6-chloro-7-methylimidazo[1,2-b]pyridazin-8-ylamino)benzonitrile from step (1a) was added trans-1,4-diaminocyclohexane (500 mg, 4.38 mmol). The mixture was allowed to melt at 165° C. for 24 hours. The melt was then cooled, water added, followed by extraction with dichloromethane. The organic layer was concentrated in vacuo and purified by preparative HPLC to provide 4-(6-(4-trans-aminocyclohexylamino)-7-methylimidazo[1,2-b]pyridazin-8-ylamino)benzonitrile 42 mg (20%) as a TFA salt. m/e 362 (MH+).

(1c) To 4-(6-(4-trans-aminocyclohexylamino)-7-methylimidazo[1,2-b]pyridazin-8-ylamino)benzonitrile (42 mg, 0.071 mmol) from step (1b) in 2N ammonia in MeOH (10 ml) was added palladium on carbon (50 mg). The reaction mixture was allowed to shake in a PARR apparatus for 16 hours at 55 psi of hydrogen. The catalyst was filtered and the filtrate was concentrated in vacuo. The resulting residue was purified by preparative HPLC to give 5.3 mg (10%) of the titled compound as a TFA salt. NMR (500 MHz, MeOH) δ ppm 8.01 (1H, d, J=2.0 Hz), 7.73 (1H, d, J=2.0 Hz), 7.36 (2H, d, J=8.5 Hz), 6.86 (2H, d, J=8.5 Hz), 4.04 (2H, s), 3.97 (1H, m), 3.17 (1H, m), 2.27 (2H, m), 2.15 (2H, m), 2.12 (3H, s), 1.57 (4H, m). LC/MS, m/e 366 (M+1). HPLC Rt, 0.91 min. Waters Sunfire C18 column (4.6×50 mm). 0%-100% B. Solvent B: (90% MeOH, 10% H2O, 0.1% TFA). Solvent A: (10% MeOH, 90% H2O, 0.1% TFA). Gradient, start % B=0, final % B=100, gradient time 4 min, hold at 100% B 1 min, flow rate 4 mL/min.

Example XXXVI(1)

6-(3-Amino-1,2-benzisoxazol-5-yl)-N-phenylimidazo[1,2-b]pyridazin-8-amine

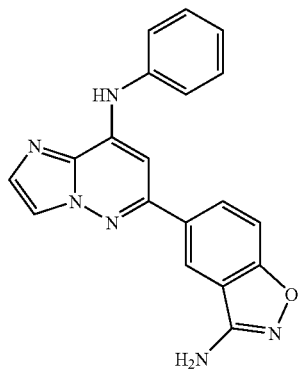

(1a) A solution of potassium t-butoxide in THF (4.73 mL, 4.73 mmol) was added dropwise to a solution of N-(4-methoxybenzyl)aniline (0.92 g, 4.3 mmol) in THF (10 mL) at 0° C. The solution was warmed to RT for 15 minutes, recooled to 0° C. and a solution of 8-bromo-6-chloroimidazo[1,2-b]pyridazine (1.0 g, 4.30 mmol) from Example 1, step 1b, in THF (10 mL) was added in rapidly. The solution was stirred at 0° C. for 30 minutes and then at RT for 30 minutes. The reaction solution was concentrated in vacuo. The resulting residue was purified by flash chromatography eluting with 10% ethyl acetate/heptane to provide 0.75 g (48%) of 6-chloro-N-(4-methoxybenzyl)-N-phenyl imidazo[1,2-b]pyridazin-8-amine.

(1b) To a vial was added 6-chloro-N-(4-methoxybenzyl)-N-phenyl imidazo[1,2-b]pyridazin-8-amine (150 mg, 0.411 mmol) from (1a), 3-cyano-4-fluorophenylboronic acid (74.6 mg, 0.452 mmol), potassium phosphate (174 mg, 0.822 mmol), tris(dibenzylideneacetone)dipalladium (2.0 mg, 0.002 mmol) and 1,2,3,4,5-pentaphenyl-1'-(di-t-butylphosphino)ferrocene (CTC-Q-Phos) (5.8 mg, 0.008 mmol) in toluene (2 mL) under nitrogen. The solution was heated to 100° C. for 10 hours. After checking the reaction solution which showed no reaction, more palladium reagent (2.0 mg), ligand (5.8 mg) and boronic acid (74.6 mg) were added. After heating at 100° C. for another 24 hours, the reaction went to completion with no SM left. The crude product mixture was filtered through celite, concentrated in vacuo to provide 2-fluoro-5-(8-((4-methoxybenzyl)(phenyl)amino)imidazo[1,2-b]pyridazin-6-yl)benzonitrile which was used as is in the next reaction. LC/MS, m/e 450 (M+1). HPLC Rt, 3.60 min. Waters Sunfire C18 column (4.6×50 mm). 0%-100% B. Solvent B: (90% MeOH, 10% $H_2O$, 0.1% TFA). Solvent A: (10% MeOH, 90% $H_2O$, 0.1% TFA). Gradient, start % B=0, final % B=100, gradient time 4 min, hold at 100% B 1 min, flow rate 4 mL/min.

(1c) To a solution of acetohydroxamic acid (42 mg, 0.556 mmol) in DMF (1 mL) was added a solution of potassium t-butoxide in THF (0.56 mL, 0.56 mmol). The reaction solution was stirred at RT for 15 minutes and then a solution of 2-fluoro-5-(8-((4-methoxybenzyl)(phenyl)amino)imidazo[1,2-b]pyridazin-6-yl)benzonitrile (25 mg, 0.056 mmol) from (1b) in DMF (1 mL) was added. The reaction solution was stirred at RT for 24 hours. The solution was diluted with methanol and purified by preparative HPLC to give 5-(8-((4-methoxybenzyl)(phenyl)amino)imidazo[1,2-b]pyridazin-6-yl)benzo[d]isoxazol-3-amine. LC/MS, m/e 463 (M+1). HPLC Rt, 3.13 min. Waters Sunfire C18 column (4.6×50 mm). 0%-100% B. Solvent B: (90% MeOH, 10% $H_2O$, 0.1% TFA). Solvent A: (10% MeOH, 90% $H_2O$, 0.1% TFA). Gradient, start % B=0, final % B=100, gradient time 4 min. hold at 100% B 1 min, flow rate 4 mL/min.

(1d) To a solution of 5-(8-((4-methoxybenzyl)(phenyl)amino)imidazo[1,2-b]pyridazin-6-yl)benzo[d]isoxazol-3-amine from (1c) was added TFA (1 mL) and the solution stirred at RT for 1 hour. The reaction solution was concentrated in vacuo, diluted with methanol and purified by preparative HPLC to provide the titled compound (13.20 mg, 70%). $^1$H NMR (500 MHz, $CD_3OD$) δ ppm 8.3 (1H, s), 8.21 (1H, d=2.2 Hz), 8.11 (1H, m), 7.97 (1H, m), 7.52 (4H, m), 7.3 (1H, m), 7.1 (1H, m), 7.07 (1H, d, J=8.8 Hz). LC/MS, m/e 343 (M+1). HPLC Rt, 2.63 min. Waters Sunfire C18 column (4.6×50 mm). 0%-100% B. Solvent B: (90% MeOH, 10% $H_2O$, 0.1% TFA). Solvent A: (10% MeOH, 90% $H_2O$, 0.1% TFA). Gradient, start % B=0, final % B=100, gradient time 4 min, hold at 100% B 1 min, flow rate 4 mL/min.

Example XXXVII(1)

6-(3-Amino-1,2-benzisoxazol-6-yl)-N-phenylimidazo[1,2-b]pyridazin-8-amine

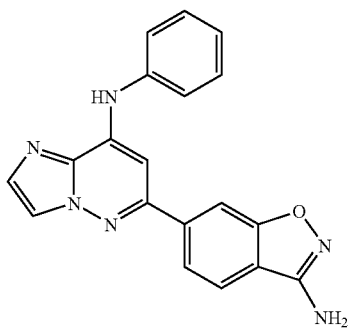

(1a) To a vial was added 6-chloro-N-(4-methoxybenzyl)-N-phenyl imidazo[1,2-b]pyridazin-8-amine (100 mg, 0.274 mmol) from Example XXXVI(1) step (1a), 4-cyano-3-fluorophenylboronic acid (49.7 mg, 0.302 mmol), tetrakis(triphenylphosphine) palladium (17.4 mg, 0.015 mmol) and cesium carbonate (295 mg, 0.905 mmol in water (0.2 mL)) and DMF (2 mL). The solution was heated to 100° C. for 10 hours. The crude product mixture was filtered through celite, concentrated in vacuo and purified by preparative HPLC to give 2-fluoro-4-(8-((4-methoxybenzyl)(phenyl)amino)imidazo[1,2-b]pyridazin-6-yl)benzonitrile (30 mg, 24%). LC/MS, m/e 463 (M+1). HPLC Rt, 3.80 min. Waters Sunfire C18 column (4.6×50 mm). 0%-100% B. Solvent B: (90% MeOH, 10% $H_2O$, 0.1% TFA). Solvent A: (10% MeOH, 90% $H_2O$, 0.1% TFA). Gradient, start % B=0, final % B=100, gradient time 4 min hold at 100% B 1 min, flow rate 4 mL/min.

(1b) To a solution of acetohydroxamic acid (50 mg, 0.667 mmol) in DMF (1 mL) was added a solution of potassium t-butoxide in THF (0.667 mL, 0.667 mmol). The reaction solution was stirred at RT for 15 minutes and then a solution of 2-fluoro-4-(8-((4-methoxybenzyl)(phenyl)amino)imidazo[1,2-b]pyridazin-6-yl)benzonitrile (30 mg, 0.067 mmol) from (X) in DMF (1 mL) was added. The reaction solution was stirred at RT for 24 hours. The solution was diluted with methanol and purified by preparative HPLC to give 6-(8-((4-methoxybenzyl)(phenyl)amino)imidazo[1,2-b]pyridazin-6-yl)benzo[d]isoxazol-3-amine. LC/MS, m/e 463 (M+1). HPLC Rt, 3.08 min. Waters Sunfire C18 column (4.6×50 mm). 0%-100% B. Solvent B: (90% MeOH, 10% $H_2O$, 0.1% TFA). Solvent A: (10% MeOH, 90% $H_2O$, 0.1% TFA). Gradient, start % B=0, final % B=100, gradient time 4 min. hold at 100% B 1 min, flow rate 4 mL/min.

(1c) To a solution of 6-(8-((4-methoxybenzyl)(phenyl)amino)imidazo[1,2-b]pyridazin-6-yl)benzo[d]isoxazol-3-amine from (1b) was added TFA (1 mL) and the solution stirred at RT for 1 hour. The reaction solution was concentrated in vacuo and then diluted with methanol and purified by preparative HPLC to provide the titled compound (3.90 mg, 17%). $^1$H NMR (500 MHz, $CD_3OD$) δ ppm 8.26 (1H, s), 7.92 (1H, s), 7.86 (1H, d, J=8.6 Hz), 7.80 (1H, d, J=8.25 Hz), 7.52 (4H, m), 7.35 (1H, t, J=7.15 Hz), 7.27 (1H, s). LC/MS, m/e 343 (M+1). HPLC Rt, 2.52 min. Waters Sunfire C18 column (4.6×50 mm). 0%-100% B. Solvent B: (90% MeOH, 10% $H_2O$, 0.1% TFA). Solvent A: (10% MeOH, 90% $H_2O$, 0.1% TFA). Gradient, start % B=0, final % B=100, gradient time 4 min, hold at 100% B 1 min, flow rate 4 mL/min.

Example XXXVIII(1)

$N^6$-(trans-4-Aminocyclohexyl)-7-(3-chlorophenyl)-$N^8$-phenylimidazo[1,2-b]pyridazine-6,8-diamine

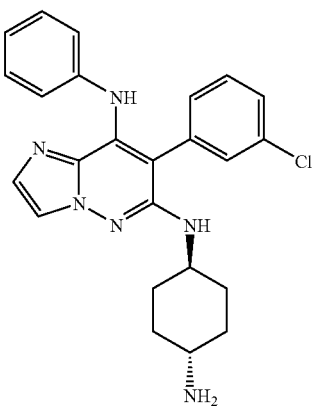

(1a) To a flask was added ethyl 2-(3-chlorophenyl)-2-oxoacetate (1.8 g, 8.47 mmol) and acetic anhydride (1.60 ml, 16.93 mmol) in DCE (5 ml) at RT. To the resulting solution was added titanium(IV) chloride (16.93 ml, 16.93 mmol) and tributylamine (2.42 ml, 10.16 mmol). The solution was heated to reflux for 12 hours. The solution was then cooled in ice, and a solution of ammonium chloride was added. The mixture was stirred for 30 min. LC/MS indicated all starting material was gone. The solution was washed with 1×$NH_4Cl$, 1N HCl, water, dried and concentrated in vacuo to provide 3-(3-chlorophenyl)furan-2,5-dione which was used as is in the next reaction. LC/MS, m/e 209 (M+1). HPLC Rt, 2.89 min. Waters Sunfire C18 column (4.6×50 mm). 0%-100% B. Solvent B: (90% MeOH, 10% $H_2O$, 0.1% TFA). Solvent A: (10% MeOH, 90% $H_2O$, 0.1% TFA). Gradient, start % B=0, final % B=100, gradient time 4 min. hold at 100% B 1 min, flow rate 4 mL/min.

(1b) To a 25 mL flask was added 3-(3-chlorophenyl)furan-2,5-dione (1.7 g, 8.15 mmol) from (1a) and hydrazine hydrate (0.476 mL, 9.78 mmol) in water (6 mL) and acetic acid (4 mL). The resulting mixture was refluxed for 18 hours. The solution was cooled and placed in the refrigerator for 1 hour. The resulting precipitate was filtered and dried, then purified by flash chromatography eluting with 5% methanol/dichloromethane to give 4-(3-chlorophenyl)pyridazine-3,6-diol.

(1c) To a vial was added 4-(3-chlorophenyl)pyridazine-3,6-diol (0.2 g, 0.898 mmol) from (1b) and phosphorus oxychloride (0.837 mL, 8.98 mmol). The reaction was stirred for 24 h at 100° C. The excess reagent was removed in vacuo and the residue was dissolved in dichloromethane, washed 2× with sodium bicarbonate solution, dried and concentrated to give 3,6-dichloro-4-(3-chlorophenyl)pyridazine (0.43 g). LC/MS, m/e 258 (M+1). HPLC Rt, 3.22 min. Waters Sunfire C18 column (4.6×50 mm). 0%-100% B. Solvent B: (90% MeOH, 10% $H_2O$, 0.1% TFA). Solvent A: (10% MeOH, 90% $H_2O$, 0.1% TFA). Gradient, start % B=0, final % B=100, gradient time 4 min. hold at 100% B 1 min, flow rate 4 mL/min.

(1d) 3,6-dichloro-4-(3-chlorophenyl)pyridazine from (1c) was processed as described in Example XIII (1) steps (1a-e) to provide the titled compound (4.9 mgs, 27%). $^1$H NMR (500 MHz, $CD_3OD$) δ ppm 8.04 (1H, s), 7.75 (1H, s), 7.46 (2H, d, J=8.80 Hz), 7.29 (2H, d, J=8.25 Hz), 7.19 (2H, t, J=7.97 Hz), 7.02 (1H, t, J=7.42 Hz), LC/MS, m/e 433 (M+1). HPLC Rt, 2.28 min. Waters Sunfire C18 column (4.6×50 mm). 0%-100% B. Solvent B: (90% MeOH, 10% $H_2O$, 0.1% TFA). Solvent A: (10% MeOH, 90% $H_2O$, 0.1% TFA). Gradient, start % B=0, final % B=100, gradient time 4 min, hold at 100% B 1 min, flow rate 4 mL/min.

Compounds having the formula (Ia) were prepared according to procedures similar to Example XXXVIII(1), where in $R_1$, $R_2$, $R_3$, X and Y have the values listed in Table 14, using the appropriate starting materials and substantially the same procedures as indicated.

TABLE 14

| Exp | Name | $R_1$ | $R_2$ | $R_3$ | X | Y | LC/MS m/z (M + 1) |
|---|---|---|---|---|---|---|---|
| | $N^6$-(trans-4-Aminocyclohexyl)-7-(4-chlorophenyl)-$N^8$-phenylimidazo[1,2-b]pyridazine-6,8-diamine | H | H | 4-PhCl | NH—⟨phenyl⟩— | NH⋯⟨cyclohexyl⟩—$NH_2$ | 434 |

*For substituents X and Y, substitution on the core (formula Ia) occurs at the available nitrogen atom

Example XXXIX(1)

8-Anilino-6-((3S)-3-piperidinylamino)imidazo[1,2-b]pyridazine-3-carbonitrile

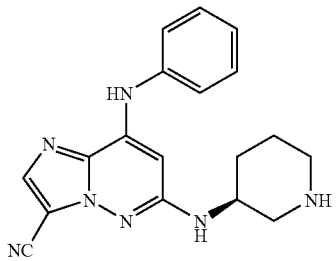

(1a) 6-Chloro-8-((4-methoxybenzyl)(phenyl)amino)imidazo[1,2-b]pyridazine-3-carbonitrile (100 mg, 0.257 mmol) from example XXXI, step (1b) and (S)-3-amino-1-benzylpiperidine (195 mg, 1.026 mmol) were combined in a 1-dram vial and heated at 160° C. for 6 h. The reaction was cooled to room temperature, dissolved in DCM (2 mL) and loaded onto to a 12 g silica gel column and eluted with 5%-100% EtOAc/heptane to give (S)-6-(1-benzylpiperidin-3-ylamino)-8-((4-methoxybenzyl)(phenyl)amino)imidazo[1,2-b]pyridazine-3-carbonitrile (55 mg, 40%). LCMS m/z (544, M+1).

(1b) 6-(1-Benzylpiperidin-3-ylamino)-8-((4-methoxybenzyl)(phenyl)amino)imidazo[1,2-b]pyridazine-3-carbonitrile from step (1a) (50 mg, 0.092 mmol) was dissolved in DCE (2 ml) and treated with 1-chloroethyl chloroformate (0.030 ml, 0.276 mmol). The mixture was heated at 85° C. overnight. The solvent was removed in vacuo to give a slurry that was suspended in MeOH (2 mL). The mixture was heated at 85° C. for 5 h. The mixture was cooled to room temperature. and purified on a reverse-phase HPLC to give the titled compound (17 mg, 0.039 mmol, 42.9%) as a TFA salt. LCMS, m/z (334, M+1). HPLC Rt, 2.47 min. Sunfire C18 column (4.6×50 mm). 0%-100% B. Solvent B: (90% MeOH, 10% $H_2O$, 0.1% TFA). Solvent A: (10% MeOH, 90% $H_2O$, 0.1% TFA). Gradient, start % B=0, final % B=100, gradient time 4 min, hold at 100% B 1 min, flow rate 4 mL/min. 1H NMR (400 MHz, MeOD) δ ppm 7.96 (s, 1H), 7.39-7.48 (m, 2H), 7.33-7.38 (m, 2H), 7.18-7.24 (m, 1H), 6.27 (s, 1H), 4.11 (m, 1H), 3.64 (m, 1H), 3.25 (m, 1H), 3.01 (m, 2H), 2.02-2.14 (m, 2H), 1.78-1.90 (m, 1H), 1.62-1.72 (m, 1H).

Example XL(1)

3-((6-((trans-4-Aminocyclohexyl)amino)-7-isopropylimidazo[1,2-b]pyridazin-8-yl)amino)phenol

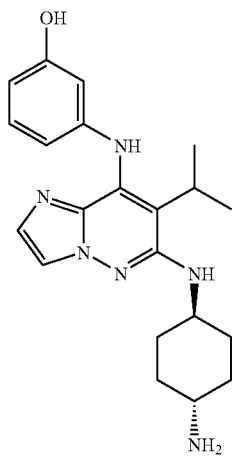

(1a) To a vial was added N6-(4-trans-aminocyclohexyl)-N8-(3-(benzyloxy)phenyl)-7-(isopropyl)imidazo[1,2-b]pyridazine-6,8-diamine (20.2 mg, 0.043 mmol) prepared by the method described in Example XXXIII(1) in dichloromethane (2 mL). To the reaction solution at RT was added a solution of boron tribromide (0.1 mL, 1M). The reaction was stirred for 1 h at RT. The solution was quenched with methanol, concentrated in vacuo and purified by preparative HPLC to provide the titled compound (10.50 mg, 65%). $^1$H NMR (500 MHz, $CD_3OD$) δ ppm 8.00 (1H, s), 7.64 (1H, s), 7.04 (1H, m), 6.20 (3H, m), 4.03 (1H, m), 3.21 (1H, m), 2.5 (1H, m), 2.27 (2H, m), 2.05 (2H, m), 1.56-1.65 (4H, m), 1.38 (6H, d, J=7.15 Hz). LC/MS, m/e 381 (M+1). HPLC Rt, 1.63 min. Waters Sunfire C18 column (4.6×50 mm). 0%-100% B. Solvent B: (90% MeOH, 10% $H_2O$, 0.1% TFA). Solvent A: (10% MeOH, 90% $H_2O$, 0.1% TFA). Gradient, start % B=0, final % B=100, gradient time 4 min, hold at 100% B 1 min, flow rate 4 mL/min.

Example LXI(1)

$N^6$-(trans-4-Aminocyclohexyl)-3-cyclopropyl-$N^8$-phenylimidazo[1,2-b]pyridazine-6,8-diamine

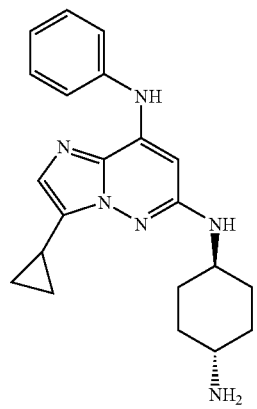

(1a) 3-Bromo-6-chloro-N-(4-methoxybenzyl)-N-phenylimidazo[1,2-b]pyridazin-8-amine (200 mg, 0.45 mmol) from Example XXXI, step (1a) and trans-1,4-cyclohexanediamine (1.1 g, 9.6 mmol) in NMP (2 mL) were heated in a microwave reactor at 200° C. for 1 h. After cooling to room temperature, the resulting mixture was poured into water and the resulting solid was collected and dried on a filter. The dry solid was dissolved in dichloromethane (4 mL) and $Boc_2O$ (159 mg) was added followed by stirring at room temperature for 1 h. Concentration and purification by flash chromatography provided tert-butyl 4-(3-bromo-8-((4-methoxybenzyl)(phenyl)amino)imidazo[1,2-b]pyridazin-6-ylamino)cyclohexylcarbamate as a light yellow solid (182 mg, 61%) LCMS [M+H]$^+$ 621.

(1b) tert-Butyl 4-(3-bromo-8-((4-methoxybenzyl)(phenyl)amino)imidazo[1,2-b]pyridazin-6-ylamino)cyclohexylcarbamate (30 mg, 0.048 mmol) from (1a) and cyclopropylboronic acid (10 mg, 0.090 mmol) in toluene were purged with argon for 15 min, then aq. $K_3PO_4$ (2M, 0.06 mL), EtOH (0.04 mL) and tetrakis(triphenylphosphine)palladium(0) were added sequentially. The mixture was heated at 120° C. for 20 h. After cooling to room temperature, the mixture was partitioned between EtOAc (20 mL) and water (5 mL) and the organic layer was washed with water, brine, dried over $MgSO_4$ and concentrated. The residue was purified by reverse phase preparative HPLC to provide tert-butyl 4-(3-cyclopropyl-8-((4-methoxybenzyl)(phenyl)amino)imidazo[1,2-b]pyridazin-6-ylamino)cyclohexylcarbamate as a cream colored oil (4.3 mg, 15%) LCMS [M+H]+ 583.

(1c) To tert-butyl 4-(3-cyclopropyl-8-((4-methoxybenzyl)(phenyl)amino)imidazo[1,2-b]pyridazin-6-ylamino)cyclohexylcarb (4 mg) from (1b) in dichloromethane at room temperature was added TFA and the resulting mixture was stirred for 30 min. then concentrated. The resulting residue was purified by reverse phase preparative HPLC to provide the titled compound as a white solid (1.5 mg). $H^1$ NMR (400 MHz, MeOH-$d_4$) δ ppm 7.42 (1H, s), 7.34 (2H, m), 7.23 (3H, m), 6.30 (1H, s), 3.64 (1H, m), 3.02 (1H, m), 2.18 (2H, m), 2.00-2.17 (3H, m), 1.43 (2H, m), 1.04 (2H, m). 0.82 (2H, m). LCMS, m/e 363 (M+1). HPLC Rt, 1.82 min. YMC S5 ODSC18 column (4.6×50 mm). 0%-100% B. Solvent B: (90% MeOH, 10% $H_2O$, 0.2% $H_3PO_4$)—Solvent A: (10% MeOH, 90% $H_2O$, 0.2% $H_3PO_4$). Gradient, start % B=0, final % B=100, gradient time 4 min, hold at 100% B 1 min, flow rate 4 mL/min.

Example LXII(1)

$N^6$-(4-Aminocyclohexyl)-$N^8$-phenyl-3-((E)-2-(4-pyridinyl)vinyl)imidazo[1,2-b]pyridazine-6,8-diamine

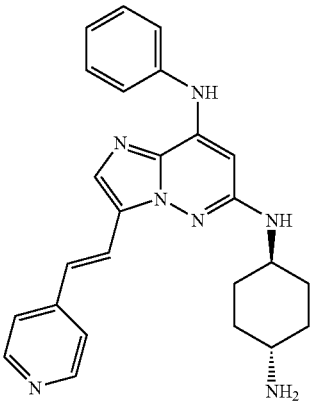

(1a) To 6-chloro-N-(4-methoxybenzyl)-N-phenylimidazo[1,2-b]pyridazin-8-amine (940 mg, 2.57 mmol) from Example X, step (1a) in chloroform (10 mL) at room temperature was added NIS in one portion and the resulting mixture was refluxed for 5 h. Concentration and purification by flash chromatography provided 6-chloro-3-iodo-N-(4-methoxybenzyl)-N-phenylimidazo[1,2-b]pyridazin-8-amine as a foamy, yellow solid (960 mg, 76%). LCMS [M+H]+ 490.

(1b) 6-chloro-3-iodo-N-(4-methoxybenzyl)-N-phenylimidazo[1,2-b]pyridazin-8-amine (120 mg, 0.25 mmol) from (1a), 4-vinylpyridine (54 μL, 0.50 mmol) and Pd(OAc)$_2$ (23 mg, 0.1 mmole) in acetonitrile (1 mL) were heated at 85° C. for 2 h. After cooling to room temperature, the mixture was partitioned between EtOAc (200 mL) and water (20 mL) and the organic layer was washed with water, brine, then dried over MgSO4 and concentrated. The resulting residue was purified by flash chromatography to provide 6-chloro-N-(4-methoxybenzyl)-N-phenyl-3-(2-(pyridin-4-yl)vinyl)imidazo[1,2-b]pyridazin-8-amine as a yellow solid (75 mg, 66%). LCMS [M+H]+ 468.

(1c) 6-chloro-N-(4-methoxybenzyl)-N-phenyl-3-(2-(pyridin-4-yl)vinyl)imidazo[1,2-b]pyridazin-8-amine (75 mg, 0.16 mmol) from (1b), sodium tert-butoxide (22 mg, 0.22 mmol), trans-1,4-cyclohexanediamine (22 mg, 0.19 mmol) and acetato(2'-di-tert-butylphosphino-1,1'-biphenyl-2-yl) palladium (II) (7.4 mg, 0.01 mmole) were purged with argon for 15 min. then toluene (0.6 mL) was added via syringe. The contents were sonicated briefly and heated at 85° C. for 2 h. After cooling to room temperature, the mixture was partitioned between EtOAc (200 mL) and water (20 mL), and the organic layer was washed with water, brine, dried over MgSO4 and concentrated. The residue was purified by reverse phase preparative HPLC to provide N6-(trans-4-aminocyclohexyl)-N8-(4-methoxybenzyl)-N8-phenyl-3-(2-(pyridin-4-yl)vinyl)imidazo[1,2-b]pyridazine-6,8-diamine as a yellow solid (32 mg, 38%). LCMS[M+H]+ 546.

(1d) To N6-(trans-4-aminocyclohexyl)-N8-(4-methoxybenzyl)-N8-phenyl-3-(2-(pyridin-4-yl)vinyl)imidazo[1,2-b]pyridazine-6,8-diamine (30 mg) from step (1c) in dichloromethane at room temperature was added excess TFA. The mixture was stirred for 30 min, concentrated, and the resulting residue was purified by reverse phase preparative HPLC to provide the titled compound as a yellow solid (21 mg). NMR (400 MHz, DMSO-$d_6$) δ ppm 9.05 (1H, s), 8.66 (2H, m), 7.78-7.90 (8H, m), 7.39-7.44 (4H, m), 7.16 (1H, m), 6.68 (1H, m), 6.26 (1H, s), 3.62 (1H, m), 3.08 (1H, m), 2.20 (2H, m), 2.02 (2H, m), 1.51-1.54 (2H, m), 1.25-1.29 (2H, m). LC/MS, m/e 426 (M+1). HPLC Rt, 1.89 min. YMC S5 ODSC18 column (4.6×50 mm). 0%-100% B. Solvent B: (90% MeOH, 10% $H_2O$, 0.2% $H_3PO_4$)—Solvent A: (10% MeOH, 90% $H_2O$, 0.2% $H_3PO_4$). Gradient, start % B=0, final % B=100, gradient time 4 min, hold at 100% B 1 min, flow rate 4 mL/min.

Example LXIII(1)

$N^6$-(trans-4-Aminocyclohexyl)-$N^8$-phenyl-3-(1-propyn-1-yl)imidazo[1,2-b]pyridazine-6,8-diamine

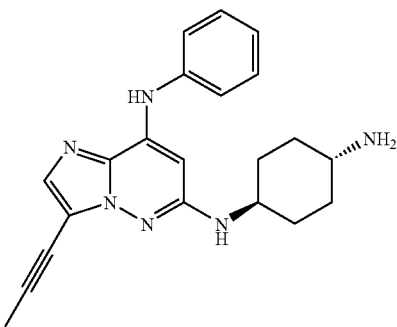

(1a) To a 2 dram vial was added trans-1,4-cyclohexyldiamine (0.040 g, 0.1 mmol) and 3-bromo-6-chloro-N-(4-methoxybenzyl)-N-phenylimidazo[1,2-b]pyridazin-8-amine (0.5 g, 4.3 mmol) from Example XXXI step (1a). The reaction was sealed and allowed to stir at 165° C. for 16 hrs. Upon cooling, the sample was dissolved in methylene chloride and washed with water. Upon separation, the organic layer was dried over Na$_2$SO$_4$, filtered and concentrated in vacuo. The brownish residue was dissolved in methanol (25%)/water (75%) mixture with 4 drops of trifloroacetic acid. The solution was purified by HPLC (5-60% methanol gradient), to provide N6-((trans)-4-aminocyclohexyl)-3-bromo-N8-(4- methoxybenzyl)-N8-phenylimidazo[1,2-b]pyridazine-6,8-diamine TFA salt as a brown solid (0.060 g (21%). m/z=(521, M+1)

(1b) To a 2 ml microwave vessel added N6-((trans)-4-aminocyclohexyl)-3-bromo-N8-(4-methoxybenzyl)-N8-phenylimidazo[1,2-b]pyridazine-6,8-diamine TFA salt (0.060 g, 0.08 mmol) from (1a), Pd(PPh$_3$)$_2$Cl$_2$ (0.005 g, 0.002 mmol), CuI (0.0015 g, 0.008 mmol) and TEA (1.6 ml, 0.05 M). The vessel was sealed and pump/purged with nitrogen 3 times. Propyne gas was then introduced via needle and the reaction was mixture was saturated over a 2 minute time interval. The reaction was heated thermally for 2 hours at 70° C. Upon cooling, the solvent was removed in vacuo and the reaction was diluted with ethyl acetate and filtered through a plug of celite. The solvent was removed providing crude N6-((trans)-4-aminocyclohexyl)-N8-(4-methoxybenzyl)-N8-phenyl-3-(prop-1-ynyl)imidazo[1,2-b]pyridazine-6,8-diamine. m/z=(481, M+1).

(1c) To a 2 dram vial was added crude N6-((trans)-4-aminocyclohexyl)-N8-(4-methoxybenzyl)-N8-phenyl-3-(prop-1-ynyl)imidazo[1,2-b]pyridazine-6,8-diamine (0.065 g, 0.13 mmol) from (1b) and a 1:1 mixture of TFA and CH$_2$Cl$_2$ (2 ml). The reaction was stirred for 2 hours, concentrated, diluted with MeOH and purified by preparative HPLC to provide the titled compound (0.0025 g, 5%) as a TFA salt. 1H NMR (400 MHz, MeOD) δ ppm 7.44 (2H, dd, 8 Hz), 7.33 (2H, d, 8 Hz), 7.18-7.26 (1H, m), 7.18-7.25 (2H, m), 6.39 (1H, s), 3.68-3.82 (1H, m), 3.06-3.21 (1H, m), 2.23-2.35 (2H, m), 2.18 (3H, s), 1.46-1.62 (2H, m), 1.25-1.41 (2H, m). LC/MS, m/z 361 (M+1). HPLC Rt, 2.30 min. Waters Sunfire C18 column (4.6×50 mm). 0%-100% B. Solvent B: (90% MeOH, 10% H$_2$O, 0.1% TFA). Solvent A: (10% MeOH, 90% H$_2$O, 0.1% TFA). Gradient, start % B=0, final % B=100, gradient time 4 min, hold at 100% B 1 min, flow rate 4 mL/min.

Example LXIV(1)

6-((trans-4-Aminocyclohexyl)amino)-8-anilino-N-4-pyridinylimidazo[1,2-b]pyridazine-3-carboxamide

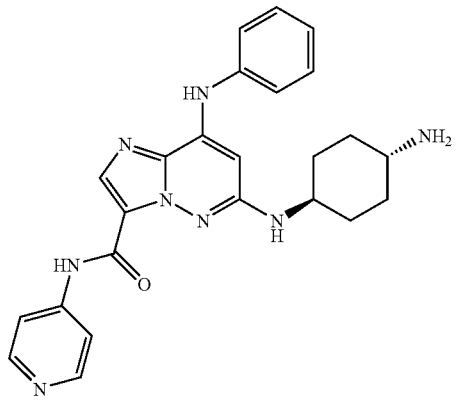

(1a) To an oven dried 25 ml shlenk flask under nitrogen was added 3-bromo-6-chloro-N-(4-methoxybenzyl)-N-phenylimidazo[1,2-b]pyridazin-8-amine (0.5 g, 1.1 mmol) from Example XXXI step (1a) and THF (5.0 ml). The solution was cooled to −78° C. and n-butyllithium was added drop-wise over 10 minutes. The reaction was allowed to stir at the depressed temperature for 1 hour. Carbon dioxide gas was then introduced via a needle purging the solution for 2 minutes. The reaction was allowed to warm to 25° C. and stir for an additional 30 minutes. Dilute 1N HCl was added taking the aqueous portion to pH=5. Ethyl acetate was added and the layers separated. The organic layer was washed with water (20 ml), then brine (10 ml), dried over Na$_2$SO$_4$, filtered and concentrated to provide 0.47 g of 6-chloro-8-((4-methoxybenzyl)(phenyl)amino)imidazo[1,2-b]pyridazine-3-carboxylic acid (98%). m/z=(410, M+1).

(1b) To a 2 dram vial was added 6-chloro-8-((4-methoxybenzyl)(phenyl)amino)-imidazo[1,2-b]pyridazine-3-carboxylic acid (0.025 g, 0.06 mmol) from (1a), EDCI (0.018 g, 0.09 mmol), HOBT (0.012 g, 0.09 mmol), 4-aminopyridine (8.46 mg, 0.09 mmol), TEA (0.025 ml, 0.18 mmol) and CH$_3$CN (1.0 ml). The reaction was stirred at 25° C. for 48 hours then concentrated to give crude 6-chloro-8-((4-methoxybenzyl)(phenyl)amino)-N-(pyridin-4-yl)imidazo[1,2-b]pyridazine-3-carboxamide. To this residue was added trans-1,4-cyclohexyldiamine (0.5 g, 4.3 mmol) and the resulting mixture was allowed to heat at 165° C. for 5 hrs. Upon cooling, the sample was dissolved in methylene chloride, and washed with water. The organics were separated, then dried over Na$_2$SO$_4$, filtered and concentrated in vacuo. To this residue was added a 1:1 mixture of CH$_2$Cl$_2$/TFA (2 ml). The solution was stirred at 25° C. for 3 hours, concentrated, diluted with MeOH and purified by preparative HPLC to provide the titled compound (0.008 g, 22%) as a TFA salt. 1H NMR (500 MHz, MeOH) δ ppm 8.74 (2H, d, J=7.15 Hz), 8.30 (2H, d, J=7.15 Hz), 8.19 (1H, s), 7.41-7.50 (2H, m), 7.31-7.41 (2H, m), 7.17-7.26 (1H, m), 6.26-6.33 (1H, m), 3.71-3.87 (1H, m), 3.10-3.23 (1H, m), 2.25-2.39 (2H, m), 2.06-2.24 (2H, m), 1.53-1.66 (2H, m), 1.35-1.52 (2H, m). LC/MS, m/z 443 (M+1). HPLC Rt, 2.34 min. Waters Sunfire C18 column (4.6×50 mm). 0%-100% B. Solvent B: (90% MeOH, 10% H$_2$O, 0.1% TFA). Solvent A: (10% MeOH, 90% H$_2$O, 0.1% TFA). Gradient, start % B=0, final % B=100, gradient time 4 min, hold at 100% B 1 min, flow rate 4 mL/min.

Example LXV(1)

6-((4-Amino-1-piperidinyl)methyl)-N-phenylimidazo[1,2-b]pyridazin-8-amine

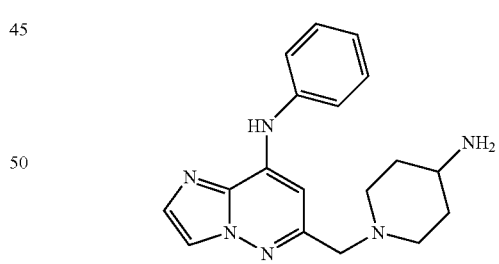

(1a) To a 20 ml microwave vial was added 6-chloro-N-(4-methoxybenzyl)-N-phenylimidazo[1,2-b]pyridazin-8-amine (0.66 g, 1.8 mmol) from Example XXXI, step (1a), zinc cyanide (0.13 g, 1.1 mmol), Pd$_2$(dba)$_3$ (0.033 g, 0.036 mmol), 1,1'-bis(diphenylphosphino)-ferrocene [dppf] (0.040 g, 0.07 mmol), zinc dust (0.012 g, 0.18 mmol) and DMA (11.0 ml, 0.17 M). The reaction mixture was sealed and pump/purged 3× with nitrogen then heated in a microwave for 20 minutes at 150° C. Upon cooling, the suspension was diluted with ethyl acetate (50 ml) and filtered through a plug of celite. To the resulting solution was added 10% LiCl solution and the layers separated. The organic layer was washed two additional times with 10% LiCl solution, then brine (1×), dried over $Na_2SO_4$, filtered and concentrated in vacuo. This residue was purified on silica gel (ISCO—80 gram) using a 30-100% ethyl acetate/heptane gradient over 20 minutes. To provide 8-((4-methoxybenzyl)(phenyl)amino)imidazo[1,2-b]pyridazine-6-carbonitrile (0.63 g, 98%). m/z=(357, M+1).

(1b) To a 25 ml round bottom flask was added 8-((4-methoxybenzyl)(phenyl)amino)imidazo[1,2-b]pyridazine-6-carbonitrile (0.62 g, 1.7 mmol) from (1a) and toluene (3.4 ml, 0.5 M) and the solution cooled to −5° C. To this was added dropwise, a 1.0 M solution of diisobutylaluminum hydride [DIBAL] in toluene (3.5 ml, 3.5 mmol) over a period of 10 minutes. The reaction was stirred at −5° C. for 1 hour and then warmed to room temperature and allowed to stir for an additional 2 hours. Dilute 1N HCl and ethyl acetate were added and the layers separated. The acidic aqueous layer was extracted 1 additional time with ethyl acetate and then basified with a 50% NaOH solution. The aqueous layer was extracted 2× with ethyl acetate and the combined organics were washed with brine (20 ml), dried over $Na_2SO_4$, filtered and concentrated in vacuo to provide crude 6-(aminomethyl)-N-(4-methoxybenzyl)-N-phenylimidazo[1,2-b]pyridazin-8-amine (0.44 g) which was used as such in the subsequent step. m/z=(360, M+1).

(1c) To a 40 ml reaction vial was added 6-(aminomethyl)-N-(4-methoxybenzyl)-N-phenylimidazo[1,2-b]pyridazin-8-amine (0.437 g, 1.2 mmol) from (1b), ethanol (5.0 ml, 0.2 M) and methyl acrylate (0.33 ml, 3.6 mmol). The vial was sealed and the reaction was heated 90° C. for 72 hours. Upon cooling, the volatiles were evaporated and the crude material was purified on silica gel (ISCO—40 gram) using a 10-70% ethyl acetate/heptane gradient over 20 minutes. This gave 0.44 g of the di-substituted product as a mixture of the methyl and ethyl esters. m/z=(532, M+1, methyl ester) and m/z=(546, M+1, ethyl ester).

(1d) The product of step (1c) (0.440 g, ~0.83 mmol) was diluted in THF (1.0 ml), cooled to 0° C. and then dropwise treated with potassium tert-butoxide (1.655 mL, 1.655 mmol). The reaction was stirred overnight at room temperature. 1 N NaOH (1.655 mL, 1.655 mmol) was added and the mixture was allowed to stir at 50° C. for 1 hour. To this was added 1 N HCl (3.31 mL, 3.31 mmol) and stirring was continued at room temperature for 4 hrs. A 50% NaOH solution was then added taking the mixture to pH~10 and this was followed by dilution with ethyl acetate. The layers were separated and the organic was washed with water, then brine, dried over $Na_2SO_4$, and concentration to dryness to provide 1-((8-((4-methoxybenzyl)(phenyl)amino)imidazo[1,2-b]pyridazin-6-yl)methyl)piperidin-4-one (0.229 g, 62.7% yield). m/z=(442, M+1).

(1e) In a 2 dram vial was added 1-((8-((4-methoxybenzyl)(phenyl)amino)imidazo[1,2-b]pyridazin-6-yl)methyl)piperidin-4-one (0.048 g, 0.109 mmol) from (1d), THF (0.362 mL) and benzylamine (0.013 mL, 0.120 mmol). The reaction was allowed to stir at room temperature for 1 hr. Sodium triacetoxyborohydride (0.092 g, 0.435 mmol) was then added and the reaction stirred for 48 hours at ambient temperature. The mixture was diluted with ethyl acetate and 1N NaOH solution and the layers separated. The organics were washed with water and the resulting aqueous solution was back-extracted with ethyl acetate (2×). The combined organics were collected, dried over $Na_2SO_4$, filtered and concentrated to provide 6-((4-(benzylamino)piperidin-1-yl)methyl)-N-(4-methoxybenzyl)-N-phenylimidazo[1,2-b]pyridazin-8-amine (0.05 g, 86% yield) which was subsequently used without further purification m/z=(532, M+1).

(1f) In a Parr bottle was added 6-((4-(benzylamino)piperidin-1-yl)methyl)-N-(4-methoxybenzyl)-N-phenylimidazo[1,2-b]pyridazin-8-amine (0.030 g, 0.056 mmol) from (1e), MeOH (7 ml), Pd/C (0.030 mg, 0.282 μmol) and AcOH (0.020 ml, 0.349 mmol). Added hydrogen to a pressure of 55 psi and let shake overnight. The suspension was filtered through celite and rinsed with MeOH, concentrated, and then diluted with TFA (1 ml). The mixture was allowed to stir at room temperature for 6 hours, concentrated and diluted with MeOH (2 ml) and purified by HPLC (10-75% MeOH/Water) to provide the title compound (0.009 g, 49.6% yield) as a TFA salt. 1H NMR (500 MHz, MeOH) δ ppm 8.08 (1H, d, J=2.75 Hz), 7.76 (1H, d, J=2.75 Hz), 7.47 (2H, dd, J=7.56, 3.44 Hz), 7.40-7.45 (2H, m), 7.25-7.31 (1H, m), 6.78 (1H, d, J=3.67 Hz), 4.40 (2H, d, J=3.21 Hz), 3.74 (2H, d, J=11.00 Hz), 3.46 (1H, d, J=3.67 Hz), 3.22 (2H, t, J=12.14 Hz), 2.25 (2H, d, J=14.20 Hz), 2.00 (2H, m). LC/MS, m/z 323 (M+1). HPLC Rt, 1.04 min. Waters Sunfire C18 column (4.6×50 mm). 0%-100% B. Solvent B: (90% MeOH, 10% $H_2O$, 0.1% TFA). Solvent A: (10% MeOH, 90% $H_2O$, 0.1% TFA). Gradient, start % B=0, final % B=100, gradient time 4 min, hold at 100% B 1 min, flow rate 4 mL/min.

Example LXVI(1)

6-((trans-4-Aminocyclohexyl)amino)-8-anilinoimidazo[1,2-b]pyridazine-7-carbonitrile

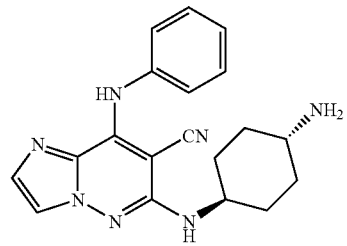

(1a) To a solution of ethyl 1H-imidazole-2-carboxylate (701 mg, 5 mmol) in DMF (20 ml) was dropwise added potassium tert-butoxide (5.50 ml, 5.50 mmol). The reaction turned cloudy in the middle of the addition. The mixture was stirred for 30 minutes before O-(4-nitrobenzoyl)hydroxylamine (911 mg, 5.00 mmol) in DMF (10 mL) was added dropwise. The reaction turned dark blue and then brown and finally orange as the addition continued. The reaction was stirred at room temperature overnight and poured into aqueous $NaHCO_3$ (150 mL) to form a clear yellow solution which was extracted with $CH_2Cl_2$ (4×200 ml). The organic layers were combined and evaporated in vacuo to provide ethyl 1-amino-1H-imidazole-2-carboxylate (760 mg, 98% yield) as a yellow solid.

(1b) In a 100 ml RB flask was added ethyl 1-amino-1H-imidazole-2-carboxylate (0.4 g, 2.58 mmol) from (1a), DCE (12.0 mL), 2-cyanoacetyl chloride (0.320 g, 3.09 mmol) and pyridine (0.417 mL, 5.16 mmol). The resulting mixture was stirred overnight under nitrogen at room temperature. The reaction was concentrated and diluted with ethyl acetate and washed with water (2×), then the aqueous was back-extracted with ethyl acetate. The organics were collected, washed with brine, dried over $Na_2SO_4$, filtered and concentrated in vacuo to provide ethyl 1-(2-cyanoacetamido)-1H-imidazole-2-carboxylate (0.38 g, 66.3% yield).

(1c) In a 40 ml reaction vial was added ethyl 1-(2-cyanoacetamido)-1H-imidazole-2-carboxylate (3.00 g, 13.50 mmol) prepared as described in (1b) and THF (2 ml). The mixture was cooled to 0° C. and potassium tert-butoxide (40.5 ml, 40.5 mmol) was added dropwise. The mixture was stirred at room temperature for 16 hours. 4.0 M HCl (10.13 ml, 40.5 mmol) in dioxane was added and the mixture was stirred for 30 min. The volatiles were evaporated to provide 6,8-dioxo-5,6,7,8-tetrahydroimidazo[1,2-b]pyridazine-7-carbonitrile which was used without purification in the following step. m/z=(177, M+1).

(1d) In a 40 ml reaction vial was added crude 6,8-dioxo-5,6,7,8-tetrahydroimidazo[1,2-b]pyridazine-7-carbonitrile (0.3 g, 1.7 mmol) from (1c) and POCl$_3$ (7.0 ml, 75.0 mmol) and the reaction was heated to 120° C. for 24 hours. The mixture was then concentrated, ice and solid sodium carbonate were added and the resulting suspension stirred for 1 hour. The mixture was filtered to provide 6,8-dichloroimidazo[1,2-b]pyridazine-7-carbonitrile (0.14 g, 39% yield) as a brown solid. m/z=(213, M+1).

(1e) In a 1 dram vial, under argon, was added 6,8-dichloroimidazo[1,2-b]pyridazine-7-carbonitrile (0.050 g, 0.235 mmol) from (1d), N-(4-methoxy)benzylaniline (0.052 g, 0.282 mmol), potassium carbonate (0.1 g, 0.704 mmol) and acetonitrile (1.0 ml). The mixture was heated to 100° C. for 6 hours, filtered through a frit and rinsed with methylene chloride. The resulting material was dry loaded onto silica and purified by ISCO (12 gram, 10-30% ethyl acetate/heptane gradient over 20 minutes) to provide 6-chloro-8-((4-methoxyphenyl)(phenyl)amino)imidazo[1,2-b]pyridazine-7-carbonitrile (0.05 g, 56.7% yield) as a yellowish solid. m/z=(390, M+1).

(1f) In a 1 dram vial was added 6-chloro-8-((4-methoxybenzyl)(phenyl)amino)imidazo[1,2-b]pyridazine-7-carbonitrile (0.019 g, 0.049 mmol) from (1e), (trans)-cyclohexane-1,4-diamine (0.011 g, 0.097 mmol), cesium carbonate (0.048 g, 0.146 mmol), Pd(OAc)$_2$ (0.547 mg, 2.437 µmol), (R)-(−)-1-[(S)-2-(dicyclohexylphosphino)ferrocenyl]ethyldi-tert-butylphosphine [JOSI-Phos] (1.351 mg, 2.437 µmol) and the solids were pump/purged with argon (3×). Dioxane (1.0 ml, 0.05 M) was added and the reaction was heated at 100° C. overnight. Upon cooling, the mixture was filtered through a frit and the resulting solution was concentrated to dryness. To this residue was added TFA (1.0 ml) and the solution was stirred for 18 hours, concentrated and purified by HPLC to provide the titled compound (0.0031 g, 18% yield) as a TFA salt. 1H NMR (500 MHz, MeOH) δ ppm 7.78 (1H, s), 7.57 (1H, s), 7.43-7.51 (2H, m), 7.31-7.40 (3H, m), 3.77-3.89 (1H, m), 3.06-3.20 (1H, m), 2.18-2.29 (2H, m), 2.09 (2H, m), 1.36-1.62 (4H, m). LC/MS, m/z 348 (M+1). HPLC Rt, 1.78 min. Waters Sunfire C18 column (4.6×50 mm). 0%-100% B. Solvent B: (90% MeOH, 10% H$_2$O, 0.1% TFA). Solvent A: (10% MeOH, 90% H$_2$O, 0.1% TFA). Gradient, start % B=0, final % B=100, gradient time 4 min, hold at 100% B 1 min, flow rate 4 mL/min.

Compounds having the formula (Ia) were prepared according to procedures similar to Example LXVI(1), where in R$_1$, R$_2$, R$_3$, X and Y have the values listed in Table 15, using the appropriate starting materials and substantially the same procedures as indicated.

TABLE 15

| Exp | Name | R$_1$ | R$_2$ | R$_3$ | X | Y | LC/MS m/z (M + 1) |
|---|---|---|---|---|---|---|---|
| LXVI(1) | 8-Anilino-6-((3S)-3-piperidinylamino)imidazo[1,2-b]pyridazine-7-carbonitrile | H | H | CN | NH—⟨phenyl⟩ | HN—⟨piperidine-NH⟩ | 334 |

*For substituents X and Y, substitution on the core (formula Ia) occurs at the available nitrogen atom Example LXVII(1)

4-((6-((trans-4-Aminocyclohexyl)amino)-3-cyanoimidazo[1,2-b]pyridazin-8-yl)amino)-N-methyl-benzenesulfonamide

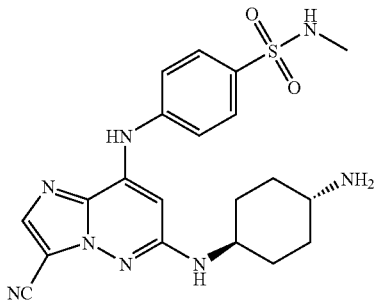

(1a) In a 100 ml round bottom flask was added 3,8-dibromo-6-chloroimidazo[1,2-b]pyridazine (0.122 g, 0.391 mmol) from Example XXIV, step (1a), 4-amino-N-methyl-benzenesulfonamide (0.080 g, 0.430 mmol), and THF (3.9 ml, 0.1 M). Potassium tert-butoxide (0.976 mL, 0.976 mmol) was added drop-wise and the reaction was stirred at 25° C. overnight. The mixture was concentrated and diluted with ethyl acetate and water. The layers were separated and the organic was washed water (20 ml), then brine (10 ml), dried over Na$_2$SO$_4$, filtered and concentrated to provide 4-(3-bromo-6-chloroimidazo[1,2-b]pyridazin-8-ylamino)-N-methylbenzenesulfonamide (0.090 g, 55.3% yield) as a brownish solid. m/z=(417, M+1).

(1b) In a microwave vial was added 4-(3-bromo-6-chloroimidazo[1,2-b]pyridazin-8-ylamino)-N-methylbenzenesulfonamide (0.068 g, 0.163 mmol) from (1a), DPPF (3.62 mg, 6.53 µmol), Pd$_2$(dba)$_3$ (2.99 mg, 3.26 µmol), and Zn(CN)$_2$ (0.031 mL, 0.490 mmol) The solids were pump/purged with nitrogen. DMA (0.326 mL) was added and the reaction was heated to 180° C. for 30 minutes, filtered through a frit and concentrated. The resulting residue was purified by HPLC (30-100% MeOH/Water) to provide 4-(6-chloro-3-cyanoimidazo[1,2-b]pyridazin-8-ylamino)-N-methylbenzenesulfonamide (0.025 g, 42% yield). m/z=(363, M+1).

(1c) In a 2 dram vial was added 4-(6-chloro-3-cyanoimidazo[1,2-b]pyridazin-8-ylamino)-N-methylbenzenesulfonamide (0.025 g, 0.069 mmol) from (1b) and (trans)-cyclohexane-1,4-diamine (0.700 g, 6.13 mmol). The mixture was heated to 165° C. for 1 hour. Upon cooling, The mixture was diluted with $CH_2Cl_2$, then washed with water, dried over $Na_2SO_4$, filtered, concentrated and purified by HPLC to provide the titled compound (0.008 g, 26.4% yield). 1H NMR (400 MHz, MeOD) δ ppm 7.91-7.99 (1H, s), 7.82-7.88 (2H, m), 7.48-7.55 (2H, m), 6.42-6.56 (1H, s), 3.68-3.84 (1H, m), 3.06-3.21 (1H, m), 2.49-2.59 (3H, s), 2.23-2.38 (2H, m), 2.04-2.17 (2H, m), 1.48-1.66 (2H, m), 1.28-1.45 (2H, m). LC/MS, m/z 441 (M+1). HPLC Rt, 2.30 min. Waters Sunfire C18 column (4.6×50 mm). 0%-100% B. Solvent B: (90% MeOH, 10% $H_2O$, 0.1% TFA). Solvent A: (10% MeOH, 90% $H_2O$, 0.1% TFA). Gradient, start % B=0, final % B=100, gradient time 4 min, hold at 100% B 1 min, flow rate 4 mL/min.

The invention claimed is:
1. A compound according to formula (I),

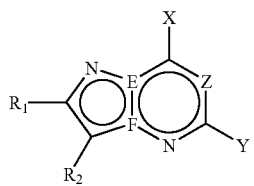

(I)

or an enantiomer, diastereomer, or a pharmaceutically-acceptable salt, thereof, wherein:
E is C;
F is N;
X is $NR_4R_5$;
Z is $CR_3$;
Y is selected from hydrogen, alkyl, substituted alkyl, alkenyl, substituted alkenyl, alkynyl, substituted alkynyl, halogen, nitro, cyano, $SR_8$, $S(O)_pR_8$, $OR_8$, $NR_6R_7$, $CO_2R_8$, $C(=O)R_8$, $O-C(=O)R_8$, $C(=O)NR_8R_9$, cycloalkyl, cycloalkenyl, cycloalkynyl, heterocyclo, aryl, and heteroaryl, provided that if Y is hydrogen then $R_4$ is phenyl substituted with a carboxamido group;
$R_1$ and $R_2$ are independently selected from (i) hydrogen, alkyl, substituted alkyl, alkenyl, substituted alkenyl, alkynyl, substituted alkynyl, halogen, nitro, cyano, $SR_{10}$, $OR_{10}$, $NR_{10}R_{11}$, $NR_{10}C(=O)R_{11}$, $CO_2R_{10}$, $C(=O)R_{10}$, $-O-C(=O)R_{10}$, $C(=O)NR_{10}R_{11}$, cycloalkyl, heterocyclo, aryl, and heteroaryl; or (ii) $R_1$ is taken together with $R_2$ and the ring atoms to which they are attached to form a fused 5-, 6-, or 7-membered cycloalkyl, aryl, heteroaryl, or cycloheteroalkyl;
$R_3$ is selected from hydrogen, halogen, alkyl, substituted alkyl, alkenyl, substituted alkenyl, alkynyl, substituted alkynyl, nitro, cyano, $SR_{13}$, $OR_{13}$, $NR_{13}R_{14}$, $NR_{13}C(=O)R_{14}$, $CO_2R_{13}$, $C(=O)R_{13}$, $-O-C(=O)R_{13}$, $-C(=O)NR_{13}R_{14}$, cycloalkyl, heterocyclo, aryl, and heteroaryl;
$R_4$, $R_5$, $R_6$, and $R_7$ are independently selected from hydrogen, alkyl, substituted alkyl, alkenyl, substituted alkenyl, alkynyl, substituted alkynyl, $OR_{15}$, $SR_{15}$, $C(=O)R_{15}$, $CO_2R_{15}$, $C(=O)NR_{15}R_{16}$, $C(W)OR_{16}$, $S(O)_pR_{17}$, $SO_2NR_{15}R_{16}$, substituted or unsubstituted cycloalkyl, heterocyclo, aryl, and heteroaryl; or (ii) $R_4$ is taken together with $R_5$ and the nitrogen atom to which they are both attached and/or $R_6$ is taken together with $R_7$ and the nitrogen atom to which they are both attached to form a substituted or unsubstituted heteroaryl or heterocyclo;

$R_8$, $R_9$, $R_{10}$, $R_{11}$, $R_{13}$, $R_{14}$, $R_{15}$, and $R_{16}$ at each occurrence are independently selected from (i) hydrogen, alkyl, substituted alkyl, alkenyl, substituted alkenyl, alkynyl, substituted alkynyl, substituted or unsubstituted cycloalkyl, aryl, heteroaryl, and heterocyclo; or (ii) together with the nitrogen atom to which they are attached, $R_8$ is taken together with $R_9$, and/or $R_{10}$ is taken together with $R_{11}$, and/or $R_{13}$ is taken together with $R_{14}$, and/or $R_{15}$ is taken together with $R_{16}$ to form a substituted or unsubstituted heteroaryl or heterocyclo;
$R_{17}$ at each occurrence is independently selected from alkyl, substituted alkyl, alkenyl, substituted alkenyl, alkynyl, substituted alkynyl, cycloalkyl, aryl, heteroaryl, and heterocyclo;
W at each occurrence is O, S, N, CN, or NH; and
p is 1 or 2,
with the following provisos:
(1) if X is NH(Me), $N(Me)_2$, NH(unsubstituted phenyl), or $NH_2$, then Y is other than hydrogen or halogen; and
(2) if $R_1$ is methyl, then X is not $N(ethyl)_2$.
2. A compound according to claim 1 having formula (Ia),

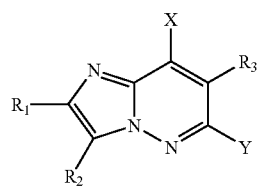

(Ia)

or an enantiomer, diastereomer, or a pharmaceutically-acceptable salt, thereof.
3. A compound according to claim 2, or an enantiomer, diastereomer, or a pharmaceutically-acceptable salt, thereof in which:
X is $NR_4R_5$;
$R_4$ is -AM;
$R_5$ is hydrogen or $C_{1-4}$alkyl;
or $R_4$ and $R_5$ together with the nitrogen atom to which they are attached form a 5-, 6- or 7-membered monocyclic heteroaryl or heterocyclo ring, or a 7- to 11-membered bicyclic heteroaryl or heterocyclo ring, each ring optionally substituted with one to three groups, $T_1$, $T_2$; and/or $T_3$;
A is a bond, $C_{1-3}$alkylene, $C_{2-4}$alkenylene, $C_{2-4}$alkynylene, $-C(O)-$, or $-SO_2-$;
M is (i) hydrogen, alkyl, alkoxy, or alkenyl; or (ii) cycloalkyl, heterocyclo, aryl, or heteroaryl, each group optionally substituted by one to three groups, $T_1$, $T_2$, and/or $T_3$;
$T_1$, $T_2$, and $T_3$ are independently selected from (i) halogen, alkyl, substituted alkyl, alkenyl, substituted alkenyl, alkynyl, substituted alkynyl, nitro, cyano, $SO_3H$ $SR_{19}$, $S(O)_pR_{21}$, $S(O)_pNR_{19}R_{20}$, $NR_{19}S(O)_pR_{21}$, $OR_{19}$, $NR_{19}R_{20}$, $NR_{19}C(=O)R_{20}$, $NR_{19}C(=O)NR_{19}R_{20}$, $CO_2R_{19}$, $C(=O)R_{19}$, $-O-C(=O)R_{19}$, $-C(=O)NR_{19}R_{20}$, cycloalkyl, heterocyclo, aryl, and heteroaryl, wherein p is one or 2; and/or (ii) two groups, $T_1$ and $T_2$, located on adjacent ring atoms are taken together with the ring atoms to which they are attached to form a fused cycloalkyl, aryl, heteroaryl, or heterocyclo;
$R_{19}$ and $R_{20}$ at each occurrence are selected independently from (i) hydrogen, alkyl, substituted alkyl, alkenyl, substituted alkenyl, cycloalkyl, aryl, heteroaryl, and heterocyclo; or (ii) $R_{19}$ and $R_{20}$ together with the nitrogen atom to which they are both attached form a heteroaryl or heterocyclo; and $R_{21}$ at each occurrence, is selected from alkyl, substituted alkyl, alkenyl, substituted alkenyl, alkynyl, substituted alkynyl, cycloalkyl, aryl, heteroaryl, and heterocyclo.

4. A compound according to claim 2, or an enantiomer, diastereomer, or a pharmaceutically-acceptable salt, thereof in which:

Y is hydrogen, halogen, $OR_8$, $NR_6R_7$, —(CH$_2$)heterocyclo, or aryl;

$R_8$ is selected from hydrogen or $C_{1-4}$alkyl optionally substituted by one to three groups selected from halogen, $C_{1-4}$alkyl, nitro, cyano, amino, $C_{1-4}$alkoxy, and OH;

$R_7$ and $R_8$ are independently selected from alkyl, cycloalkyl, heterocyclo, aryl, and heteroaryl, each group of which is optionally substituted by one to three groups, $T_4$, $T_5$, and/or $T_6$;

or $R_6$ and $R_7$ together with the nitrogen atom to which they are attached form a heteroaryl or heterocyclo ring, each ring is optionally substituted by one to three groups, $T_4$, $T_5$, and/or $T_6$;

$T_4$, $T_5$ and $T_6$ are independently selected from (i) halogen, alkyl, substituted alkyl, alkenyl, substituted alkenyl, alkynyl, substituted alkynyl, nitro, cyano, $SR_{19}$, $OR_{19}$, $NR_{19}R_{20}$, $NR_{19}C(=O)R_{20}$, $CO_2R_{19}$, $C(=O)R_{19}$, —O—C(=O)$R_{19}$, —C(=O)$NR_{19}R_{20}$, cycloalkyl, heterocyclo, aryl, and heteroaryl; and/or (ii) two groups, $T_4$ and $T_5$, substituted on adjacent ring atoms are taken together with the ring atoms to which they are attached to form a fused cycloalkyl, heterocyclo, aryl, or heteroaryl; and $R_{19}$ and $R_{20}$ at each occurrence are selected independently from (i) hydrogen, alkyl, substituted alkyl, alkenyl, substituted alkenyl, cycloalkyl, aryl, heteroaryl, and heterocyclo; or (ii) $R_{19}$ with $R_{20}$ together with the nitrogen atom to which they are both attached combine to form a heteroaryl or heterocyclo.

5. A compound according to formula (Ia),

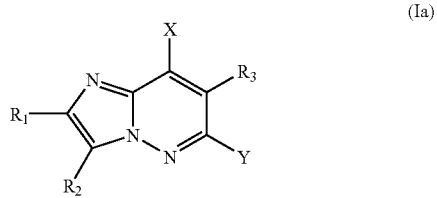

(Ia)

or an enantiomer, diastereomer, or a pharmaceutically-acceptable salt, thereof, wherein:

X is $NR_4R_5$;

Y is hydrogen, halogen, $OR_8$, $NR_6R_7$, —(CH$_2$)heterocyclo, or aryl;

$R_1$ and $R_2$ are independently selected from (i) hydrogen, alkyl, substituted alkyl, alkenyl, substituted alkenyl, alkynyl, substituted alkynyl, halogen, nitro, cyano, $SR_{10}$, $OR_{10}$, $NR_{10}R_{11}$, $NR_{10}C(=O)R_{11}$, $CO_2R_{10}$, $C(=O)R_{10}$, —O—C(=O)$R_{10}$, $C(=O)NR_{10}R_{11}$, cycloalkyl, heterocyclo, aryl, and heteroaryl; or (ii) $R_1$ is taken together with $R_2$ and the ring atoms to which they are attached to form a fused 5-, 6-, or 7-membered cycloalkyl, aryl, heteroaryl, or cycloheteroalkyl;

$R_3$ is selected from hydrogen, halogen, alkyl, substituted alkyl, alkenyl, substituted alkenyl, alkynyl, substituted alkynyl, nitro, cyano, $SR_{13}$, $OR_{13}$, $NR_{13}R_{14}$, $NR_{13}C(=O)R_{14}$, $CO_2R_{13}$, $C(=O)R_{13}$, —O—C(=O)$R_{13}$, —C(=O)$NR_{13}R_{14}$, cycloalkyl, heterocyclo, aryl, and heteroaryl;

$R_4$ is -AM;

$R_6$ is hydrogen or $C_{1-4}$alkyl;

or $R_4$ and $R_5$ together with the nitrogen atom to which they are attached form a 5-, 6- or 7-membered monocyclic heteroaryl or heterocyclo ring, or a 7- to 11-membered bicyclic heteroaryl or heterocyclo ring, each ring optionally substituted with one to three groups, $T_1$, $T_2$; and/or $T_3$;

A is a bond, $C_{1-3}$alkylene, $C_{2-4}$alkenylene, $C_{2-4}$alkynylene, —C(O)—, or —SO$_2$—;

M is (i) hydrogen, $NR_{15}R_{16}$, alkyl, alkoxy, or alkenyl; or (ii) cycloalkyl, heterocyclo, aryl, or heteroaryl, each ring optionally substituted by one to three groups, $T_1$, $T_2$, and/or $T_3$;

$R_6$ is selected from hydrogen or $C_{1-4}$alkyl optionally substituted by one to three groups selected from halogen, $C_{1-4}$alkyl, nitro, cyano, amino, $C_{1-4}$alkoxy, and OH;

$R_7$ and $R_8$ are independently selected from alkyl, cycloalkyl, heterocyclo, aryl, and heteroaryl, each group of which is optionally substituted by one to three groups, $T_4$, $T_5$, and/or $T_6$;

or $R_6$ and $R_7$ together with the nitrogen atom to which they are attached form a heteroaryl or heterocyclo ring, each ring is optionally substituted by one to three groups, $T_4$, $T_5$, and/or $T_6$;

$R_{10}$, $R_{11}$, $R_{13}$, and $R_{14}$ at each occurrence are independently selected from (i) hydrogen, $C_{1-4}$alkyl, substituted $C_{1-4}$alkyl, and an optionally substituted phenyl or 5-, 6-, or 7-membered heteroaryl or heterocyclo; or (ii) $R_{10}$ and $R_{11}$ and/or $R_{13}$, and $R_{14}$ together with the nitrogen atom they are both attached combine to form an optionally substituted 5-, 6-, or 7-membered heteroaryl or heterocyclo;

$R_{15}$ and $R_{16}$ are independently selected from (i) hydrogen, alkyl, substituted alkyl, alkenyl, substituted alkenyl, alkynyl, substituted alkynyl, cycloalkyl, aryl, heteroaryl, and heterocyclo; or (ii) together with the nitrogen atom to which they are attached $R_{15}$ is taken together with $R_{16}$ to form a heteroaryl or heterocyclo;

$T_1$, $T_2$, and $T_3$ are independently selected from (i) halogen, alkyl, substituted alkyl, alkenyl, substituted alkenyl, alkynyl, substituted alkynyl, nitro, cyano, SO$_3$H $SR_{19}$, $S(O)_pR_{21}$, $S(O)_pNR_{19}R_{20}$, $NR_{19}S(O)_pR_{21}$, $OR_{19}$, $NR_{19}R_{20}$, $NR_{19}C(=O)R_{20}$, $NR_{19}C(=O)NR_{19}R_{20}$, $CO_2R_{19}$, $C(=O)R_{19}$, —O—C(=O)$R_{19}$, —C(=O)$NR_{19}R_{20}$, cycloalkyl, heterocyclo, aryl, and heteroaryl, wherein p is one or 2; and/or (ii) two groups, $T_1$ and $T_2$, located on adjacent ring atoms are taken together with the ring atoms to which they are attached to form a fused cycloalkyl, aryl, heteroaryl, or heterocyclo;

$T_4$, $T_5$ and $T_6$ are independently selected from (i) halogen, alkyl, substituted alkyl, alkenyl, substituted alkenyl, alkynyl, substituted alkynyl, nitro, cyano, $SR_{19}$, $OR_{19}$, $NR_{19}R_{20}$, $NR_{19}C(=O)R_{20}$, $CO_2R_{19}$, $C(=O)R_{19}$, —O—C(=O)$R_{19}$, —C(=O)$NR_{19}R_{20}$, cycloalkyl, heterocyclo, aryl, and heteroaryl; and/or (ii) two groups, $T_4$ and $T_5$, substituted on adjacent ring atoms are taken together with the ring atoms to which they are attached to form a fused cycloalkyl, heterocyclo, aryl, or heteroaryl; and $R_{19}$ and $R_{20}$ at each occurrence are selected independently from (i) hydrogen, alkyl, substituted alkyl, alkenyl, substituted alkenyl, cycloalkyl, aryl, heteroaryl, and heterocyclo; or (ii) $R_{19}$ and $R_{20}$ together with the nitrogen atom to which they are both attached form a heteroaryl or heterocyclo ring; and $R_{21}$ at each occurrence, is selected from alkyl, substituted alkyl, alkenyl, substituted alkenyl, alkynyl, substituted alkynyl, cycloalkyl, aryl, heteroaryl, and heterocyclo;

with the following provisos:
(1) if X is $NH_2$, NH(Me), $N(Me)_2$, NH(unsubstituted phenyl), or $NHNH_2$, then Y is other than hydrogen or halogen; and
(2) if $R_1$ is methyl, then X is not $N(ethyl)_2$.

6. A compound according to claim 5, or an enantiomer, diastereomer, or a pharmaceutically-acceptable salt, thereof in which:

X is $NR_4R_5$;
$R_4$ is -AM;
A is a bond, —C(O)—, or —S(O)$_2$—, or $C_{1-3}$alkylene;
M is (i) hydrogen, —NH(aryl), $C_{1-6}$alkyl, $C_{2-4}$alkenyl, or —OC$_{1-4}$alkyl or (ii) $C_{3-6}$cycloalkyl, phenyl, fluorenyl, 1-naphthyl, or 2-naphthyl, each group optionally substituted by one to three groups, $T_1$, $T_2$, and/or $T_3$; or (iii) a 5-, 6- or 7-membered monocyclic or a 7- to 11-membered bicyclic heteroaryl or heterocyclo ring, each ring optionally substituted by one to three groups, $T_1$, $T_2$, and/or $T_3$; and $T_1$, $T_2$, and $T_3$ are independently selected from (i) $C_{1-4}$alkyl, substituted $C_{1-4}$alkyl, $C_{1-4}$alkyloxy, substituted $C_{1-4}$alkyloxy, $C_{1-4}$alkylthio, phenoxy, —$NR_{19}R_{20}$, halogen, hydroxy, cyano, $SO_3H$, COOH, —C(O)($R_{19}$), C(O)$NR_{19}R_{20}$, $NR_{19}$C(O)$R_{20}$, S(O)$_2R_{21}$, S(O)$_2NR_{19}R_{20}$ and $NR_{19}$(C(O)$NR_{19}R_{20}$; and/or (ii) phenyl, cyclopropyl, cyclohexyl, tetrazolyl, imidazolyl, pyrazolyl, triazolyl, thiazolyl, furyl, and morpholinyl, each group of which is optionally substituted as valence allows from one to three groups, $R_{22}$, $R_{23}$ and/or $R_{24}$; and/or (iii) two groups, $T_1$ and $T_2$, substituted on adjacent ring atoms are taken together with the ring atoms to which they are attached to form, a fused five- to seven-membered cycloalkyl, a fused phenyl or a fused 5- or 6-membered heterocyclo or heteroaryl, each group of which is optionally substituted as valence allows from one to three groups, $R_{22}$, $R_{23}$ and/or $R_{24}$; and $R_{19}$ and $R_{20}$ at each occurrence are selected independently from (i) hydrogen, —(CH$_2$)$_v$OH, and $C_{1-4}$alkyl; or (ii) —(CH$_2$)$_v$cyclohexyl, —(CH$_2$)$_v$phenyl, —(CH$_2$)$_v$morpholinyl, —(CH$_2$)$_v$pyridyl, —(CH$_2$)$_v$pyrazolyl, —(CH$_2$)$_v$cyclopropyl, —(CH$_2$)$_v$pyrrolidinyl, —(CH$_2$)$_v$piperidinyl, —(CH$_2$)$_v$furyl, —(CH$_2$)$_v$imidazolyl, —(CH$_2$)$_v$pyrimidinyl, —(CH$_2$)$_v$piperazinyl, and —(CH$_2$)$_v$pyradizinyir, each group of which is optionally substituted as valence allows from one to three groups, $R_{22}$, $R_{23}$ and/or $R_{24}$; or $R_{19}$ and $R_{20}$ are taken together with the nitrogen atom to which they are both attached to form a pyrrolindyl, morpholinyl, piperidinyl, pyradazinyl, or piperazinyl, each group of which is optionally substituted as valence allows from one to three groups, $R_{22}$, $R_{23}$ and/or $R_{24}$;

$R_{21}$ at each occurrence is selected from (i) —(CH$_2$)$_v$OH, and $C_{1-4}$alkyl; or (ii) —(CH$_2$)$_v$cyclohexyl, —(CH$_2$)$_v$phenyl, —(CH$_2$)$_v$morpholinyl, —(CH$_2$)$_v$pyridyl, —(CH$_2$)$_v$pyrazolyl, —(CH$_2$)$_v$cyclopropyl, —(CH$_2$)$_v$pyrrolidinyl, —(CH$_2$)$_v$piperidinyl, —(CH$_2$)$_v$furyl, —(CH$_2$)$_v$imidazolyl, —(CH$_2$)$_v$pyrimidinyl, —(CH$_2$)$_v$piperazinyl, and —(CH$_2$)$_v$pyradizinyl, each group of which is optionally substituted as valence allows from one to three groups, $R_{22}$, $R_{23}$ and/or $R_{24}$;

$R_{22}$, $R_{23}$, and $R_{24}$ at each occurrence, are selected independently from ($C_{1-4}$)alkyl, ($C_{2-4}$alkenyl, halogen, hydroxy, cyano, nitro, $CF_3$, =O, O($C_{1-4}$alkyl), $OCF_3$, C(=O)H, C(=O)($C_{1-4}$alkyl), $CO_2H$, $CO_2(C_{1-4}$alkyl), $NHCO_2(C_{1-4}$alkyl), —S($C_{1-4}$alkyl), —$NH_2$, $NH(C_{1-4}$alkyl)$_2$, $N(C_{1-4}$alkyl)$_2$, $N(C_{1-4}$alkyl)$_3^+$, $SO_2(C_{1-4}$alkyl), C(=O)($C_{1-4}$alkylene)$NH_2$, C(=O)($C_{1-4}$alkylene)NH(alkyl), C(=O)($C_{1-4}$alkylene)$N(C_{1-4}$alkyl)$_2$, and optionally substituted phenyl; and v is 0, 1, 2, or 3.

7. A compound according to claim 6, or an enantiomer, diastereomer, or a pharmaceutically-acceptable salt, thereof, wherein $NR_4R_5$ is selected from the following:

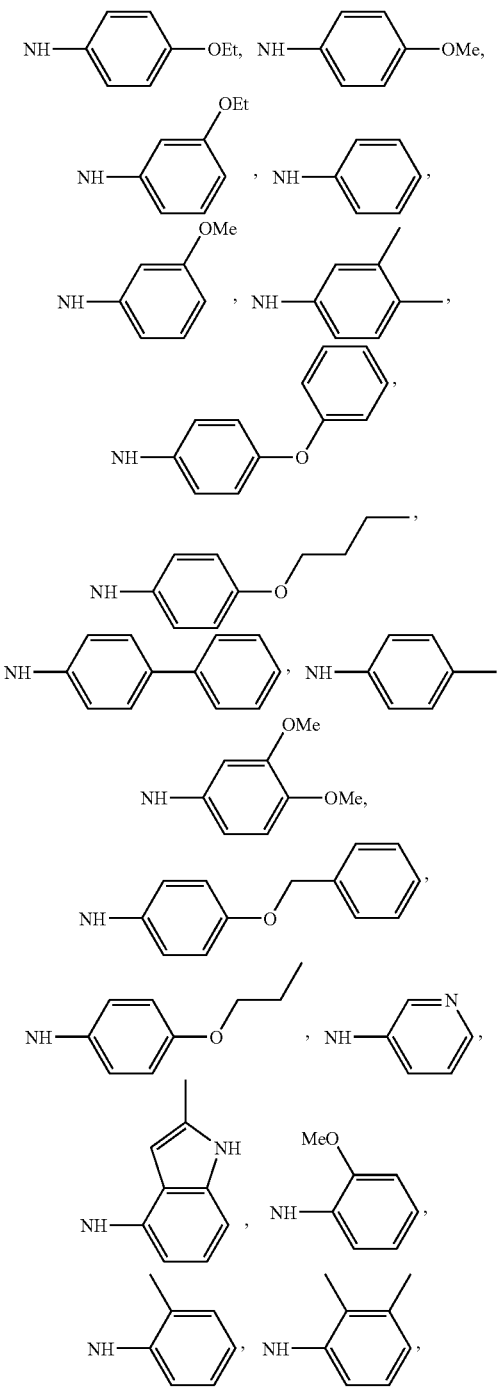

-continued
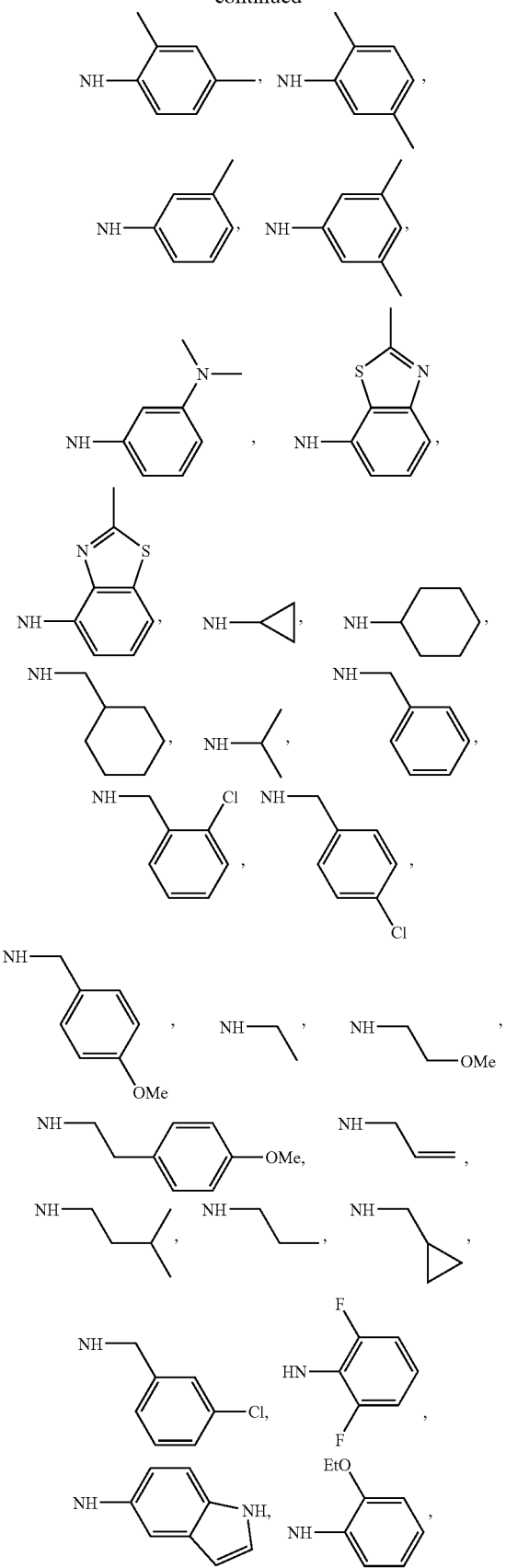
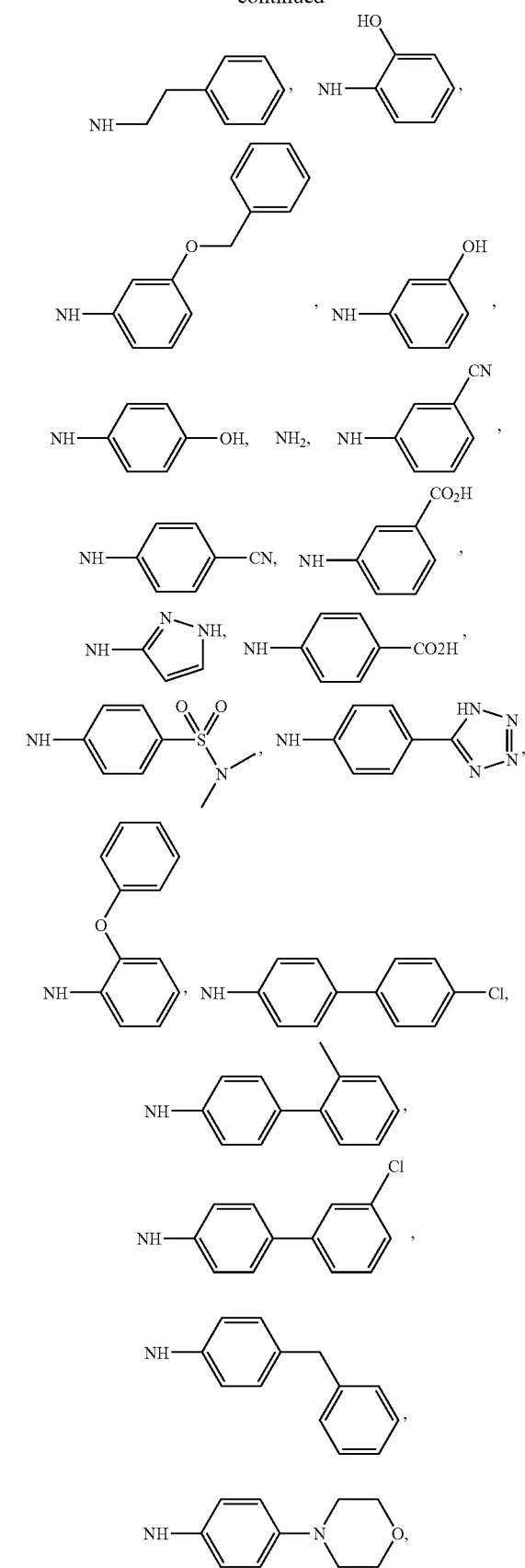

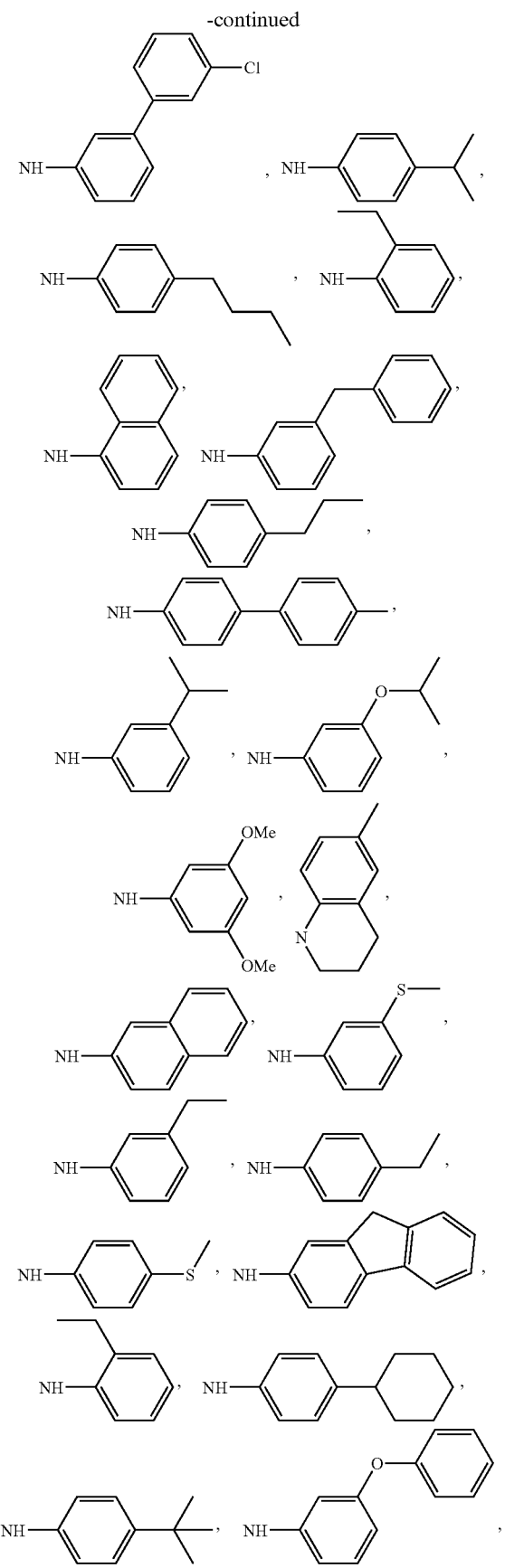
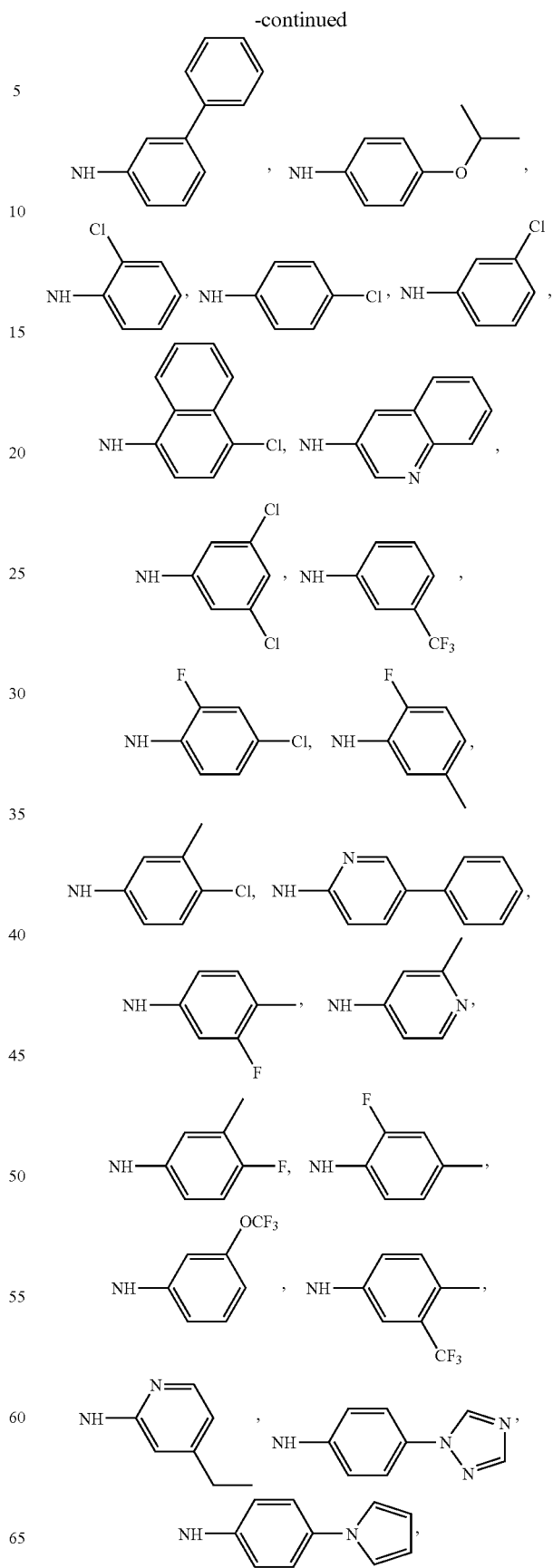

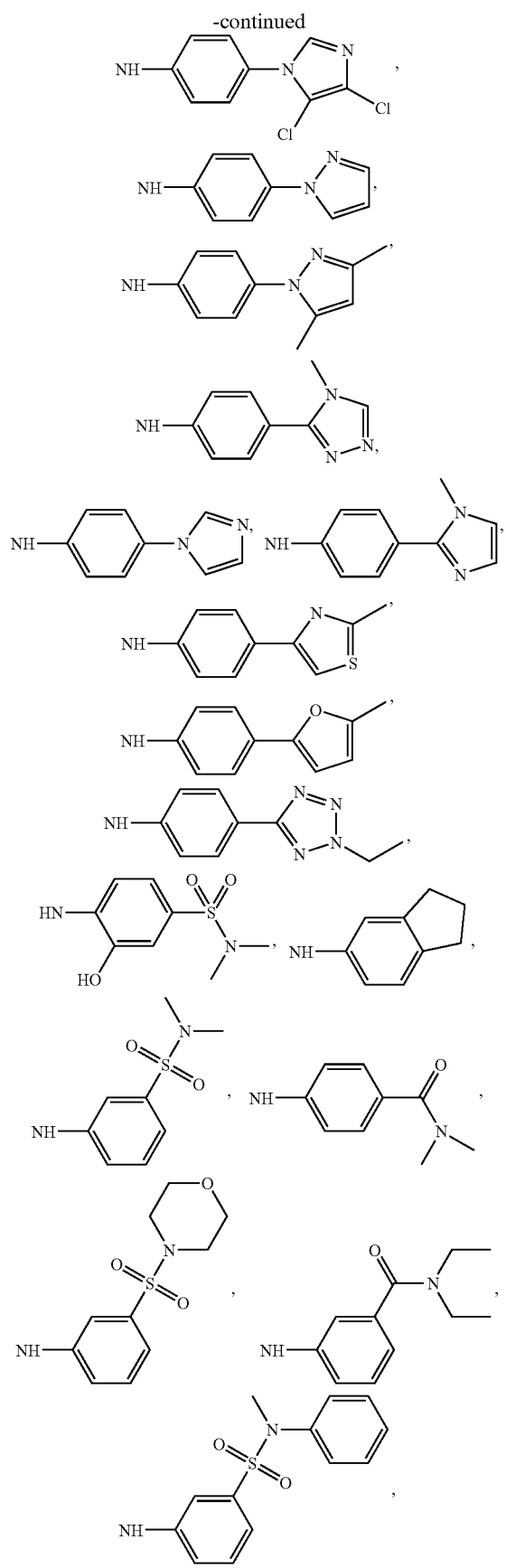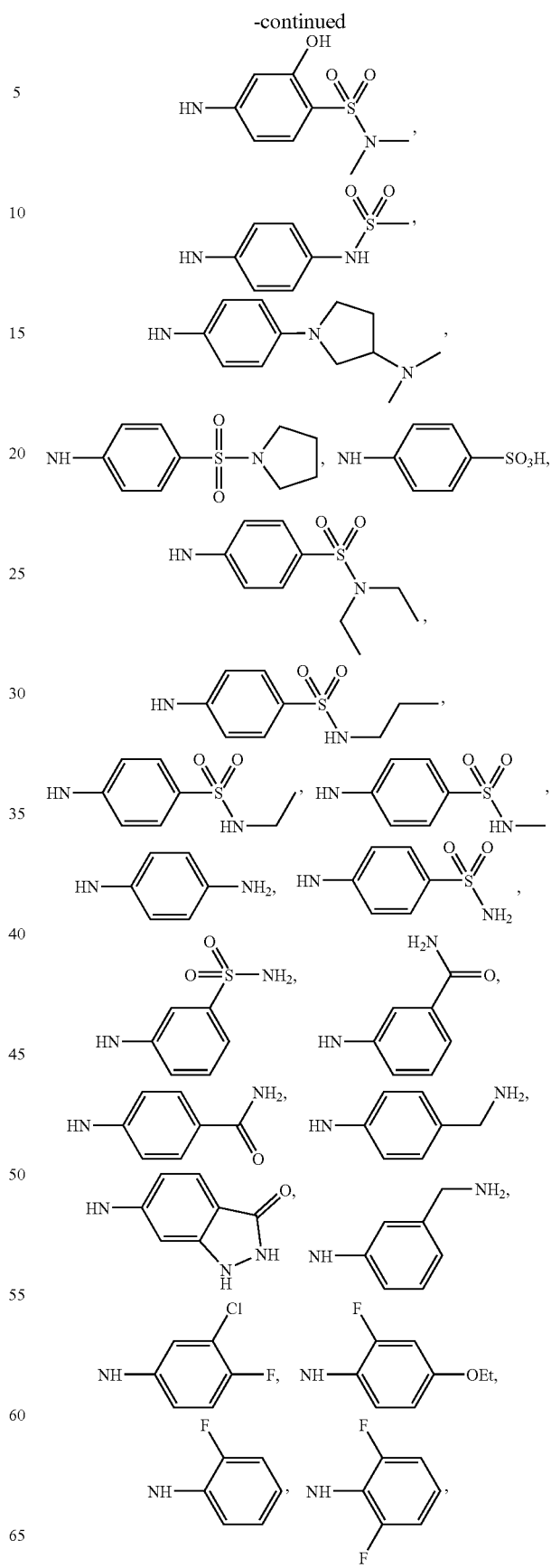

-continued
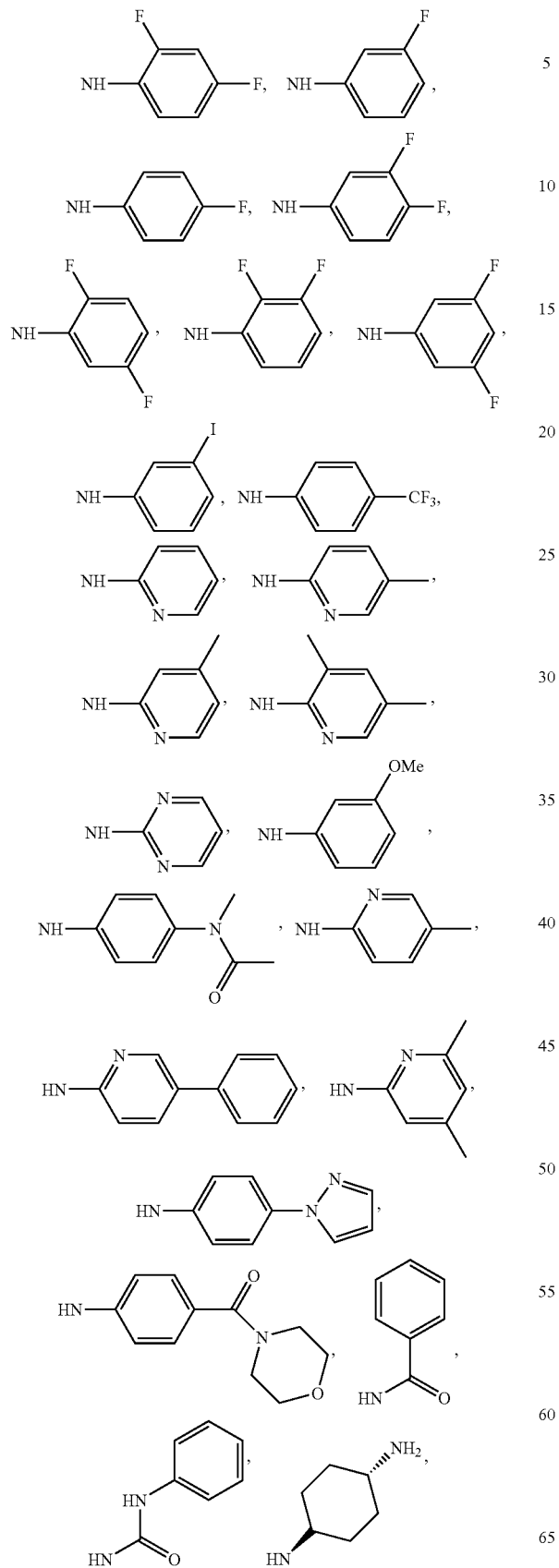
-continued
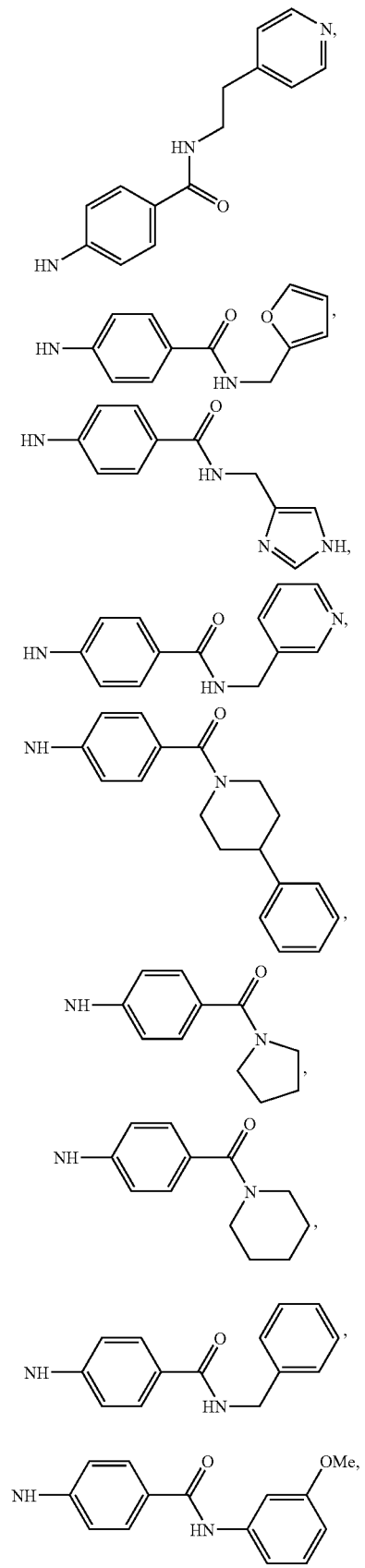

-continued
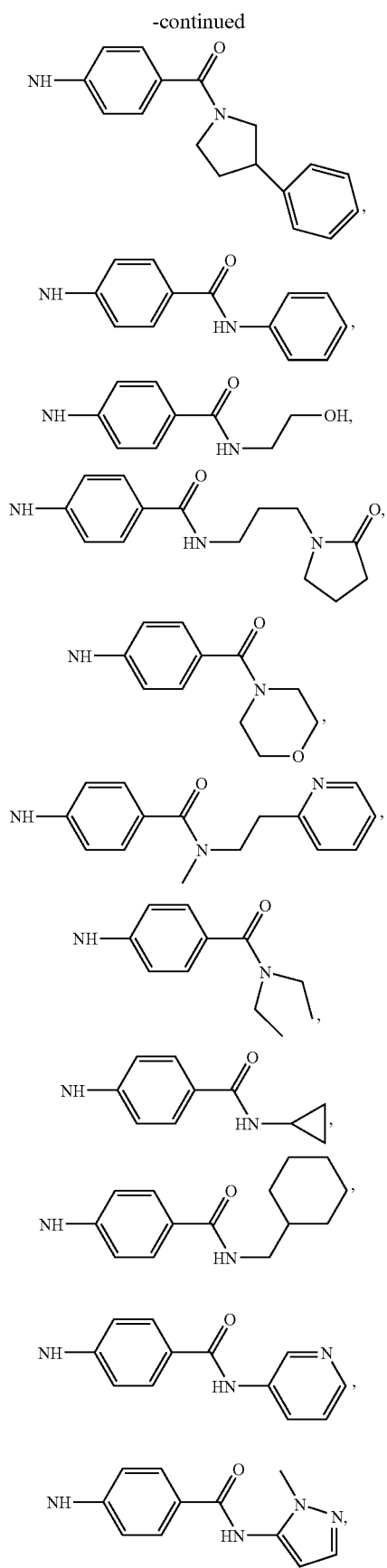
-continued
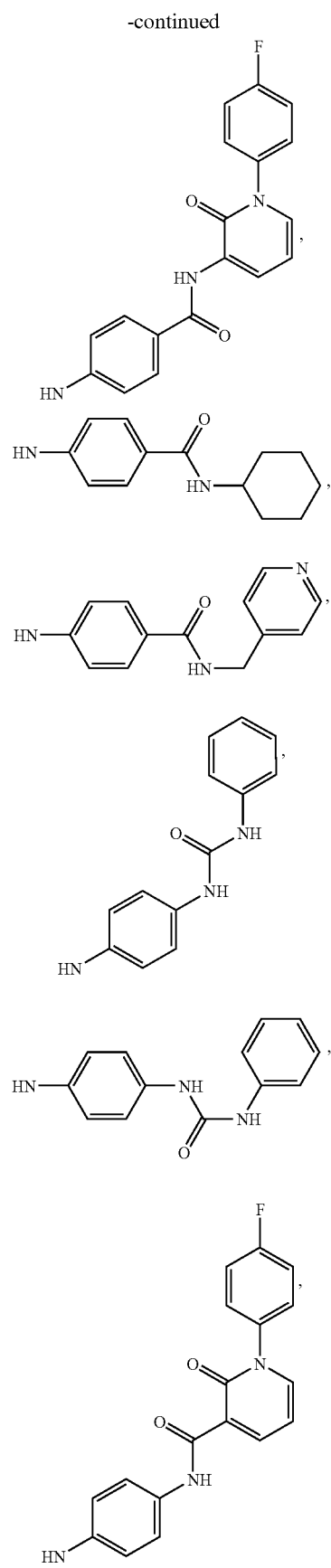

-continued

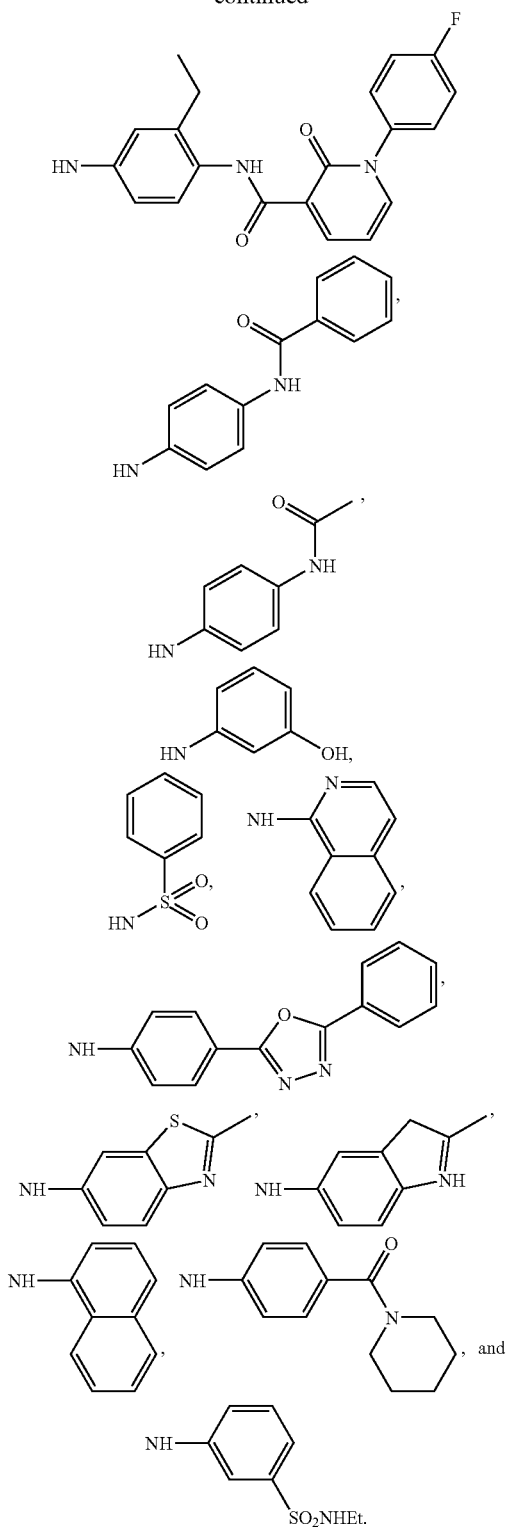

8. A compound according to claim 5, or an enantiomer, diastereomer, or a pharmaceutically-acceptable salt, thereof in which:

Y is $NR_6R_7$;

$R_6$ is selected from hydrogen or $C_{1-4}$alkyl;

$R_7$ is selected from $C_{1-4}$alkyl, cyclopentyl, cyclohexyl, bicyclo[2.2.2]octyl, pyrrolidinyl, and piperidinyl, each group of which is optionally substituted by one to three groups, $T_4$, $T_5$, and/or $T_6$;

or $R_6$ and $R_7$ together with the nitrogen atom to which they are attached form piperazinyl, piperidinyl, pyrrolidinyl, or diazepanyl, each group of which is optionally substituted by one to three groups, $T_4$, $T_5$, and/or $T_6$; and $T_4$, $T_5$, and $T_6$ are independently selected from (i) $C_{1-4}$alkyl, OH, $NH_2$, $NH(C_{1-4}$alkyl), furyl, and $N(C_{1-4}$alkyl$)_2$, and NH(pyrimidinyl) wherein the pyrimidinyl is substituted by halogen; or (ii) $C_{1-4}$alkyl substituted by cyclohexyl or OH, wherein the cyclohexyl is substituted by $NH_2$.

9. A compound according to claim 8, or an enantiomer, diastereomer, or a pharmaceutically-acceptable salt, thereof wherein $NR_6R_7$ is selected from the following:

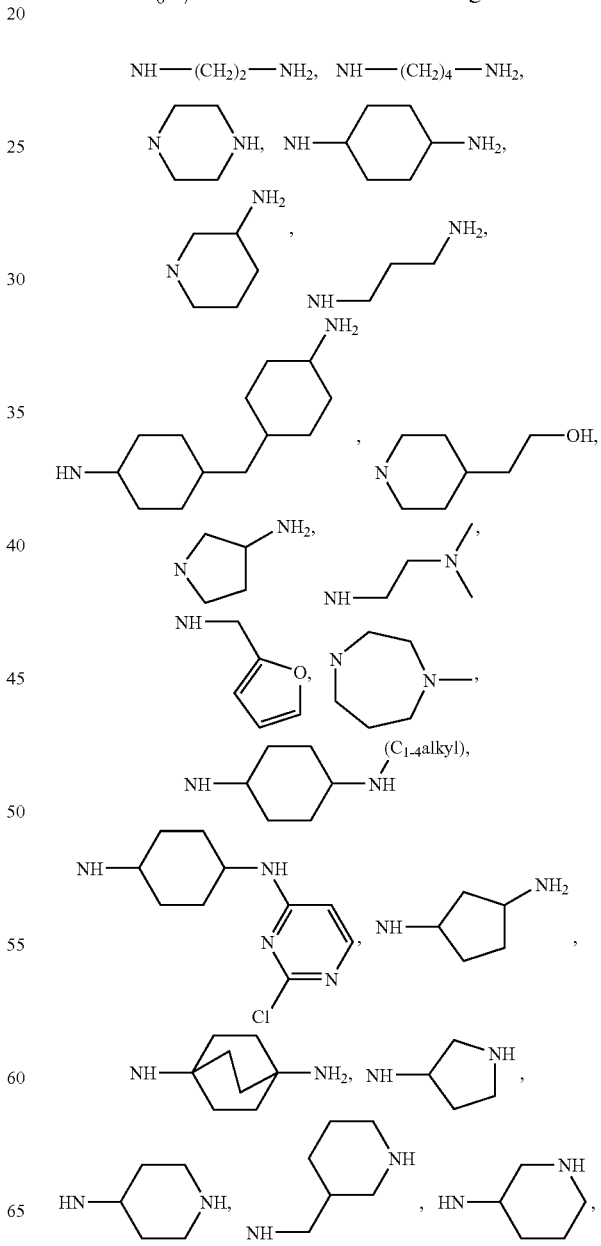

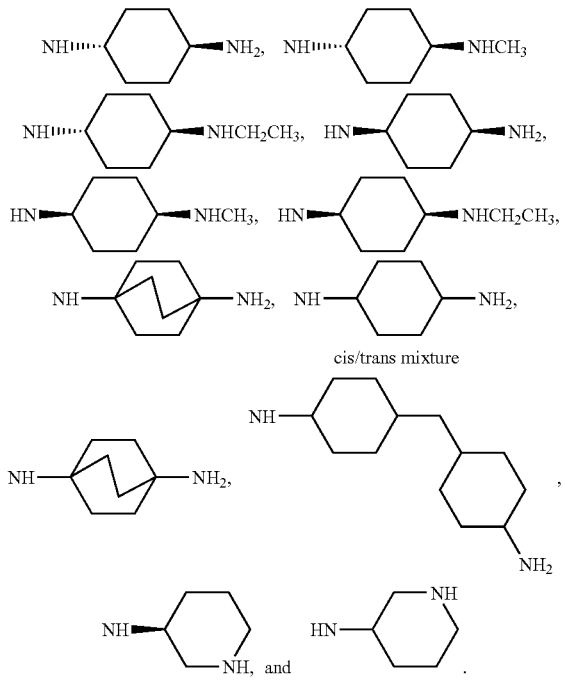

10. A compound according to claim 8, or an enantiomer, diastereomer, or a pharmaceutically-acceptable salt, thereof wherein $NR_6R_7$ is selected from:

11. A compound according to claim 5, or an enantiomer, diastereomer, or a pharmaceutically-acceptable salt, thereof wherein $R_5$ is hydrogen and $R_4$ is selected from a phenyl, pyridyl, pyrimidinyl, cyclohexyl, and piperidinyl ring, each ring optionally substituted by one to two groups, $T_1$, and/or $T_2$.

12. A compound according to claim 5, or an enantiomer, diastereomer, or a pharmaceutically-acceptable salt, thereof, in which:

$R_1$ and $R_2$ are independently selected from (i) hydrogen, halogen, $OR_{10}$, cyano, $CO_2R_{10}$, and $C(O)NR_{10}R_{11}$, or (ii) $C_{1-4}$alkyl, $C_{3-6}$cycloalkyl, $C_2$-$C_4$ alkenyl, or $C_2$-$C_4$ alkynyl, each group of which is optionally substituted;

$R_3$ is selected from (i) hydrogen, halogen, nitro, cyano, $OR_{13}$, $NR_{13}R_{14}$, $CO_2R_{13}$, $C(=O)R_{13}$, $C_{1-4}$alkyl, substituted $C_{1-4}$alkyl, cycloalkyl, aryl, and heteroaryl; and $R_{10}$, $R_{11}$, $R_{13}$, and $R_{14}$ at each occurrence are independently selected from (i) hydrogen, $C_{1-4}$alkyl, substituted $C_{1-4}$alkyl, and an optionally substituted phenyl or 5-, 6-, or 7-membered heteroaryl or heterocyclo; or (ii) $R_{10}$ and $R_{11}$ and/or $R_{13}$, and $R_{14}$ together with the nitrogen atom they are both attached combine to form an optionally substituted 5-, 6-, or 7-membered heteroaryl or heterocyclo.

13. A compound according to claim 12, wherein:
$R_1$ is hydrogen or $C_{1-4}$alkyl;
$R_2$ is cyano, halogen, $C_{1-4}$alkyl, $C_{2-4}$alkenyl(phenyl), $C_{2-4}$alkenyl(heteroaryl), cyclopropyl, propynyl, or $C(O)NR_{10}R_{11}$;
$R_3$ is hydrogen, halogen, $C_{1-4}$alkyl, substituted $C_{1-4}$alkyl, or aryl;
$R_{10}$ and $R_{11}$, at each occurrence are independently selected from hydrogen, $C_{1-4}$alkyl, substituted $C_{1-4}$alkyl, an optionally substituted phenyl, and an optionally substituted heteroaryl wherein the heteroaryl is selected from pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl, indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl, carbazolyl, benzidolyl, phenanthrollinyl, acridinyl, phenanthridinyl, and xanthenyl.

14. A compound selected from the following:
(i) $N^6$-(trans-4-aminocyclohexyl)-$N^8$-[4-(ethyloxy)phenyl]imidazo[1,2-b]pyridazine-6,8-diamine,
$N^6$-(2-aminoethyl)-$N^8$-(4-(ethyloxy)phenyl)imidazo[1,2-b]pyridazine-6,8-diamine;
$N^6$-(4-aminobutyl)-$N^8$-(4-(ethyloxy)phenyl)imidazo[1,2-b]pyridazine-6,8-diamine;
7-chloro-N-(4-(ethyloxy)phenyl)-6-(1-piperazinyl)imidazo[1,2-b]pyridazin-8-amine;
$N^6$-(trans-4-aminocyclohexyl)-$N^8$-(4-(methyloxy)phenyl)imidazo[1,2-b]pyridazine-6,8-diamine;
$N^6$-(trans-4-aminocyclohexyl)-$N^8$-(3-(ethyloxy)phenyl)imidazo[1,2-b]pyridazine-6,8-diamine;
$N^6$-(trans-4-aminocyclohexyl)-$N^8$-phenyl)imidazo[1,2-b]pyridazine-6,8-diamine;
$N^6$-(trans-4-aminocyclohexyl)-$N^8$-(3-(methyloxy)phenyl)imidazo[1,2-b]pyridazine-6,8-diamine;
$N^6$-(trans-4-aminocyclohexyl)-$N^8$-(3,4-dimethylphenyl)imidazo[1,2-b]pyridazine-6,8-diamine;
$N^6$-(trans-4-aminocyclohexyl)-$N^8$-(4-(phenyloxy)phenyl)imidazo[1,2-b]pyridazine-6,8-diamine;
$N^6$-(trans-4-aminocyclohexyl)-$N^8$-(4-(butyloxy)phenyl)imidazo[1,2-b]pyridazine-6,8-diamine;
$N^6$-(trans-4-aminocyclohexyl)-$N^8$-4-biphenylylimidazo[1,2-b]pyridazine-6,8-diamine;
$N^6$-(trans-4-aminocyclohexyl)-$N^8$-(4-methylphenyl)imidazo[1,2-b]pyridazine-6,8-diamine;
$N^6$-(trans-4-aminocyclohexyl)-$N^8$-(3,4-bis(methyloxy)phenyl)imidazo[1,2-b]pyridazine-6,8-diamine;
$N^6$-(trans-4-aminocyclohexyl)-$N^8$-(4-(phenylmethyl)oxy)phenylimidazo[1,2-b]pyridazine-6,8-diamine;
$N^6$-(trans-4-aminocyclohexyl)-$N^8$-(4-(propyloxy)phenyl)imidazol[1,2-b]pyridazine-6,8-diamine;
$N^6$-(trans-4-aminocyclohexyl)-$N^8$-pyridin-3-ylimidazo[1,2-b]pyridazine-6,8-diamine;
$N^6$-(trans-4-aminocyclohexyl)-$N^8$-(2-methyl-1H-indol-5-yl)imidazo[1,2-b]pyridazine-6,8-diamine;
$N^6$-(trans-4-aminocyclohexyl)-$N^8$-methyl-1H-phenylimidazo[1,2-b]pyridazine-6,8-diamine;
$N^6$-(trans-4-aminocyclohexyl)-$N^8$-[2-(methyloxy)phenyl]imidazo[1,2-b]pyridazine-6,8-diamine;
$N^6$-(trans-4-aminocyclohexyl)-$N^8$-(2-methylphenyl)imidazo[1,2-b]pyridazine-6,8-diamine;

$N^6$-(trans-4-aminocyclohexyl)-$N^8$-(2,3-dimethylphenyl)imidazo[1,2-b]pyridazine-6,8-diamine;
$N^6$-(trans-4-aminocyclohexyl)-$N^8$-(2,4-dimethylphenyl)imidazo[1,2-b]pyridazine-6,8-diamine;
$N^6$-(trans-4-aminocyclohexyl)-$N^8$-(2,5-dimethylphenyl)imidazo[1,2-b]pyridazine-6,8-diamine;
$N^6$-(trans-4-aminocyclohexyl)-$N^8$-(3-methylphenyl)imidazo[1,2-b]pyridazine-6,8-diamine;
$N^6$-(trans-4-aminocyclohexyl)-$N^8$-(3,5-dimethylphenyl)imidazo[1,2-b]pyridazine-6,8-diamine;
$N^6$-(trans-4-aminocyclohexyl)-$N^8$-[3-(dimethylamino)phenyl]imidazo[1,2-b]pyridazine-6,8-diamine;
$N^6$-(trans-4-aminocyclohexyl)-$N^8$-(2-methyl-1,3-benzothiazol-6-yl)imidazo[1,2-b]pyridazine-6,8-diamine;
$N^6$-(trans-4-aminocyclohexyl)-$N^8$-(2-methyl-1,3-benzothiazol-5-yl)imidazo[1,2-b]pyridazine-6,8-diamine;
$N^6$-(trans-4-aminocyclohexyl)$N^8$-cyclopropylimidazo[1,2-b]pyridazine-6,8-diamine;
$N^6$-(trans-4-aminocyclohexyl)-$N^8$-cyclohexylimidazo[1,2-b]pyridazine-6,8-diamine;
$N^6$-(trans-4-aminocyclohexyl)-$N^8$-(cyclohexyl methyl)imidazo[1,2-b]pyridazine-6,8-diamine;
$N^6$-(trans-4-aminocyclohexyl)-$N^8$-(1-methylethyl)imidazo[1,2-b]pyridazine-6,8-diamine;
$N^6$-(trans-4-aminocyclohexyl)-$N^8$-(phenyl methyl)imidazo[1,2-b]pyridazine-6,8-diamine;
$N^6$-(trans-4-aminocyclohexyl)-$N^8$-[(2-chlorophenyl)methyl]imidazo[1,2-b]pyridazine-6,8-diamine;
$N^6$-(trans-4-aminocyclohexyl)-$N^8$-((4-chlorophenyl)methyl)imidazo[1,2-b]pyridazine-6,8-diamine;
$N^6$-(trans-4-aminocyclohexyl)-$N^8$-((4-(methyloxy)phenyl)methylimidazo[1,2-b]pyridazine-6,8-diamine;
$N^6$-(trans-4-aminocyclohexyl)-$N^8$-ethylimidazo[1,2-b]pyridazine-6,8-diamine;
$N^6$-(trans-4-aminocyclohexyl)-$N^8$-(2-(methyloxy)ethyl)imidazo[1,2-b]pyridazine-6,8-diamine;
$N^6$-(trans-4-aminocyclohexyl)-$N^8$-(2-(4-(methyloxy)phenyl)ethyl)imidazo[1,2-b]pyridazine-6,8-diamine;
$N^6$-(trans-4-aminocyclohexyl)-$N^8$-2-propen-1-ylimidazo[1,2-b]pyridazine-6,8-diamine;
$N^6$-(trans-4-aminocyclohexyl)-$N^8$-(3-methylbutyl)imidazo[1,2-b]pyridazine-6,8-diamine;
$N^6$-(trans-4-aminocyclohexyl-$N^8$-propylimidazo[1,2-b]pyridazine-6,8-diamine;
$N^6$-(trans-4-aminocyclohexyl)-$N^8$-(cyclopropylmethyl)imidazo[1,2-b]pyridazine-6,8-diamine;
$N^6$-(trans-4-aminocyclohexyl)-$N^8$-((3-chlorophenyl)methylimidazo[1,2-b]pyridazine-6,8-diamine;
6-(3-amino-1-piperidinyl)-N-(4-(ethyloxy)phenyl)imidazo[1,2-b]pyridazin-8-amine;
$N^6$-(3-aminopropyl)-$N^8$-(4-(ethyloxy)phenyl)imidazo[1,2-b]pyridazine-6,8-diamine;
$N^6$-(trans-4-aminocyclohexyl)-$N^8$-(2,6-difluorophenyl)imidazo[1,2-b]pyridazine-6,8-diamine;
$N^6$-(4-((4-aminocyclohexyl)methyl)cyclohexyl)-$N^8$-(4-(ethyloxy)phenyl)imidazo[1,2-b]pyridazine-6,8-diamine;
2-(1-(8-((4-(ethyloxy)phenyl)amino)imidazo[1,2-b]pyridazin-6-yl)-4-piperidinyl)ethanol;
$N^6$-(trans-4-aminocyclohexyl)-$N^8$-1H-indol-5-ylimidazo[1,2-b]pyridazine-6,8-diamine;
$N^6$-(trans-4-aminocyclohexyl)-$N^8$-(2-(ethyloxy)phenyl)imidazo[1,2-b]pyridazine-6,8-diamine;
6-(3-amino-1-pyrrolidinyl)-N-(4-(ethyloxy)phenylimidazo[1,2-b]pyridazin-8-amine
$N^6$-(trans-4-aminocyclohexyl)-$N^8$-(2-phenylethyl)imidazo[1,2-b]pyridazine-6,8-diamine;
N-(4-(ethyloxy)phenyl)-6-(1-piperazinyl)imidazo[1,2-b]pyridazin-8-amine
$N^6$-(2-(dimethylamino)-ethyl)-$N^8$-(4-(ethyloxy)phenyl)imidazo[1,2-b]pyridazine-6,8-diamine;
$N^6$-(4-(ethyloxy)phenyl)-$N^8$-(2-furanylmethyl)imidazo[1,2-b]pyridazine-6,8-diamine;
N-(4-(ethyloxy)phenyl)-6-(4-methyl-1,4-diazepan-1-yl)imidazo[1,2-b]pyridazin-8-amine;
2-((6-((trans-4-aminocyclohexyl)amino)imidazo[1,2-b]pyridazin-8-yl)amino)phenol;
$N^6$-(trans-4-aminocyclohexyl)-$N^8$-(3-((phenylmethyl)oxy)phenyl)imidazo[1,2-b]pyridazine-6,8-diamine;
3-((6-((trans-4-aminocyclohexylamino)imidazo[1,2-b]pyridazin-8-yl)amino)phenol;
4-((6-((trans-4-aminocyclohexyl)amino)imidazo[1,2-b]pyridazin-8-yl)amino)phenol;
$N^6$-(trans-4-aminocyclohexyl)imidazo[1,2-b]pyridazine-6,8-diamine;
3-((6-((trans-4-aminocyclohexyl)amino)imidazo[1,2-b]pyridazin-8-yl)amino)benzonitrile;
4-((6-((trans-4-aminocyclohexyl)amino)imidazo[1,2-b]pyridazin-8-yl)amino)benzonitrile,
3-((6-((trans-4-aminocyclohexyl)amino)imidazo[1,2-b]pyridazin-8-yl)amino)benzoic acid;
$N^6$-(trans-4-aminocyclohexyl)-$N^8$-1H-pyrazol-3-ylimidazo[1,2-b]pyridazine-6,8-diamine;
4-((6-((trans-4-aminocyclohexyl)amino)imidazo[1,2-b]pyridazin-8-yl)amino)benzoic acid;
4-((6-((trans-4-aminocyclohexyl)amino)imidazo[1,2-b]pyridazin-8-yl)amino)-N,N-dimethylbenzenesulfonamide;
$N^6$-(trans-4-aminocyclohexyl)-$N^8$-(4-(1H-tetrazol-5-yl)phenyl)imidazo[1,2-b]pyridazine-6,8-diamine;
$N^6$-(trans-4-(ethylamino)cyclohexyl)$N^8$-phenylimidazo[1,2-b]pyridazine-6,8-diamine;
$N^6$-(trans-4-(methylamino)cyclohexyl)-$N^8$-phenylimidazo[1,2-b]pyridazine-6,8-diamine;
$N^6$-(trans-4-aminocyclohexyl)-$N^8$-(2-(phenyloxy)phenyl)imidazo[1,2-b]pyridazine-6,8-diamine;
$N^6$-(trans-4-aminocyclohexyl)-$N^8$-(4'-chloro-4-biphenylyl)imidazo[1,2-b]pyridazine-6,8-diamine;
$N^6$-(trans-4-aminocyclohexyl)-$N^8$-(2'-methyl-4-biphenylyl)imidazo[1,2-b]pyridazine-6,8-diamine;
$N^6$-(trans-4-aminocyclohexyl)-$N^8$-(3'-chloro-4-biphenylyl)imidazo[1,2-b]pyridazine-6,8-diamine;
$N^6$-(trans-4-aminocyclohexyl)-$N^8$-(4-(phenylmethyl)phenyl)imidazo[1,2-b]pyridazine-6,8-diamine;
$N^6$-(trans-4-aminocyclohexyl)-$N^8$-(4-(4-morpholinyl)phenyl)imidazo[1,2-b]pyridazine-6,8-diamine;
$N^6$-(trans-4-aminocyclohexyl)-$N^8$-(3'-chloro-3-biphenylyl)imidazol[1,2-b]pyridazine-6,8-diamine;
$N^6$-(trans-4-aminocyclohexyl)-$N^8$-(4-(1-methylethyl)phenyl)imidazo[1,2-b]pyridazine-6,8-diamine;
$N^6$-(trans-4-aminocyclohexyl)-$N^8$-(4-butylphenyl)imidazo[1,2-b]pyridazine-6,8-diamine;
$N^6$-(trans-4-aminocyclohexyl)-$N^8$-(5,6,7,8-tetrahydro-1-naphthalenyl)imidazo[1,2-b]pyridazine-6,8-diamine;
$N^6$-(trans-4-aminocyclohexyl)-$N^8$-1-naphthalenylimidazo[1,2-b]pyridazine-6,8-diamine;
$N^6$-(trans-4-aminocyclohexyl)-$N^8$-(3-(phenylmethyl)phenyl)imidazo[1,2-b]pyridazine-6,8-diamine;
$N^6$-(trans-4-aminocyclohexyl)-$N^8$-(4-propylphenyl)imidazo[1,2-b]pyridazine-6,8-diamine;
$N^6$-(trans-4-aminocyclohexyl)-$N^8$-(4'-methyl-4-biphenylyl)imidazo[1,2-b]pyridazine-6,8-diamine;
$N^6$-(trans-4-aminocyclohexyl)-$N^8$-(3-(1-methylethyl)phenyl)imidazo[1,2-b]pyridazine-6,8-diamine;

$N^6$-(trans-4-aminocyclohexyl)-$N^8$-(3-((1-methylethyl)oxy)phenyl)imidazo[1,2-b]pyridazine-6,8-diamine;
$N^6$-(trans-4-aminocyclohexyl)-$N^8$-(3,5-bis(methyloxy)phenyl)imidazo[1,2-b]pyridazine-6,8-diamine;
trans-N-(8-(6-methyl-3,4-dihydro-1(2H)-quinolinyl)imidazo[1,2-b]pyridazin-6-yl)-1,4-cyclohexanediamine;
$N^6$-(trans-4-aminocyclohexyl)-$N^8$-2-naphthalenylimidazo[1,2-b]pyridazine-6,8-diamine;
$N^6$-(trans-4-aminocyclohexyl)-$N^8$-(3-(methylsulfanyl)phenyl)imidazo[1,2-b]pyridazine-6,8-diamine;
$N^6$-(trans-4-aminocyclohexyl)-$N^8$-(3-ethylphenyl)imidazo[1,2-b]pyridazine-6,8-diamine;
$N^6$-(trans-4-aminocyclohexyl)-$N^8$-(4-ethylphenyl)imidazo[1,2-b]pyridazine-6,8-diamine;
$N^6$-(trans-4-aminocyclohexyl)-$N^8$-(4-(methylsulfanyl)phenyl)imidazo[1,2-b]pyridazine-6,8-diamine;
$N^6$-(trans-4-aminocyclohexyl)-$N^8$-9H-fluoren-2-ylimidazo[1,2-b]pyridazine-6,8-diamine;
$N^6$-(trans-4-aminocyclohexyl)-$N^8$-(2-ethylphenyl)imidazo[1,2-b]pyridazine-6,8-diamine;
$N^6$-(trans-4-aminocyclohexyl)-$N^8$-(4-cyclohexylphenyl)imidazo[1,2-b]pyridazine-6,8-diamine;
$N^6$-(trans-4-aminocyclohexyl)-$N^8$-(4-(1,1-dimethylethyl)phenyl)imidazo[1,2-b]pyridazine-6,8-diamine;
$N^6$-(trans-4-aminocyclohexyl)-$N^8$-(3-(phenyloxy)phenylimidazo[1,2-b]pyridazine-6,8-diamine;
$N^6$-(trans-4-aminocyclohexyl)-$N^8$-3-biphenylylimidazo[1,2-b]pyridazine-6,8-diamine;
$N^6$-(trans-4-aminocyclohexyl)-$N^8$-(4-((1-methylethyl)oxy)phenyl)imidazo[1,2-b]pyridazine-6,8-diamine;
$N^6$-(trans-4-aminocyclohexyl)-$N^8$-(2-chlorophenyl)imidazo[1,2-b]pyridazine-6,8-diamine;
$N^6$-(trans-4-aminocyclohexyl)-$N^8$-(4-chlorophenyl)imidazo[1,2-b]pyridazine-6,8-diamine;
$N^6$-(trans-4-aminocyclohexyl)-$N^8$-(3-chlorophenyl)imidazo[1,2-b]pyridazine-6,8-diamine;
$N^6$-(trans-4-aminocyclohexyl)-$N^8$-(4-chloro-1-naphthalenyl)imidazo[1,2-b]pyridazine-6,8-diamine;
$N^6$-(trans-4-aminocyclohexyl)-$N^8$-3-quinolinylimidazo[1,2-b]pyridazine-6,8-diamine;
$N^6$-(trans-4-aminocyclohexyl)-$N^8$-(3,5-dichlorophenyl)imidazo[1,2-b]pyridazine-6,8-diamine;
$N^6$-(trans-4-aminocyclohexyl)-$N^8$-(3-(trifluoromethyl)phenyl)imidazo[1,2-b]pyridazine-6,8-diamine;
$N^6$-(trans-4-aminocyclohexyl)-$N^8$-(4-chloro-2-fluorophenyl)imidazo[1,2-b]pyridazine-6,8-diamine;
$N^6$-(trans-4-aminocyclohexyl)-$N^8$-(2-fluoro-5-methylphenyl)imidazo[1,2-b]pyridazine-6,8-diamine;
$N^6$-(trans-4-aminocyclohexyl)-$N^8$-(4-chloro-3-methylphenyl)imidazo[1,2-b]pyridazine-6,8-diamine;
$N^6$-(trans-4-aminocyclohexyl)-$N^8$-(5-phenyl-2-pyridinyl)imidazo[1,2-b]pyridazine-6,8-diamine;
$N^6$-(trans-4-aminocyclohexyl)-$N^8$-(3-fluoro-4-methylphenyl)imidazo[1,2-b]pyridazine-6,8-diamine;
$N^6$-(trans-4-aminocyclohexyl)-$N^8$-(2-methyl-4-pyridinyl)imidazo[1,2-b]pyridazine-6,8-diamine;
$N^6$-(trans-4-aminocyclohexyl)-$N^8$-(4-fluoro-3-methylphenyl)imidazo[1,2-b]pyridazine-6,8-diamine;
$N^6$-(trans-4-aminocyclohexyl)-$N^8$-(2-fluoro-4-methylphenyl)imidazo[1,2-b]pyridazine-6,8-diamine;
$N^6$-(trans-4-aminocyclohexyl)-$N^8$-(3-((trifluoromethyl)oxy)phenyl)imidazo[1,2-b]pyridazine-6,8-diamine;
$N^6$-(trans-4-aminocyclohexyl)-$N^8$-(4-methyl-3-(trifluoromethyl)phenyl)imidazo[1,2-b]pyridazine-6,8-diamine;
$N^6$-(trans-4-aminocyclohexyl)-$N^8$-(4-ethyl-2-pyridinyl)imidazo[1,2-b]pyridazine-6,8-diamino;
$N^6$-(trans-4-aminocyclohexyl)-$N^8$-(4-(1H-1,2,4-triazol-1-yl)phenyl)imidazo[1,2-b]pyridazine-6,8-diamine;
$N^6$-(trans-4-aminocyclohexyl)-$N^8$-(4-(1H-pyrrol-1-yl)phenyl)imidazo[1,2-b]pyridazine-6,8-diamine;
$N^6$-(trans-4-aminocyclohexyl)-$N^8$-(4-(4,5-dichloro-1H-imidazol-1-yl)phenyl)imidazo[1,2-b]pyridazine-6,8-diamine;
$N^6$-(trans-4-aminocyclohexyl)-$N^8$-(4-(1H-pyrazol-1-yl)phenyl)imidazo[1,2-b]pyridazine-6,8-diamine;
$N^6$-(trans-4-aminocyclohexyl)-$N^8$-(4-(3,5-dimethyl-1H-pyrazol-1-yl)phenylimidazo[1,2-b]pyridazine-6,8-diamine;
$N^6$-(trans-4-aminocyclohexyl)-$N^8$-(4-(4-methyl-4H-1,2,4-triazol-3-yl)phenyl)imidazo[1,2-b]pyridazine-6,8-diamine;
$N^6$-(trans-4-aminocyclohexyl)-$N^8$-(4-(1H-imidazol-1-yl)phenyl)imidazo[1,2-b]pyridazine-6,8-diamine;
$N^6$-(trans-4-aminocyclohexyl)-$N^8$-(4-(1-methyl-1H-imidazol-2-yl)phenyl)imidazo[1,2-b]pyridazine-6,8-diamine;
$N^6$-(trans-4-aminocyclohexyl)-$N^8$-(4-(2-methyl-1,3-thiazol-4-yl)phenyl)imidazo[1,2-b]pyridazino-6,8-diamine;
$N^6$-(trans-4-aminocyclohexyl)-$N^8$-(4-(5-methyl-2-furanyl)phenyl)imidazo[1,2-b]pyridazine-6,8-diamino;
$N^6$-(trans-4-aminocyclohexyl)-$N^8$-(4-(2-ethyl-2H-tetrazol-5-yl)phenyl)imidazo[1,2-b]pyridazino-6,8-diamine;
4-((6-((trans-4-aminocyclohexyl)amino)imidazo[1,2-b]pyridazin-8-yl)amino)-3-hydroxy-N,N-dimethylbenzenesulfonamide;
$N^6$-(trans-4-aminocyclohexyl)-$N^8$-(2,3-dihydro-1H-inden-5-yl)imidazo[1,2-b]pyridazine-6,8-diamine;
3-((6-((trans-4-aminocyclohexyl)amino)imidazo[1,2-b]pyridazin-8-yl)amino)-N,N-dimethylbenzenesulfonamide;
4-((6-((trans-4-aminocyclohexyl)amino)imidazo[1,2-b]pyridazin-8-yl)amino)-N,N-dimethylbenzamide;
$N^6$-(trans-4-((2-chloro-4-pyrimidinyl)amino)cyclohexyl)-$N^8$-phenylimidazo[1,2-b]pyridazine-6,8-diamine;
$N^6$-(3-aminocyclopentyl)-$N^8$-phenylimidazo[1,2-b]pyridazine-6,8-diamine;
$N^6$-(trans-4-aminocyclohexyl)-$N^8$-(3-(4-morpholinylsulfonyl)phenyl)imidazo[1,2-b]pyridazine-6,8-diamine;
3-((6-((trans-4-aminocyclohexyl)amino)imidazo[1,2-b]pyridazin-8-yl)amino)-N,N-diethylbenzamide
3-((6-((trans-4-aminocyclohexyl)amino)imidazo[1,2-b]pyridazin-8-yl)amino)-N-methyl-N-phenylbenzenesulfonamide;
4-((6-((trans-4-aminocyclohexyl)amino)imidazo[1,2-b]pyridazin-8-yl)amino)-2-hydroxy-N,N-dimethylbenzenesulfonamide
$N^6$-(4-aminobicyclo[2.2.2]oct-1-yl)-$N^8$-phenylimidazo[1,2-b]pyridazine-6,8-diamine;
N-(4-((6-((trans-4-aminocyclohexyl)amino)imidazo[1,2-b]pyridazin-8-yl)amino)phenyl)methanesulfonamide;
$N^6$-(trans-4-aminocyclohexyl)-$N^8$-(4-(3-(dimethylamino)-1-pyrrolidinyl)phenyl)imidazo[1,2-b]pyridazine-6,8-diamine;
$N^6$-(trans-4-aminocyclohexyl)-$N^8$-(4-(1-pyrrolidinylsulfonyl)phenyl)imidazo[1,2-b]pyridazine-6,8-diamine;
4-((6-((trans-4-aminocyclohexyl)amino)imidazo[1,2-b]pyridazin-8-yl)amino)benzenesulfonic acid;
4-((6-((trans-4-aminocyclohexyl)amino)imidazo[1,2-b]pyridazin-8-yl)amino)-N,N-diethylbenzenesulfonamide;

4-((6-trans-4-aminocyclohexyl)amino)imidazo[1,2-b]pyridazin-8-yl)amino)-N-propylbenzenesulfonamide;
4-((6-((trans-4-aminocyclohexyl)amino)imidazo[1,2-b]pyridazin-8-yl)amino)-N-ethylbenzenesulfonamide;
4-((6-((trans-4-aminocyclohexyl)amino)imidazo[1,2-b]pyridazin-8-yl)amino)-N-methylbenzenesulfonamide;
$N^6$-(trans-4-aminocyclohexyl)-$N^8$-(4-aminophenyl)imidazo[1,2-b]pyridazine-6,8-diamine;
4-((6-((trans-4-aminocyclohexyl)amino)imidazo[1,2-b]pyridazin-8-yl)amino)benzenesulfonamide;
3-((6-((trans-4-aminocyclohexyl)amino)imidazo[1,2-b]pyridazin-8-yl)amino)benzenesulfonamide;
3-((6-((trans-4-aminocyclohexyl)amino)imidazo[1,2-b]pyridazin-8-yl)amino)benzamide;
4-((6-((trans-4-aminocyclohexyl)amino)imidazo[1,2-b]pyridazin-8-yl)amino)benzamide;
$N^6$-(trans-4-aminocyclohexyl)-$N^8$-(4-(aminomethyl)phenyl)imidazo[1,2-b]pyridazine-6,8-diamine;
6-((6-((trans-4-aminocyclohexyl)amino)imidazo[1,2-b]pyridazin-8-yl)amino)-1,2-dihydro-3H-indazol-3-one;
$N^6$-(trans-4-aminocyclohexyl)-$N^8$-(3-(aminomethyl)phenyl)imidazo[1,2-b]pyridazine-6,8-diamine;
$N^6$-(trans-4-aminocyclohexyl)-$N^8$-(2,6-difluorophenyl)imidazo[1,2-b]pyridazine-6,8-diamine;
$N^6$-(trans-4-aminocyclohexyl)-7-chloro-$N^8$-[4-(ethyloxy)phenyl]imidazo[1,2-b]pyridazine-6,8-diamine;
$N^6$-(3-aminopropyl)-$N^8$-[4-(ethyloxy)phenyl]imidazo[1,2-b]pyridazine-6,8-diamine;
$N^6$-(trans-4-aminocyclohexyl)-$N^8$-(2-fluorophenyl)imidazo[1,2-b]pyridazine-6,8-diamine;
$N^6$-(trans-4-aminocyclohexyl)-$N^8$-(2,6-difluorophenyl)imidazo[1,2-b]pyridazine-6,8-diamine;
$N^6$-(trans-4-aminocyclohexyl)-$N^8$-(2,4-difluorophenyl)imidazo[1,2-b]pyridazine-6,8-diamine;
$N^6$-(trans-4-aminocyclohexyl)-$N^8$-(3-fluorophenyl)imidazo[1,2-b]pyridazine-6,8-diamine;
$N^6$-(trans-4-aminocyclohexyl)-$N^8$-(4-fluorophenyl)imidazo[1,2-b]pyridazine-6,8-diamine;
$N^6$-(trans-4-aminocyclohexyl)-$N^8$-(3,4-difluorophenyl)imidazo[1,2-b]pyridazine-6,8-diamine;
$N^6$-(trans-4-aminocyclohexyl)-$N^8$-(2,5-difluorophenyl)imidazo[1,2-b]pyridazine-6,8-diamine;
$N^6$-(trans-4-aminocyclohexyl)-$N^8$-(2,3-difluorophenyl)imidazo[1,2-b]pyridazine-6,8-diamine;
$N^6$-(trans-4-aminocyclohexyl)-$N^8$-(3,5-difluorophenyl)imidazo[1,2-b]pyridazine-6,8-diamine;
$N^6$-(trans-4-aminocyclohexyl)-$N^8$-(3-iodophenyl)imidazo[1,2-b]pyridazine-6,8-diamine;
$N^6$-(trans-4-aminocyclohexyl)-$N^8$-[4-(trifluoromethyl)phenyl]imidazo[1,2-b]pyridazine-6,8-diamine;
$N^6$-(trans-4-aminocyclohexyl)-$N^8$-pyridin-2-ylimidazo[1,2-b]pyridazine-6,8-diamine;
$N^6$-(trans-4-aminocyclohexyl)-$N^8$-(4-methylpyridin-2-yl)imidazo[1,2-b]pyridazine-6,8-diamine;
$N^6$-(trans-4-aminocyclohexyl)-$N^8$-(5-methylpyridin-2-yl)imidazo[1,2-b]pyridazine-6,8-diamine;
$N^6$-(trans-4-aminocyclohexyl)-$N^8$-(4,6-dimethylpyridin-2-yl)imidazo[1,2-b]pyridazine-6,8-diamine;
$N^6$-(trans-4-aminocyclohexyl)-$N^8$-pyrimidin-2-ylimidazo[1,2-b]pyridazine-6,8-diamine;
$N^6$-(trans-4-aminocyclohexyl)-$N^8$-[4-(ethyloxy)phenyl]-7-methylimidezo[1,2-b]pyridazine-6,8-diamine;
$N^6$-(trans-4-aminocyclohexyl)-7-ethyl-$N^8$-[4-(ethyloxy)phenyl]imidezo[1,2-b]pyridazine-6,8-diamine;
$N^6$-(trans-4-aminocyclohexyl)-7-methyl-$N^8$-phenylimidazo[1,2-b]pyridazine-6,8-diamine;
$N^6$-(trans-4-aminocyclohexyl)-$N^8$-(3,4-dimethylphenyl)-7-methylimidazo[1,2-b]pyridazine-6,8-diamine;
$N^6$-(trans-4-aminocyclohexyl)-7-methyl-$N^8$-(4-methylphenyl)imidazo[1,2-b]pyridazine-6,8-diamine;
$N^6$-(trans-4-aminocyclohexyl)-7-methyl-$N^8$-[3-(methyloxy)phenyl]imidazo[1,2-b]pyridazine-6,8-diamine;
$N^6$-(trans-4-aminocyclohexyl)-$N^8$-biphenyl-4-yl-7-methylimidazo[1,2-b]pyridazine-6,8-diamine;
$N^6$-(trans-4-aminocyclohexyl)-7-methyl-$N^8$-[4-(propyloxy)phenyl]imidazo[1,2-b]pyridazine-6,8-diamine;
4-((6-((trans-4-aminocyclohexyl)amino)-7-methylimidazo[1,2-b]pyridazin-8-yl)amino)benzoic acid;
4-((6-((4-aminocyclohexyl)amino)-7-methylimidazo[1,2-b]pyridazin-8-yl)amino)-N,N-dimethylbenzenesulfonamide;
N-(4-((6-((trans-4-aminocyclohexyl)amino)-7-methylimidazo[1,2-b]pyridazin-8-yl)amino)phenyl)-N-methylacetamide;
$N^6$-(trans-4-aminocyclohexyl)-7-ethyl-$N^8$-phenylimidazo[1,2-b]pyridazine-6,8-diamine;
$N^6$-(trans-4-aminocyclohexyl)-7-chloro-$N^8$-[4-(ethyloxy)phenyl]imidazo[1,2-b]pyridazine-6,8-diamine;
$N^8$-[4-(ethyloxy)phenyl]-$N^6$-piperidin-3-ylimidazo[1,2-b]pyridazine-6,8-diamine;
$N^8$-[4-(ethyloxy)phenyl]-$N^6$-pyrrolidin-3-ylimidazo[1,2-b]pyridazine-6,8-diamine;
$N^8$-[4-(ethyloxy)phenyl]-$N^6$-piperidin-4-ylimidazo[1,2-b]pyridazine-6,8-diamine;
6-(3-amino-1-piperidinyl)-N-(4-(ethyoxy)phenyl)imidazo[1,2-b]pyridazin-8-amine;
$N^8$-(4-(ethyloxy)phenyl))-7-methyl-$N^6$-3-piperidinyl)imidazo[1,2-b]pyridazine-6,8-diamine;
$N^8$-phenyl-$N^6$-3-piperidinylimidazo[1,2-b]pyridazine-6,8-diamine;
6-[(3S)-3-aminopyrrolidin-1-yl]-N-[4-(ethyloxy)phenyl]imidazo[1,2-b]pyridazin-8-amine;
$N^2$-(trans-4-aminocyclohexyl)-$N^4$-[4-(ethyloxy)phenyl]pyrazolo[1,5-a][1,3,5]triazine-2,4-diamine;
Imidazo[2,1-f][1,2,4]triazine-2,4-diamine;  $N^2$-(trans-4-aminocyclohexyl)-$N^4$-(4-ethoxyphenyl)-;
$N^6$-(cis-4-aminocyclohexyl)-$N^8$-[4-(ethyloxy)phenyl]-7-methylimidazo[1,2-b]pyridazine-6,8-diamine;
$N^6$-(cis-4-aminocyclohexyl)-$N^8$-(5-methyl-2-pyridinyl)imidazo[1,2-b]pyridazine-6,8-diamine;
$N^6$-(cis-4-aminocyclohexyl)-$N^8$-phenylimidazo[1,2-b]pyridazine-6,8-diamine;
$N^6$-(cis-4-aminocyclohexyl)-7-methyl-$N^8$-phenylimidazo[1,2-b]pyridazine-6,8-diamine;
$N^6$-(cis-4-aminocyclohexyl)-$N^8$-(4-(ethyloxy)phenyl)imidazo[1,2-b]pyridazine-6,8-diamine;
$N^6$-(cis-4-aminocyclohexyl)-$N^8$-(3,4-dimethylphenyl)imidazo[1,2-b]pyridazine-6,8-diamine;
$N^6$-(cis-4-aminocyclohexyl)-$N^8$-(5-phenyl-2-pyridinyl)imidazo[1,2-b]pyridazine-6,8-diamine;
4-((6-((cis-4-aminocyclohexyl)amino)imidazo[1,2-b]pyridazin-8-yl)amino)-N,N-dimethylbenzenesulfonamide;
$N^6$-(cis-4-aminocyclohexyl)-$N^8$-(4-methylphenyl)imidazo[1,2-b]pyridazine-6,8-diamine;
$N^6$-(cis-4-aminocyclohexyl)-$N^8$-(4,6-dimethyl-2-pyridinyl)imidazo[1,2-b]pyridazine-6,8-diamine;
$N^6$-(cis-4-aminocyclohexyl)-$N^8$-(4-(1H-pyrazol-1-yl)phenyl)imidazo[1,2-b]pyridazine-6,8-diamine;
$N^6$-(cis-4-aminocyclohexyl)-$N^8$-(4-(4-morpholinylcarbonyl)phenyl)imidazo[1,2-b]pyridazine-6,8-diamine;
$N^6$-(trans-4-aminocyclohexyl)-7-methyl-$N^8$-(2-methylphenyl)imidazo[1,2-b]pyridazine-6,8-diamine;

N⁶-(trans-4-aminocyclohexyl)-N⁸-(2-fluorophenyl)-7-methylimidazo[1,2-b]pyridazine-6,8-damine;
N⁶-(cis-4-aminocyclohexyl)-7-methyl-N⁸-(2-methyl phenyl)imidazo[1,2-b]pyridazine-6,8-diamine;
N⁶-(cis-4-aminocyclohexyl)-N⁸-(2-fluorophenyl)-7-methylimidazo[1,2-b]pyridazine-6,8-diamine;
N⁶-(6-((trans-4-aminocyclohexyl)amino)imidazo[1,2-b]pyridazin-8-yl)benzamide;
1-(6-((trans-4-aminocyclohexyl)amino)imidazo[1,2-b]pyridazin-8-yl)-3-phenylurea;
N,N'-bis(4-trans-aminocyclohexyl)imidazo[1,2-b]pyridazine-6,8-diamine;
N⁶-(trans-4-aminocyclohexyl)-N⁸-(4-ethyloxyphenyl)-7-phenylimidazo[1,2-b]pyridazine-6,8-diamine;
N⁶-(trans-4-aminocyclohexyl)-N⁸-(phenyl)-7-phenylimidazo[1,2-b]pyridazine-6,8-diamine;
N⁶-(cis-4-aminocyclohexyl)-N⁸-(phenyl)-7-phenylimidazo[1,2-b]pyridazine-6,8-diamine;
N⁶-(cis-4-aminocyclohexyl)-N⁸-(4-ethoxyphenyl)-7-phenylimidazo[1,2-b]pyridazine-6,8-diamine;
4-(6-((trans-4-aminocyclohexyl)amino)imidazo[1,2-b]pyridazin-8-yl)amino)-N-(2-(4-pyridinyl)ethyl)benzamide
4-((6-((trans-4-aminocyclohexyl)amino)imidazo[1,2-b]pyridazin-8-yl)amino)-N-(2-furanylmethyl)benzamide;
4-((6-((trans-4-aminocyclohexyl)amino)imidazo[1,2-b]pyridazin-8-yl)amino)-N-(1H-imidazol-4-ylmethyl)benzamide;
4-((6-((trans-4-aminocyclohexyl)amino)imidazo[1,2-b]pyridazin-8-yl)amino)-N-(3-pyridinylmethyl)benzamide;
N⁶-(trans-4-aminocyclohexyl)-N⁸-(4-((4-phenyl-1-piperidinyl)carbonyl)phenyl)imidazo[1,2-b]pyridazine-6,8-diamine;
N⁶-(trans-4-aminocyclohexyl)-N⁸-(4-(1-pyrrolidinylcarbonyl)phenylimidazo[1,2-b]pyridazine-6,8-diamine;
N⁶-(trans-4-aminocyclohexyl)-N⁸-(4-(1-piperidinylcarbonyl)phenyl)imidazo[1,2-b]pyridazine-6,8-diamine;
4-((6-((trans-4-aminocyclohexyl)amino)imidazo[1,2-b]pyridazin-8-yl)amino)-N-(phenylmethyl)benzamide;
4-((6-((trans-4-aminocyclohexyl)amino)imidazo[1,2-b]pyridazin-8-yl)amino)-N-(3-(methyloxy)phenyl)benzamide;
N⁶-(trans-4-aminocyclohexyl)-N⁸-(4-((3-phenyl-1-pyrrolidinyl)carbonyl)phenyl)imidazo[1,2-b]pyridazine-6,8-diamine;
3-((6-((trans-4-aminocyclohexyl)amino)imidazo[1,2-b]pyridazin-8-yl)amino)-N-phenylbenzamide;
4-((6-((trans-4-aminocyclohexyl)amino)imidazo[1,2-b]pyridazin-8-yl)amino)-N-(2-hydroxyethyl)benzamide;
4-((6-((trans-4-aminocyclohexylamino)imidazo[1,2-b]pyridazin-8-yl)amino)-N-(3-(2-oxo-1-pyrrolidinyl)propyl)benzamide;
N⁶-(trans-4-aminocyclohexyl)-N⁸-(4-(4-morpholinylcarbonyl)phenyl)imidazo[1,2-b]pyridazine-6,8-diamine;
4-((6-((trans-4-aminocyclohexyl)amino)imidazo[1,2-b]pyridazin-8-yl)amino)-N-methyl-N-(2-(2-pyridinyl)ethyl)benzamide;
4-((6-((trans-4-aminocyclohexyl)amino)imidazo[1,2-b]pyridazin-8-yl)amino)-N,N-diethylbenzamide;
4-((6-((trans-4-aminocyclohexyl)amino)imidazo[1,2-b]pyridazin-8-yl)amino)-N-cyclopropylbenzamide;
4-((6-((trans-4-aminocyclohexyl)amino)imidazo[1,2-b]pyridazin-8-yl)amino)-N-(cyclohexylmethyl)benzamide;
4-((6-((trans-4-aminocyclohexyl)amino)imidazo[1,2-b]pyridazin-8-yl)amino)-N-3-pyridinylbenzamide;
4-((6-((trans-4-aminocyclohexyl)amino)imidazo[1,2-b]pyridazin-8-yl)amino)-N-(1-methyl-1H-pyrazol-5-yl)benzamide;
4-((6-((trans-4-aminocyclohexyl)amino)imidazo[1,2-b]pyridazin-8-yl)amino)-N-(1-(4-fluorophenyl)-2-oxo-1,2-dihydro-3-pyridinyl)benzamide;
4-((6-((trans-4-aminocyclohexyl)amino)imidazo[1,2-b]pyridazin-8-yl)amino)-N-phenylbenzamide;
4-((6-((trans-4-aminocyclohexyl)amino)imidazo[1,2-b]pyridazin-8-yl)amino)-N-cyclohexylbenzamide;
4-((6-((trans-4-aminocyclohexyl)amino)imidazo[1,2-b]pyridazin-8-yl)amino)-N-(4-pyridinylmethyl)benzamide;
1-(4-((6-((trans-4-aminocyclohexyl)amino)imidazo[1,2-b]pyridazin-8-yl)amino)phenyl)-3-phenylurea;
1-(4-((6-((cis-4-aminocyclohexyl)amino)-7-methylimidazo[1,2-b]pyridazin-8-yl)amino)phenyl)-3-phenylurea;
1-(4-((6-((trans-4-aminocyclohexyl)amino)-7-methylimidazo[1,2-b]pyridazin-8-yl)amino)phenyl)-3-phenylurea;
N-(4-((6-((trans-4-aminocyclohexyl)amino)imidazo[1,2-b]pyridazin-8-yl)amino)phenyl)-1-(4-fluorophenyl)-2-oxo-1,2-dihydro-3-pyridinecarboxamide;
N-(4-((6-((trans-4-aminocyclohexyl)amino)imidazo[1,2-b]pyridazin-8-yl)amino)-phenyl)-1-(4-fluorophenyl)-2-oxo-1,2-dihydro-3-pyridinecarboxamide
N-(4-((6-((trans-4-aminocyclohexyl)amino)imidazo[1,2-b]pyridazin-8-yl)amino)-2-ethyl phenyl)-1-(4-fluorophenyl)-2-oxo-1,2-dihydro-3-pyridinecarboxamide;
N-(4-((6-((trans-4-aminocyclohexyl)amino)imidazo[1,2-b]pyridazin-8-yl)amino)phenyl)benzamide;
N-(4-((6-((trans-4-aminocyclohexyl)amino)imidazo[1,2-b]pyridazin-8-yl)amino)phenyl)acetamide;
3-((6-((trans-4-aminocyclohexyl)amino)-7-methylimidazo[1,2-b]pyridazin-8-yl)amino)phenol;
N-(4-((6-chloroimidazo[1,2-b]pyridazin-8-yl)amino)phenyl)-1-(4-fluorophenyl)-2-oxo-1,2-dihydro-3-pyridinecarboxamide;
1-(4-fluorophenyl)-N-(4-(imidazo[1,2-b]pyridazin-8-ylamino)phenyl)-2-oxo-3-piperidinecarboxamide;
1-(4-fluorophenyl)-N-(4-(imidazo[1,2-b]pyridazin-8-ylamino)phenyl)-2-oxo-1,2-dihydro-3-pyridinecarboxamide;
6-((trans-4-aminocyclohexyl)amino)-8-((4-(ethyloxy)phenyl)amino)imidazo[1,2-b]pyridazine-3-carbonitrile;
6-((trans-4-aminocyclohexyl)amino)-8-(phenylamino)imidazo[1,2-b]pyridazine-3-carbonitrile;
6-((4-trans-aminocyclohexyl)amino)-7-methyl-8-(phenylamino)imidazo[1,2-b]pyridazine-3-carbonitrile;
6-((trans)-4-aminocyclohexylamino)-7-ethyl-8-(phenylamino)imidazo[1,2-b]pyridazine-3-carbonitrile;
6-((trans-4-aminocyclohexyl)amino)-8-anilino-7-isopropylimidazo[1,2-b]pyridazine-3-carbonitrile;
N⁶-(trans-4-aminocyclohexyl)-N⁸-(4-(ethyloxy)phenyl)-3-fluoroimidazo[1,2-b]pyridazine-6,8-diamine;
N⁶-(trans-4-aminocyclohexyl)-N⁸-(4-(ethyloxy)phenyl)-3-methylimidazo[1,2-b]pyridazine-6,8-diamine;
N⁶-(trans-4-aminocyclohexyl)-N⁸-(4-(ethyloxy)phenyl)-2,3-dimethyl imidazo[1,2-b]pyridazine-6,8-diamine;
N-(6-((trans-4-aminocyclohexyl)amino)imidazo[1,2-b]pyridazin-8-yl)benzenesulfonamide;
6-((trans-4-aminocyclohexyl)oxy)-8-anilinoimidazo[1,2-b]pyridazine-3-carbonitrile;

6-((trans-4-aminocyclohexyl)amino)-8-anilinoimidazo[1,2-b]pyridazine-3-carboxamide;

$N^6$-(trans-4-aminocyclohexyl)-7-ethyl-$N^8$-phenylimidazo[1,2-b]pyridazine-6,8-diamine;

$N^6$-(trans-4-aminocyclohexyl)-7-ethyl-$N^8$-[4-(ethyloxy)phenyl]imidazo[1,2-b]pyridazine-6,8-diamine;

$N^6$-(trans-4-Aminocyclohexyl)-7-benzyl-$N^8$-phenylimidazo[1,2-b]pyridazine-6,8-diamine;

3-((6-((trans-4-Aminocyclohexyl)amino)-7-isopropylimidazo[1,2-b]pyridazin-8-yl)amino)-N-ethylbenzenesulfonamide;

4-((6-((trans-4-Aminocyclohexyl)amino)-7-isopropylimidazo[1,2-b]pyridazin-8-yl)amino)-N-ethylbenzenesulfonamide;

4-((6-((trans-4-Aminocyclohexyl)amino)-7-isopropylimidazo[1,2-b]pyridazin-8-yl)amino)-N-phenylbenzamide;

$N^6$-(trans-4-Aminocyclohexyl)-7-isopropyl-$N^8$-3-pyridinylimidazo[1,2-b]pyridazine-6,8-diamine;

$N^6$-(trans-4-Aminocyclohexyl)-$N^8$-(3-ethoxyphenyl)-7-isopropylimidazo[1,2-b]pyridazine-6,8-diamine;

$N^6$-(trans-4-Aminocyclohexyl)-$N^8$-(4-ethoxyphenyl)-7-isopropyl imidazo[1,2-b]pyridazine-6,8-diamine;

4-((6-((trans-4-Aminocyclohexyl)amino)-7-isopropylimidazo[1,2-b]pyridazin-8-yl)amino)phenol;

$N^6$-(trans-4-Aminocyclohexyl)-$N^8$-(4-(aminomethyl)phenyl)-7-methylimidazo[1,2-b]pyridazine-6,8-diamine;

6-(3-Amino-1,2-benzisoxazol-5-yl)-N-phenyl imidazo[1,2-b]pyridazin-8-amine;

6-(3-Amino-1,2-benzisoxazol-6-yl)-N-phenylimidazo[1,2-b]pyridazin-8-amine;

$N^6$-(trans-4-Aminocyclohexyl)-7-(3-chlorophenyl)-$N^8$-phenylimidazo-6,8-diamine;

$N^6$-(trans-4-Aminocyclohexyl)-7-(4-chlorophenyl)-$N^8$-phenylimidazo[1,2-b]pyridazine-6,8-diamine 8-Anilino-6-((3S)-3-piperidinylamino)imidazo[1,2-b]pyridazine-3-carbonitrile;

3-((6-((trans-4-Aminocyclohexyl)amino)-7-isopropylimidazo[1,2-b]pyridazin-8-yl)amino)phenol;

$N^6$-(trans-4-Aminocyclohexyl)-3-cyclopropyl-$N^8$-phenylimidazo[1,2-b]pyridazine-6,8-diamine $N^6$-(4-Aminocyclohexyl)-$N^8$-phenyl-3((E)-2-(4-pyridinyl)vinyl)imidazo[1,2-b]pyridazine-6,8-diamine;

$N^6$-(trans-4-Aminocyclohexyl)-$N^8$-phenyl-3-(1-propyn-1-yl)imidazo[1,2-b]pyridazine-6,8-diamine;

6-((trans-4-Aminocyclohexyl)amino)-8-anilino-N-4-pyridinylimidazo[1,2-b]pyridazine-3-carboxamide;

6-((4-Amino-1-piperidinyl)methyl)-N-phenylimidazo[1,2-b]pyridazin-8-amine;

6-((trans-4-Aminocyclohexyl)amino)-8-anilinoimidazo[1,2-b]pyridazine-7-carbonitrile;

8-Anilino-6-((3S)-3-piperidinylamino)imidazo[1,2-b]pyridazine-7-carbonitrile; and 4-((6-((trans-4-Aminocyclohexyl)amino)-3-cyanoimidazo[1,2-b]pyridazin-8-yl)amino)-N-methylbenzenesulfonamide;

ii) or an enantiomer, diastereomer, or a pharmaceutically-acceptable salt of (i), thereof.

15. A pharmaceutical composition comprising one or more compounds according to claim 1 or 14 and a pharmaceutically acceptable carrier or diluent.

16. A method of treating rheumatoid arthritis, comprising administering to a mammal in need of such treatment a therapeutically effective amount of a compound according to claim 1 or 14.

* * * * *

UNITED STATES PATENT AND TRADEMARK OFFICE
CERTIFICATE OF CORRECTION

PATENT NO. : 7,723,336 B2
APPLICATION NO. : 11/689132
DATED : May 25, 2010
INVENTOR(S) : Wayne Vaccaro et al.

It is certified that error appears in the above-identified patent and that said Letters Patent is hereby corrected as shown below:

On the Title Page, Item (56) "OTHER PUBLICATIONS"
line 4, delete "Rhematol." and insert -- Rheumatol. --, therefor.

In the Claims:
Claim 4, col. 159, line 12, delete "$R_8$" and insert -- $R_6$ --, therefor.

Claim 5, col. 160, line 5, delete "$R_6$" and insert -- $R_5$ --, therefor.

Claim 6, col. 161, line 31, delete "$NR_{19}(C(O)NR_{19}R_{20}$;" and insert -- $NR_{19}C(O)NR_{19}R_{20}$; --, therefor.

Claim 6, col. 161, line 50, delete "-$(CH_2)_v$pyradizinyir," and insert-- -$(CH_2)_v$pyradizinyl, --, therefor.

Claim 7, col. 173, line 10, after " 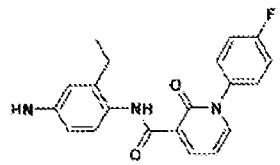 " insert -- , --.

Claim 10, col. 175, line 15, after "  " insert -- , --.

Claim 13, col. 176, line 8, delete "$R_{11}$," and insert -- $R_{11}$ --, therefor.

Claim 13, col. 176, line 22, delete "phenanthrollinyl," and insert -- phenanthrolinyl, --, therefor.

Claim 14, col. 176, line 37, delete "-phenyl)imidazo" and insert --phenylimidazo --, therefor.

Claim 14, col. 176, line 57, delete "imidazol" and insert -- imidazo --, therefor.

Signed and Sealed this
Twelfth Day of April, 2011

David J. Kappos
*Director of the United States Patent and Trademark Office*

CERTIFICATE OF CORRECTION (continued)
U.S. Pat. No. 7,723,336 B2

In the Claims:

Claim 14, col. 176, line 62, delete "-1H-" and insert -- -$N^8$- --, therefor.

Claim 14, col. 177, line 17, delete "$N^8$-" and insert -- -$N^8$- --, therefor.

Claim 14, col. 177, line 32, delete "methylimidazo" and insert -- methyl)imidazo --, therefor.

Claim 14, col. 177, lines 47-48, delete "methylimidazo" and insert -- methyl)imidazo --, therefor.

Claim 14, col. 177, lines 64-65, delete "phenylimidazo" and insert -- phenyl)imidazo --, therefor.

Claim 14, col. 178, line 3, delete "-ethyl)" and insert -- ethyl) --, therefor.

Claim 14, col. 178, line 5, delete "$N^6$-(4-(ethyloxy)phenyl)-$N^8$-" and insert -- $N^8$-(4-(ethyloxy)phenyl)-$N^6$- --, therefor.

Claim 14, col. 178, line 13, delete "((trans-4-aminocyclohexyl" and insert -- ((trans-4-aminocyclohexyl) --, therefor.

Claim 14, col. 178, line 34, delete "$N^8$-" and insert -- -$N^8$- --, therefor.

Claim 14, col. 179, lines 7-8, delete "-$N^8$-2-naphthalenyl)imidazo" and insert -- -$N^8$-2-naphthalenylimidazo --, therefor.

Claim 14, col. 179, lines 25-26, delete "phenylimidazo" and insert -- phenyl)imidazo --, therefor.

Claim 14, col. 180, line 11, delete "phenylimidazo" and insert -- phenyl)imidazo --, therefor.

Claim 14, col. 180, line 22, delete "pyridazino-" and insert -- pyridazine- --, therefor.

Claim 14, col. 180, line 27, delete "pyridazino-" and insert -- pyridazine- --, therefor.

Claim 14, col. 181, line 63, delete "-methylimidezo" and insert -- -methylimidazo --, therefor.

Claim 14, col. 181, line 65, delete "imidezo" and insert -- imidazo --, therefor.

Claim 14, col. 182, line 29, delete "(4-(ethyoxy)" and insert -- (4-(ethyloxy) --, therefor.

Claim 14, col. 182, lines 31-32, delete "$N^8$-(4-(ethyloxy)phenyl))-7-methyl-$N^6$-3-piperidinyl)imidazo[1,2-b]pyridazine-6,8-diamine;" and insert -- $N^8$-(4-(ethyloxy)phenyl)-7-methyl-$N^6$-3-piperidinylimidazo[1,2-b]pyridazine-6,8-diamine; --, therefor.

CERTIFICATE OF CORRECTION (continued)
U.S. Pat. No. 7,723,336 B2

In the Claims:

Claim 14, col. 183, line 2, delete "8-damine;" and insert -- 8-diamine; --, therefor.

Claim 14, col. 183, line 7, delete "$N^6$-" and insert -- N- --, therefor.

Claim 14, col. 183, line 21, delete "4-(6" and insert -- 4-((6 --, therefor.

Claim 14, col. 183, lines 22-23, after "benzamide" insert -- ; --.

Claim 14, col. 184, line 29, after "pyridinecarboxamide" insert -- ; --.

Claim 14, col. 185, line 34, delete "phenylimidazo-6,8-diamine;" and insert -- phenylimidazo[1,2-b]pyridazine-6,8-diamine; --, therefor.

Claim 14, col. 186, line 2, after "diamine" insert -- ; --.

Claim 14, col. 186, line 8, after "diamine" insert -- ; --.